US007687466B2

(12) United States Patent
Mickle et al.

(10) Patent No.: US 7,687,466 B2
(45) Date of Patent: *Mar. 30, 2010

(54) ABUSE-RESISTANT AMPHETAMINE PRODRUGS

(75) Inventors: Travis Mickle, Coralville, IA (US); Suma Krishnan, Belvedere, CA (US); Barney Bishop, Annandale, VA (US); Christopher Lauderback, Blacksburg, VA (US); James Scott Moncrief, Christiansburg, VA (US); Robert Oberlender, Blacksburg, VA (US); Thomas Piccariello, Blacksburg, VA (US); Bernhard J. Paul, Lexington, MA (US); Christopher A. Verbicky, Broadalbin, NY (US)

(73) Assignee: Shire LLC, Florence, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/201,794

(22) Filed: Aug. 29, 2008

(65) Prior Publication Data

US 2009/0131516 A1     May 21, 2009

Related U.S. Application Data

(63) Continuation of application No. 11/400,304, filed on Apr. 10, 2006, which is a continuation-in-part of application No. 10/857,619, filed on Jun. 1, 2004, now Pat. No. 7,223,735, and a continuation-in-part of application No. 10/858,526, filed on Jun. 1, 2004, now Pat. No. 7,105,486, which is a continuation-in-part of application No. PCT/US03/05525, filed on Feb. 24, 2003.

(60) Provisional application No. 60/759,958, filed on Jan. 19, 2006, provisional application No. 60/756,548, filed on Jan. 6, 2006, provisional application No. 60/681,170, filed on May 16, 2005, provisional application No. 60/669,386, filed on Apr. 8, 2005, provisional application No. 60/669,385, filed on Apr. 8, 2005, provisional application No. 60/567,801, filed on May 5, 2004, provisional application No. 60/473,929, filed on May 29, 2003, provisional application No. 60/362,082, filed on Mar. 7, 2002, provisional application No. 60/358,368, filed on Feb. 22, 2002.

(51) Int. Cl.
*A61K 38/00* (2006.01)
*A61K 51/00* (2006.01)
*A61K 31/785* (2006.01)
*G01N 33/53* (2006.01)
*G01N 33/00* (2006.01)

(52) U.S. Cl. .................... 514/17; 424/1.69; 424/78.16; 436/901; 436/111; 514/18; 514/12; 514/2

(58) Field of Classification Search .................. 514/12, 514/2, 15, 44, 554; 530/300
See application file for complete search history.

(56) References Cited

U.S. PATENT DOCUMENTS

| 3,028,395 A | 4/1962 | Gillingham |
| 3,028,430 A | 4/1962 | Gillingham |
| 3,676,492 A | 7/1972 | Biel et al. |
| 3,706,831 A | 12/1972 | Plotnikoff et al. |
| 3,843,696 A | 10/1974 | Wagner et al. |
| 3,846,399 A | 11/1974 | Hirschmann et al. |
| 3,878,187 A | 4/1975 | Schneider et al. |
| 3,884,898 A | 5/1975 | Schneider |
| 3,975,342 A | 8/1976 | Gross |
| 3,998,799 A | 12/1976 | Bodor et al. |
| 4,000,280 A | 12/1976 | Florvall et al. |
| 4,025,501 A | 5/1977 | Leute |
| 4,040,907 A | 8/1977 | Ullman et al. |
| 4,043,989 A | 8/1977 | Schneider et al. |
| 4,064,235 A | 12/1977 | Yanaihara et al. |
| 4,064,236 A | 12/1977 | Dorn et al. |
| 4,297,346 A | 10/1981 | Rips et al. |
| 4,356,166 A | 10/1982 | Peterson et al. |

(Continued)

FOREIGN PATENT DOCUMENTS

EP          0187547          7/1986

(Continued)

OTHER PUBLICATIONS

Amidon, G., et al., "A Theoretical Basis for a Biopharmaceutic Drug Classification: The Correlation of in Vitro Drug Product Dissolution and in Vivo Bioavailability," *Pharmaceutical Research*, 12(3): 413-420 (1995).
Amidon, G.L., et al., "5'-Amino Acid Esters of Antiviral Nucleosides, Acyclovir, and AZT are Absorbed by the Intestinal PEPT1 Peptide Transporter," *Pharm Res*, 16(2):175 (1999).
Balimane, P., et al., "Effect of Ionization on the Variable Uptake of Valacyclovir via the Human Intestinal Peptide Transporter (hPepT1) in CHP cells," *Biopharm Drug Dispos*, 21(5):165-174 (2000).

(Continued)

*Primary Examiner*—Maury Audet
(74) *Attorney, Agent, or Firm*—Darby & Darby P.C.

(57) ABSTRACT

The invention describes compounds, compositions, and methods of using the same comprising a chemical moiety covalently attached to amphetamine. These compounds and compositions are useful for reducing or preventing abuse and overdose of amphetamine. These compounds and compositions find particular use in providing an abuse-resistant alternative treatment for certain disorders, such as attention deficit hyperactivity disorder (ADHD), ADD, narcolepsy, and obesity. Oral bioavailability of amphetamine is maintained at therapeutically useful doses. At higher doses bioavailability is substantially reduced, thereby providing a method of reducing oral abuse liability. Further, compounds and compositions of the invention decrease the bioavailability of amphetamine by parenteral routes, such as intravenous or intranasal administration, further limiting their abuse liability.

14 Claims, 68 Drawing Sheets

U.S. PATENT DOCUMENTS

| | | | |
|---|---|---|---|
| 4,399,121 A | 8/1983 | Albarella et al. | |
| 4,427,660 A | 1/1984 | Schiffman et al. | |
| 4,457,907 A | 7/1984 | Porter | |
| 4,552,864 A | 11/1985 | Antoni et al. | |
| 4,650,675 A | 3/1987 | Borel et al. | |
| 4,801,575 A | 1/1989 | Pardridge | |
| 4,863,735 A | 9/1989 | Kohn et al. | |
| 4,902,505 A | 2/1990 | Pardridge et al. | |
| 4,960,790 A | 10/1990 | Stella et al. | |
| 4,976,962 A | 12/1990 | Bichon et al. | |
| 5,026,827 A | 6/1991 | Miyazaki et al. | |
| 5,073,641 A | 12/1991 | Bundgaard et al. | |
| 5,087,616 A | 2/1992 | Myers et al. | |
| 5,169,933 A | 12/1992 | Anderson et al. | |
| 5,183,883 A | 2/1993 | Tanaka et al. | |
| 5,219,564 A | 6/1993 | Zalipsky et al. | |
| 5,233,025 A | 8/1993 | Miyazaki et al. | |
| 5,238,714 A | 8/1993 | Wallace et al. | |
| 5,362,831 A | 11/1994 | Mongelli et al. | |
| 5,470,997 A | 11/1995 | Buechler et al. | |
| 5,501,987 A | 3/1996 | Ordonez et al. | |
| 5,529,915 A | 6/1996 | Phillips et al. | |
| 5,534,496 A | 7/1996 | Lee et al. | |
| 5,670,477 A | 9/1997 | Poduslo et al. | |
| 5,762,909 A | 6/1998 | Uzgiris | |
| 5,767,227 A | 6/1998 | Latham et al. | |
| 5,846,743 A | 12/1998 | Janmey et al. | |
| 5,851,536 A | 12/1998 | Yager et al. | |
| 5,882,645 A | 3/1999 | Toth et al. | |
| 5,891,459 A | 4/1999 | Cooke et al. | |
| 5,898,033 A | 4/1999 | Swadesh et al. | |
| 5,910,569 A | 6/1999 | Latham et al. | |
| 5,935,988 A | 8/1999 | Matzke et al. | |
| 5,948,750 A | 9/1999 | Garsky et al. | |
| 5,952,294 A | 9/1999 | Lazo et al. | |
| 5,977,163 A | 11/1999 | Li et al. | |
| 6,005,004 A | 12/1999 | Katz et al. | |
| 6,030,941 A | 2/2000 | Summerton et al. | |
| 6,043,230 A | 3/2000 | Arimilli et al. | |
| 6,048,736 A | 4/2000 | Kosak | |
| 6,074,659 A | 6/2000 | Kunz et al. | |
| 6,093,391 A | 7/2000 | Kabanov et al. | |
| 6,235,718 B1 | 5/2001 | Balasubramanium et al. | |
| 6,255,285 B1 | 7/2001 | Kotake et al. | |
| 6,258,836 B1 | 7/2001 | Shashoua | |
| 6,306,993 B1 | 10/2001 | Rothbard et al. | |
| 6,309,633 B1 | 10/2001 | Ekwuribe et al. | |
| 6,384,020 B1 * | 5/2002 | Flanner et al. | 514/53 |
| 6,407,137 B2 | 6/2002 | Shashoua | |
| 6,458,842 B1 | 10/2002 | Dickinson et al. | |
| 6,632,922 B1 | 10/2003 | Deming et al. | |
| 6,680,365 B1 | 1/2004 | Deming | |
| 6,686,446 B2 | 2/2004 | Deming et al. | |
| 6,716,452 B1 | 4/2004 | Piccariello et al. | |
| 6,740,641 B2 | 5/2004 | Gao et al. | |
| 6,784,186 B1 | 8/2004 | Jackson et al. | |
| 6,913,768 B2 | 7/2005 | Couch et al. | |
| 7,105,486 B2 | 9/2006 | Mickle et al. | |
| 2001/0031873 A1 | 10/2001 | Greenwald et al. | |
| 2002/0098999 A1 | 7/2002 | Gallop et al. | |
| 2002/0099013 A1 | 7/2002 | Piccariello et al. | |
| 2002/0115725 A1 | 8/2002 | Epstein et al. | |
| 2002/0151526 A1 | 10/2002 | Gallop et al. | |
| 2002/0151529 A1 | 10/2002 | Cundy et al. | |
| 2002/0173468 A1 | 11/2002 | Lerchen et al. | |
| 2002/0183390 A1 | 12/2002 | Javitt | |
| 2003/0077297 A1 | 4/2003 | Chen et al. | |
| 2004/0131680 A1 | 7/2004 | Goldenheim et al. | |
| 2004/0132968 A1 | 7/2004 | Reed et al. | |
| 2004/0204434 A1 | 10/2004 | Shafer et al. | |
| 2005/0038121 A1 | 2/2005 | Mickle et al. | |
| 2005/0054561 A1 | 3/2005 | Mickle et al. | |
| 2005/0176645 A1 | 8/2005 | Mickle et al. | |

FOREIGN PATENT DOCUMENTS

| | | |
|---|---|---|
| EP | 0634999 | 1/1995 |
| FR | 1421130 | 3/1966 |
| GB | 1091089 | 11/1967 |
| GB | 1112347 | 5/1968 |
| JP | 55007242 | 1/1980 |
| JP | 55028915 | 2/1980 |
| JP | 4112858 | 4/1992 |
| JP | 7165684 | 6/1995 |
| NL | 6414901 | * 12/1964 |
| NL | 6414901 | 7/1965 |
| WO | WO-9320048 | 10/1993 |
| WO | WO-9320079 A1 | 10/1993 |
| WO | WO-9411021 A1 | 5/1994 |
| WO | WO-9512605 | 5/1995 |
| WO | WO-9514033 | 5/1995 |
| WO | WO-9736616 | 10/1997 |
| WO | WO-9804277 | 2/1998 |
| WO | WO-9848824 | 11/1998 |
| WO | WO-9939691 A2 | 8/1999 |
| WO | WO-9949901 A1 | 10/1999 |
| WO | WO-0234237 | 5/2002 |
| WO | WO-03034980 | 5/2003 |
| WO | WO-2005-032474 | 4/2005 |
| WO | WO-2006121552 | 11/2006 |

OTHER PUBLICATIONS

Balimane, P., et al., "Direct Evidence for Peptide Transporter (PepT1)-Mediated Uptake of a Nonpeptide Prodrug, Valacyclovir," *Biochem Biophys Res Commun*, 250(2):246-251 (1998).

Bunevicius, R., "Effects of Thyroxine as Compared with Thyroxine Plus Triiodothyronine in Patients with Hypothyroidism," *The New England Journal of Medicine*, 340(6): 424-429 (1999).

Burnette, Thimysta C., et al., "Metabolic Disposition of the Acyclovir Prodrug Valaciclovir in the Rat," *Drug Metabolism and Disposition*, 22(1):60-64 (1994).

Canaris, G., "The Colorado Thyroid Disease Prevalence Study," Archives Internal Medicine Articles and Abstracts, 160(4) (2000).

De Vrueh, Remco L.A., et al, "Transport of L-Valine-Acyclovir Via the Oligopeptide Transporter in the Human Intestinal Cell Line, Caco-2," *Journal of Pharmacology and Experimental Therapeutics*, 286(2):1166-1170 (1988).

Friedrichsen, G.M., et al., "Model Prodrugs Designed for the Intestinal Peptide Transporter. A Synthetic Approach for Coupling of Hydroxy-Containing Compounds to Dipeptides," *Eur J Pharm Sci*, 14(1):13-19 (2001, Abstract.

Guo, A., et al., "Interactions of a Nonpeptidic Drug, Valacyclovir, with the Human Intestinal Peptide Transporter (hPEPT1) Expressed in a Mammalian Cell Line," *Pharmacol Exp Ther*, 289(1):448-454 (1999), Abstract.

Han H., et al., "5'-Amino Acid Esters of Antiviral Nucleosides, Acyclovir, and AZT and Absorbed by the Intestinal PEPT1 Peotide Transporter," *Pharm Res*, 15(8):1154-1159 (1998).

Han, H.K., et al., "Cellular Uptake Mechanism of Amino Acid Ester prodrugs in Caco-2hPEPT1 Cells Overexpressing a Human Peptide Transporter," *Pharm Res*, 15(9):1382-1386 (1998).

Han, Hyo-Kyung, et al., "Targeted Prodrug Design to Optimize Drug Delivery," *AAPS PharmSci*, 2(1): Article 6 (2000).

Havranova, Marie et al., "A High-Molecular Mass Derivative of Trypsin-Kallikrein Inhibitor for Potential Medical Use, II," *Hoppe-Seyler's Z. Physiol. Chem.*, 363:295-303 (1982).

Herrera-Ruiz, D., et al., "Spatial Expression Patterns of Peptide Transporters in the Human and Rat Gastrointestinal Tracts, Caco-2 in vitro Cell Culture Model, and Multiple Human Tissues," *AAPS PharmSci*, 3(1):E9 (2001).

Hosztafi, S. et al. "Synthesis and Analgetic Activity of Nicotinic Esters of Morphine Derivatives," Arzneim.-Forsch./Drug Res. 43(II), Nr. 11 (1993).

Knutter, I, et al., "A Novel Inhibitor of the Mammalian Peptide Transporter PEPT1," *Biochemistry*, 40(14):4454-4458 (2001).

Kovacs, J., et al., "Glutamic and Aspartic Anhydrides. Rearrangement of N-Carboxyglutamic 1,5-Anhydride to the Leuchs' Anhydride and Conversion of the Latter to Pyroglutamic Acid," *J. Am. Chem. Soc.*, 85(12): 1839-1844 (1963).

Kramer, Werner et al., "Intestinal Absorption of Peptides by Coupling to Bile Acids," *The Journal of Biochemistry*, 269(14):10621-10627 (1994).

Leibach, F.H, et al., "Peptide Transporters in the Intestine and the Kidney," *Annu Rev Nutri*, 16:99-119 (1996).

Li, Chun, et al., "Complete Regression of Well-Established Tumors Using a Novel Water-Soluble Poly(L-Glutamic Acid)-Paclitaxel Conjugate," *Cancer Res*, 58:2404-2409 (1998).

Marriq, Claudine, et al., "Amino Acid Sequence of the Unique 3,5,3'-Triiodothyronine-Containing Sequence from Porcine Thyroglobulin," *Biochemical and Biophysical Research Communications*, 112(1):206-213 (1983).

Negishi, Naoki, et al., "Coupling of Naltrexone to Biodegradable Poly (α-Amino Acids)," *Pharmaceutical Research*, 4(4):305-310 (1987).

Nishida, Koyo, et al., "Pharmacokinetic Analysis of in Vivo Metabolism of Amino Acid or Dipeptide Conjugates of Salicylic Acid in Rabbit Intestinal Microorganisms," *Pharmaceutical Research*, 11(1):160-164 (1994).

Oh, D., et al., "Estimating the Fraction Dose Absorbed from Suspensions of Poorly Soluble Compounds in Humans: A Mathematical Model," *Pharmaceutical Research*, vol. 10, No. 2 (1993).

Oh, DM, et al., "Drug Transport and Targeting. Intestinal Transport," *Pharma Biotechnol*, 12:59-88 (1999), Abstract.

Okada, Masahiko, et al., "Synthesis of Glycopeptide-conjugates via Ring-Opening Polymerization of Sugar-Substituted α-Amino Acid N-Carboxyanhydrides (GlycoNCAs)," *Proc. Japan Acad.*, 73:205-209 (1997).

Orten, James M. et al., "Thyroxine," *Human Biochemistry*, 9$^{th}$ Ed., C.V. Mosby Company, St. Louis,pp. 401-405 (1975).

Pade, V., et al., "Link Between Drug Absorption Solubility and Permeability Measurements in Caco-2 Cells," *Journal of Pharmaceutical Sciences*, vol. 87, No. 12 (1998).

Rawitch, Allen B., et al., "The Isolation of Identical Thyroxine Containing Amino Acid Sequences from Bovine, Ovine and Porcine Thyroglobulins," *Biochemical and Biophysical Research Communications*, 118(2):423-429 (1984).

Ryser, Hugues J.P., et al., "Conjugation of Methotrexate to Poly (L-lysine) Increases Drug Transport and Overcomes Drug Resistance in Cultured Cells," *Proc. Natl. Acad. Sci. USA*, 75(8):3867-3870 (1978).

Sawada, Kyoko, et al., "Recognition of L-Amino Acid Ester Compounds by Rat Peptide Transporters PEPT1 and PEPT2," *Journal of Pharmacology and Experimental Therapeutics*, 291(2):705-709 (1999).

Schmidt, Brigitte F., et al., "Peptide-Linked 1,3-Dialkyl-3-acyltriazenes: Gastrin Receptor Directed Antineoplastic Alkylating Agents," *Journal of Medicinal Chemistry*, 37(22):3812-3817 (1994).

Shen, H., et al., "Developmental Expression of PEPT1 and PEPT2 in Rat Small Intestine, Colon, and Kidney," *Pediatr Res*, 49(6):789-795 (2001), Abstract.

Shiraga, T., et al., "Cellular and Molecular Mechanisms of Dietary Regulation on Rat Intestinal H+/Peptide Transporter PepT1," *Gastroenterology*, 116(2):354-362 (1999), Abstract.

Tamai, I., et al., "Improvement of L-dopa Absorption by Dipeptidyl Derivation, Utilizing Peptide Transporter PepT1," *J. Pharma. Sci.*, 87(12):1542-1546 (1988), Abstract.

Toft, A., "Thyroid Hormone Replacement—One Hormone or Two?," *The New England Journal of Medicine*, vol. 340, No. 6 (1999).

Toth, Istvan, "A Novel Chemical Approach to Drug Delivery: Lipidic Amino Acid Conjugates," *Journal of Drug Targeting*, 2:217-239 (1994).

Zunino, Franco, et al., "Anti-Tumor Activity of Daunorubicin Linked to Poly-L-Aspartic Acid," *International Journal of Cancer*, 30:465-470 (1982).

Zunino, Franco, et al., "Comparison of Antitumor Effects of Daunorubicin Covalently Linked to Poly-L-Amino Acid Carriers," *European Journal of Cancer & Clinical Oncology*, 20(3):121-125 (1984).

Bai, J.P.F. et al., Gastrointestinal Transport of Peptide and Protein Drugs and Prodrugs, In: Welling PG, Balant LP, eds. Handbook of Experimental Pharmacology. Heidelberg: Springer-Verlag; 1994:110:189-206.

Schenk, J., The functioning neuronal transporter for dopamine: kinetic mechanisms and effects of amphetamines, cocaine and methyphenidata, Progress in Drug Research, vol. 59, 2002.

Hughes, et al. Lipidic Peptides. III: Lipidic Amino Acid and Oligomer Conjugates of Morphine, Journal of Pharmaceutical Sciences, vol. 80, No. 12, Dec. 1991.

International Search Report for PCT/US04/17204 dated Oct. 15, 2004.

International Search Report for PCT/US03/05525 dated Oct. 9, 2003.

Weber et al., "Synthesis, In Vitro Skin Permeation Studies, and PLS-Analysis of New Naproxen Derivatives," Pharmaceutical Research, 2001; 18(5):600-607.

Kinoshita et al., "Serum Leucine Aminopeptidase Assay Using a Dialysis Membrane-Covered Glassy-Carbon Electrode," Japanese J. of Clin. Chem., 1993; 22: 143-146.

Franssen et al., "Low Molecular Weight Proteins as Carriers for Renal Drug Targeting. Preparation of Drug-Protein Conjugates and Drug-Spacer Derivatives and Their Catabolism in Renal Cortex Homogenates and Lysosomal Lysates," J. Med. Chem., 1992; 35: 1246-1259.

International Search Report for PCT/US03/17009 dated Sep. 3, 2003.

Bennett, et al., "Drug-Coupled Poly(Amino Acids) as Polymeric Prodrugs" Journal of Bioactive and Compatible Polymers, vol. 3, Jan. 1988, pp. 44-52, XP08078115.

Kuchimanchi, et al., "Intestinal Absorption and biodistribution of Cosalane and its Amino Acid Conjugagtes: Novel anti-HIV Agents", International Journal of Pharmaceutics, vol. 231, No. 2, Jan. 14, 2002, pp. 197-211, ISSN: 0378-5173.

Adler, et al., *Double-Blind, Placebo-Controlled Study of the Efficacy and Safety of Lisdexamfetamine Dimesylate in Adults with Attention-Deficit/Hyperactivity Disorder*, Clinical Psychiatry, 69:9, Sep. 2008 pp. 1364-1373.

Barkley, et al, *Unrecognized Attention-Deficit/Hyperactivity Disorder in Adults Presenting with Other Psychiatric Disorders*, CNS Spectr. 13:11, Nov. 2008, pp. 977-984.

Bukstein, *Substance Abuse in Patients with Attention-Deficit/Hyperactivity Disorder*, Medscape J Med., 2008; 10(1):24, 10 pages.

Faraone, *Interpreting Estimates of Treatment Effects*, Implications for Managed Care, P&T, Dec. 2008, vol. 33 No. 12, pp. 700-701.

Faraone, *Lisdexamfetamine Dimesylate: the first long-acting prodrug stimulant treatment for attention deficit/hyperactivity disorder*, Child and Adolescent Psychiatry Research, 2008, pp. 1565-1574.

Findling, *Long-Term Effectiveness and Safety of Lisdexamfetamine Dimesylate in School-Aged Children with Attention-Deficit/Hyperactivity Disorder*, CNS Spectr. 13:7, Jul. 2008, pp. 614-620.

Biederman, *Lisdexamfetamine Dimesylate and Mixed Amphetamine Salts Extended-Release in Children with ADHD: A Double-Blind, Placebo-Controlled, Crossover Analog Classroom Study*, Biol Psychiatry 2007, 62:970-976.

Erratum—Biederman, , *Lisdexamfetamine Dimesylate and Mixed Amphetamine Salts Extended-Release in Children with ADHD: A Double-Blind, Placebo-Controlled, Crossover Analog Classroom Study*, Biol Psychiatry 2007, 1 page.

Biederman, et al., *Efficacy and Tolerability of Lisdexamfetamine Dimesylate (NRP-104) in Children with Attention—Deficit/Hyperactivity Disorder: A Phase III, Multicenter, Randomized, Double-Blind, Forced Dose, Parallel-Group Study*, American Psychiatric Associate, May 20-25, 2006, Clinical Therapeutics, vol. 29, No. 3, 2007; pp. 450-463.

Blick, et al., *Lisdexamfetamine*, ADIS Drug Profile, 2007, pp. 129-135.

Goodman, *Lisdexamfetamine Dimesylate: The First Prodrug Stimulant*, Psychiatry, Aug. 2007, pp. 39-45.

Krishnan et al., *An Evaluation of the Chytochrome P450 Inhibition Potential of Lisdexamfetamine in Human Liver Microsomes*, Drug Metabolism and Disposition, 2007, pp. 180-184.

Krishnan, et al., *Toxicity Profile of Lisdexamfetamine Dimesylate in Three Independent Rat Toxicology Studies*, Basic & Clinical Pharmacology, 2007, 101, 233-240.

Heal, *New perspectives from microdialysis studies in freely-moving, spontaneously hypertensive rats on the pharmacology drugs for the treatment of ADHD*, Pharmacology, Biochemistry and Behavior, 90, 2008, pp. 184-197.

Jasinksi et al., *Human Pharmacology of Intravenous Lisdexamfetamine Dimesylate: abuse liability in adult stimulant abusers*, Journal of Psychopharmacology, 2008, pp. 1-9.

Krishnan et al., *Relative Bioavailability of Lisdexamfetamine 70-mg Capsules in Fasted and Fed Healthy Adult Volunteers and in Solution: a Single-Dose, Crossover Pharmacokinetic Study*, The Journal of Clinical Pharmacology, 2008, 48: pp. 293-302.

Krishnan, et al., *Multiple daily-dose pharmacokinetics of Lisdexamfetamine Dimesylate in healthy adult volunteers*, Current Medical Research and Opinion, vol. 24, No. 1, 2008, pp. 33-40.

Krishnan et al., *Metabolism, Distribution and Elimination of Lisdexamfetamine Dimesylate*, Clinical Drug Investigation, vol. 28, No. 12, 2008, pp. 745-755.

Manos, *Pharmacologic Treatment of ADHD: Road Conditions in Driving Patients to Successful Outcomes*, Medscape J Med., 2008: 10(1):5, 13 pages.

Riggs, *Non-medical use and abuse of commonly prescribed medications*, Current Medical Research and Opinion, vol. 24, No. 3, 2008, pp. 869-877.

Lopez, *Effect of Lisdexamfetamine Dimesylate on Parent-Rated Measures in Children Aged 6 to 12 Years with Attention-Deficit/Hyperactivity Disorder: A Secondary Analysis*, Postgraduate Medicine, vol. 120, Issue 3, Sep. 2008, pp. 89-101.

Findling, *Evolution of the Treatment of Attention-Deficit/Hyperactivity Disorder in Children: A Review*, Clinical Therapeutics/vol. 30, Nov. 5, 2008, pp. 942-957.

Furukawa, et al.: "Effects of pGlu-His-pro-amphetamine (TRH-amphetamine) guinea-pig: Antagonistic effect of amphetamine on TRH response", European Journal of Pharmacology, Elsevier BV., NL, vol. 112, No. 2, Jun. 7, 1985_pp. 237-241, XP025547293.

Physician's Desk Reference, "Acuprin 18 Adult Low Dose Aspirin Contains 81 Mg of Enteric Coated Aspirin", Jan. 1, 1996, XP002932207, 2 pages.

Kumar, et al., "Safety and pharmacokinetics of abacavir (1592U89) following oral administration of escalating single doses in human immunodeficiency virus type 1-infected adults," Antimicrobial Agents and Chemotherapy, vol. 43, No. 3, Mar. 1999, pp. 603-608, XP002530985.

Leopold, et al., "In vivo pharmacokinetic study for the assessment of poly(L-aspartic acid) as a drug carrier for colon-specific drug delivery," Journal of Pharmacokinetics and Biopharmaceuticals, vol. 23, No. 4, 1995, pp. 397-406, XP002530986.

Li et al., "Drug-coupled Poly(amino acids) as Polymeric Prodrugs," Journal of Bioactive and Compatible Polymers, Lancaster, PA, vol. 3, No. 1, Jan. 1, 1988, pp. 44-52, XP008078115.

Weisler et al., *Long-Term Safety and Efficacy of Lisdexamfetamine Dimesylate in Adults with Attention Deficit/Hyperactivity Disorder* (Oct. 30, 2008-Nov. 2, 2008).

Manos et al., *Lisdexamfetamine Dimesylate as Treatment for Attention-Deficit/Hyperactivity Disorder in Children Previously Treated with Mixed Amphetamine Salts Extended Release: Parental Impressions* (Nov. 12, 2008-Nov. 15, 2008).

Krishnan et al, *Lisdexamfetamine Dimesylate (NRP-104)—GLP in Vitro Human Cytochrome P450 Inhibitory Drug-Drug Interaction Study* (May 20, 2006).

Arora et al., *Bioavailability of Lisdexamfetamine Dimesylate in Healthy Volunteers when Administered With or Without Food* (Oct. 6, 2006).

Krishnan, *A Multiple Dose Single-Arm Pharmacokinetics Study of Oral Lisdexamfetamine (LDX; NRP104) in Healthy Adult Volunteers* (Jun. 14, 2006).

Boyle et al., *Pharmacokinetics of NRP 104 (Lisdexamfetamine Dimesylate) Following Administration of a Single Intranasal, Intravenous or Oral Dose in Rats* (Jun. 14, 2006).

Biederman et al., *Improvements in Symptoms of ADHD in School-Aged Children with Lisdexamfetamine (NRP 104) and Mixed-Amphetamine Salts, Extended-Release versus Placebo* (May 24, 2006).

Biederman et al., *Efficacy and Safety of Lisdexamfetamine (NRP 104) in Children Aged 6-12 with ADHD* (May 24, 2006).

Jasinski et al., *Abuse Liability of Intravenous, L-lysine-d-amphetamine (NRP104)* (Jun. 17, 2006-Jun. 22, 2006).

Sep. 15, 2009 Communication in European Application No. 06769808.

\* cited by examiner a. Single Amino Acid Amphetamine Prodrugs b. Dipeptide Amphetamine Prodrugs from Amphetamine c. Dipeptide Amphetamine Prodrugs from Single Amino Acid Prodrugs d. Tripeptide Amphetamine Prodrugs from Amphetamine e. Tripeptide Amphetamine Prodrugs from Single Amino Acid Prodrugs $R^1, R^2, R^3$ = independent amino acid side-chains

Oral Formulation: Solution, 0.2 mg/mL in water

ABUSE-RESISTANT AMPHETAMINE PRODRUGS

CROSS REFERENCE RELATED APPLICATIONS

This application is a continuation of U.S. application Ser. No. 11/400,304, filed Apr. 10, 2006, which in turn, (a) claims benefit under 35 U.S.C. 119(e) to U.S. Provisional Application Nos. 60/669,385 filed Apr. 8, 2005, 60/669,386 filed Apr. 8, 2005, 60/681,170 filed May 16, 2005, 60/756,548 filed Jan. 6, 2006, and 60/759,958 filed Jan. 19, 2006; (b) is a continuation-in-part of U.S. application Ser. No. 10/857,619 filed Jun. 1, 2004, now U.S. Pat. No. 7,223,735, which claims the benefit of under 35 U.S.C. 119(e) to U.S. Provisional Application Nos. 60/473,929 filed May 29, 2003 and 60/567,801 filed May 5, 2004; and (c) is a continuation-in-part of U.S. application Ser. No. 10/858,526 filed Jun. 1, 2004, now U.S. Pat. No. 7,105,486, which, in turn, is a continuation-in-part of international application PCT/US03/05525 filed Feb. 24, 2003, which claims priority to U.S. Provisional Application Nos. 60/358,368 filed Feb. 22, 2002 and 60/362,082 filed Mar. 7, 2002; application Ser. No. 10/858,526 also claims benefit under 35 U.S.C. 119(e) to U.S. Provisional Application Nos. 60/473,929 filed May 29, 2003 and 60/567,801 filed May 5, 2004. All of the above-identified applications are hereby incorporated by reference in their entirety.

FIELD OF THE INVENTION

The invention relates to amphetamine compounds, more particularly to amphetamine prodrugs comprising amphetamine covalently bound to a chemical moiety. The invention also relates to pharmaceutical compositions comprising the amphetamine compounds, and to methods of manufacturing, delivering, and using the amphetamine compounds.

BACKGROUND OF THE INVENTION

Amphetamines stimulate the central nervous system (CNS) and have been used medicinally to treat various disorders including attention deficit hyperactivity disorder (ADHD), obesity, and narcolepsy. In children with ADHD, potent CNS stimulants have been used for several decades as a drug treatment given either alone or as an adjunct to behavioral therapy. While methylphenidate (Ritalin®) has been the most frequently prescribed stimulant, the prototype of the class, amphetamine (alpha-methyl phenethylamine) has been used all along and increasingly so in recent years. (Bradley C, Bowen M, "Amphetamine (benzedrine) therapy of children's behavior disorders." American Journal of Orthopsychiatry 11: 92-103 (1941).

Because of their stimulating effects, amphetamines, including amphetamine derivatives and analogs, are subject to abuse. A user can become dependent over time on these drugs and their physical and psychological effects, even when the drugs are used for legitimate therapeutic purposes. Legitimate amphetamine users that develop drug tolerances are especially susceptible to becoming accidental addicts as they increase dosing in order to counteract their increased tolerance of the prescribed drugs. Additionally, it is possible for individuals to inappropriately self-administer higher than prescribed quantities of the drug or to alter either the product or the route of administration (e.g., inhalation (snorting), injection, and smoking), potentially resulting in immediate release of the active drug in quantities larger than prescribed. When taken at higher than prescribed doses, amphetamines can cause temporary feelings of exhilaration and increased energy and mental alertness.

Recent developments in the abuse of prescription drug products increasingly raise concerns about the abuse of amphetamine prescribed for ADHD. The National Survey on Drug Use and Health (NSDUH), estimates that in 2003, 1.2 million Americans aged 12 and older abused stimulants, such as amphetamines. The high abuse potential has earned amphetamines Schedule II status according to the Controlled Substances Act (CSA). Schedule II classification is reserved for those drugs that have accepted medical use but have the highest potential for abuse.

Sustained release formulations of amphetamines, e.g., Adderall XR®, have an increased abuse liability relative to the single dose tablets because each tablet of the sustained release formulation contains a higher concentration of amphetamine. It may be possible for substance abusers to obtain a high dose of amphetamine with rapid onset by crushing the tablets into powder and snorting it or by dissolving the powder in water and injecting it. Sustained release formulations may also provide uneven release.

Additional information about amphetamines and amphetamine abuse can be found in U.S. Publication No. 2005/0054561 (U.S. Ser. No. 10/858,526).

The need exists for additional amphetamine compounds, especially abuse resistant amphetamine compounds. Further, the need exists for amphetamine pharmaceutical compositions that provide sustained release and sustained therapeutic effect.

Figure 8:
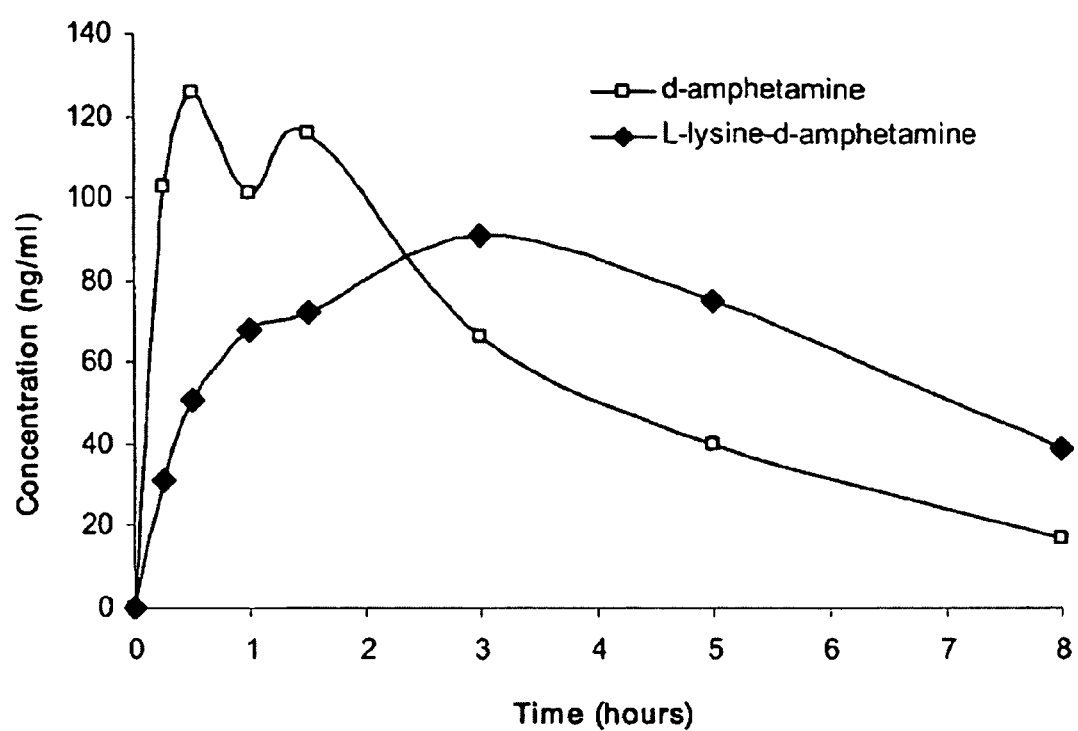
Figure 9:
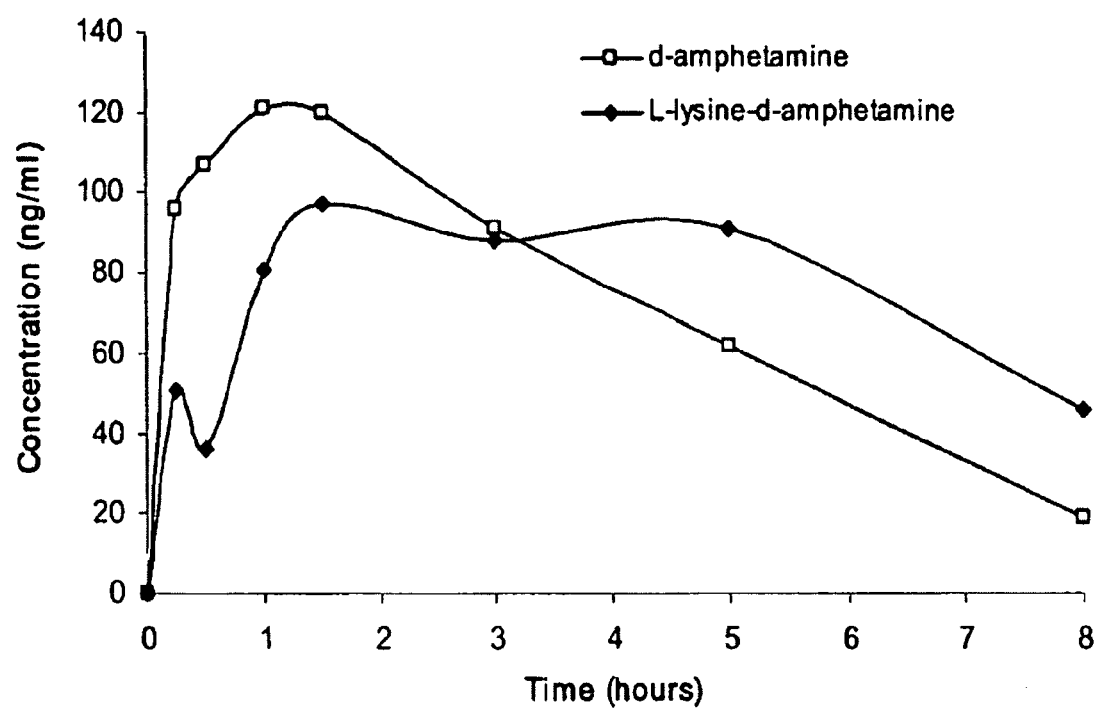
Figure 10:
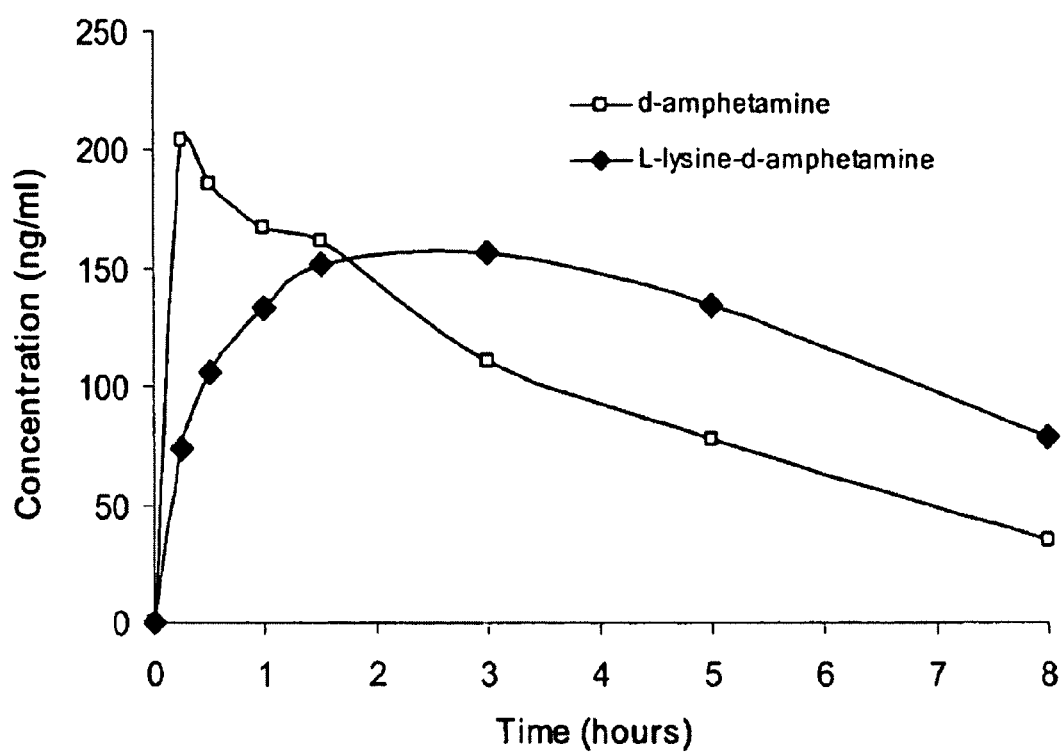
Figure 11:
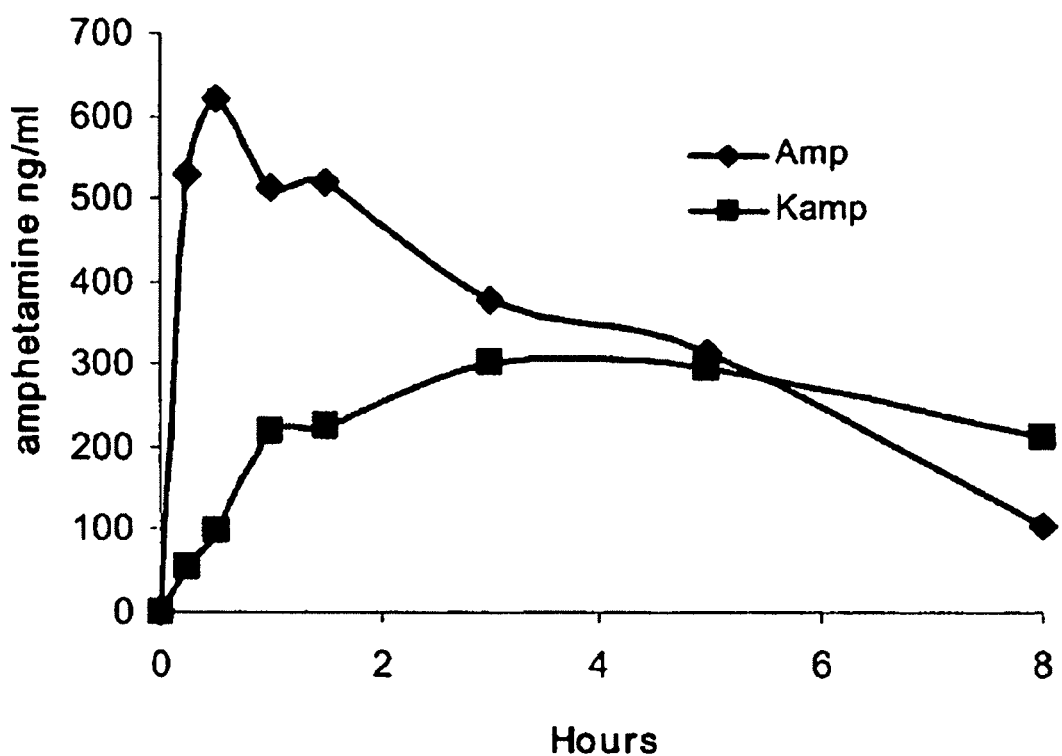
Figure 12:
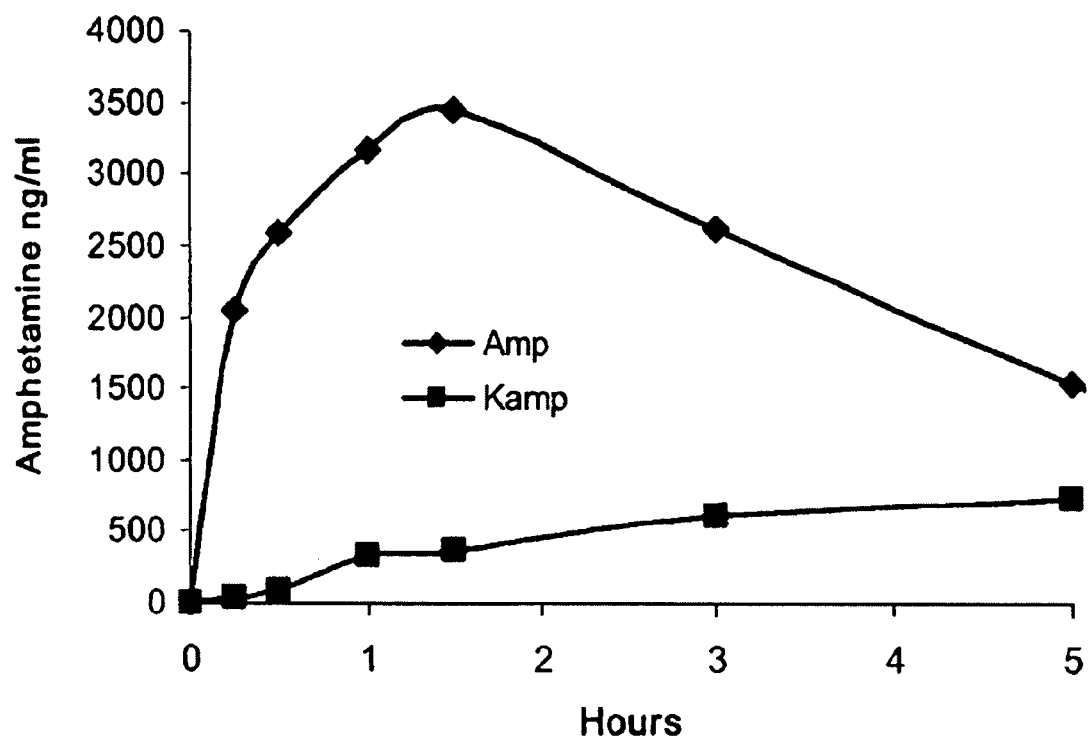
Figure 13:
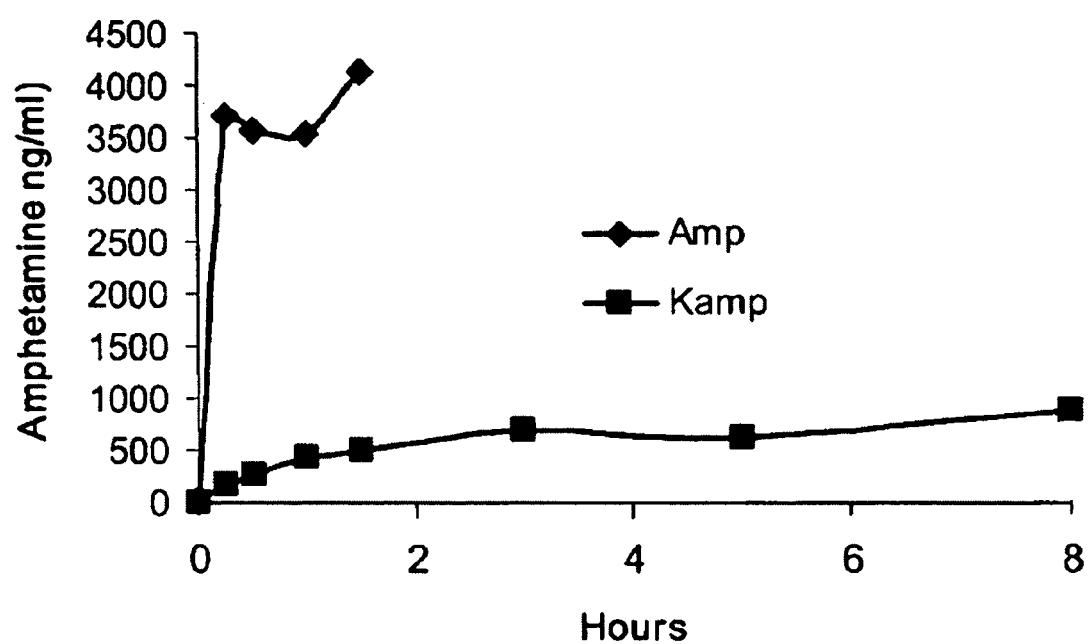
Figure 14:
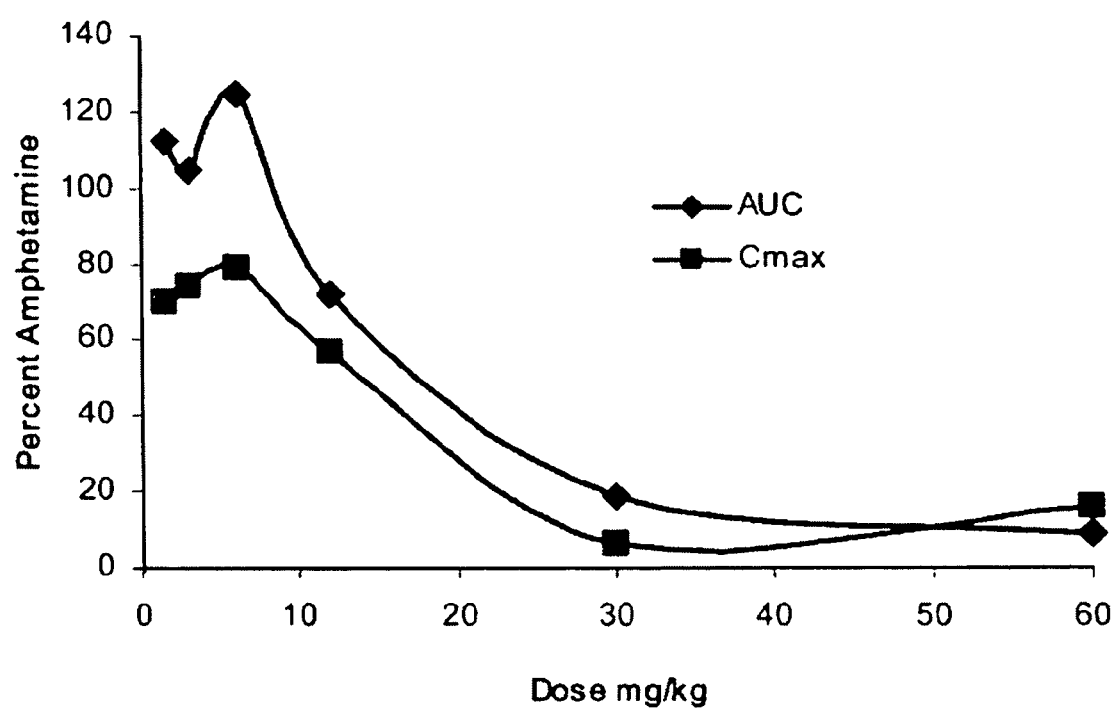
Figure 15:
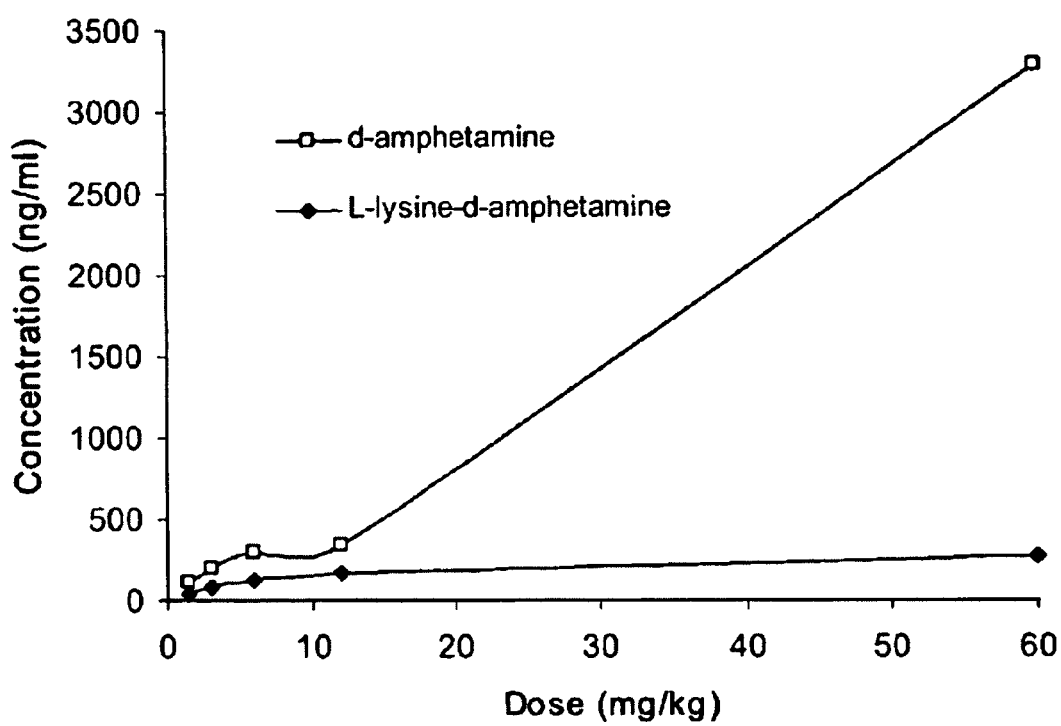
Figure 16:
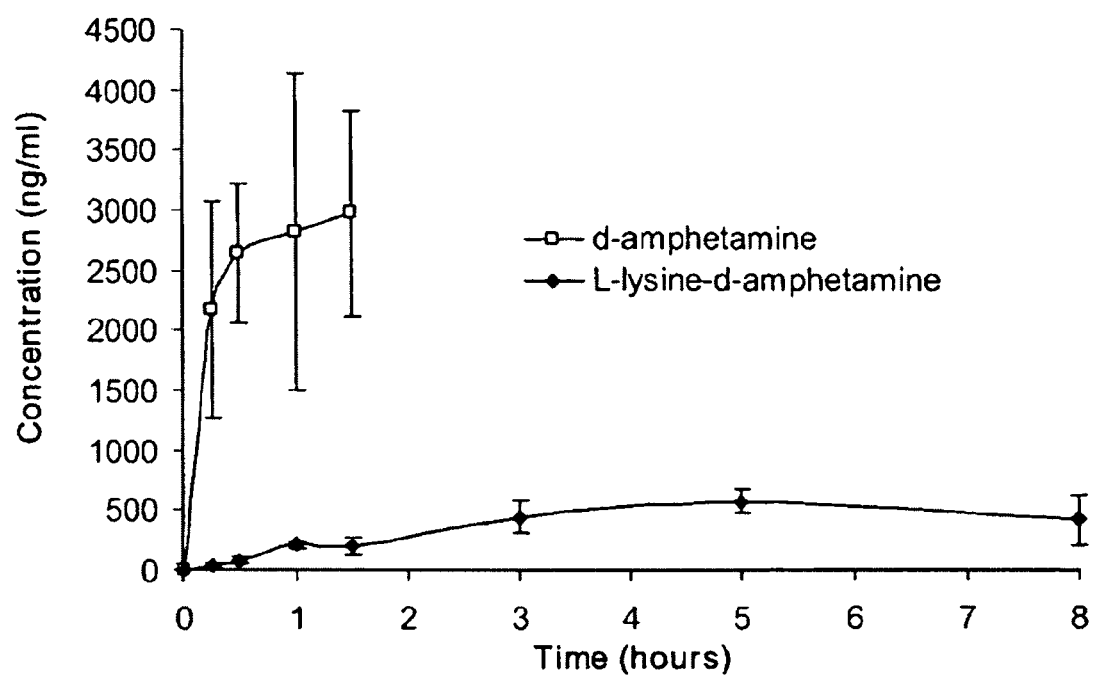
Figure 17:
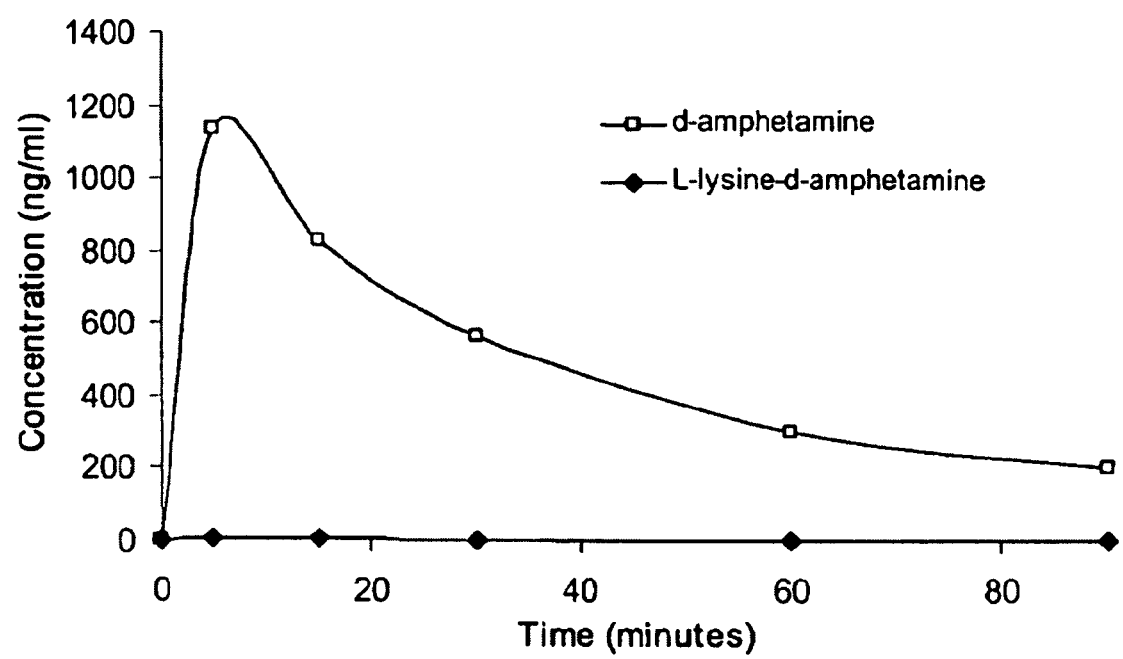

The following Figures (FIG. 8-FIG. 16) depict results obtained from studies of oral administration of d-amphetamine sulfate or L-lysine-d-amphetamine dimesylate to rats (ELISA analysis):

FIG. 8. Plasma concentrations of d-amphetamine (at dose 1.5 mg/kg d-amphetamine base).
FIG. 9. Plasma concentrations of d-amphetamine (at dose 3 mg/kg d-amphetamine base).
FIG. 10. Plasma concentrations of d-amphetamine (at dose 6 mg/kg d-amphetamine base).
FIG. 11. Plasma concentrations of d-amphetamine (at dose 12 mg/kg d-amphetamine base).
FIG. 12. Plasma concentrations of d-amphetamine (at dose 30 mg/kg d-amphetamine base).
FIG. 13. Plasma concentrations of d-amphetamine (at dose 60 mg/kg d-amphetamine base).
FIG. 14. Percent bioavailability (AUC and $C_{max}$) of L-lysine-d-amphetamine dimesylate compared to d-amphetamine sulfate at doses 1.5, 3, 6, 12, 30, and 60 mg/kg d-amphetamine base.
FIG. 15. Plasma concentrations of d-amphetamine at 30-minutes post-dose for escalating doses of d-amphetamine base.
FIG. 16. Plasma concentrations of d-amphetamine (at dose 60 mg/kg d-amphetamine base).
FIG. 17. Plasma concentrations of d-amphetamine following intranasal administration of L-lysine-d-amphetamine hydrochloride or d-amphetamine sulfate (at dose 3 mg/kg d-amphetamine base) to rats (ELISA analysis).

Figure 18:
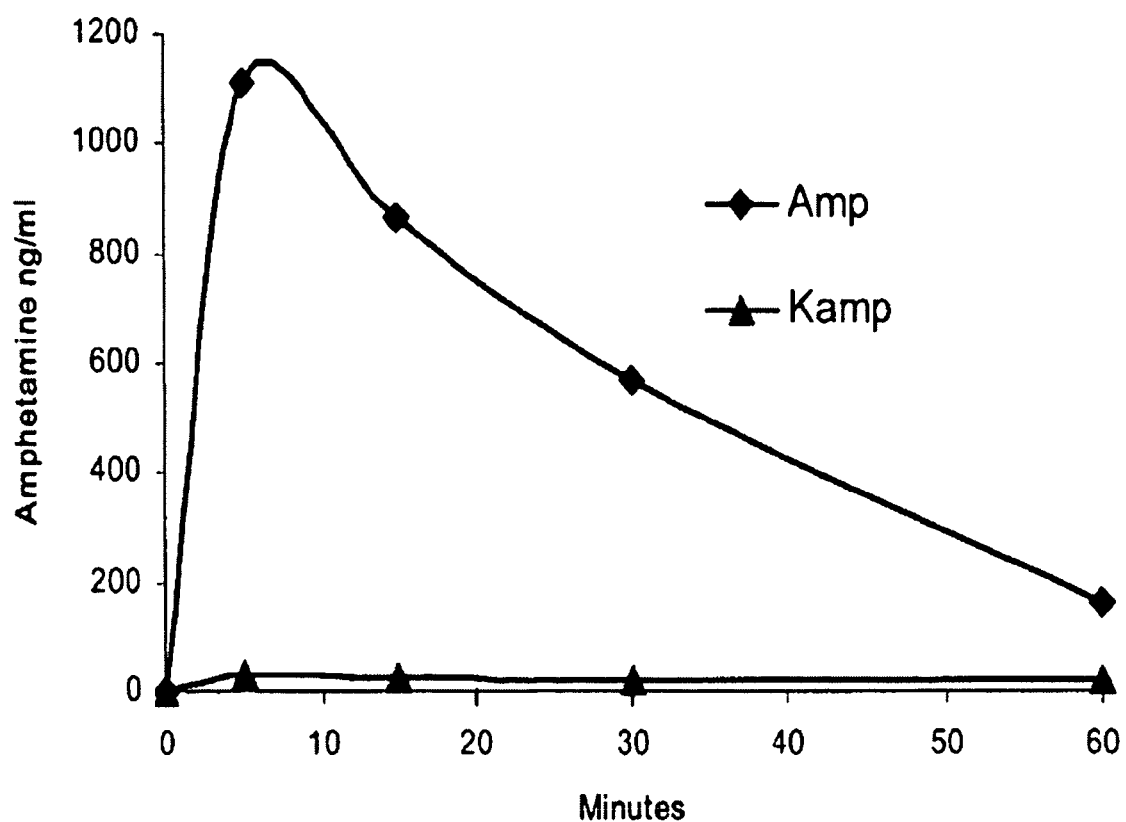

FIG. 18. Plasma concentrations of d-amphetamine following intranasal administration of L-lysine-d-amphetamine dimesylate or d-amphetamine sulfate (at dose 3 mg/kg d-amphetamine base) to rats (ELISA analysis).

Figure 19:
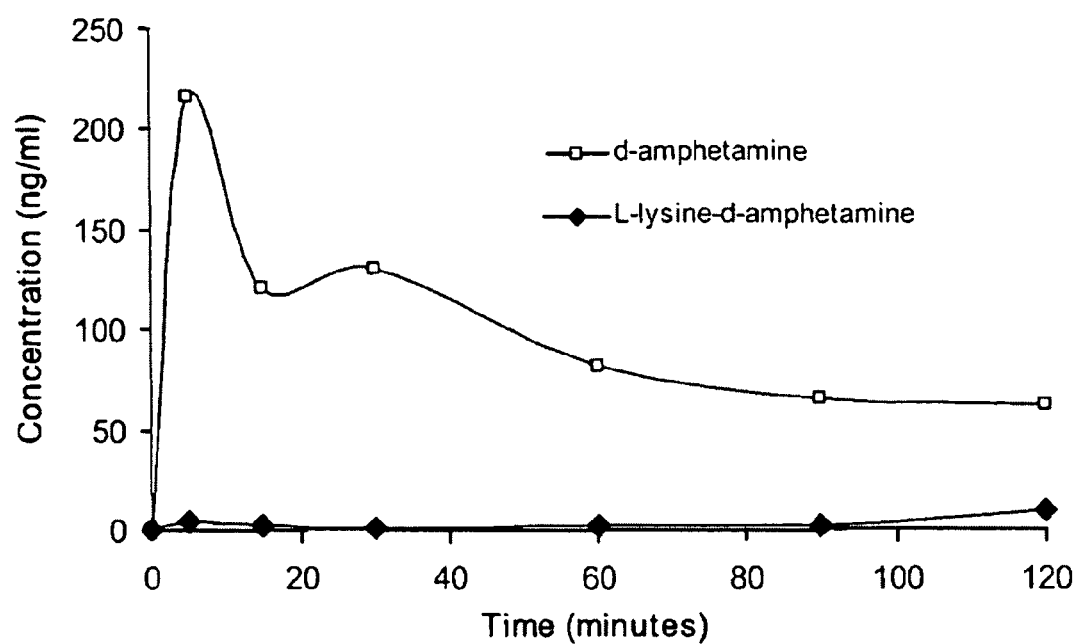

FIG. 19. Plasma concentrations of d-amphetamine following bolus intravenous administration of L-lysine-d-amphetamine dimesylate or d-amphetamine sulfate (at dose 1.5 mg/kg d-amphetamine base) to rats (ELISA analysis).

Figure 20:
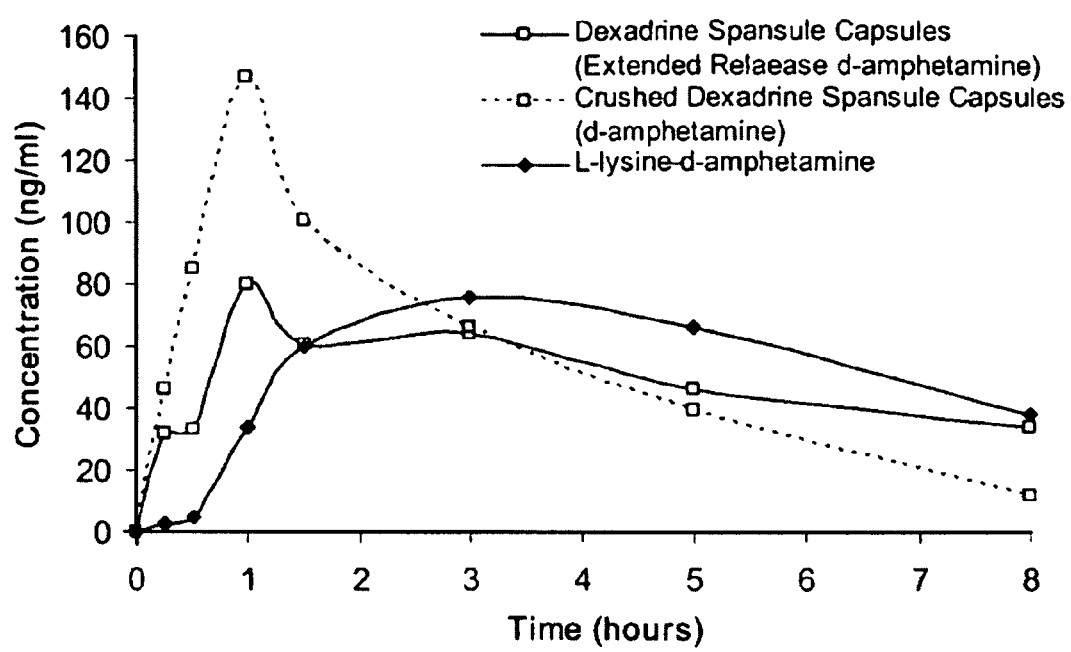

FIG. 20. Plasma concentrations of d-amphetamine levels following oral administration of Dexedrine Spansule® capsules, crushed Dexedrine Spansule® capsules, or L-lysine-d-amphetamine dimesylate (at dose 3 mg/kg d-amphetamine base) to rats (ELISA analysis).

Figure 21A:
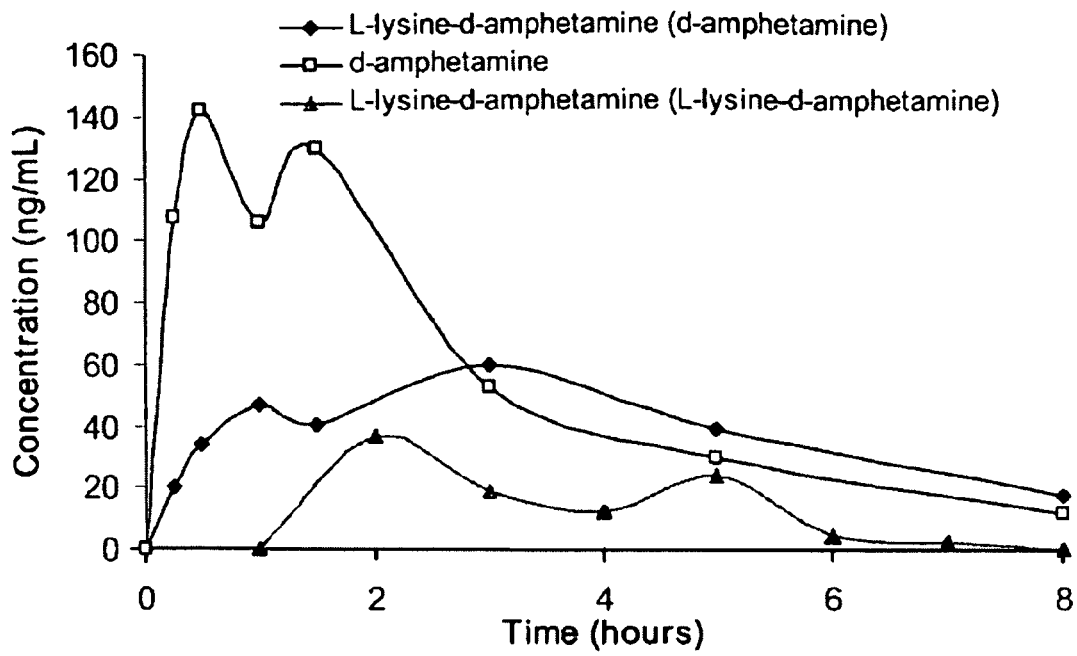
Figure 21B:
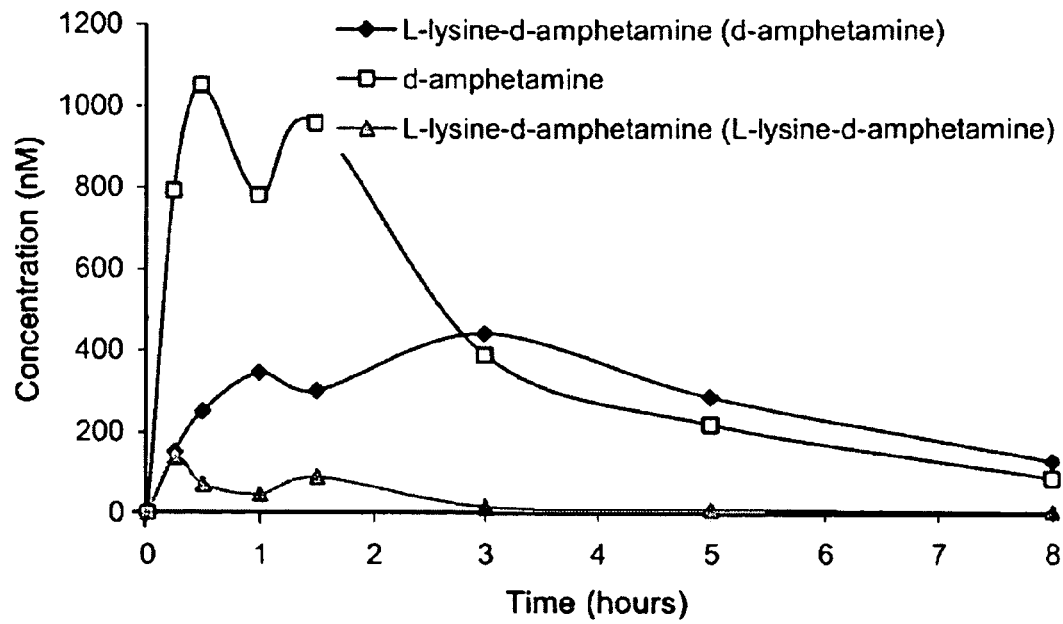

The following Figures (FIG. 21-FIG. 30) depict results obtained from studies of oral administration of d-amphetamine sulfate or L-lysine-d-amphetamine dimesylate to rats (LC/MS/MS analysis):

FIG. 21A and FIG. 21B. Plasma concentrations of d-amphetamine in ng/mL (FIG. 21A) and in nM (FIG. 21B) (at dose 1.5 mg/kg d-amphetamine base).

Figure 22A:
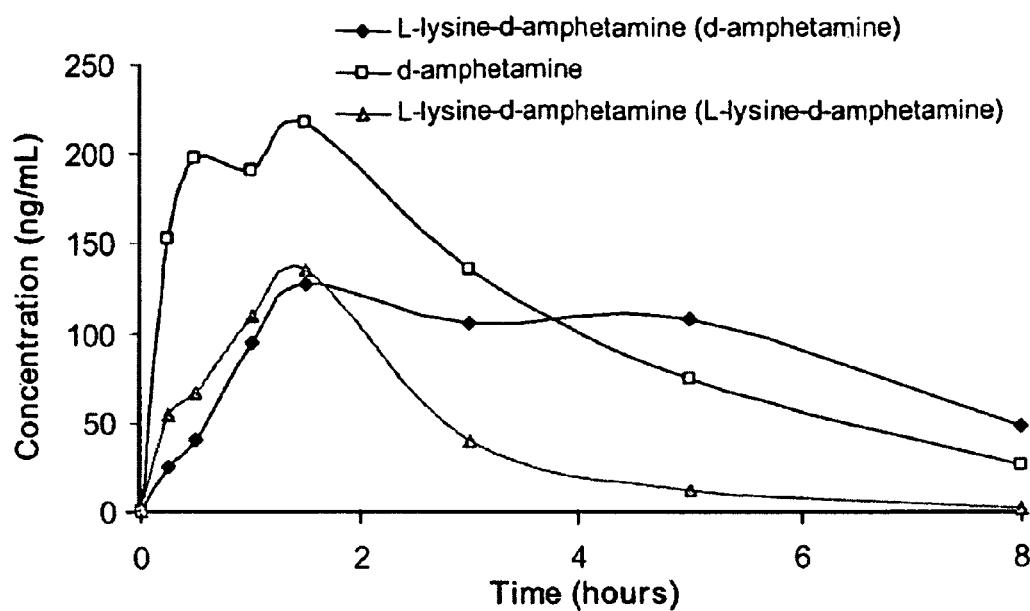
Figure 22B:
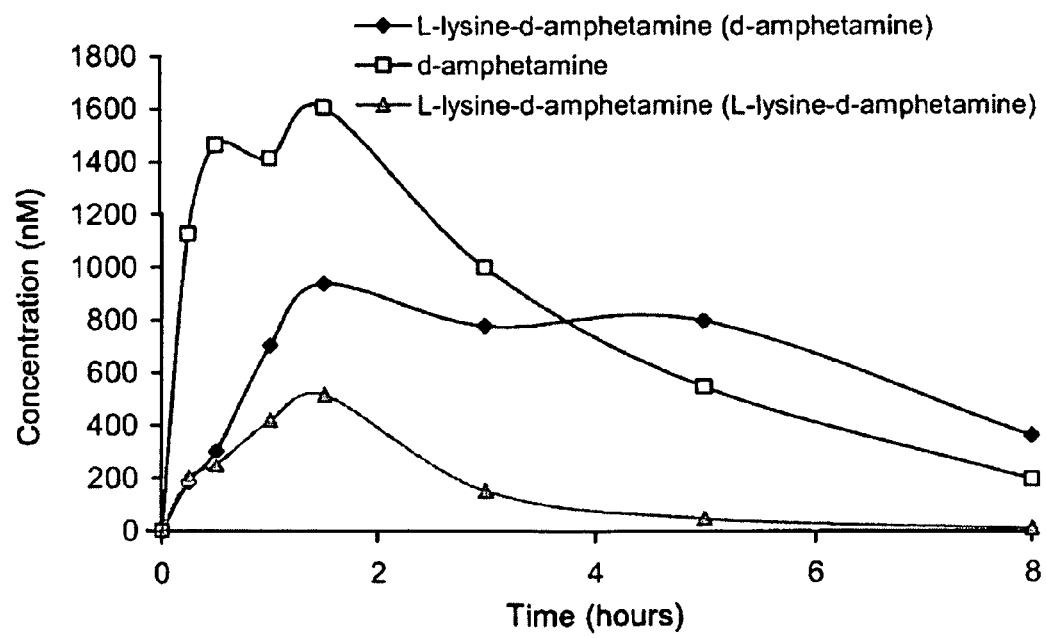

FIG. 22A and FIG. 22B. Plasma concentrations of d-amphetamine in ng/mL (FIG. 22A) and in nM (FIG. 22B) (at dose 3 mg/kg d-amphetamine base).

Figure 23A:
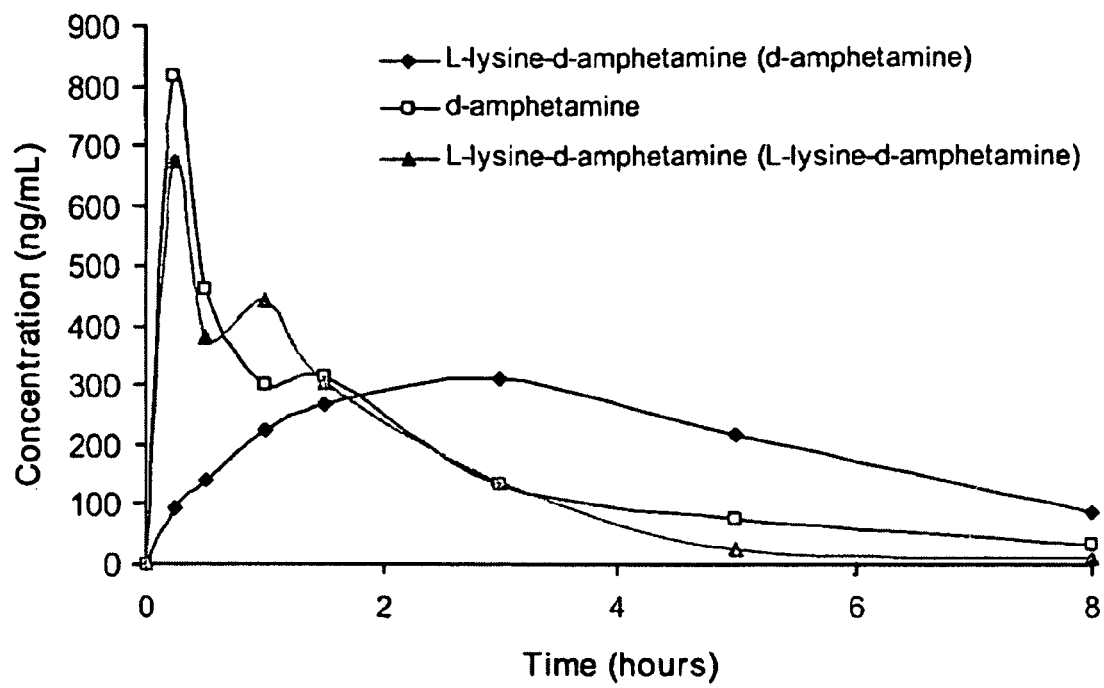
Figure 23B:
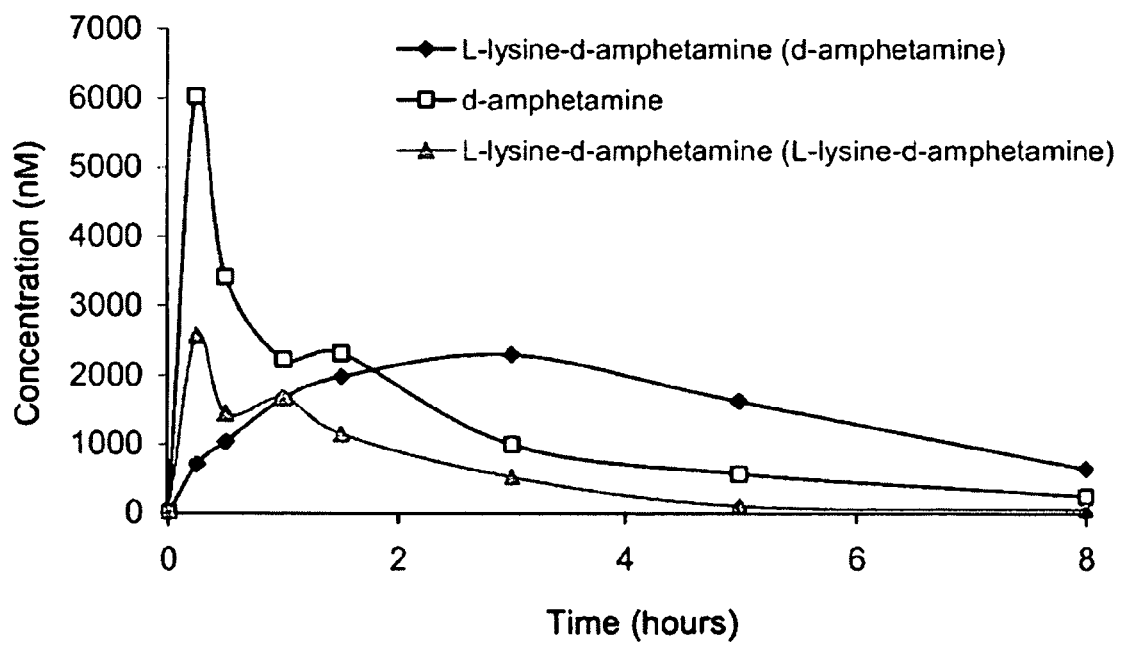

FIG. 23A and FIG. 23B. Plasma concentrations of d-amphetamine in ng/mL (FIG. 23A) and in nM (FIG. 23B) (at dose 6 mg/kg d-amphetamine base).

Figure 24A:
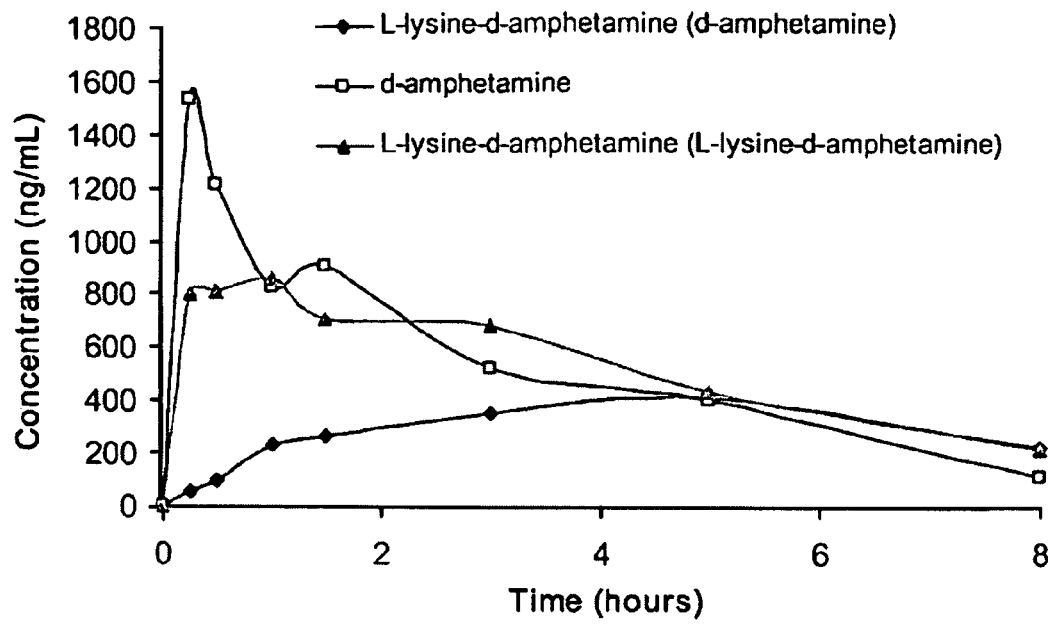
Figure 24B:
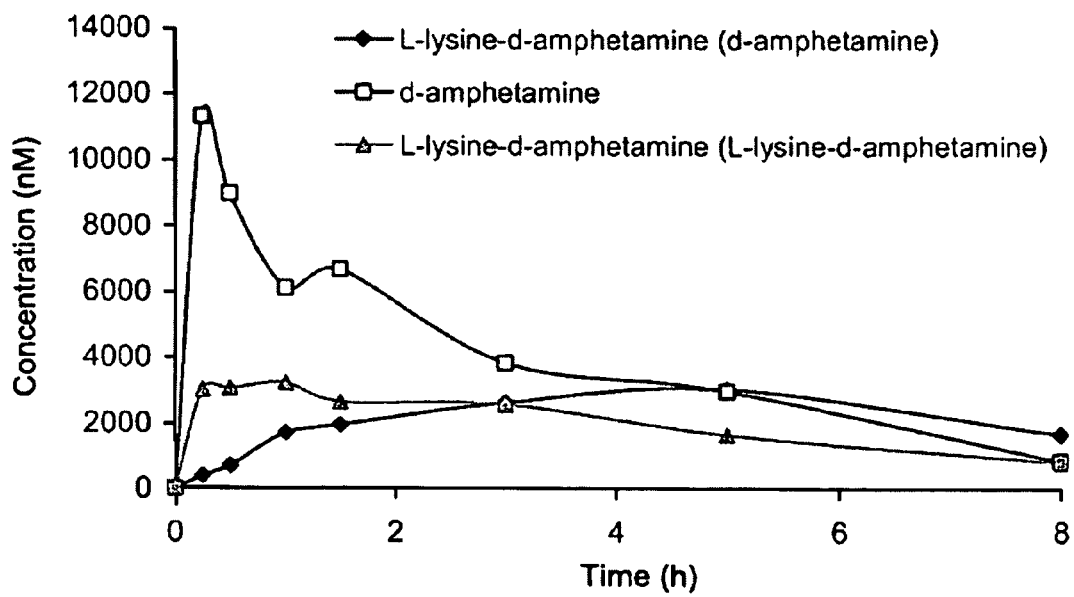

FIG. 24A and FIG. 24B. Plasma concentrations of d-amphetamine in ng/mL (FIG. 24A) and in nM (FIG. 24B) (at dose 12 mg/kg d-amphetamine base).

Figure 25A:
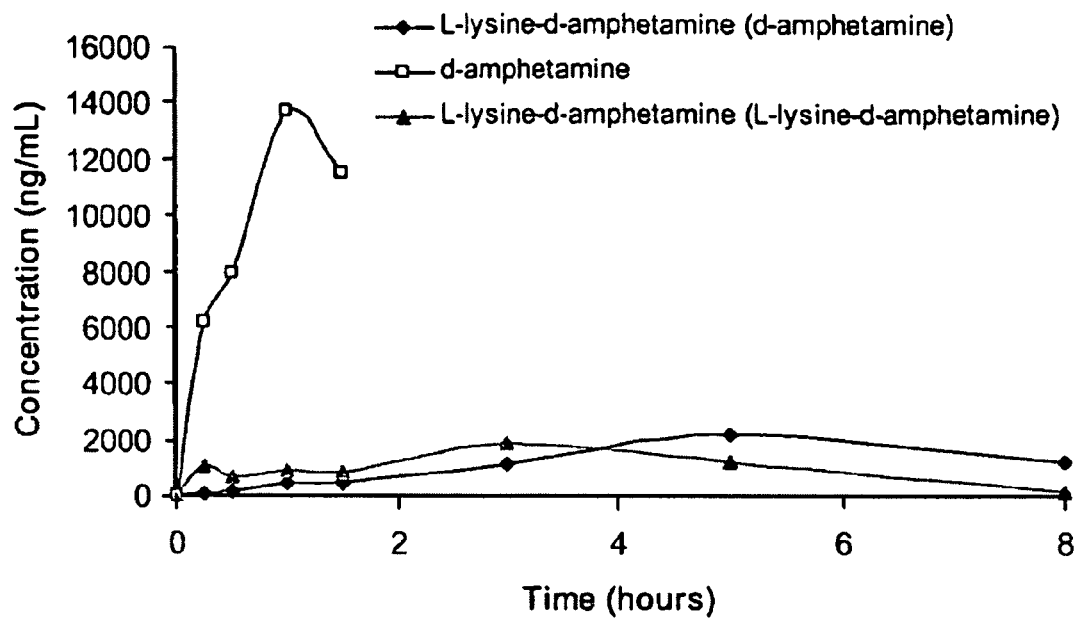
Figure 25B:
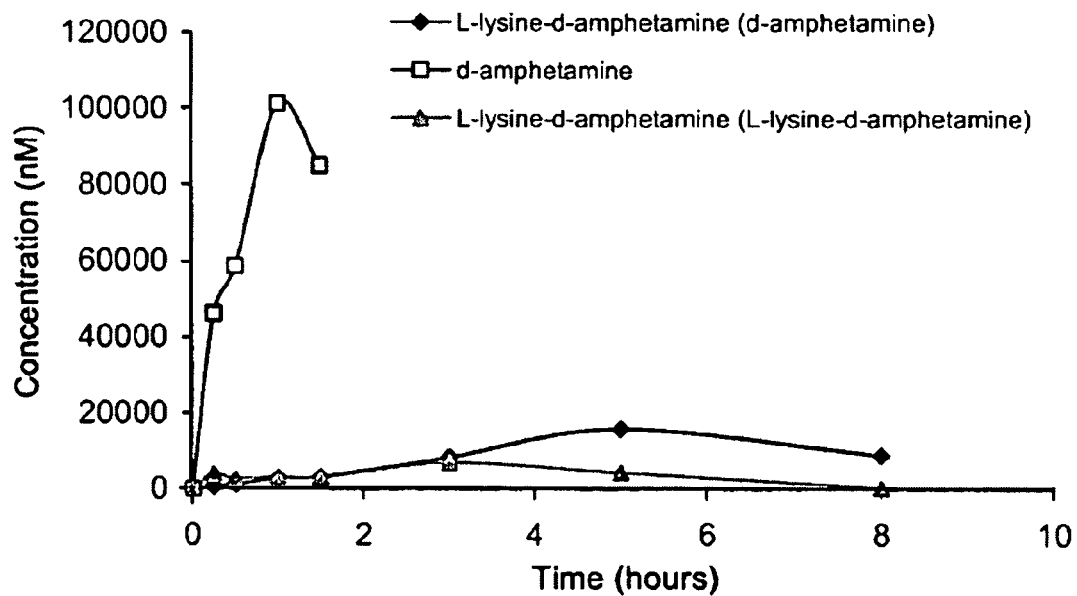

FIG. 25A and FIG. 25B. Plasma concentrations of d-amphetamine in ng/mL (FIG. 25A) and in nM (FIG. 25B) (at dose 60 mg/kg d-amphetamine base).

Figure 26:
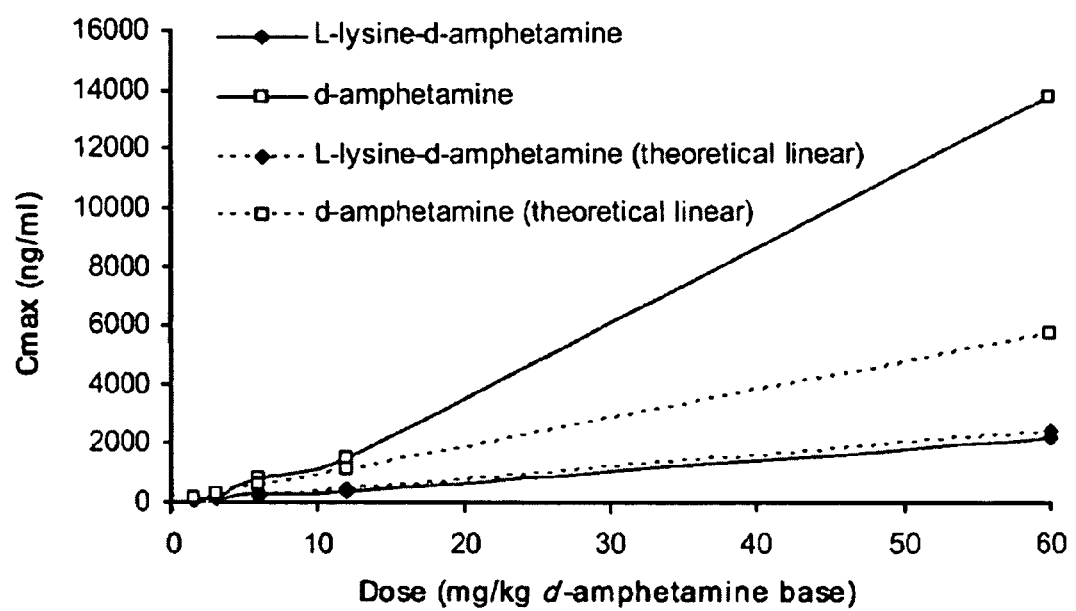

FIG. 26. Comparative bioavailability ($C_{max}$) of L-lysine-d-amphetamine and d-amphetamine in proportion to escalating human equivalent doses.

Figure 27:
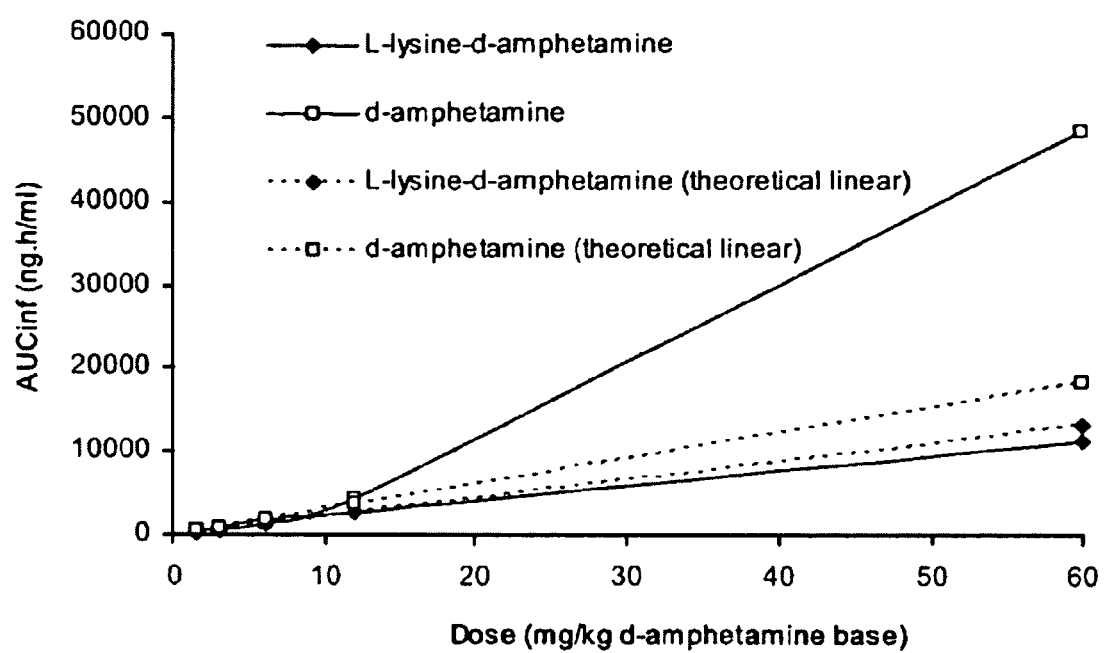

FIG. 27. Comparative bioavailability ($AUC_{inf}$) of L-lysine-d-amphetamine and d-amphetamine in proportion to escalating doses of d-amphetamine base.

Figure 28:
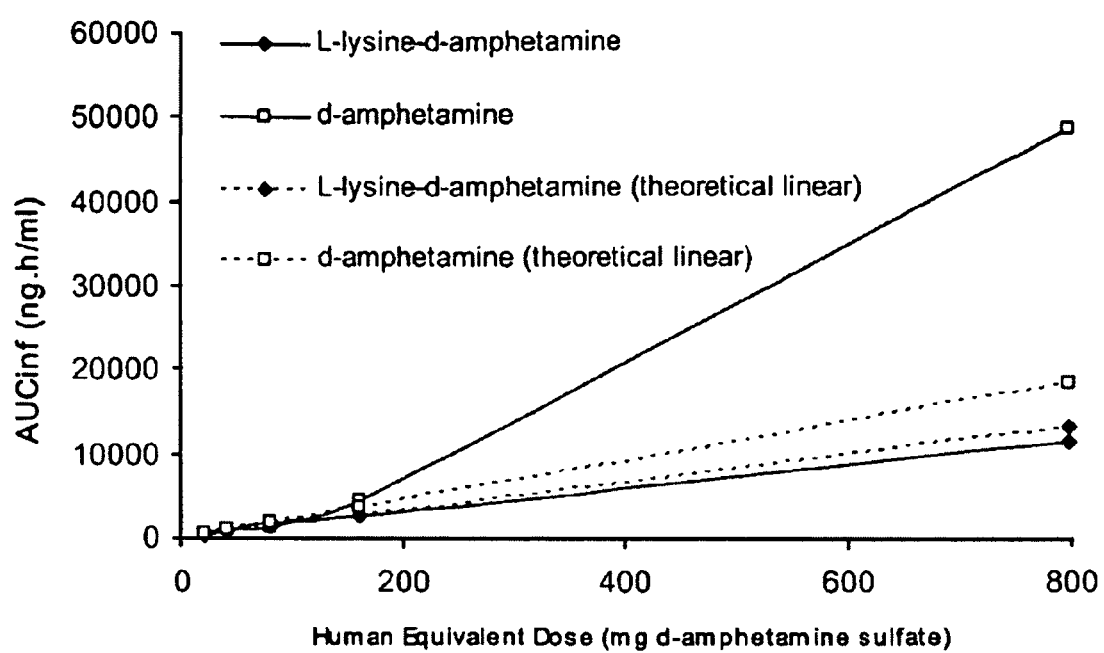

FIG. 28. Comparative bioavailability ($AUC_{inf}$) of L-lysine-d-amphetamine and d-amphetamine in proportion to escalating human equivalent doses.

Figure 29:
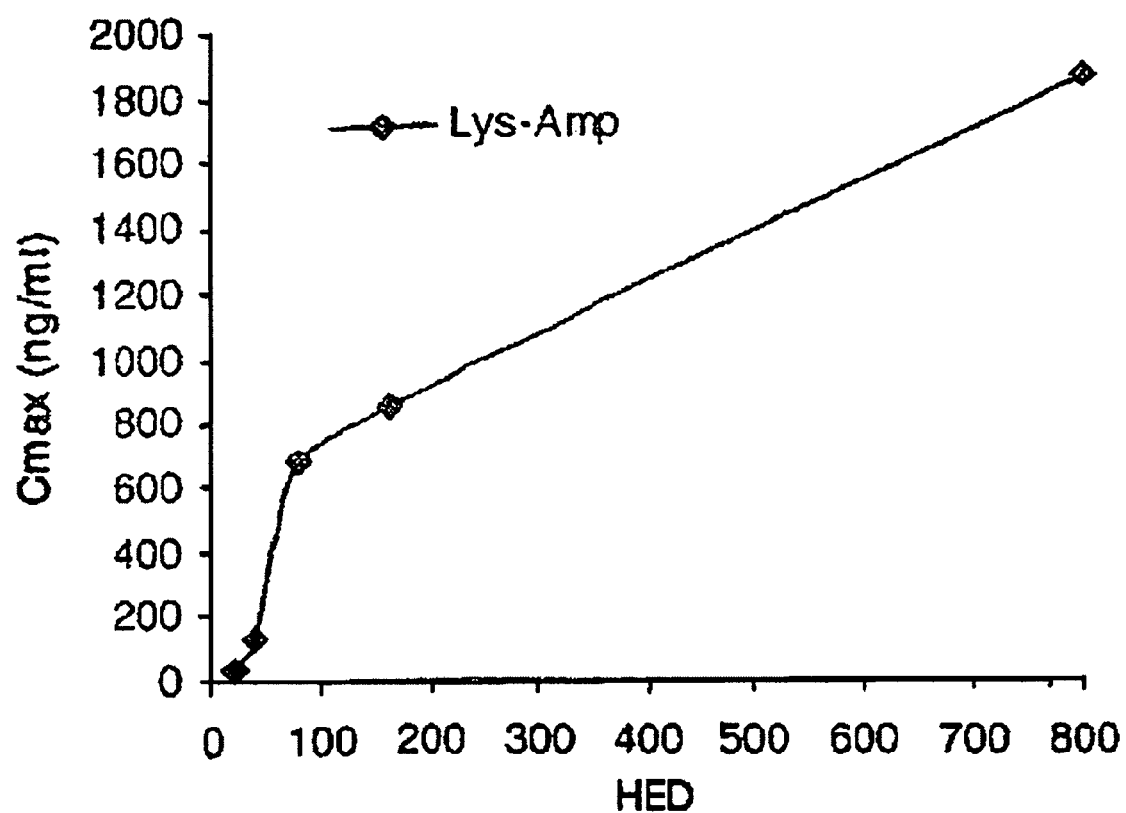

FIG. 29. Comparative bioavailability ($C_{max}$) of intact L-lysine-d-amphetamine in proportion to escalating human equivalent doses.

Figure 30:
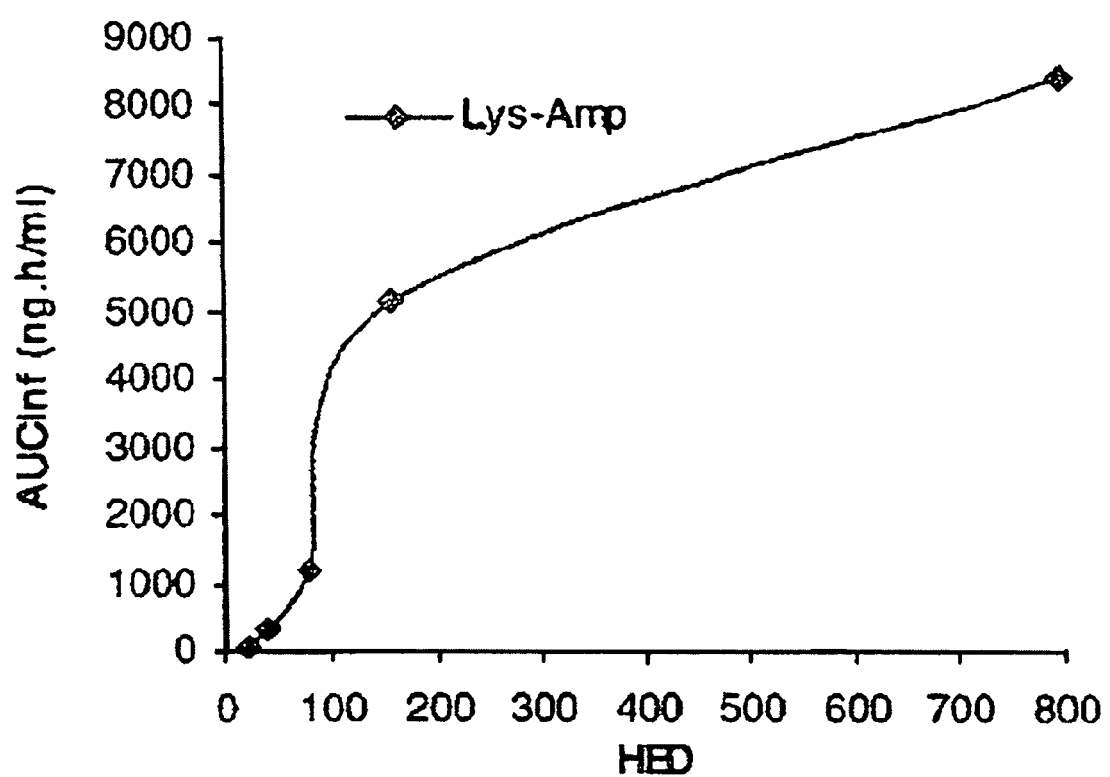

FIG. 30. Comparative bioavailability ($AUC_{inf}$) of intact L-lysine-d-amphetamine in proportion to escalating human equivalent doses.

Figure 31:
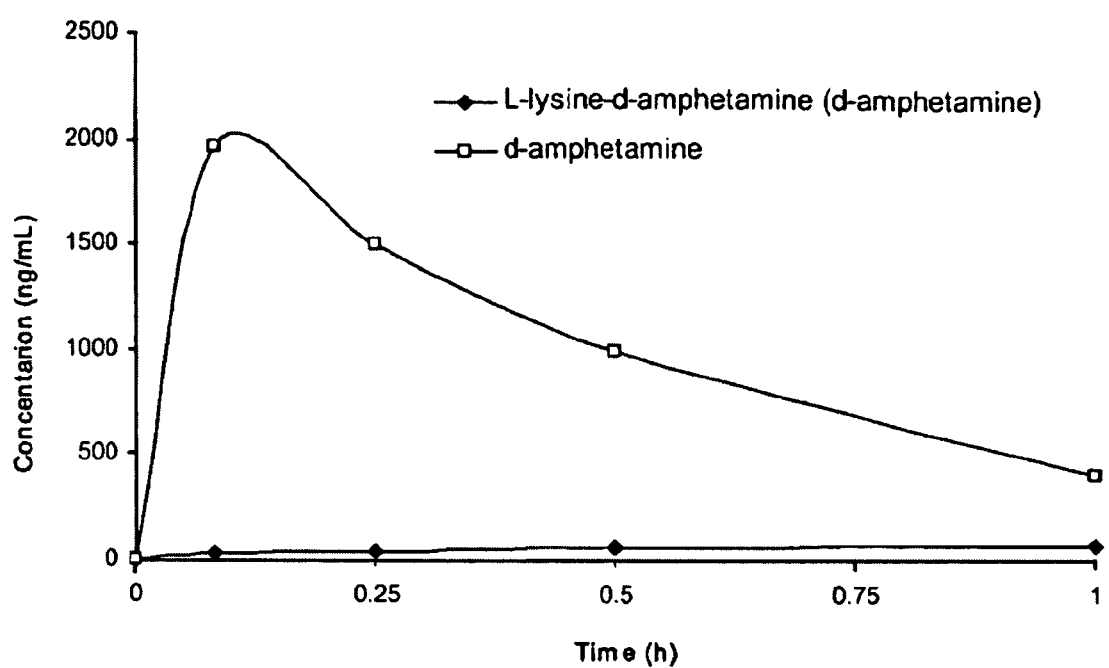

FIG. 31. Plasma concentrations of d-amphetamine following intranasal administration of L-lysine-d-amphetamine dimesylate or d-amphetamine sulfate (at dose 3 mg/kg d-amphetamine base) to rats (LC/MS/MS analysis).

Figure 32A:
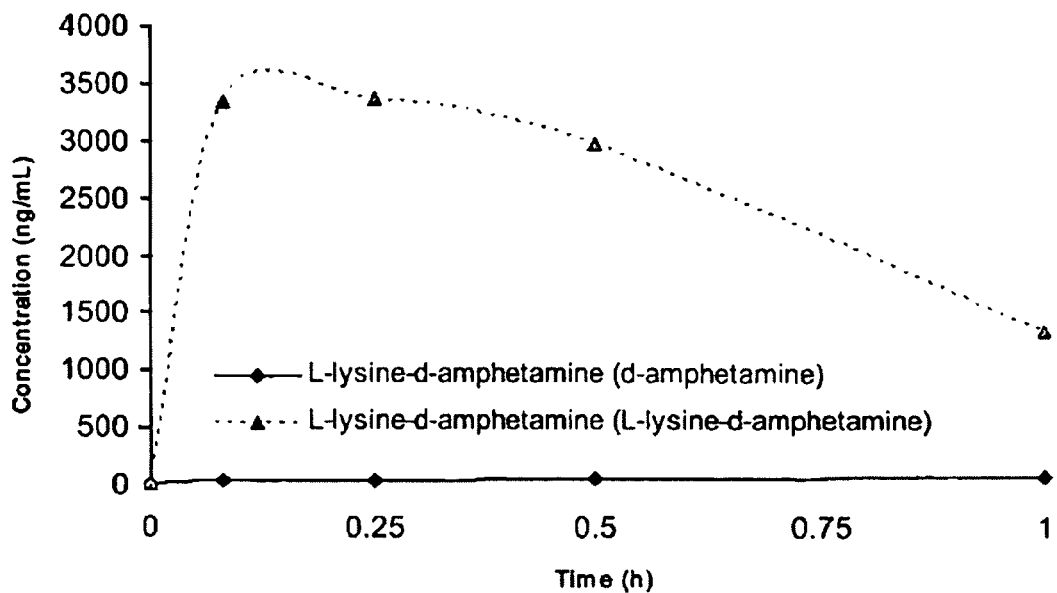
Figure 32B:
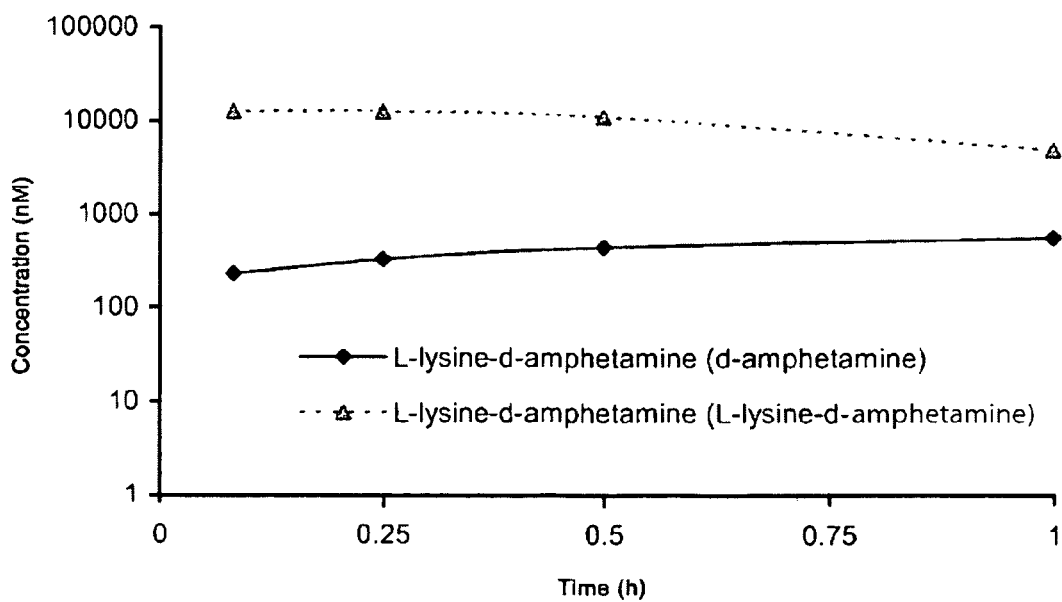

FIG. 32A and FIG. 32B. Plasma concentrations of d-amphetamine and L-lysine-d-amphetamine in ng/mL (FIG. 32A) and in nM (FIG. 32B), following intranasal administration of L-lysine-d-amphetamine dimesylate or d-amphetamine sulfate (at dose 3 mg/kg d-amphetamine base) to rats (LC/MS/MS analysis).

Figure 33:
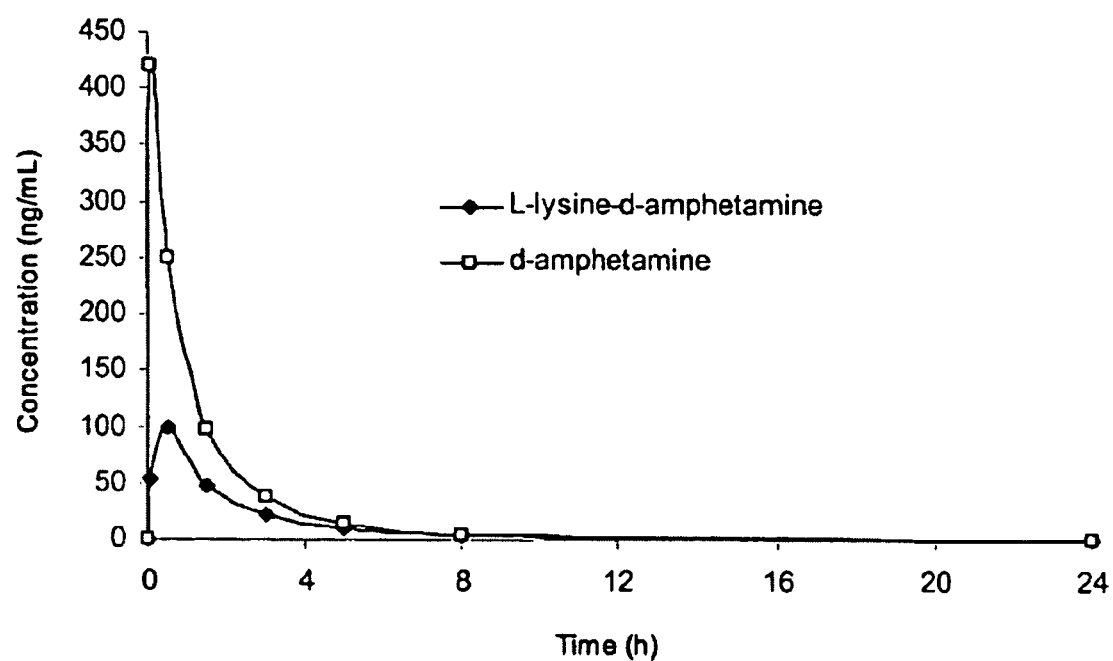

FIG. 33. Plasma concentrations of d-amphetamine following bolus intravenous administration of L-lysine-d-amphetamine dimesylate or d-amphetamine sulfate (at dose 1.5 mg/kg d-amphetamine base) to rats (LC/MS/MS analysis).

Figure 34A:
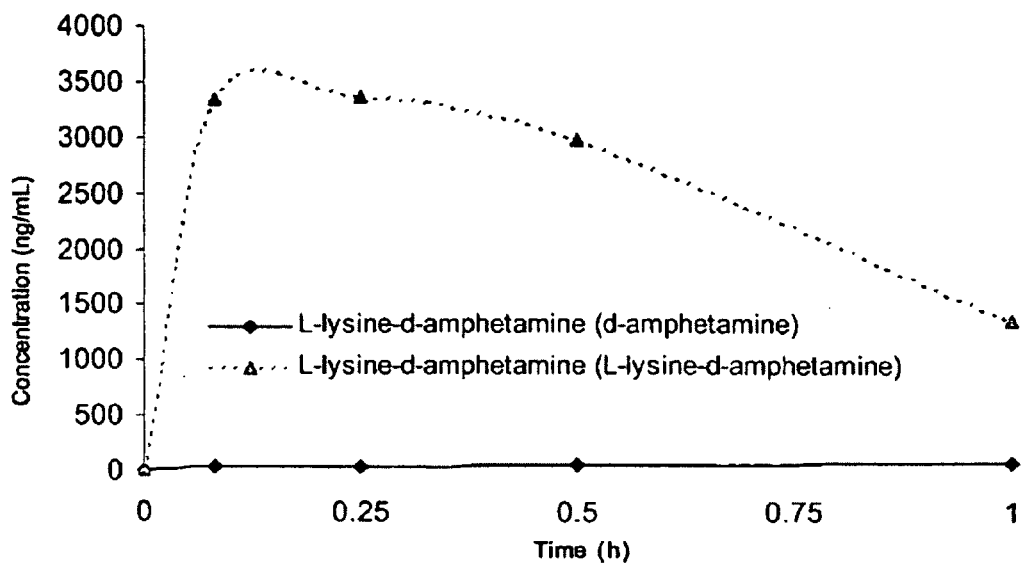
Figure 34B:
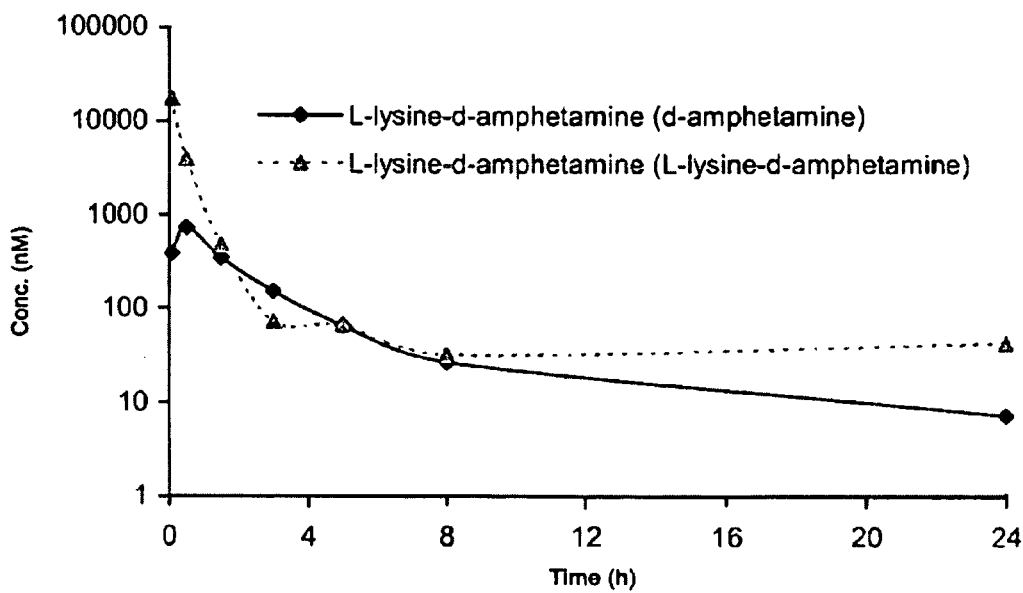

FIG. 34A and FIG. 34B. Plasma concentrations of d-amphetamine in ng/mL (FIG. 34A) and in nM (FIG. 34B), following intravenous administration of L-lysine-d-amphetamine dimesylate or d-amphetamine sulfate (at dose 1.5 mg/kg d-amphetamine base) to rats (LC/MS/MS analysis).

Figure 35:
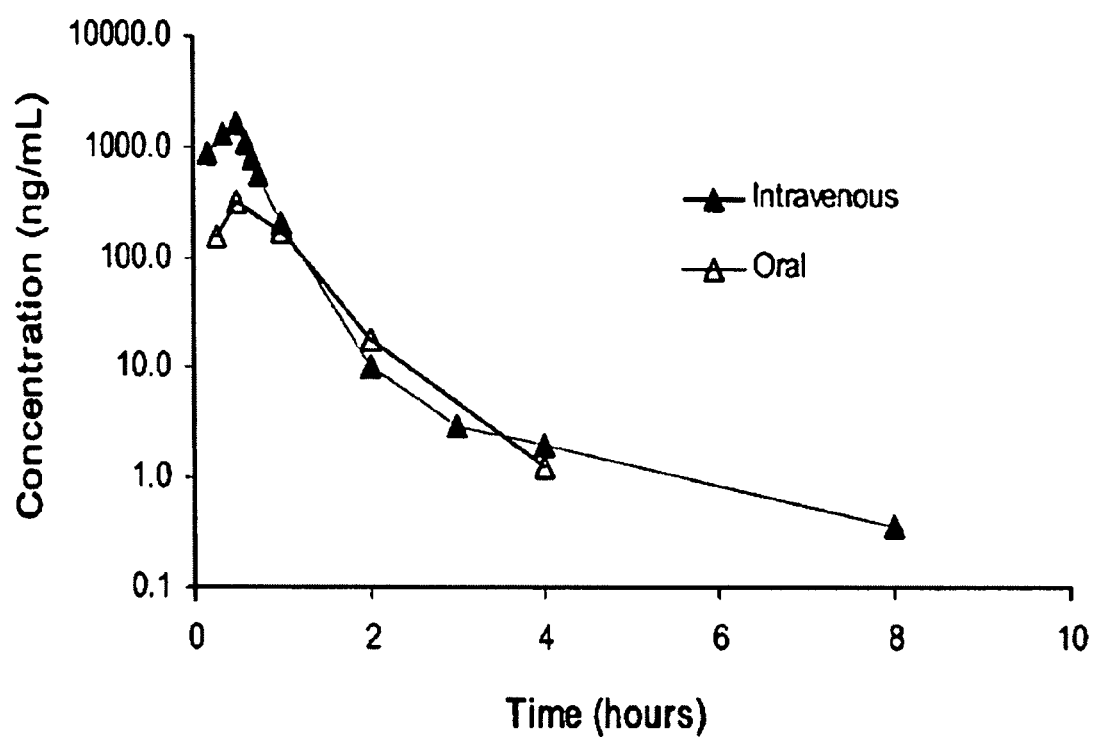

The following Figures (FIG. 35-FIG. 40) depict results obtained from studies of oral and intravenous administration (at dose 1 mg/kg d-amphetamine base) of d-amphetamine sulfate or L-lysine-d-amphetamine dimesylate to conscious male beagle dogs (LC/MS/MS analysis):

FIG. 35. Mean plasma concentration time profile of L-lysine-d-amphetamine following intravenous or oral administration of L-lysine-d-amphetamine (n=3).

Figure 36:
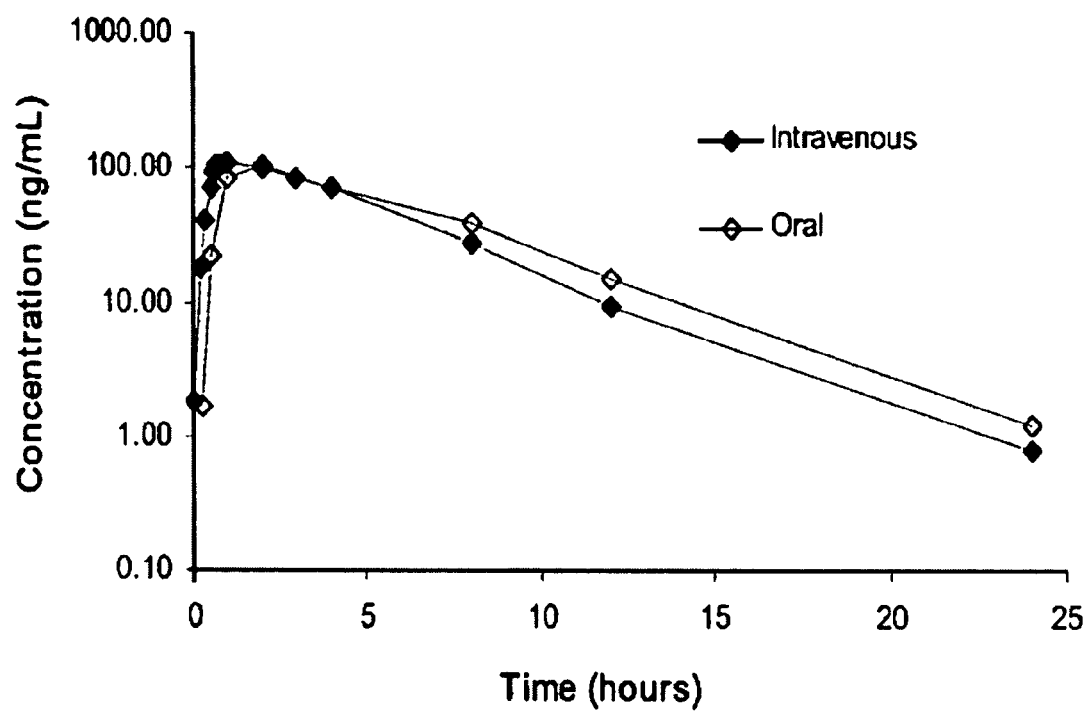

FIG. 36. Plasma concentration time profile of d-amphetamine following intravenous or oral administration of L-lysine-d-amphetamine (n=3).

Figure 37A:
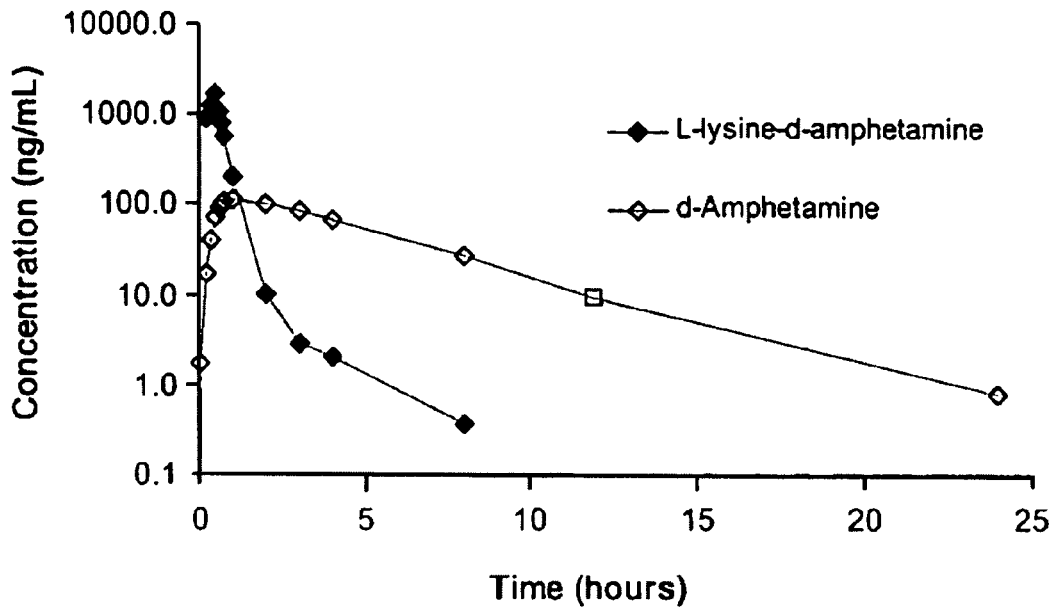
Figure 37B:
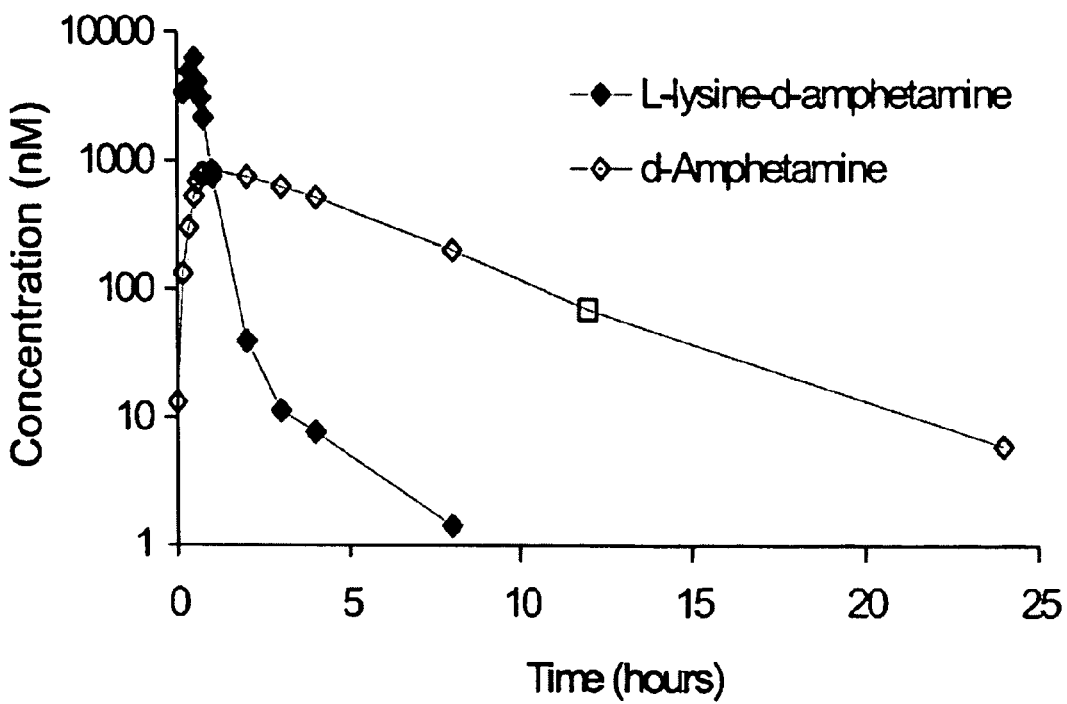

FIG. 37A and FIG. 37B. Mean plasma concentration time profile of L-lysine-d-amphetamine and d-amphetamine levels in ng/ml (FIG. 37A) and in nM (FIG. 37B), following intravenous administration of L-lysine-d-amphetamine (n=3).

Figure 38A:
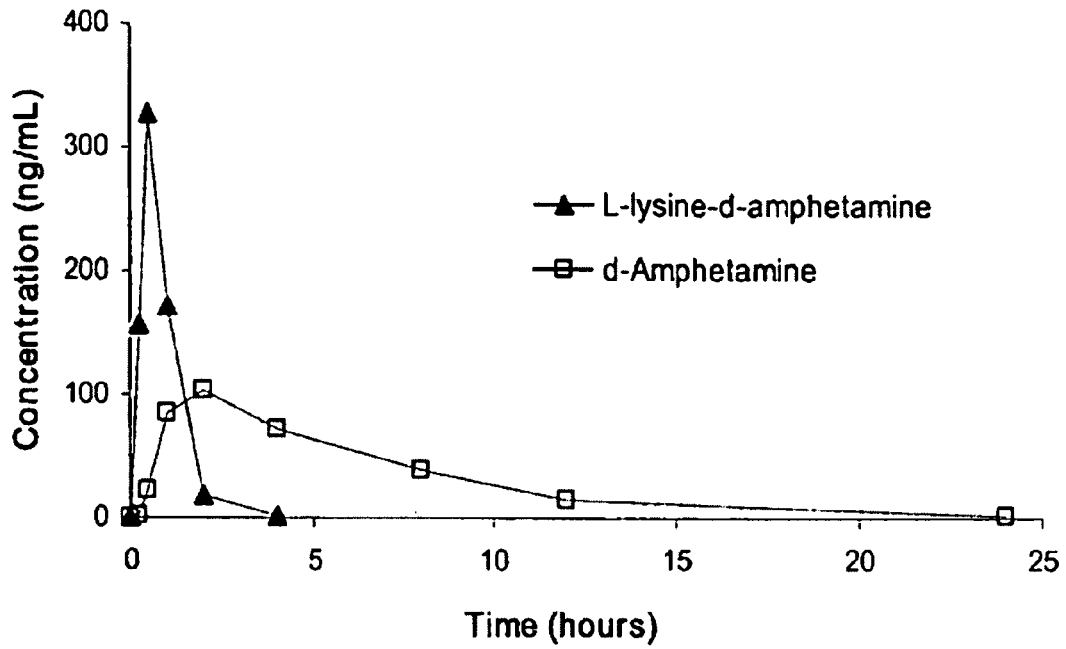
Figure 38B:
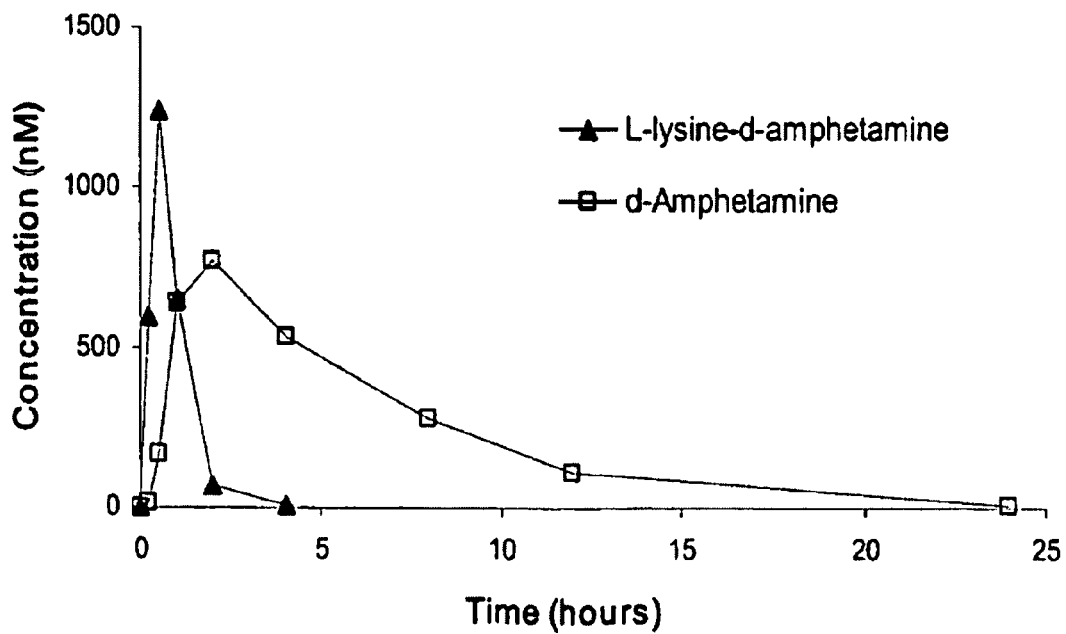

FIG. 38A and FIG. 38B. Mean plasma concentration time profile of L-lysine-d-amphetamine and d-amphetamine levels in ng/ml (FIG. 38A) and in nM (FIG. 38B), following oral administration of L-lysine-d-amphetamine (n=3).

Figure 39A:
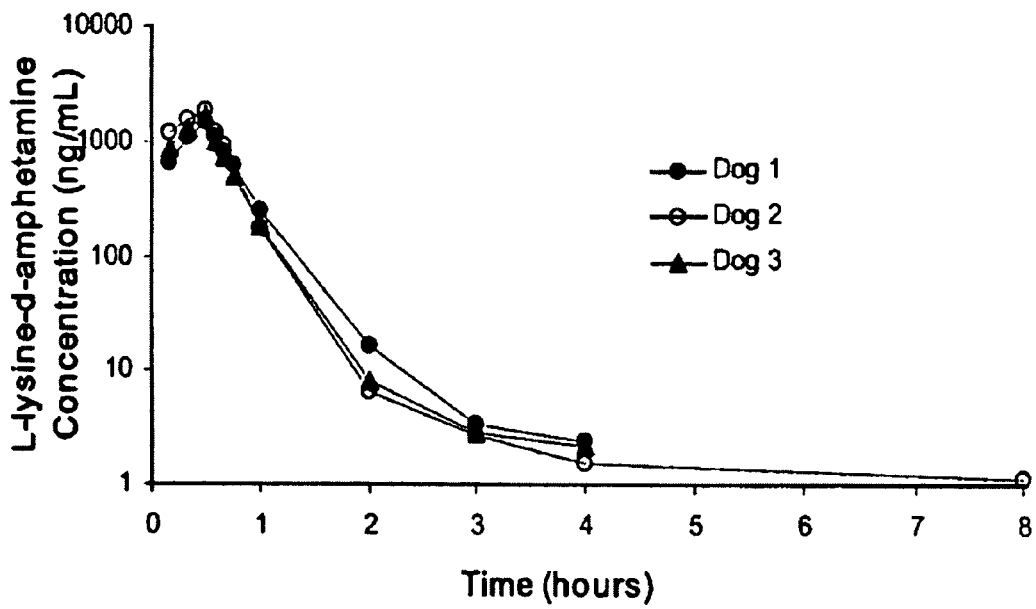
Figure 39B:
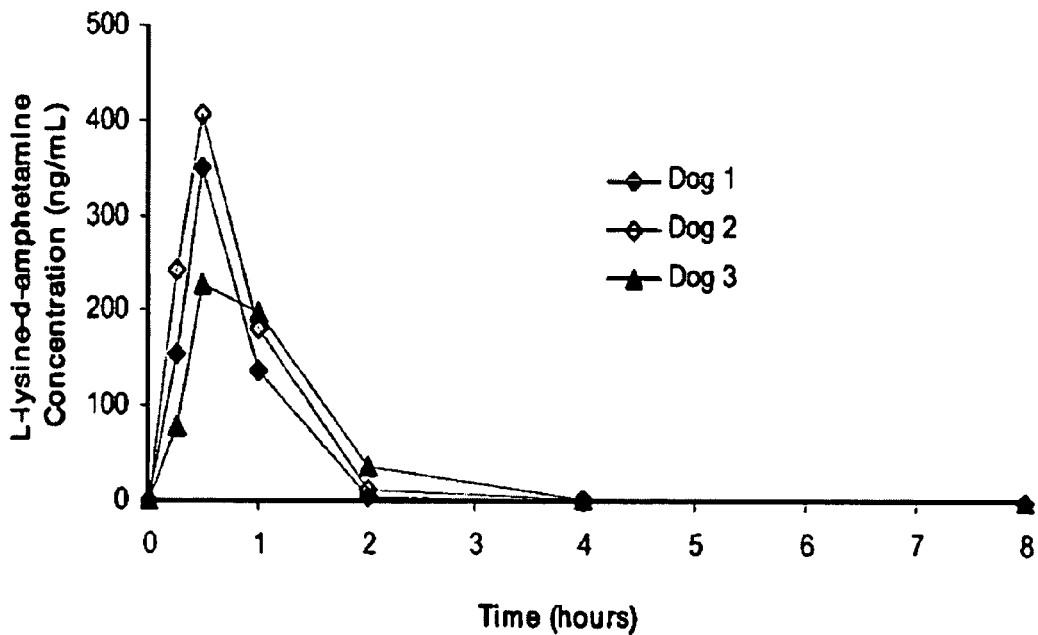

FIG. 39A and FIG. 39B. Individual plasma concentration time profile of L-lysine-d-amphetamine following intravenous administration (FIG. 39A) or oral administration (FIG. 39B) of L-lysine-d-amphetamine.

Figure 40A:
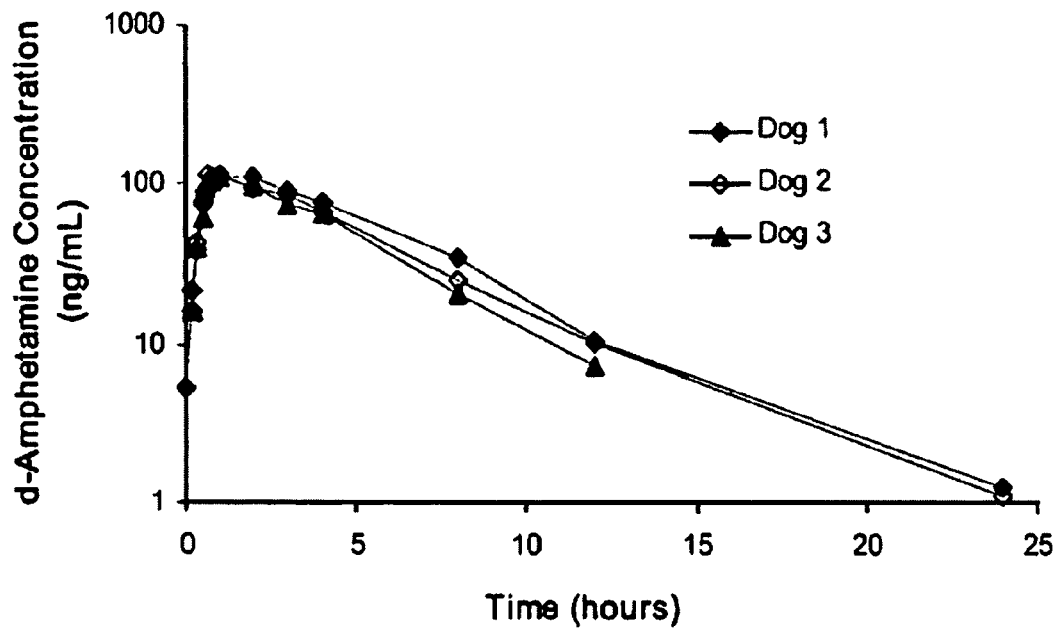
Figure 40B:
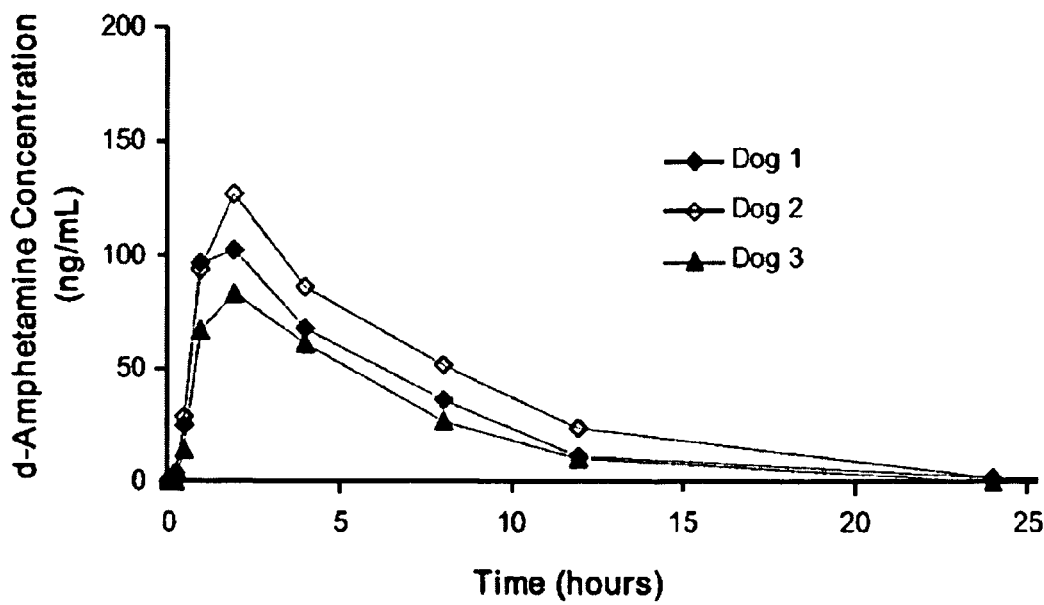

FIG. 40A and FIG. 40B. Individual plasma concentration time profile of d-amphetamine following intravenous administration (FIG. 40A) or oral administration (FIG. 40B) of L-lysine-d-amphetamine.

Figure 41:
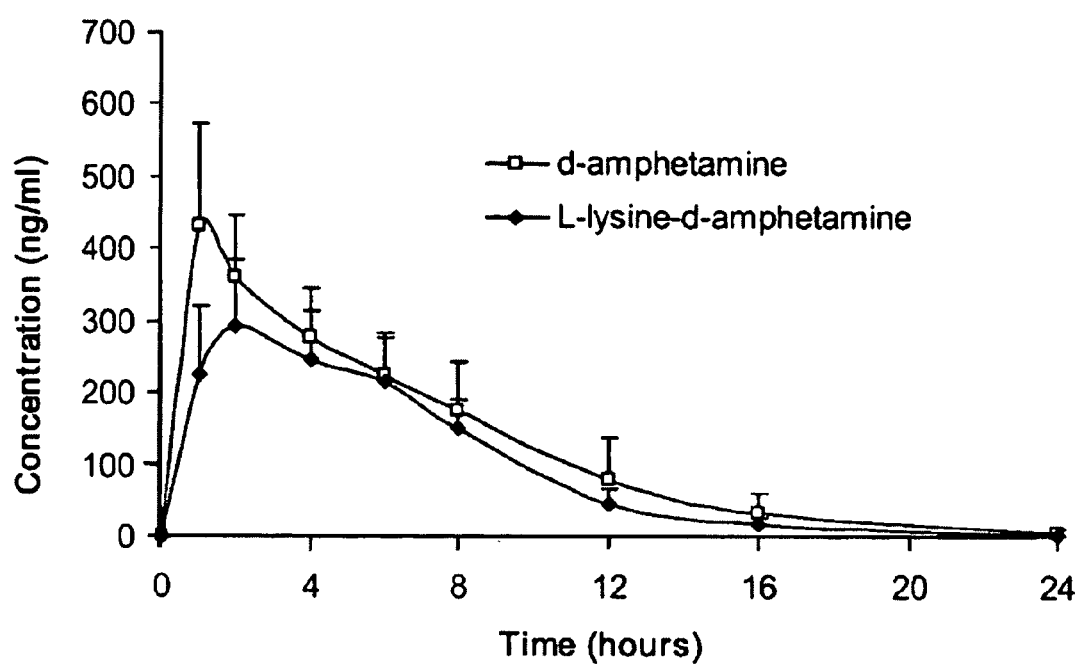

FIG. 41. Plasma concentrations of d-amphetamine following oral administration of L-lysine-d-amphetamine dimesylate or d-amphetamine sulfate (at dose 1.8 mg/kg d-amphetamine base) to male dogs.

Figure 42:
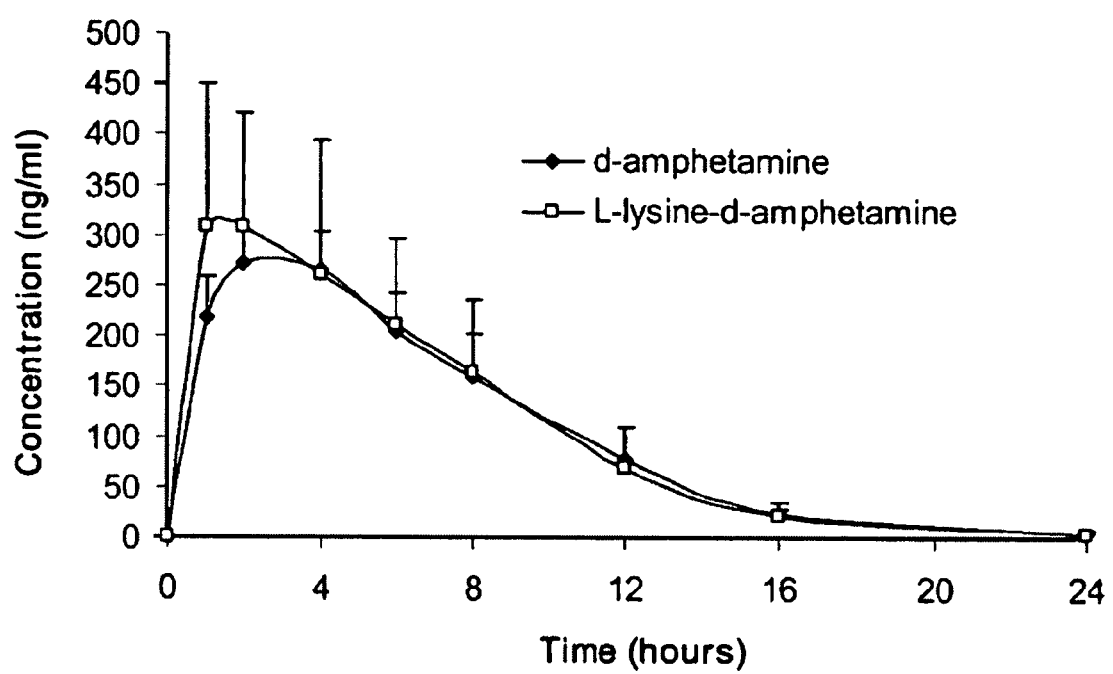

FIG. 42. Plasma concentrations of d-amphetamine following oral administration of L-lysine-d-amphetamine dimesylate or d-amphetamine sulfate (at dose 1.8 mg/kg d-amphetamine base) to female dogs.

Figure 43:
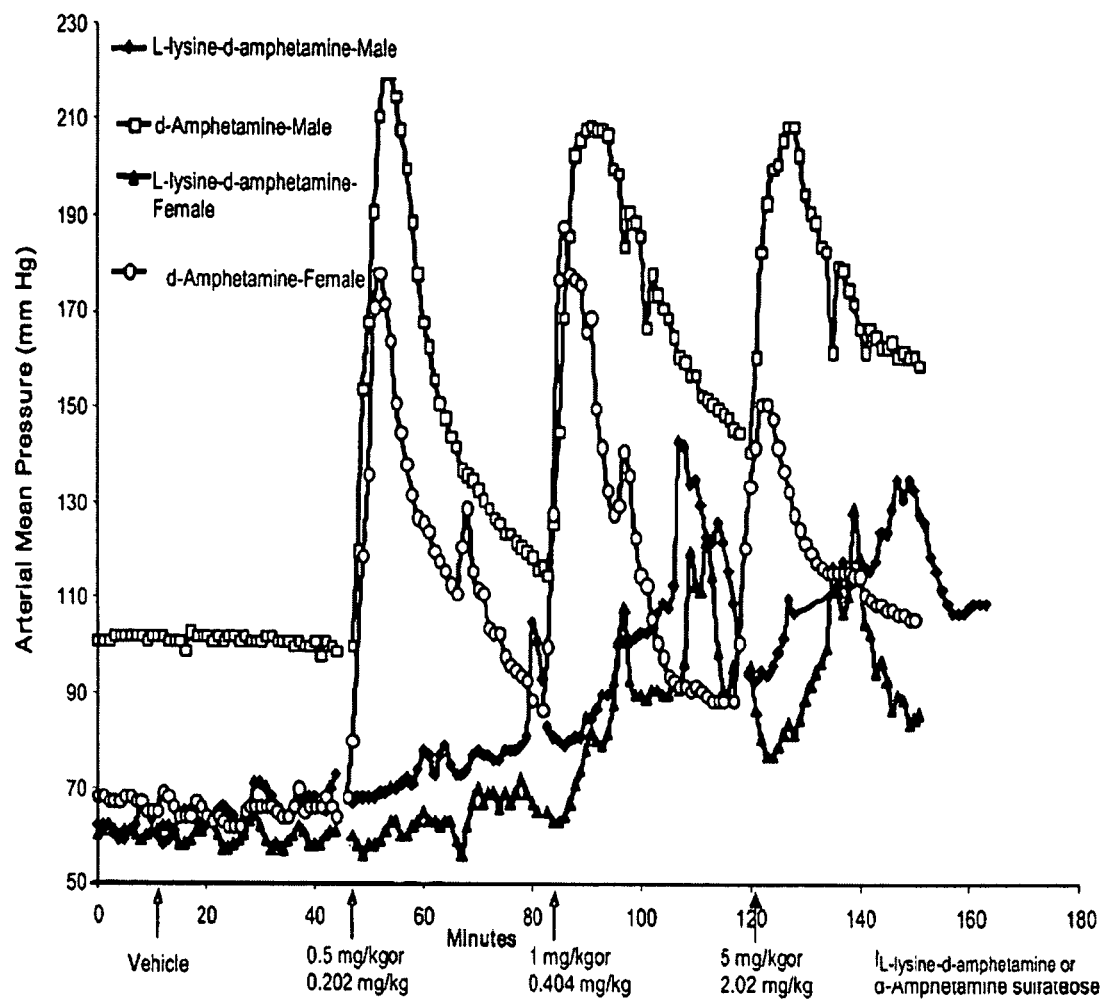

FIG. 43. Mean blood pressure following intravenous injection of increasing amounts of L-lysine-d-amphetamine dimesylate or d-amphetamine in male and female dogs.

Figure 44:
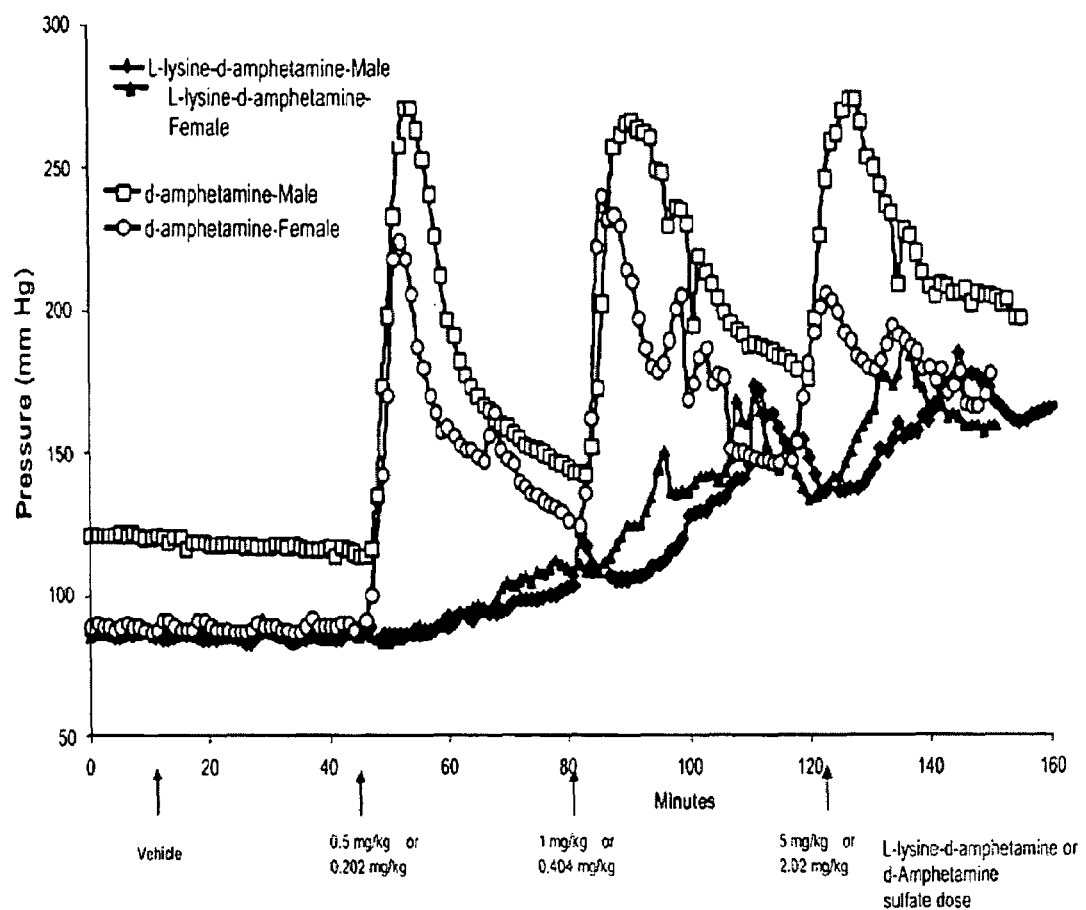

FIG. 44. Left ventricular blood pressure following intravenous injection of increasing amounts of L-lysine-d-amphetamine dimesylate or d-amphetamine in male and female dogs.

Figure 45:
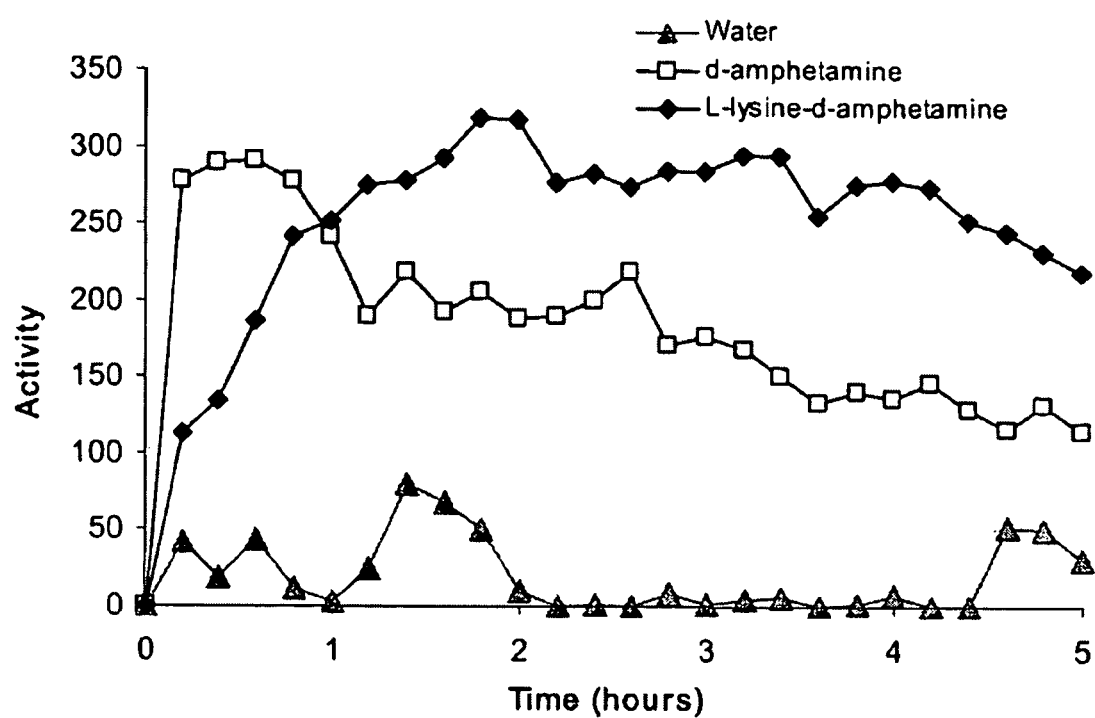

The following Figures (FIG. 45-FIG. 49) depict results obtained from studies of oral (at dose 6 mg/kg d-amphetamine base), intranasal (at dose 1 mg/kg d-amphetamine base), and intravenous administration (at dose 1 mg/kg d-amphetamine base) of d-amphetamine sulfate or L-lysine-d-amphetamine hydrochloride to rats:

FIG. 45. Locomotor activity of rats following oral administration (5 hour time-course).

Figure 46:
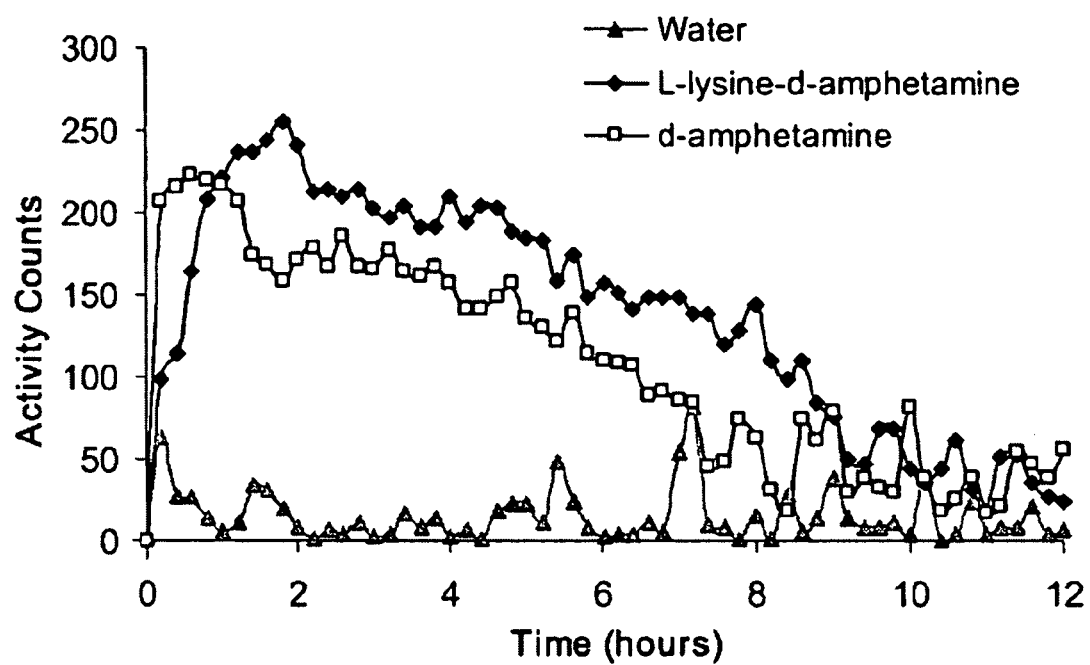

FIG. 46. Locomotor activity of rats following oral administration (12 hour time-course).

Figure 47:
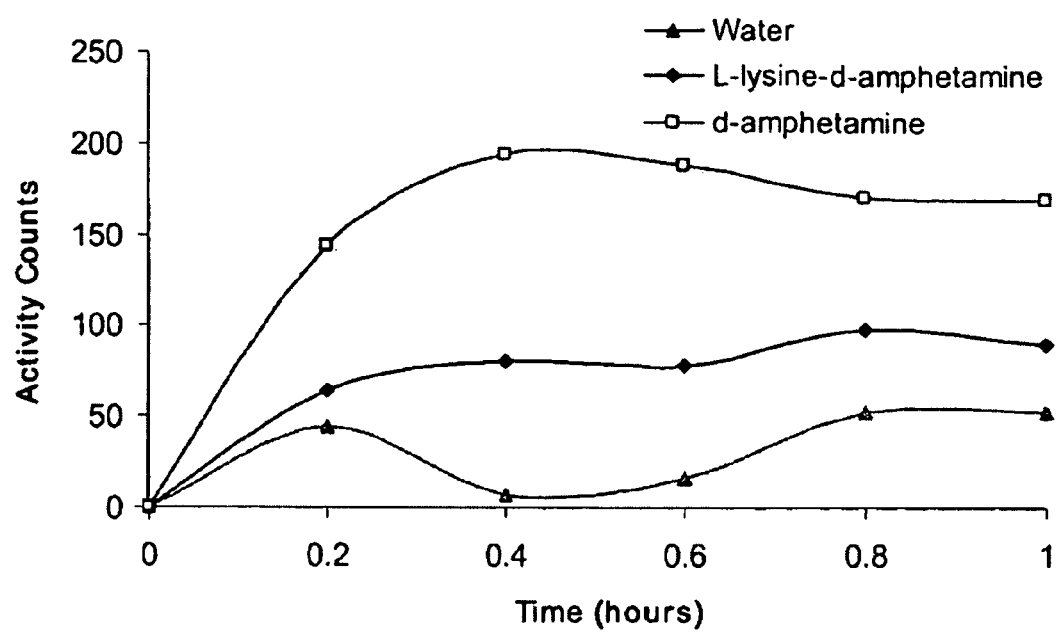

FIG. 47. Locomotor activity of rats following intranasal administration (1 hour time-course).

Figure 48:
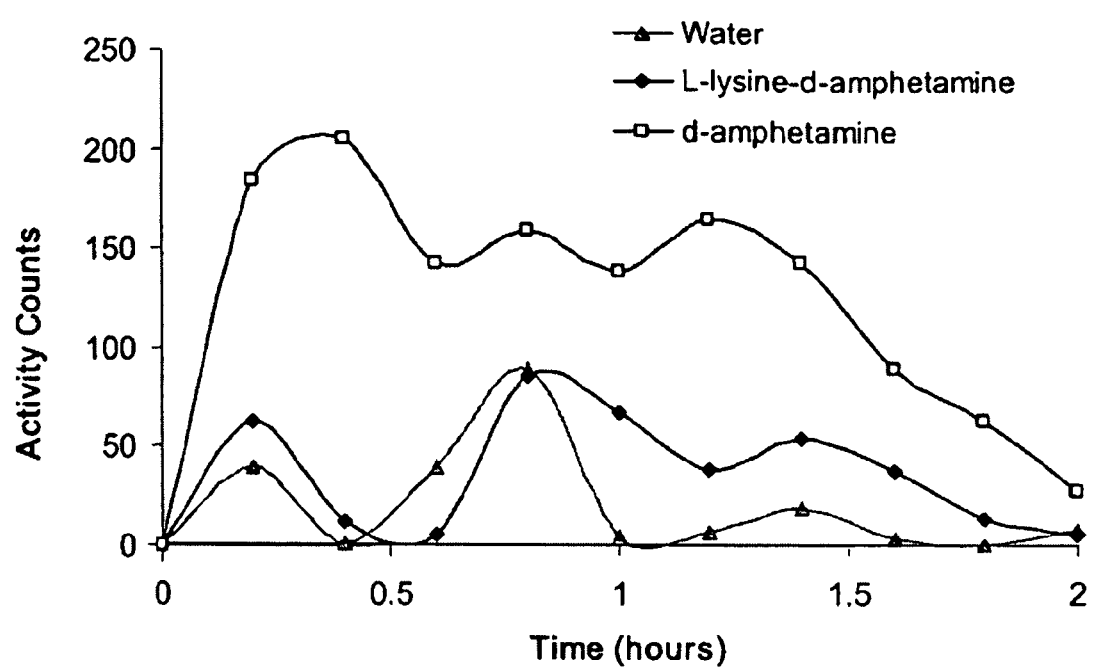

FIG. 48. Locomotor activity of rats following intranasal administration (with carboxymethylcellulose) (2 hour time-course).

Figure 49:
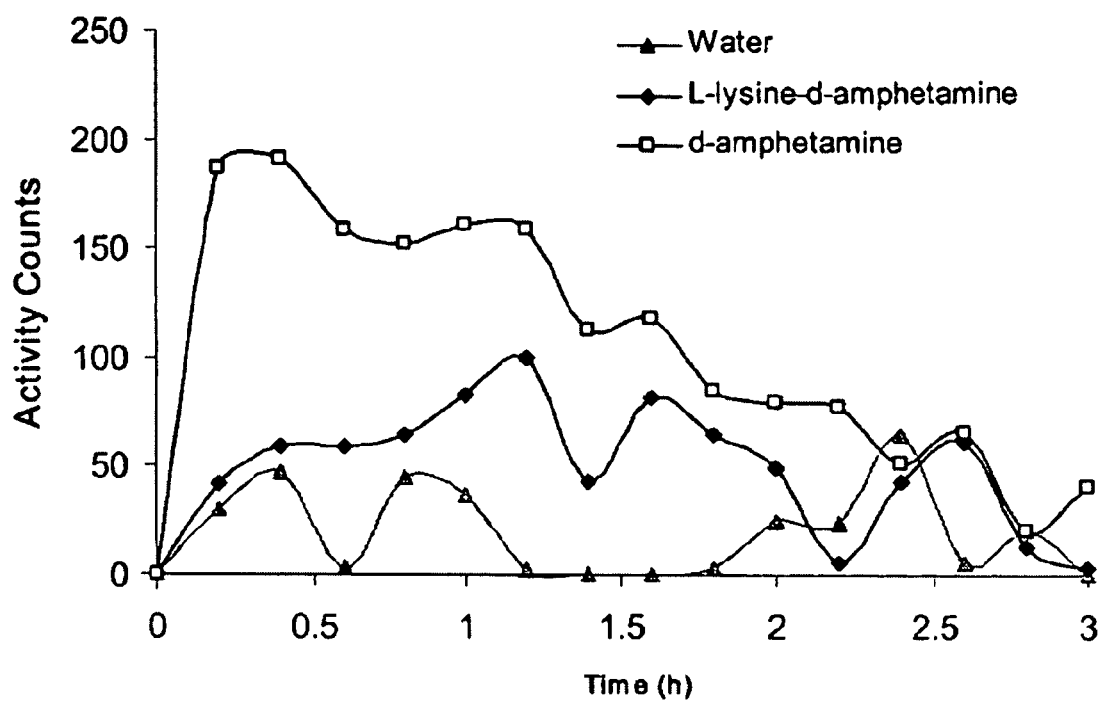

FIG. 49. Locomotor activity of rats following intravenous administration (3 hour time-course).

Figure 50:
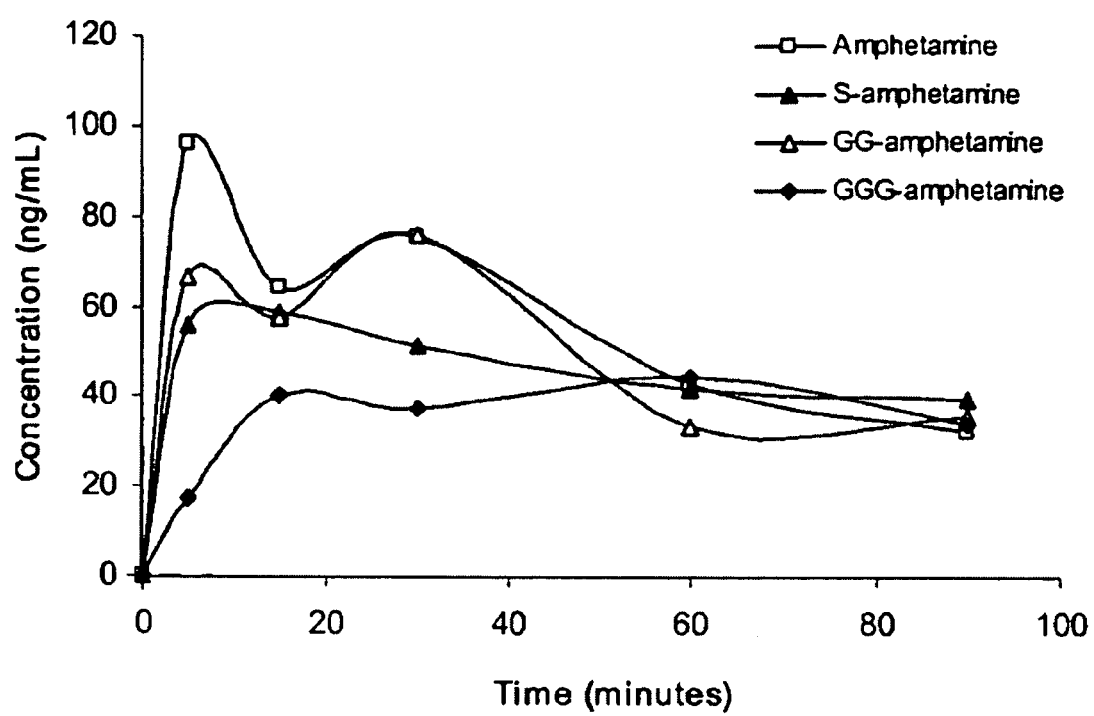

The following Figures (FIG. 50-FIG. 58) depict results obtained from studies of oral, intranasal, and intravenous administration of d-amphetamine or amphetamine conjugate hydrochloride salts to rats (ELISA analysis):

FIG. 50. Intranasal bioavailability of abuse-resistant amphetamine amino acid, di-, and tri-peptide conjugates.

Figure 51:
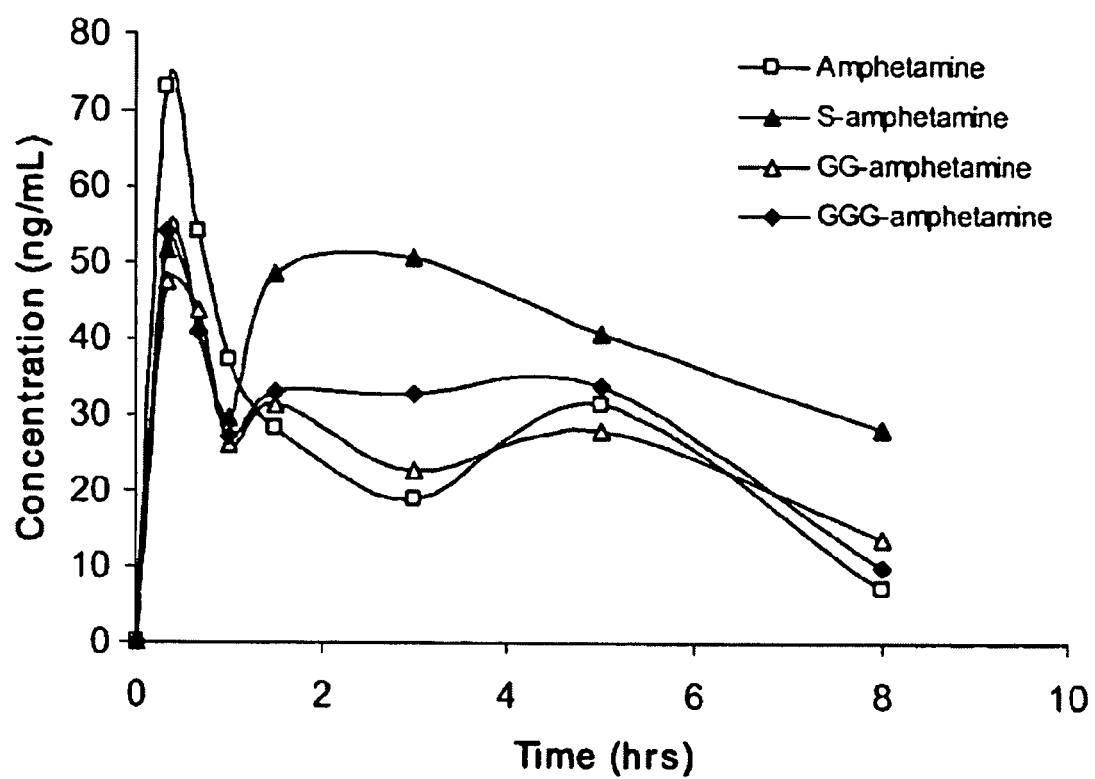

FIG. 51. Oral bioavailability of abuse-resistant amphetamine amino acid, di-, and tri-peptide conjugates.

Figure 52:
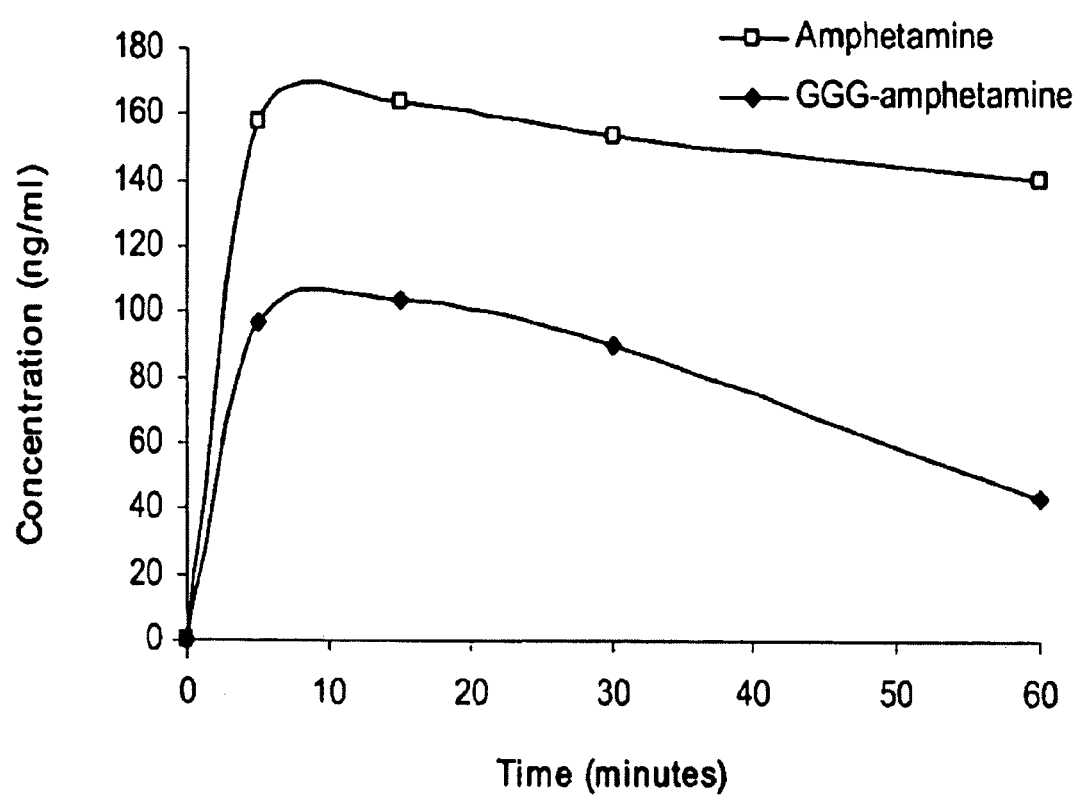

FIG. 52. Intravenous bioavailability of an abuse-resistant amphetamine tri-peptide conjugate.

Figure 53:
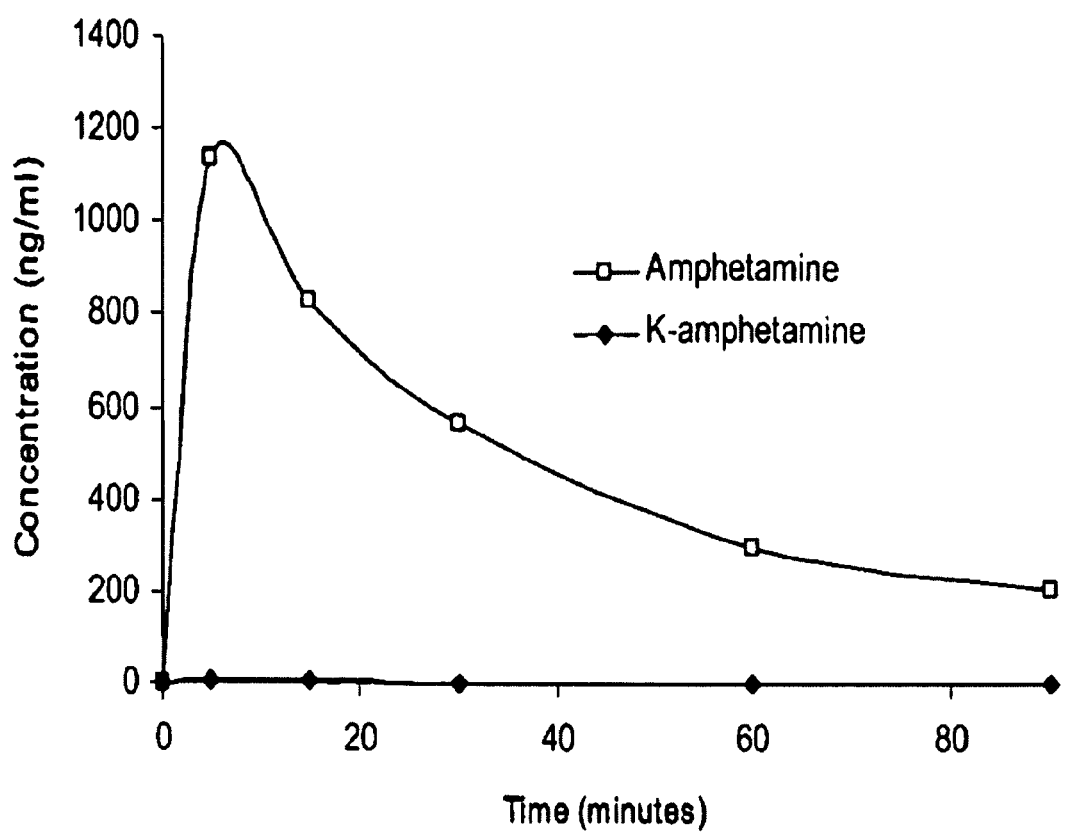

FIG. 53. Intranasal bioavailability of an abuse-resistant amphetamine amino acid conjugate.

Figure 54:
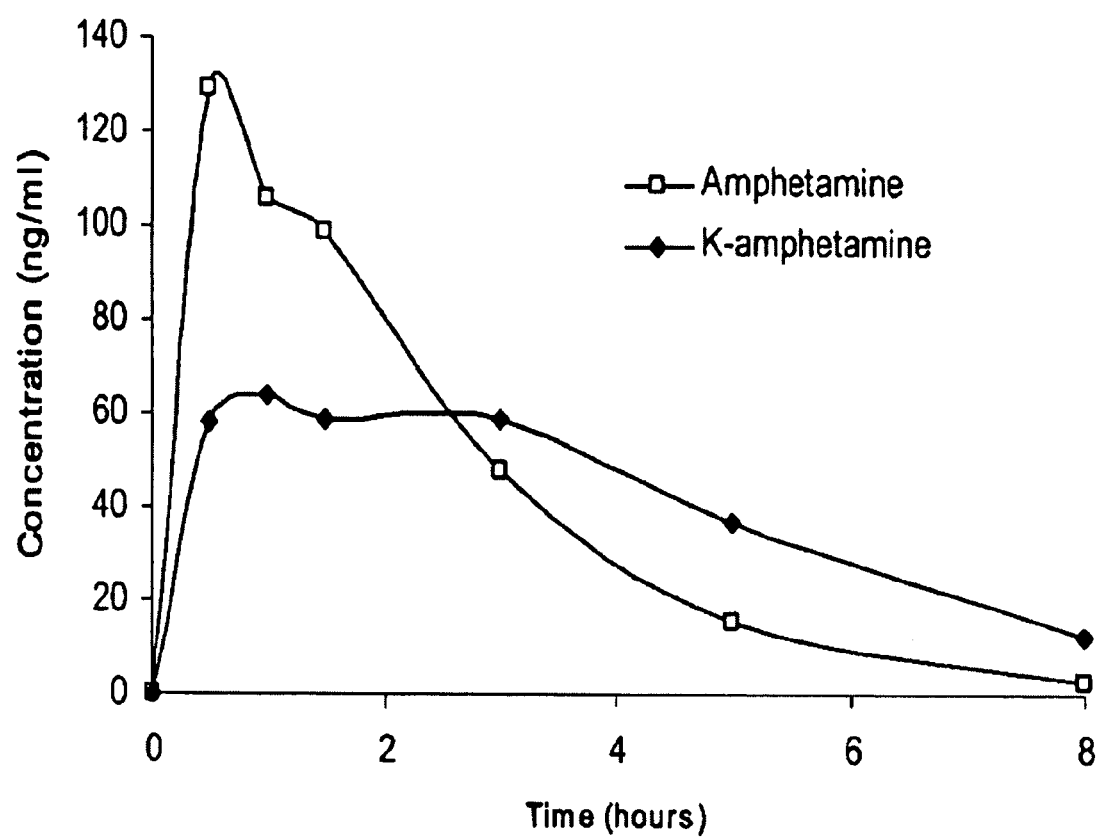

FIG. 54. Oral bioavailability of an abuse-resistant amphetamine amino acid conjugate.

Figure 55:
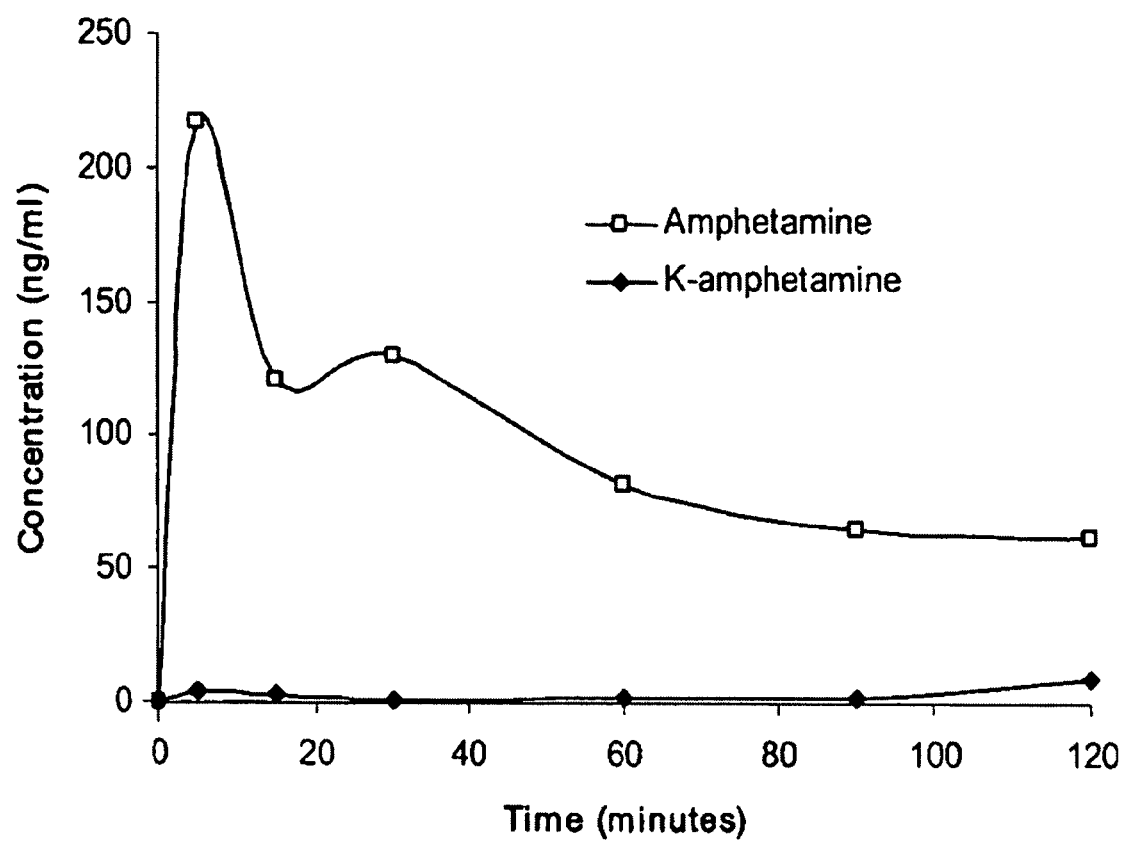

FIG. 55. Intravenous bioavailability of an abuse-resistant amphetamine amino acid conjugate.

Figure 56:
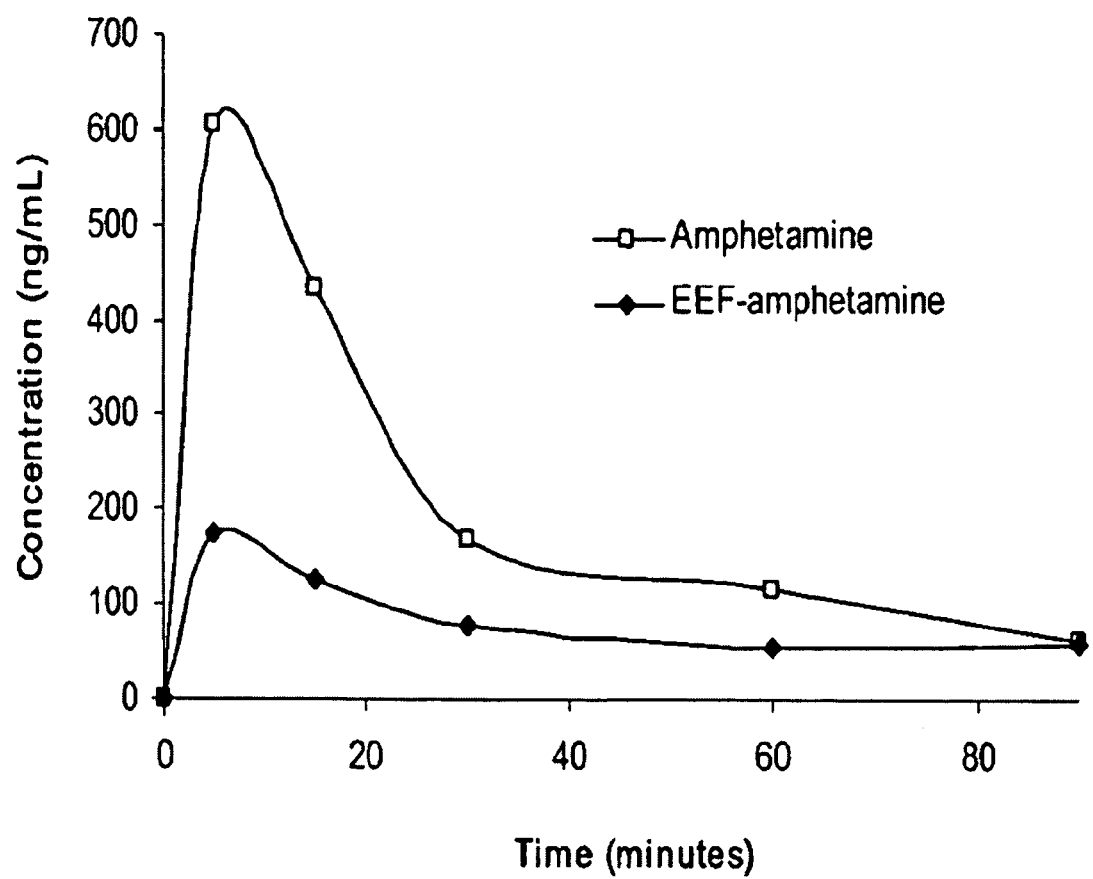

FIG. 56. Intranasal bioavailability of an abuse-resistant amphetamine amino tri-peptide conjugate.

Figure 57:
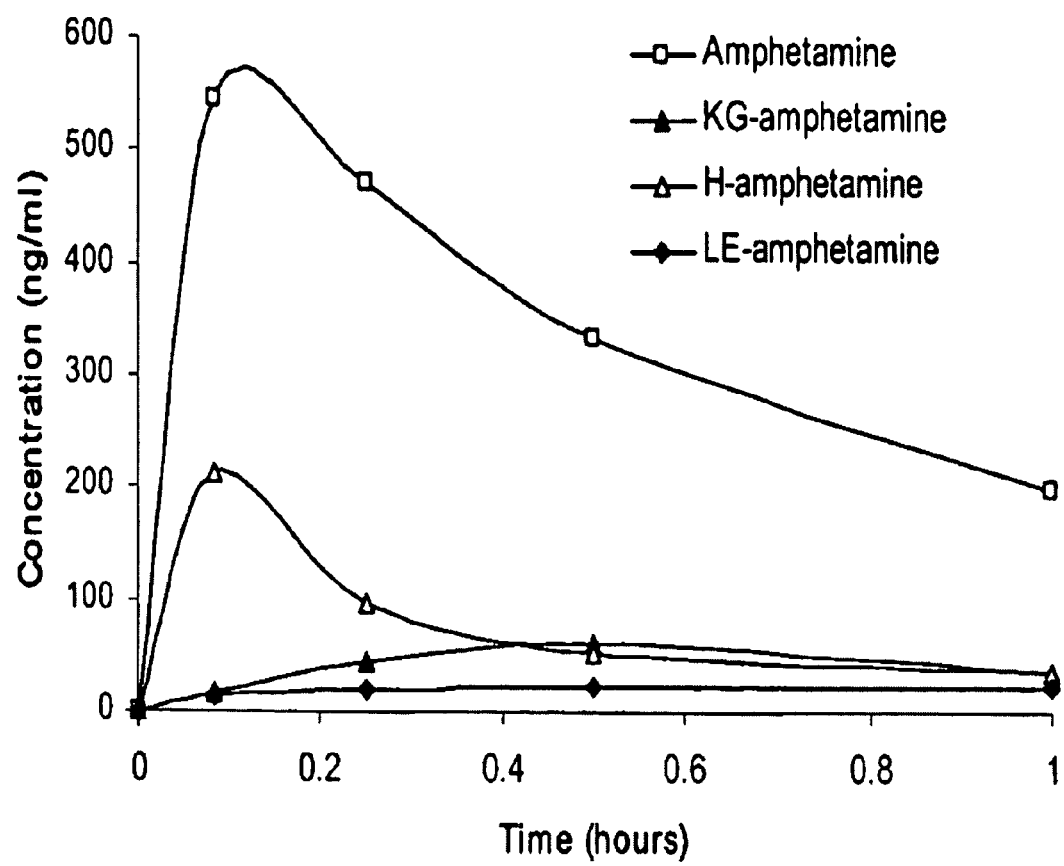

FIG. 57. Intranasal bioavailability of abuse-resistant amphetamine amino acid-, and di-peptide conjugates.

Figure 58:
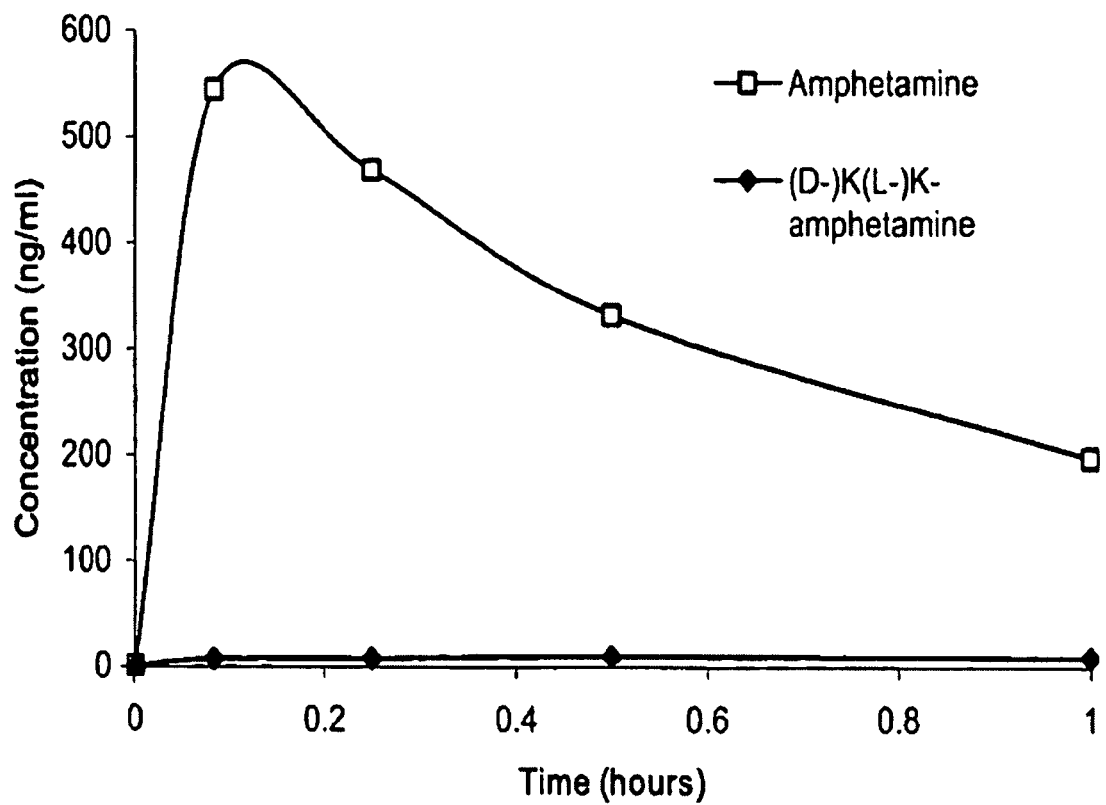

FIG. 58. Intranasal bioavailability of an abuse-resistant amphetamine di-peptide conjugate containing D- and L-amino acid isomers.

Figure 59A:
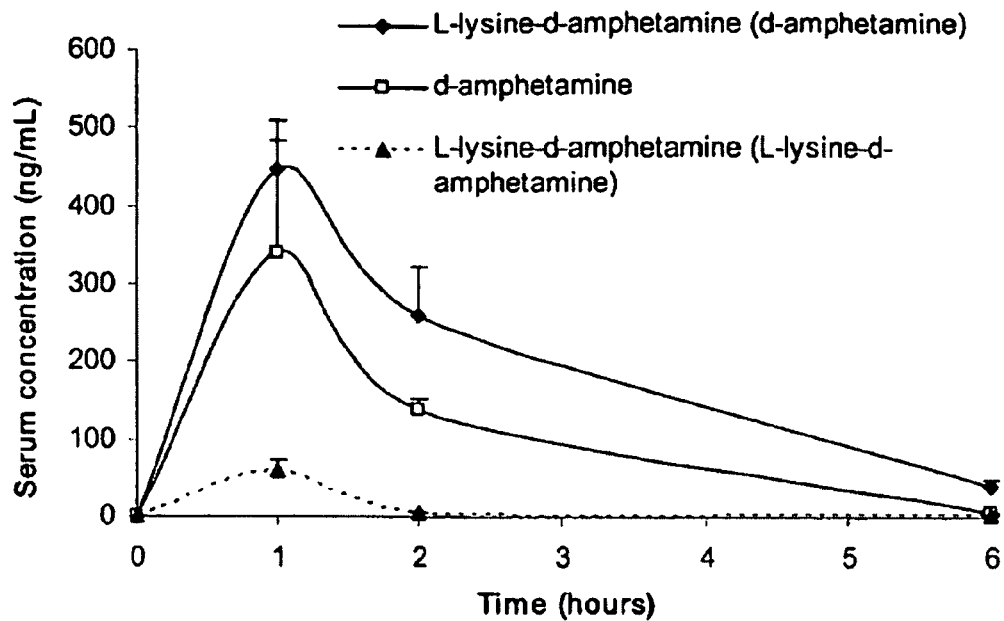
Figure 59B:
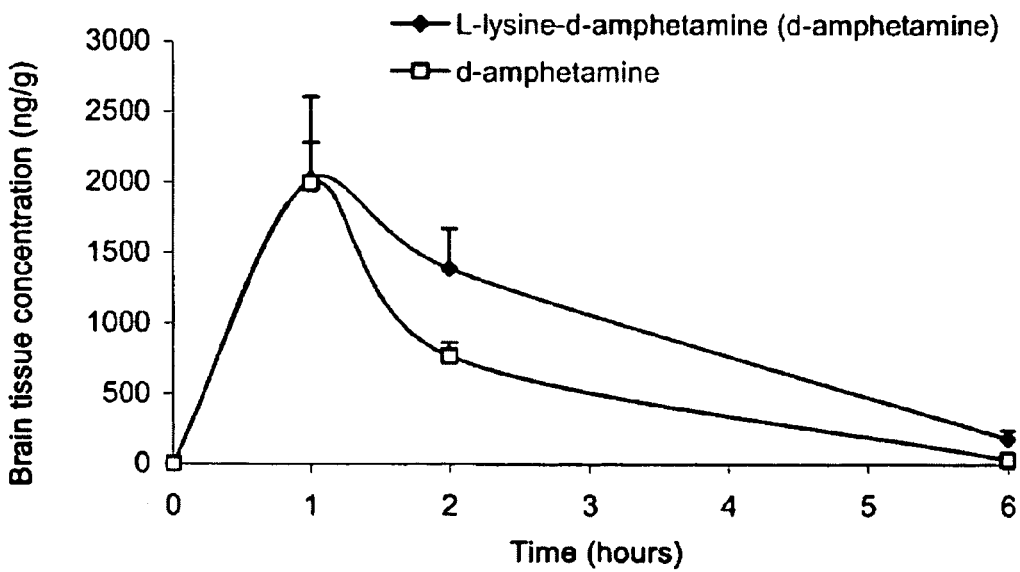

FIG. 59A and FIG. 59B. Plasma concentrations of d-amphetamine and L-lysine-d-amphetamine in ng/mL for the serum levels (FIG. 59A) and in ng/g for brain tissue (FIG. 59B), following oral administration of L-lysine-d-amphetamine hydrochloride or d-amphetamine sulfate (at dose 5 mg/kg d-amphetamine base) to rats (LC/MS/MS analysis).

Figure 60:
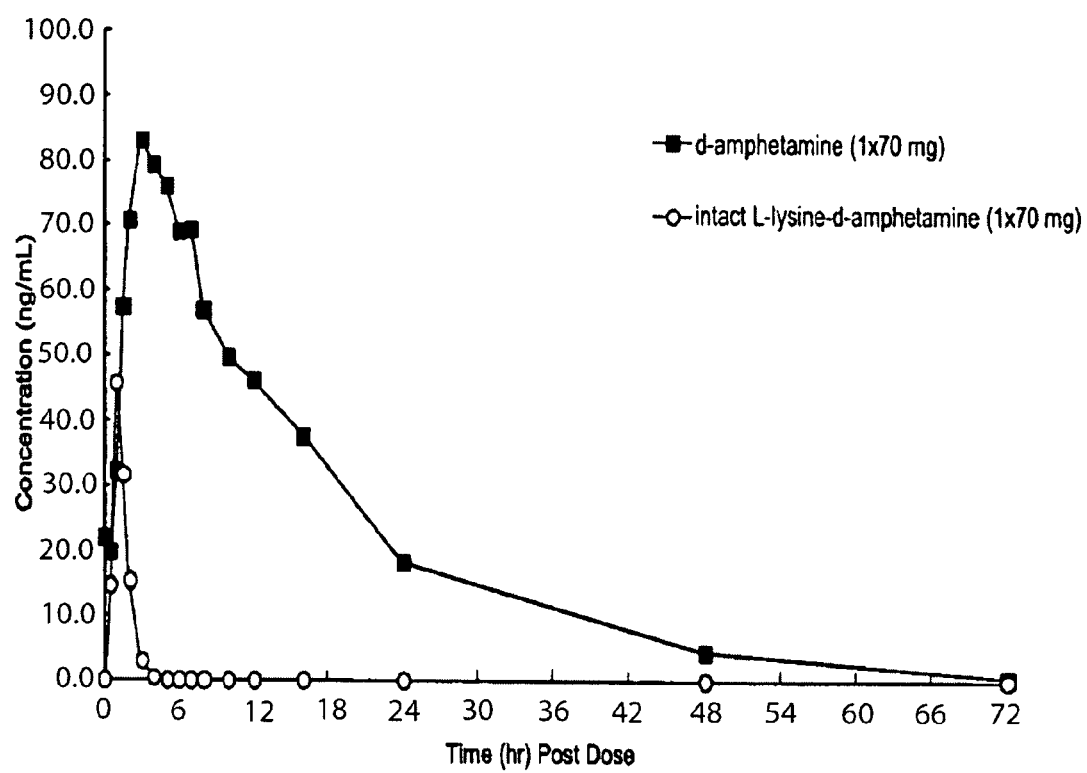

FIG. 60. Steady-state plasma d-amphetamine and L-lysine-d-amphetamine levels obtained from clinical studies of oral administration of L-lysine-d-amphetamine dimesylate 70 mg to humans (LC/MS/MS analysis).

Figure 61A:
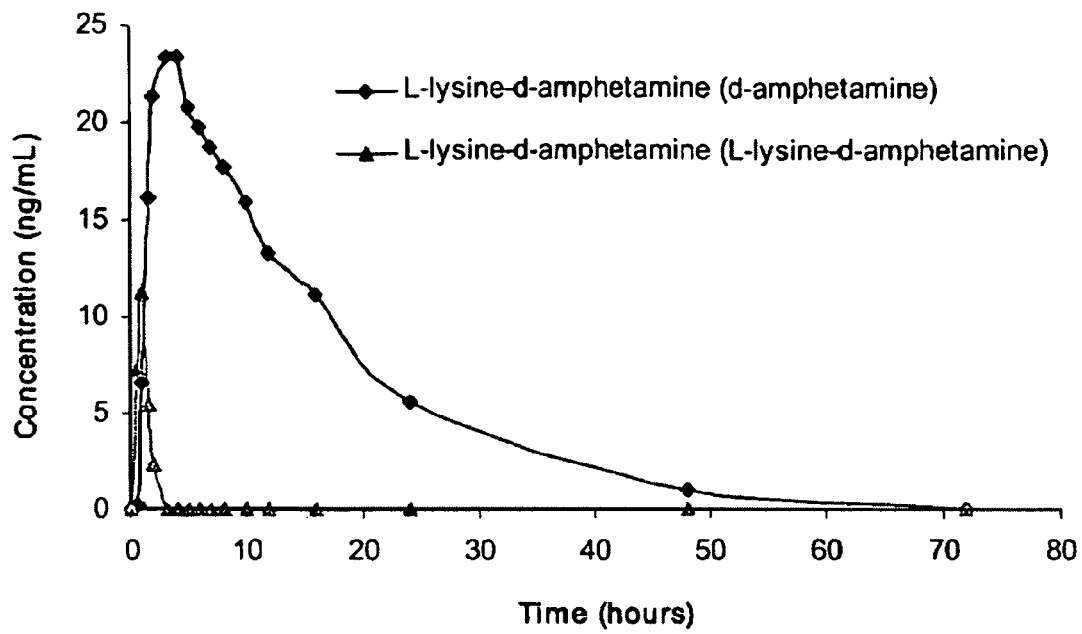
Figure 61B:
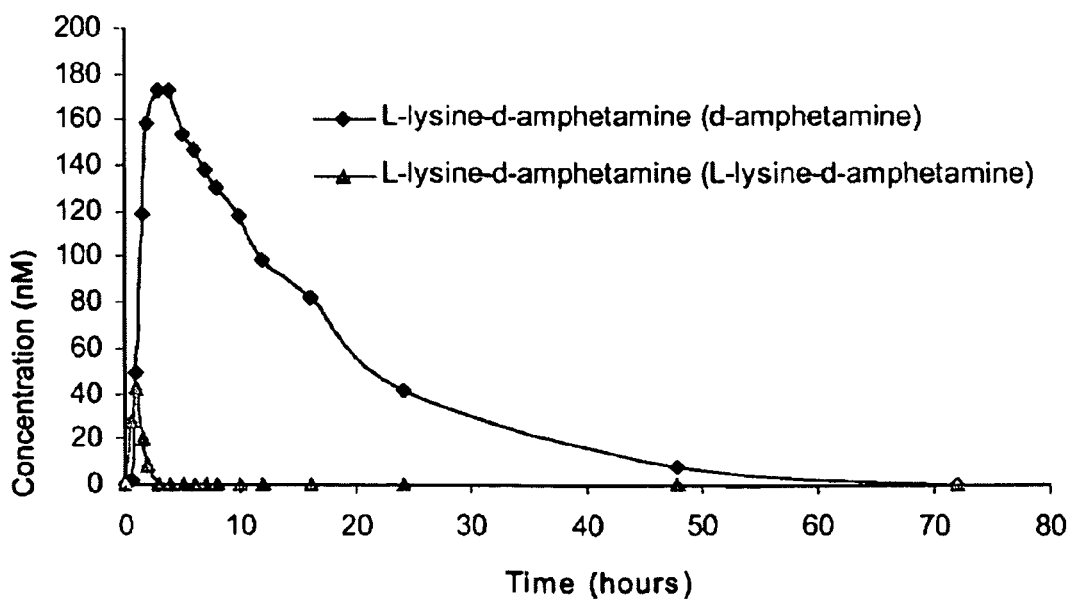

The following Figures (FIG. 61-FIG. 70) depict results obtained from clinical studies of oral administration of L-lysine-d-amphetamine dimesylate to humans (LC/MS/MS analysis):

FIG. 61A and FIG. 61B. Plasma d-amphetamine and L-lysine-d-amphetamine levels (FIG. 61A, ng/mL; FIG. 61B, nM) over a 72 hour period following oral administration of L-lysine-d-amphetamine (25 mg L-lysine-d-amphetamine dimesylate containing 7.37 mg d-amphetamine base) to humans.

Figure 62A:
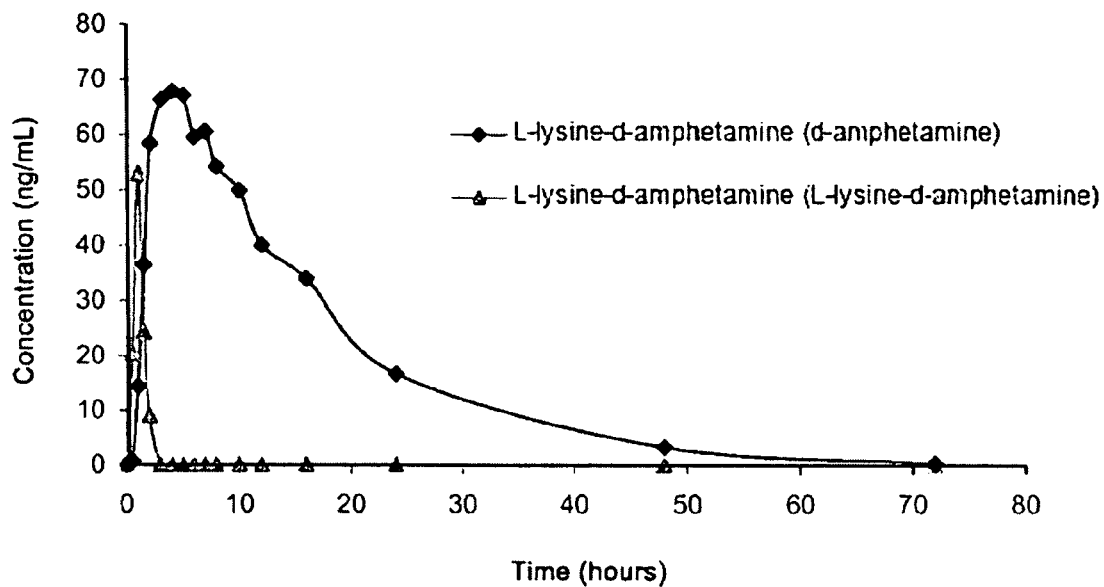
Figure 62B:
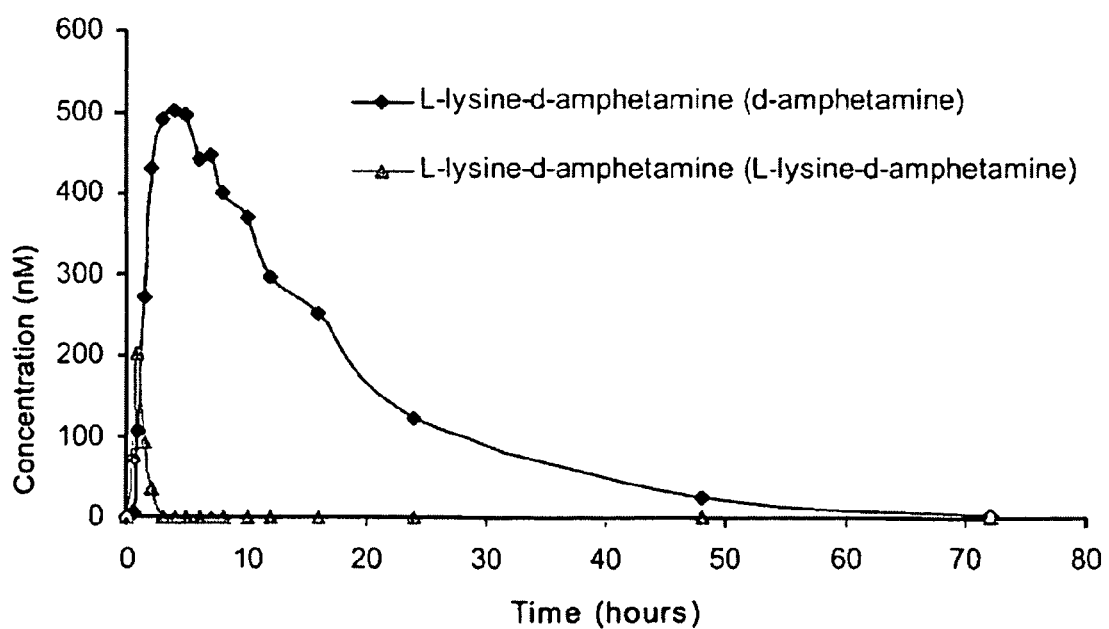

FIG. 62A and FIG. 62B. Plasma d-amphetamine and L-lysine-d-amphetamine levels (FIG. 62A, ng/mL; FIG. 62B, nM) over a 72 hour period following oral administration of L-lysine-d-amphetamine (75 mg L-lysine-d-amphetamine dimesylate containing 22.1 mg d-amphetamine base) to humans.

Figure 63A:
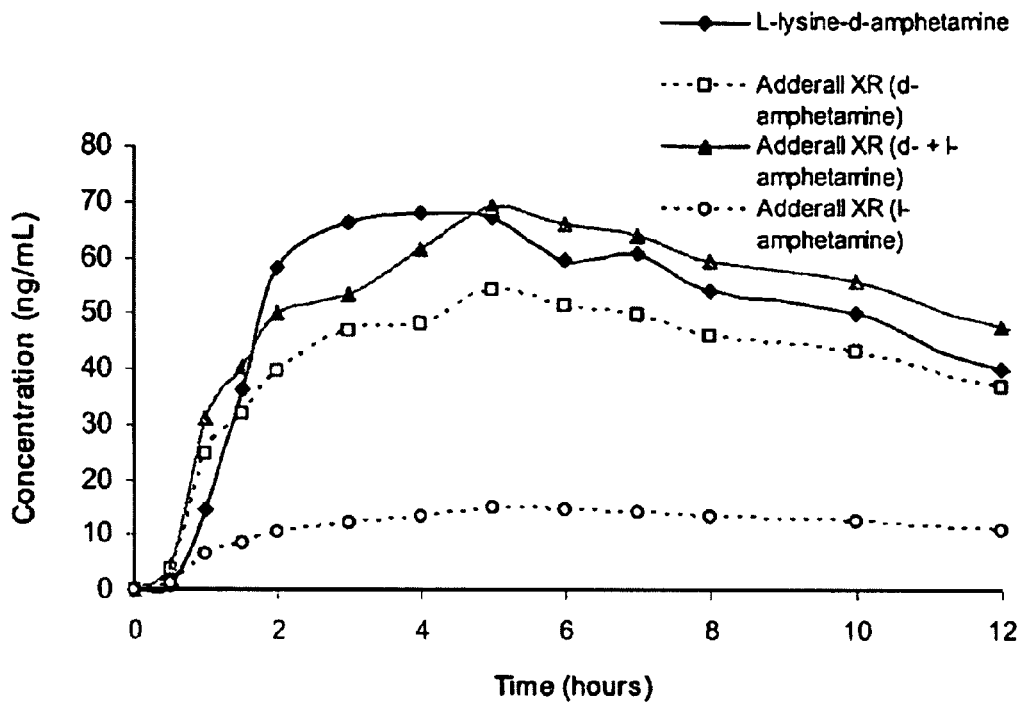
Figure 63B:
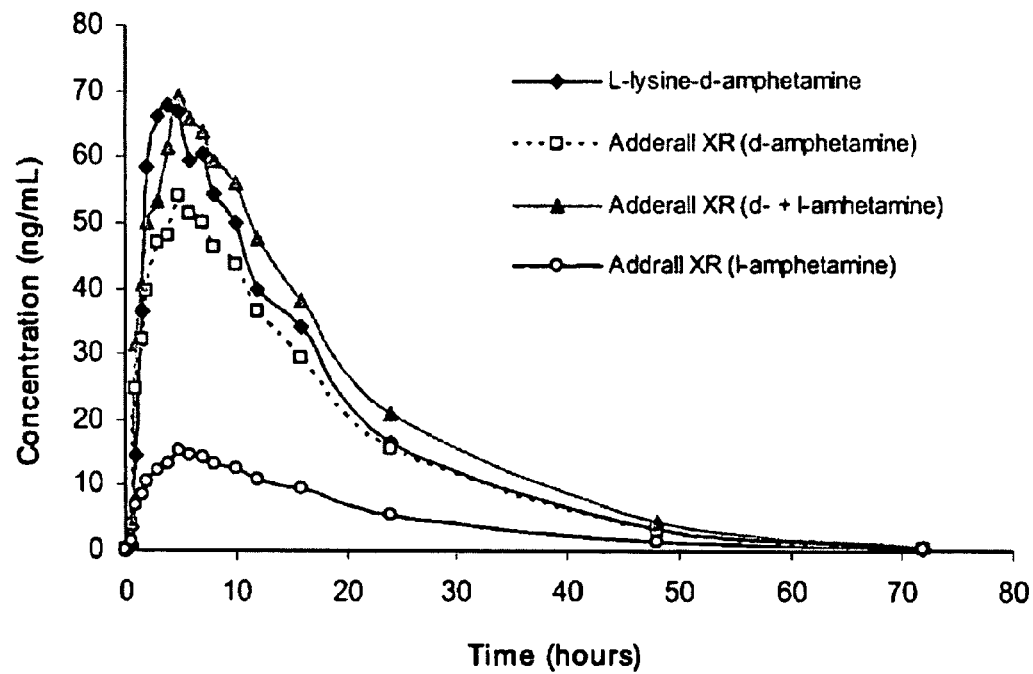

FIG. 63A and FIG. 63B. Plasma d-amphetamine levels (FIG. 63A, 0-12 hours; FIG. 63B, 0-72 hours) following oral administration of L-lysine-d-amphetamine (75 mg L-lysine-d-amphetamine dimesylate containing 22.1 mg d-amphetamine base) or Adderall XR® (35 mg containing 21.9 mg amphetamine base) to humans.

Figure 64A:
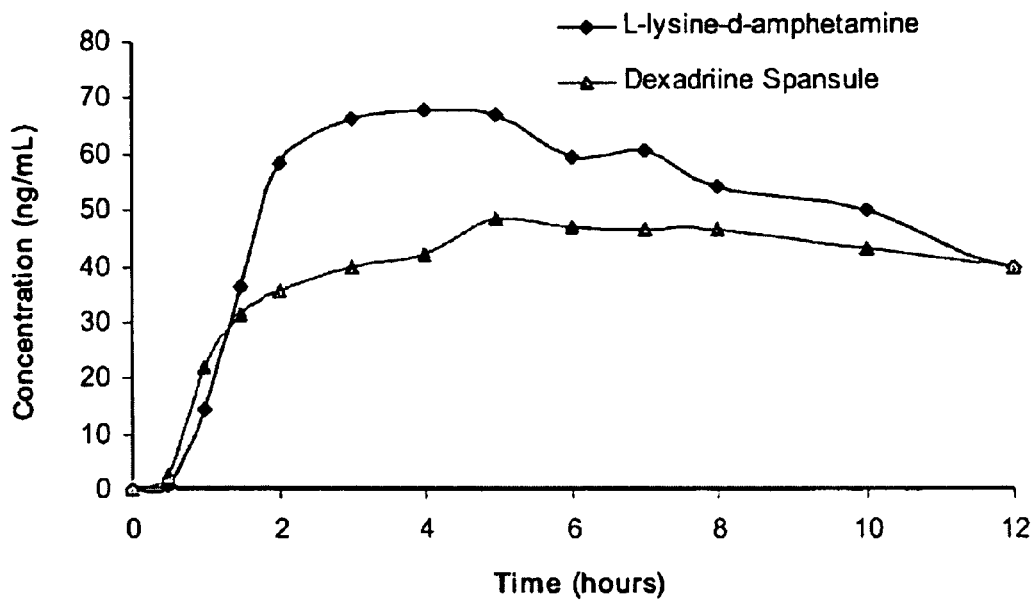
Figure 64B:
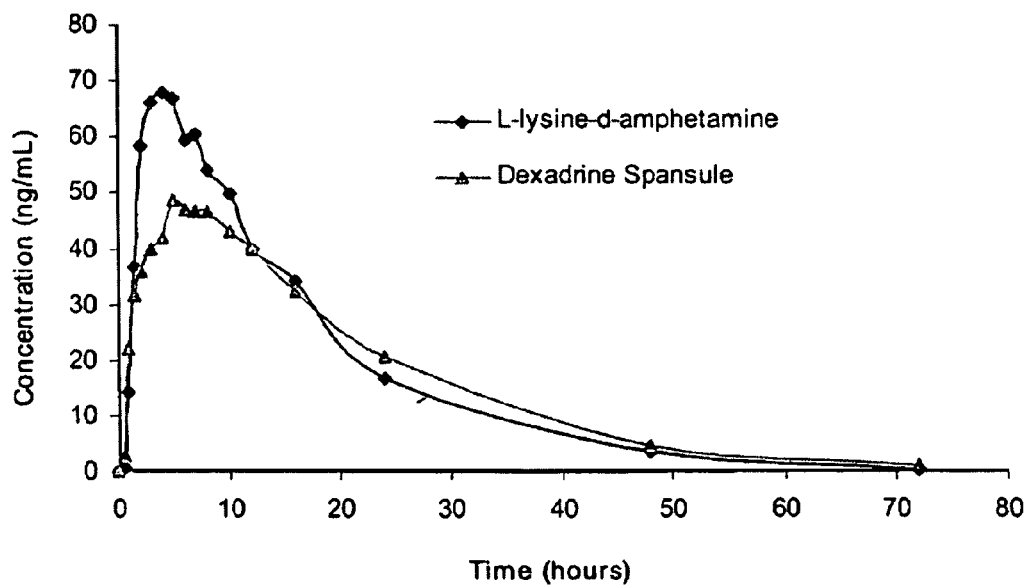

FIG. 64A and FIG. 64B. Plasma d-amphetamine levels (FIG. 64A, 0-12 hours; FIG. 64B, 0-72 hours) following oral administration of L-lysine-d-amphetamine (75 mg L-lysine-d-amphetamine dimesylate containing 22.1 mg d-amphetamine base) or Dexedrine Spansule® (30 mg containing 22.1 mg amphetamine base) to humans.

Figure 65:
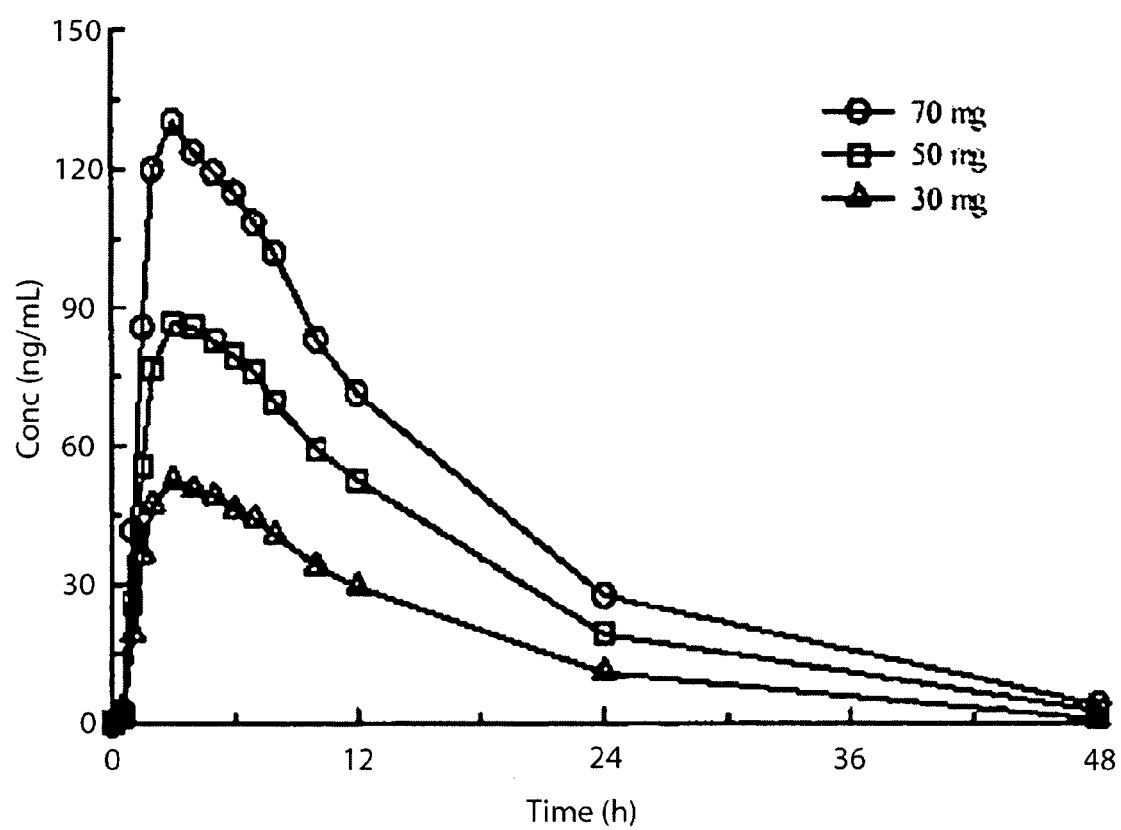

FIG. 65. Mean plasma concentration of d-amphetamine after oral administration of single 30 mg, 50 mg, and 70 mg doses of L-lysine-d-amphetamine dimesylate under fasted conditions to pediatric patients with ADHD.

Figure 66:
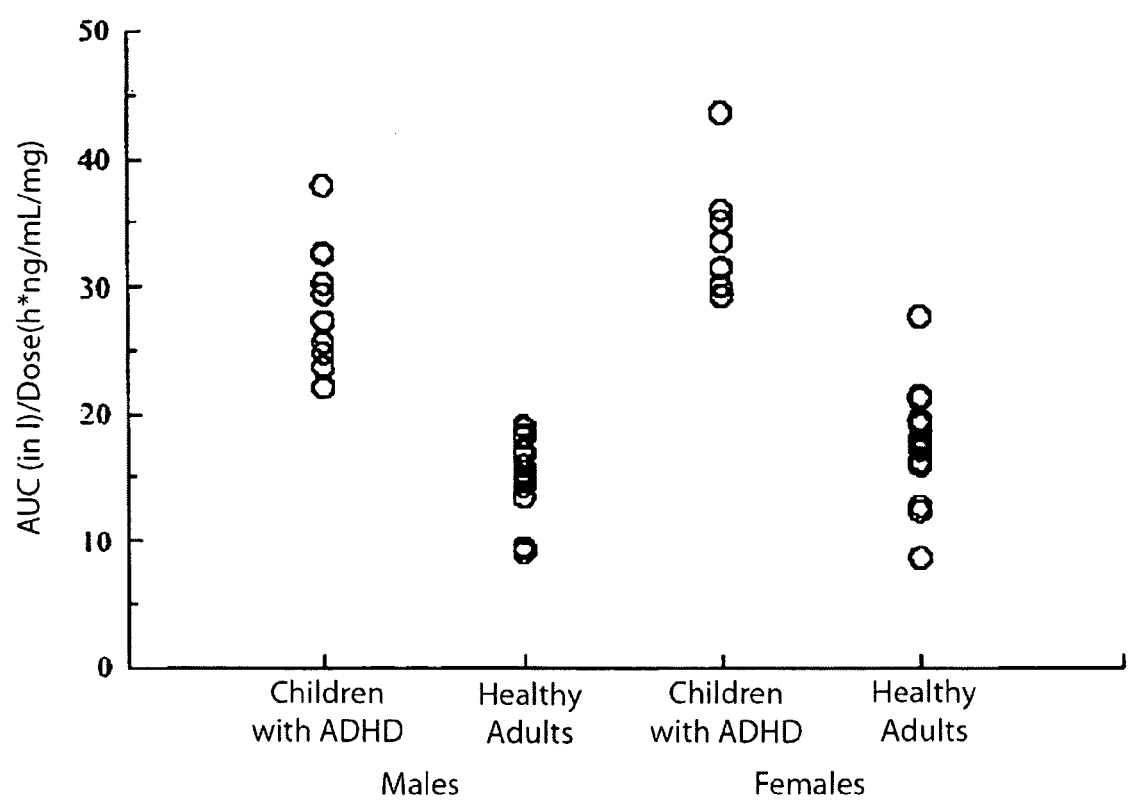

FIG. 66. Relationship between the dose-normalized AUC of d-amphetamine and gender after oral administration of L-lysine-d-amphetamine dimesylate capsules once daily to healthy adult volunteers and children with ADHD.

Figure 67:
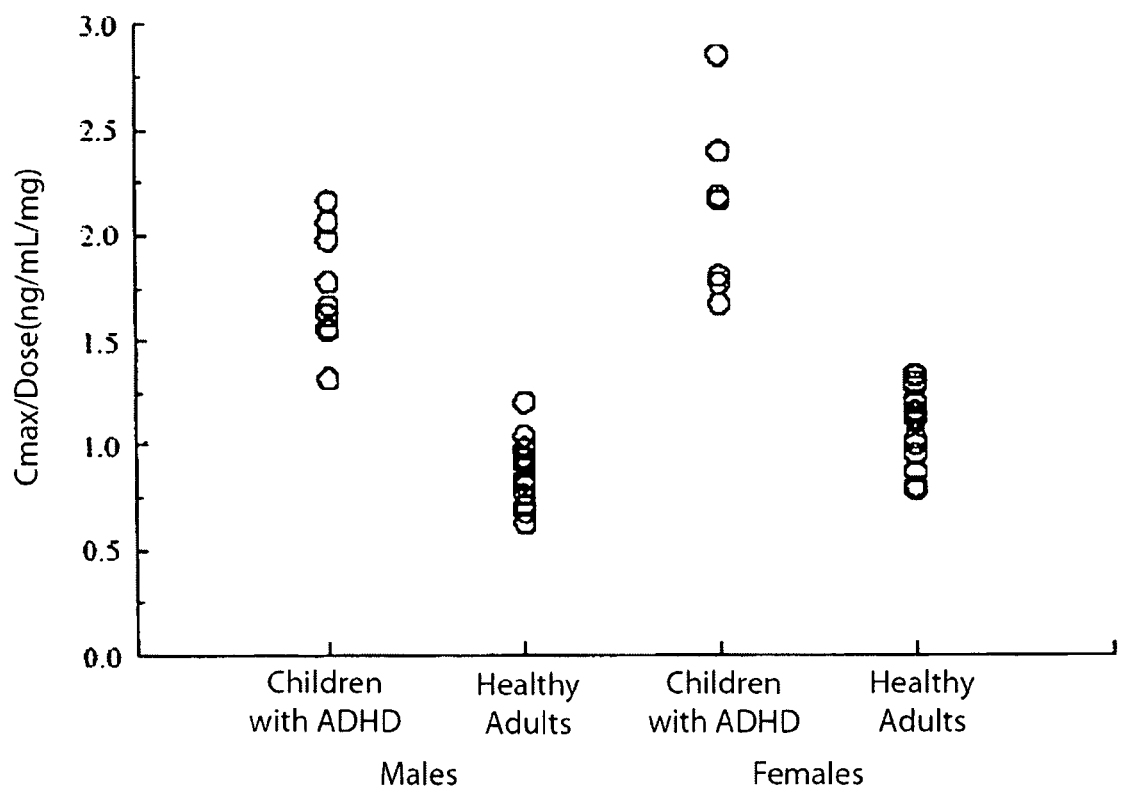

FIG. 67. Relationship between the dose-normalized maximum plasma concentration of d-amphetamine and gender after oral administration of L-lysine-d-amphetamine dimesylate capsules once daily to healthy adult volunteers and children with ADHD.

Figure 68:
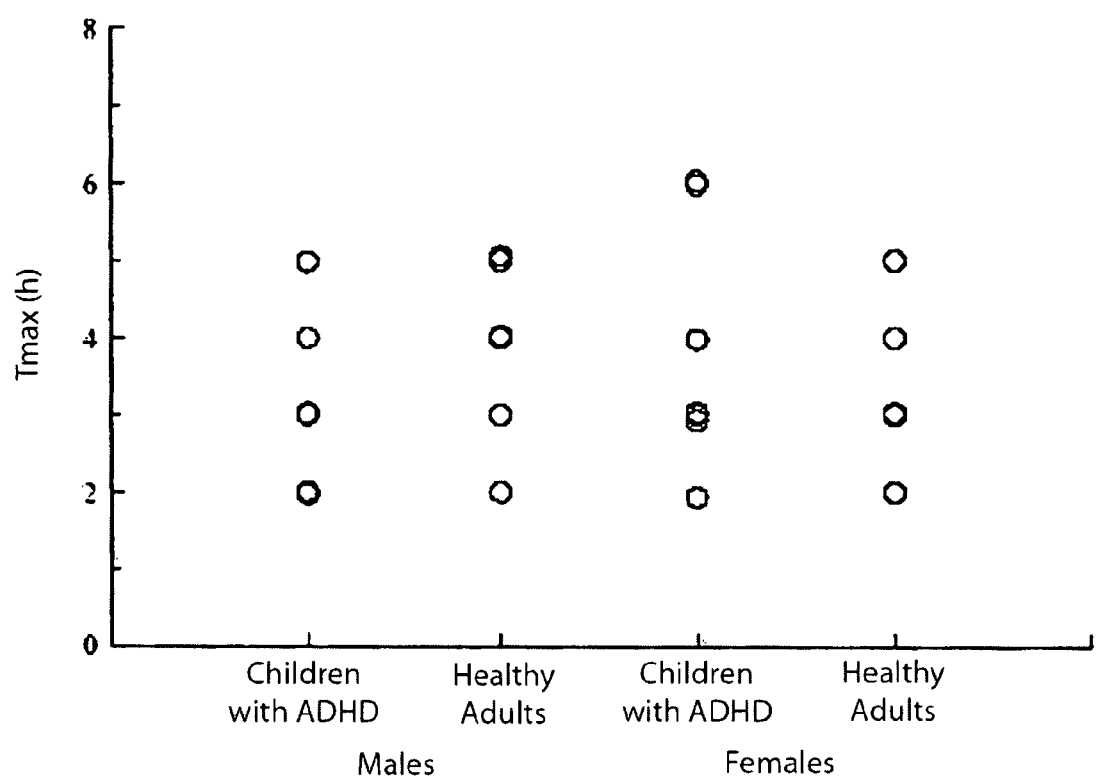

FIG. 68. Relationship between the dose-normalized time to maximum concentration of d-amphetamine and gender after oral administration of L-lysine-d-amphetamine dimesylate capsules once daily to healthy adult volunteers and children with ADHD.

Figure 69:
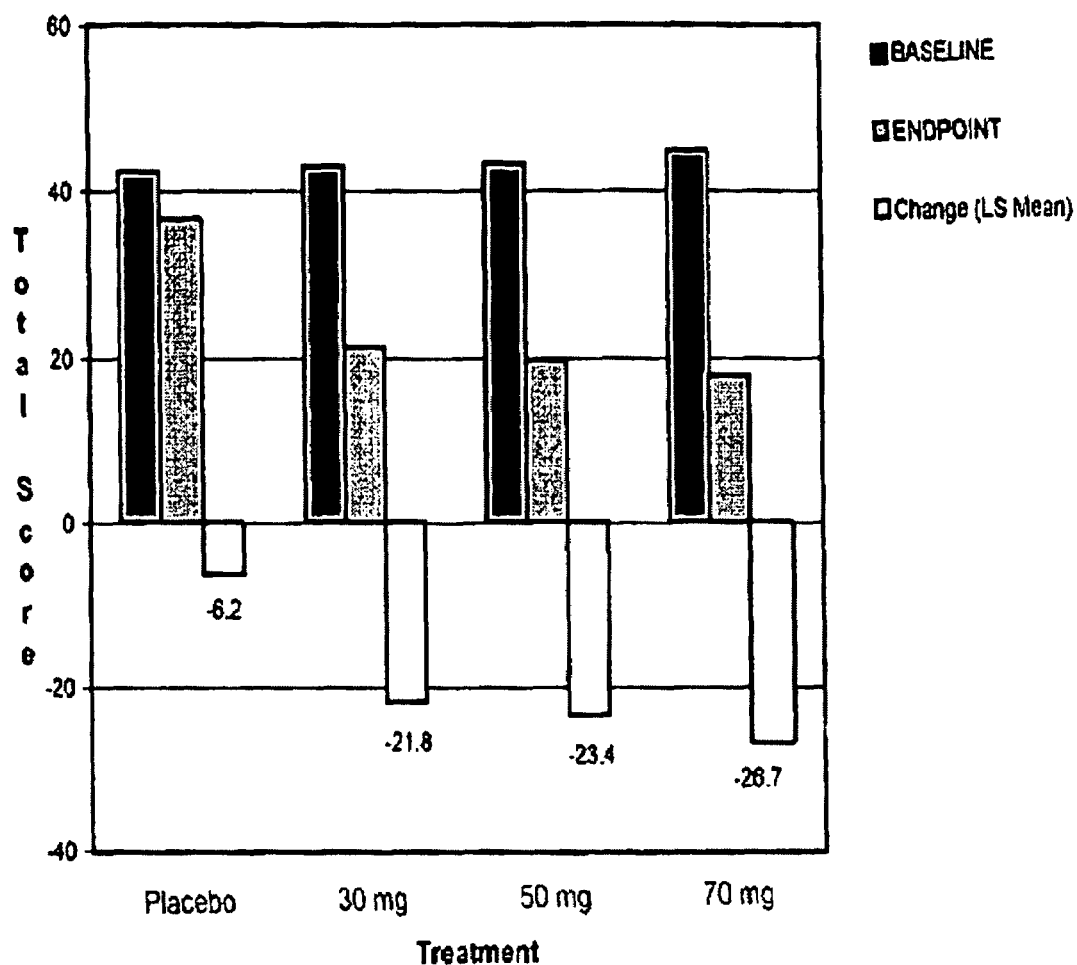

FIG. 69. ADHD-RS at endpoint for pediatric clinical study.

Figure 70:
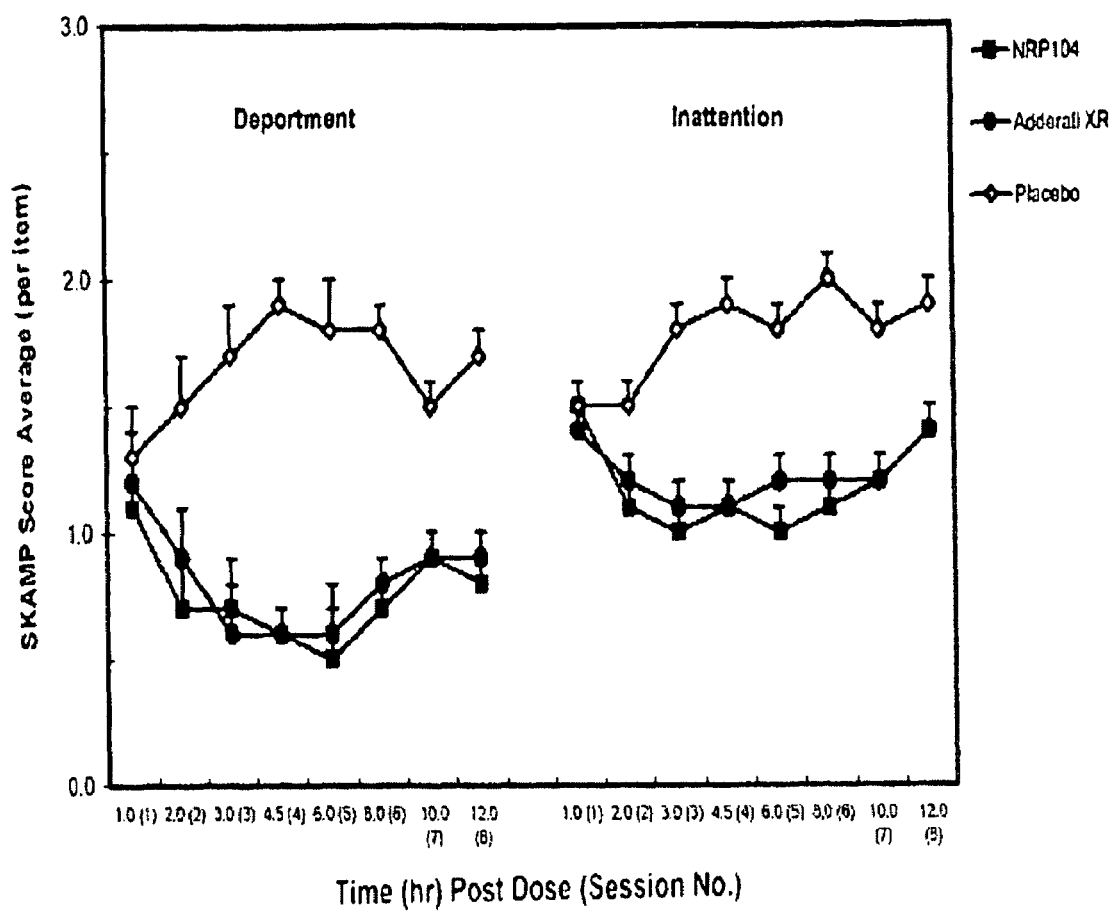

FIG. 70. SKAMP score (efficacy) vs. time for pediatric clinical study.

DETAILED DESCRIPTION OF THE INVENTION

The invention provides amphetamine prodrugs comprising amphetamine covalently bound to a chemical moiety. The amphetamine prodrugs can also be characterized as conjugates in that they possess a covalent attachment. They may also be characterized as conditionally bioreversible derivatives ("CBDs") in that the amphetamine prodrug preferably remains inactive until oral administration releases the amphetamine from the chemical moiety.

In one embodiment, the invention provides an amphetamine prodrug of Formula I:

$$A\text{-}X_n\text{-}Z_m \quad (I)$$

wherein A is an amphetamine;

each X is independently a chemical moiety;

each Z is independently a chemical moiety that acts as an adjuvant and is different from at least one X;

n is an increment from 1 to 50, preferably 1 to 10; and m is an increment from 0 to 50, preferably 0.

When m is 0, the amphetamine prodrug is a compound of Formula (II):

$$A\text{-}X_n \quad (II)$$

wherein each X is independently a chemical moiety.

Formula (II) can also be written to designate the chemical moiety that is physically attached to the amphetamine:

$$A\text{-}X_1\text{---}(X)_{n-1} \quad (III)$$

wherein A is an amphetamine; $X_1$ is a chemical moiety, preferably a single amino acid; each X is independently a chemical moiety that is the same as or different from $X_1$; and n is an increment from 1 to 50.

The amphetamine, A, can be any of the sympathomimetic phenethylamine derivatives which have central nervous system stimulant activity such as amphetamine, or any derivative, analog, or salt thereof. Exemplary amphetamines include, but are not limited to, amphetamine, methamphetamine, methylphenidate, p-methoxyamphetamine, methylenedioxyamphetamine, 2,5-dimethoxy-4-methylamphetamine, 2,4,5-trimethoxyamphetamine, and 3,4-methylenedioxymethamphetamine, N-ethylamphetamine, fenethylline, benzphetamine, and chlorphentermine as well as the amphetamine compounds of Adderall®; actedron; actemin; adipan; akedron; allodene; alpha-methyl-(±)-benzeneethanamine; alpha-methylbenzeneethanamine; alpha-methylphenethylamine; amfetamine; amphate; anorexine; benzebar; benzedrine; benzyl methyl carbinamine; benzolone; beta-amino propylbenzene; beta-phenylisopropylamine; biphetamine; desoxynorephedrine; dietamine; DL-amphetamine; elastonon; fenopromin; finam; isoamyne; isomyn; mecodrin; monophos; mydrial; norephedrane; novydrine; obesin; obesine; obetrol; octedrine; oktedrin; phenamine; phenedrine; phenethylamine, alpha-methyl-; percomon; profamina; profetamine; propisamine; racephen; raphetamine;

rhinalator, sympamine; simpatedrin; simpatina; sympatedrine; and weckamine. Preferred amphetamines include methamphetamine, methylphenidate, and amphetamine, with amphetamine being most preferred.

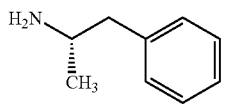

d-amphetamine

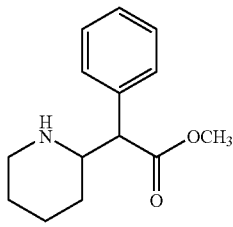

Methylphenidate

The amphetamine can have any stereogenic configuration, including both dextro- and levo-isomers. The dextro-isomer, particularly dextroamphetamine, is preferred.

Preferably, the amphetamine is an amphetamine salt. Pharmaceutically acceptable salts, e.g., non-toxic, inorganic and organic acid addition salts, are known in the art. Exemplary salts include, but are not limited to, 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, finnarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphateldiphosphate, picrate, pivalate, polygalacturonate, propionate, p-toluenesulfonate, saccharate, salicylate, stearate, subacetate, succinate, sulfate, sulfosaliculate, suramate, tannate, tartrate, teoclate, thiocyanate, tosylate, triethiodide, undecanoate, and valerate salts, and the like. (See Berge et al. (1977) "Pharmaceutical Salts", J Pharm. Sci. 66:1-19). A preferred amphetamine salt is the mesylate salt (e.g., as in L-lysine-d-amphetamine dimesylate).

Particular salts may be less hygroscopic thereby facilitating handling. In a preferred embodiment, the amphetamine prodrug has a water content (Karl Fischer analysis) of about 0% to about 5%, about 0.1% to about 3%, about 0.25% to about 2%, or increments therein. When the amphetamine prodrug is formulated into a pharmaceutical composition, the pharmaceutical composition preferably has a water content of about 1% to about 10%, about 1% to about 8%, about 2% to about 7%, or increments therein.

Throughout this application, the term "increment" is used to define a numerical value in varying degrees of precision, e.g., to the nearest 10, 1, 0.1, 0.01, etc. The increment can be rounded to any measurable degree of precision. For example, the range 1 to 100 or increments therein includes ranges such as 20 to 80, 5 to 50, 0.4 to 98, and 0.04 to 98.05.

The amphetamine is bound to one or more chemical moieties, denominated X and Z. A chemical moiety can be any moiety that decreases the pharmacological activity of amphetamine while bound to the chemical moiety as compared to unbound (free) amphetamine. The attached chemical moiety can be either naturally occurring or synthetic. Exemplary chemical moieties include, but are not limited to, peptides, including single amino acids, dipeptides, tripeptides, oligopeptides, and polypeptides; glycopeptides; carbohydrates; lipids; nucleosides; nucleic acids; and vitamins. Preferably, the chemical moiety is generally recognized as safe ("GRAS").

"Carbohydrates" include sugars, starches, cellulose, and related compounds, e.g., $(CH_2O)_n$ wherein n is an integer larger than 2, and $C_n(H_2O)_{n-1}$ wherein n is an integer larger than 5. The carbohydrate can be a monosaccharide, disaccharide, oligosaccharide, polysaccharide, or a derivative thereof (e.g., sulfo- or phospho-substituted). Exemplary carbohydrates include, but are not limited to, fructose, glucose, lactose, maltose, sucrose, glyceraldehyde, dihydroxyacetone, erythrose, ribose, ribulose, xylulose, galactose, mannose, sedoheptulose, neuraminic acid, dextrin, and glycogen.

A "glycopeptide" is a carbohydrate linked to an oligopeptide. Similarly, the chemical moiety can also be a glycoprotein, glyco-amino-acid, or glycosyl-amino-acid. A "glycoprotein" is a carbohydrate (e.g., a glycan) covalently linked to a protein. A "glyco-amino-acid" is a carbohydrate (e.g., a saccharide) covalently linked to a single amino acid. A "glycosyl-amino-acid" is a carbohydrate (e.g., a saccharide) linked through a glycosyl linkage (O—, N—, or S—) to an amino acid.

A "peptide" includes a single amino acid, a dipeptide, a tripeptide, an oligopeptide, a polypeptide, or a carrier peptide. An oligopeptide includes from 2 to 70 amino acids.

Preferably, the chemical moiety is a peptide, more particularly a single amino acid, a dipeptide, or a tripeptide. The peptide preferably comprises fewer than 70 amino acids, fewer than 50 amino acids, fewer than 10 amino acids, or fewer than 4 amino acids. When the chemical moiety is one or more amino acids, the amphetamine is preferably bound to lysine, serine, phenylalanine, or glycine. In another embodiment, the amphetamine is preferably bound to lysine, glutamic acid, or leucine. In one embodiment, the amphetamine is bound to lysine and optional additional chemical moieties, e.g., additional amino acids. In a preferred embodiment, the amphetamine is bound to a single lysine amino acid.

In one embodiment, the chemical moiety is from 1 to 12 amino acids, preferably 1 to 8 amino acids. In another embodiment, the number of amino acids is 1, 2, 3, 4, 5, 6, or 7. In another embodiment, the molecular weight of the chemical moiety is below about 2,500 kD, more preferably below about 1,000 kD, and most preferably below about 500 kD.

Each amino acid can be any one of the L- or D-enantiomers, preferably L-enantiomers, of the naturally occurring amino acids: alanine (Ala or A), arginine (Arg or R), asparagine (Asn or N), aspartic acid (Asp or D), cysteine (Cys or C), glycine (Gly or G), glutamic acid (Glu or E), glutamine (Gln or Q), histidine (His or H), isoleucine (Ile or I), leucine (Leu or L), lysine (Lys or K), methionine (Met or M), proline (Pro or P), phenylalanine (Phe or F), serine (Ser or S), tryptophan (Trp or W), threonine (Thr or T), tyrosine (Tyr or Y), and valine (Val or V). In a preferred embodiment, the peptide comprises only naturally occurring amino acids and/or only L-amino acids. Each amino acid can be an unnatural, non-standard, or synthetic amino acids, such as aminohexanoic acid, biphenylalanine, cyclohexylalanine, cyclohexylglycine, diethylglycine, dipropylglycine, 2,3-diaminoproprionic acid, homophenylalanine, homoserine, homotyrosine, naphthylalanine, norleucine, ornithine, phenylalanine (4-fluoro), phenylalanine(2,3,4,5,6-pentafluoro), phenylalanine(4-nitro), phenylglycine, pipecolic acid, sarcosine, tetrahydroisoquinoline-3-carboxylic acid, and tert-leucine. Preferably, synthetic amino acids with alkyl side chains are selected from $C_1$-$C_{17}$ alkyls, preferably $C_1$-$C_6$ alkyls. In one embodiment, the peptide comprises one or more amino acid alcohols, e.g., serine and threonine. In another embodiment, the peptide comprises one or more N-methyl amino acids, e.g., N-methyl aspartic acid.

In one embodiment, the peptides are utilized as base short chain amino acid sequences and additional amino acids are added to the terminus or side chain. In another embodiment, the peptide may have an one or more amino acid substitutions. Preferably, the substitute amino acid is similar in structure, charge, or polarity to the replaced amino acid. For instance, isoleucine is similar to leucine, tyrosine is similar to phenylalanine, serine is similar to threonine, cysteine is similar to methionine, alanine is similar to valine, lysine is similar to arginine, asparagine is similar to glutamine, aspartic acid is similar to glutamic acid, histidine is similar to proline, and glycine is similar to tryptophan.

The peptide can comprise a homopolymer or heteropolymer of naturally occurring or synthetic amino acids. For example, the side chain attachment of amphetamine to the peptide can be a homopolymer or heteropolymer containing glutamic acid, aspartic acid, serine, lysine, cysteine, threonine, asparagine, arginine, tyrosine, or glutamine.

Exemplary peptides include Lys, Ser, Phe, Gly-Gly-Gly, Leu-Ser, Leu-Glu, homopolymers of Glu and Leu, and heteropolymers of $(Glu)_n$-Leu-Ser. In a preferred embodiment, the peptide is Lys, Ser, Phe, or Gly-Gly-Gly.

In one embodiment, the chemical moiety has one or more free carboxy and/or amine terminal and/or side chain group other than the point of attachment to the amphetamine. The chemical moiety can be in such a free state, or an ester or salt thereof.

The chemical moiety can be covalently attached to the amphetamine either directly or indirectly through a linker. Covalent attachment may comprise an ester or carbonate bond. The site of attachment typically is determined by the functional group(s) available on the amphetamine. For example, a peptide can be attached to an amphetamine via the N-terminus, C-terminus, or side chain of an amino acid. For additional methods of attaching amphetamine to various exemplary chemical moieties, see U.S. application Ser. No. 10/156,527, PCT/US03/05524, and PCT/US03/05525, each of which is hereby incorporated by reference in its entirety.

Figure 1:
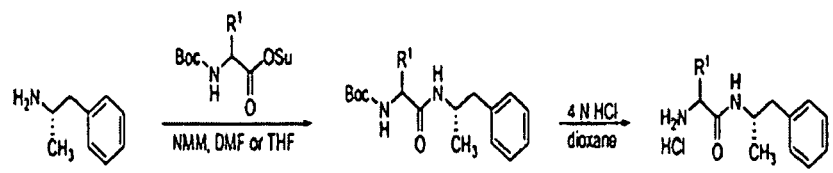
FIG. 1. Synthesis of peptide amphetamine conjugates.
Figure 1:
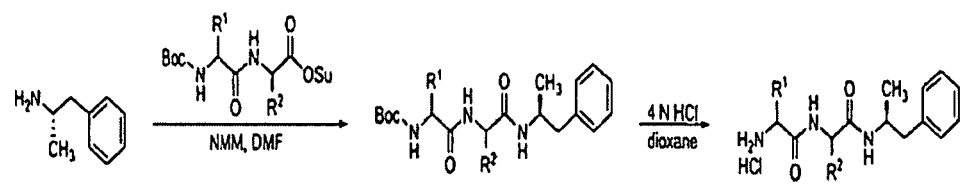
Figure 1:
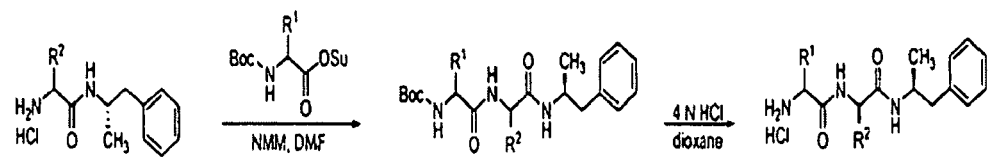
Figure 1:
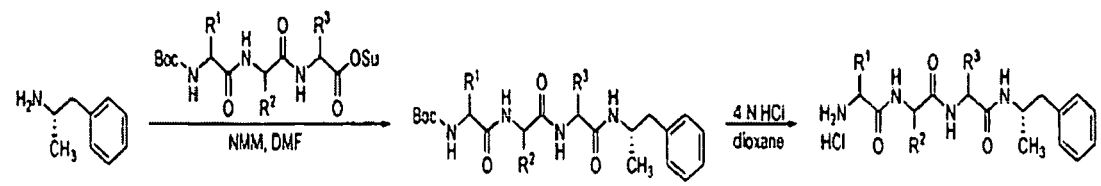
Figure 1:
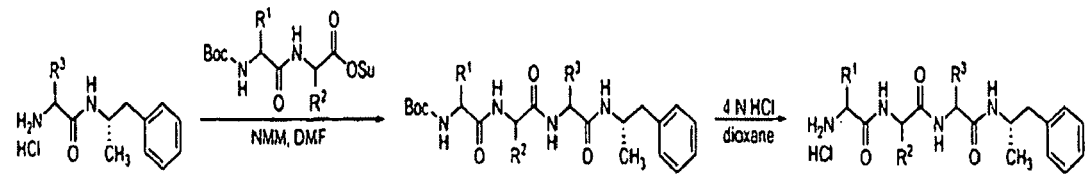
Figure 2:
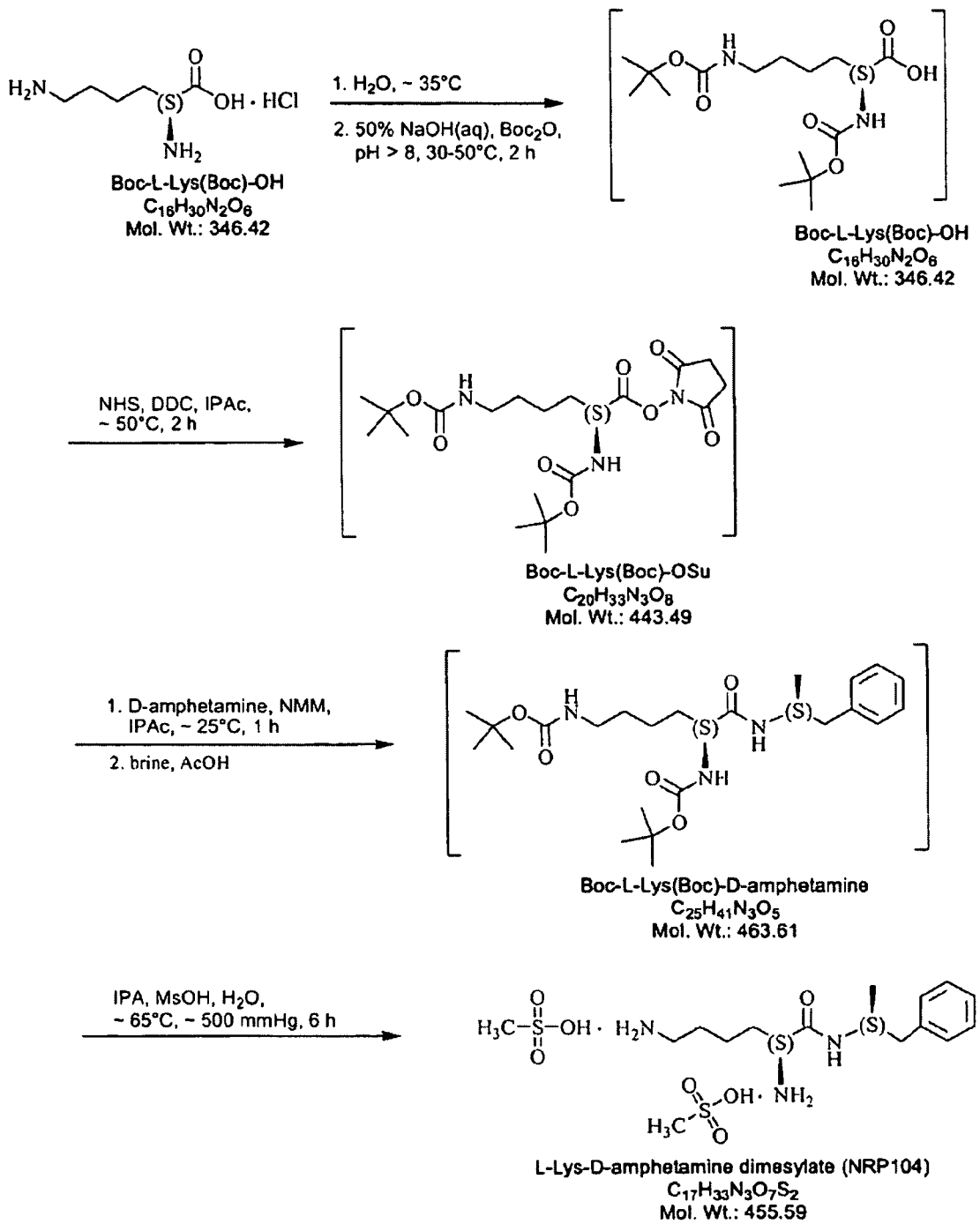
FIG. 2. Synthesis of lysine amphetamine dimesylate.
Figure 3:
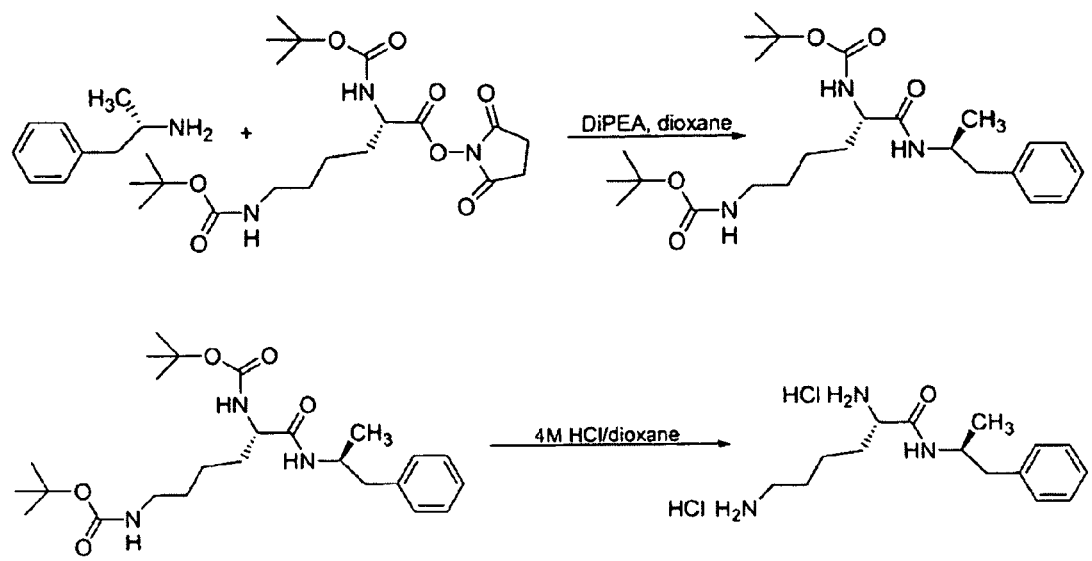
FIG. 3. Synthesis of lysine amphetamine HCl.
Figure 4:
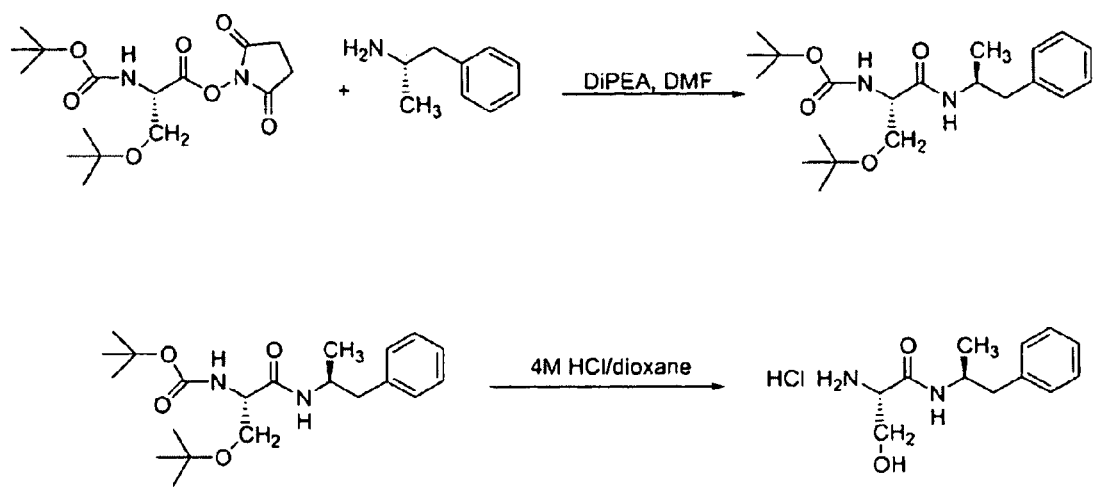
FIG. 4. Synthesis of serine amphetamine conjugate.
Figure 5:
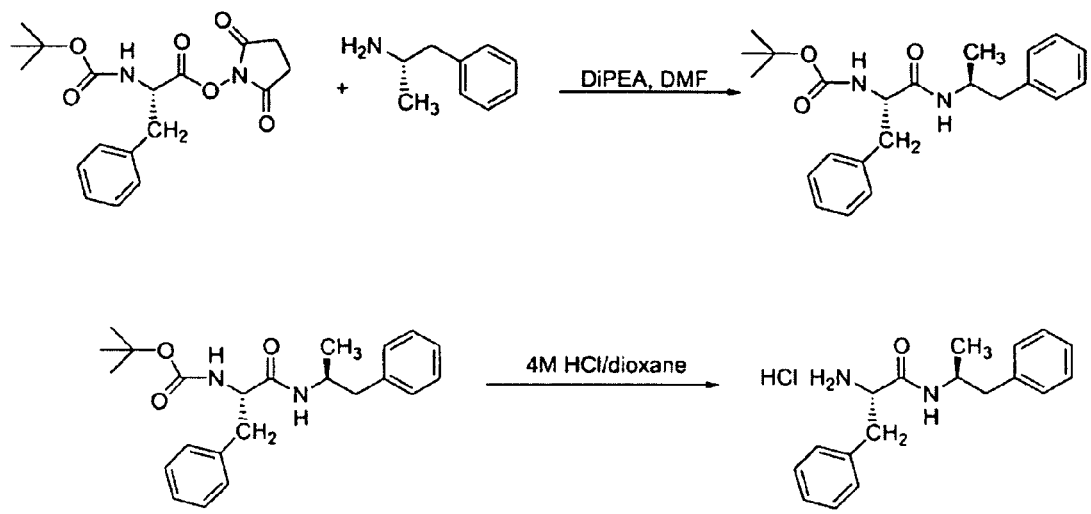
FIG. 5. Synthesis of phenylalanine amphetamine conjugate.
Figure 6:
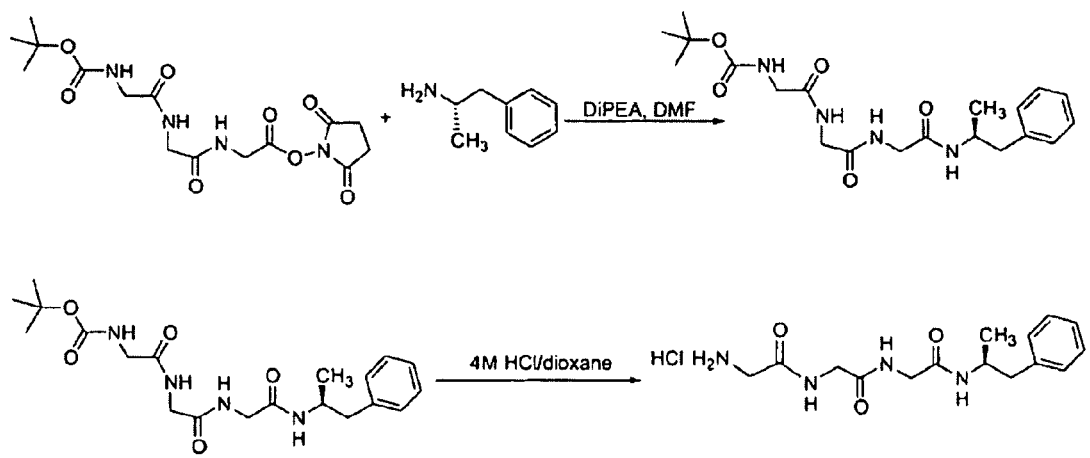
FIG. 6. Synthesis of triglycine amphetamine conjugate.

The amphetamine prodrug compounds described above can be synthesized as described in Example 1 and FIG. 1. Preferably, additional purification and/or crystallization steps are not necessary to yield a highly pure product. In one embodiment, the purity of the amphetamine prodrug is at least about 95%, more preferably at least about 96%, 97%, 98%, 98.5%, 99%, 99.5%, 99.9%, or increments therein. For the synthesis of L-lysine-d-amphetamine, known impurities include Lys-Lys-d-amphetamine, Lys(Lys)-d-amphetamine, d-amphetamine, Lys(Boc)-d-amphetamine, Boc-Lys-d-amphetamine, and Boc-Lys(Boc)-d-amphetamine. In one embodiment, the presence of any single impurity is less than about 3%, more preferably less than about 2%, 1%, 0.5%, 0.25%, 0.15%, 0.1%, 0.05%, or increments therein.

In one embodiment, the amphetamine prodrug (a compound of one of the formulas described above) may exhibit one or more of the following advantages over free amphetamines. The amphetamine prodrug may prevent overdose by exhibiting a reduced pharmacological activity when administered at higher than therapeutic doses, e.g., higher than the prescribed dose. Yet when the amphetamine prodrug is administered at therapeutic doses, the amphetamine prodrug may retain similar pharmacological activity to that achieved by administering unbound amphetamine, e.g., Adderall XR®. Also, the amphetamine prodrug may prevent abuse by exhibiting stability under conditions likely to be employed by illicit chemists attempting to release the amphetamine. The amphetamine prodrug may prevent abuse by exhibiting reduced bioavailability when it is administered via parenteral routes, particularly the intravenous ("shooting"), intranasal ("snorting"), and/or inhalation ("smoking") routes that are often employed in illicit use. Thus, the amphetamine prodrug may reduce the euphoric effect associated with amphetamine abuse. Thus, the amphetamine prodrug may prevent and/or reduce the potential of abuse and/or overdose when the amphetamine prodrug is used in a manner inconsistent with the manufacturer's instructions, e.g., consuming the amphetamine prodrug at a higher than therapeutic dose or via a non-oral route of administration.

Use of phrases such as "decreased", "reduced", "diminished", or "lowered" includes at least a 10% change in pharmacological activity with greater percentage changes being preferred for reduction in abuse potential and overdose potential. For instance, the change may also be greater than 25%, 35%, 45%, 55%, 65%, 75%, 85%, 95%, 96%, 97%, 98%, 99%, or other increments greater than 10%.

Use of the phrase "similar pharmacological activity" means that two compounds exhibit curves that have substantially the same AUC, $C_{max}$, $T_{max}$, $C_{min}$, and/or $t_{1/2}$ parameters, preferably within about 30% of each other, more preferably within about 25%, 20%, 10%, 5%, 2%, 1%, or other increments less than 30%.

Preferably, the amphetamine prodrug exhibits an unbound amphetamine oral bioavailability of at least about 60% AUC (area under the curve), more preferably at least about 70%, 80%, 90%, 95%, 96%, 97%, 98%, 99%, or other increments greater than 60%. Preferably, the amphetamine prodrug exhibits an unbound amphetamine parenteral, e.g., intranasal, bioavailability of less than about 70% AUC, more preferably less than about 50%, 30%, 20%, 15%, 10%, 5%, 4%, 3%, 2%, 1%, or other increments less than 70%. For certain treatments, it is desirable that the amphetamine prodrug exhibits both the oral and parenteral bioavailability characteristics described above. See, e.g., Table 61.

Preferably, the amphetamine prodrug remains inactive until oral administration releases the amphetamine. Without being bound by theory, it is believed that the amphetamine prodrug is inactive because the attachment of the chemical moiety reduces binding between the amphetamine and its biological target sites (e.g., human dopamine ("DAT") and norepinephrine ("NET") transporter sites). (See Hoebel, B. G., L. Hernandez, et al., "Microdialysis studies of brain norepinephrine, serotonin, and dopamine release during ingestive behavior, Theoretical and clinical implications." Ann NY Acad Sci 575: 171-91 (1989)). The chemical moiety attachment may reduce binding between amphetamine and DAT and/or NET in part because the amphetamine prodrug cannot cross the blood-brain barrier. The amphetamine prodrug is activated by oral administration, that is, the amphetamine is released from the chemical moiety by hydrolysis, e.g., by enzymes in the stomach, intestinal tract, or blood serum. Because oral administration facilitates activation, activation is reduced when the amphetamine prodrug is administered via parenteral routes often employed by illegal users.

Further, it is believed that the amphetamine prodrug is resistant to abuse and/or overdose due to a natural gating mechanism at the site of hydrolysis, namely the gastrointestinal tract. This gating mechanism is thought to allow the release of therapeutic amounts of amphetamine from the amphetamine prodrug, but limit the release of higher amounts of amphetamine.

In another embodiment, the toxicity of the amphetamine prodrug is substantially lower than that of the unbound amphetamine. For example, in a preferred embodiment, the acute toxicity is 1-fold, 2-fold, 3-fold, 4-fold, 5-fold, 6-fold, 7-fold, 8-fold, 9-fold, 10-fold less, or increments therein less lethal than oral administration of unbound amphetamine.

Preferably, the amphetamine prodrug provides a serum release curve that does not increase above amphetamine's toxicity level when administered at higher than therapeutic doses. The amphetamine prodrug may exhibit a reduced rate of amphetamine absorption and/or an increased rate of clearance compared to the free amphetamine. The amphetamine prodrug may also exhibit a steady-state serum release curve. Preferably, the amphetamine prodrug provides bioavailability but prevents $C_{max}$ spiking or increased blood serum concentrations. Pharmacokinetic parameters are described in the Examples below, particularly the clinical pharmacokinetic Examples. In one embodiment, the amphetamine prodrug provides similar pharmacological activity to the clinically measured pharmacokinetic activity of L-lysine-d-amphetamine dimesylate. For example, the pharmacological parameters (AUC, $C_{max}$, $T_{max}$, $C_{min}$, and/or $t_{1/2}$) are preferably within 80% to 125%, 80% to 120%, 85% to 125%, 90% to 110%, or increments therein, of the given values. It should be recognized that the ranges can, but need not be symmetrical, e.g., 85% to 105%. For the pediatric study, the pharmacokinetic parameters of d-amphetamine released from L-lysine-d-amphetamine dimesylate are listed in Table 72.

The amphetamine prodrug may exhibit delayed and/or sustained release characteristics. Delayed release prevents rapid onset of pharmacological effects, and sustained release is a desirable feature for particular dosing regimens, e.g., once a day regimens. The amphetamine prodrug may achieve the release profile independently. Alternatively, the amphetamine prodrug may be pharmaceutically formulated to enhance or achieve such a release profile. It may be desirable to reduce the amount of time until onset of pharmacological effect, e.g., by formulation with an immediate release product.

Accordingly, the invention also provides methods comprising providing, administering, prescribing, or consuming an amphetamine prodrug. The invention also provides pharmaceutical compositions comprising an amphetamine prodrug. The formulation of such a pharmaceutical composition can optionally enhance or achieve the desired release profile.

In one embodiment, the invention provides methods for treating a patient comprising administering a therapeutically effective amount of an amphetamine prodrug, i.e., an amount sufficient to prevent, ameliorate, and/or eliminate the symptoms of a disease. These methods can be used to treat any disease that may benefit from amphetamine-type drugs including, but not limited to: attention deficit disorders, e.g., ADD and ADHD, and other learning disabilities; obesity; Alzheimer's disease, amnesia, and other memory disorders and impairments; fibromyalgia; fatigue and chronic fatigue; depression; epilepsy; obsessive compulsive disorder (OCD); oppositional defiant disorder (ODD); anxiety; resistant depression; stroke rehabilitation; Parkinson's disease; mood disorder; schizophrenia; Huntington's disorder; dementia, e.g., AIDS dementia and frontal lobe dementia; movement disfunction; apathy; Pick's disease; Creutzfeldt-Jakob disease, sleep disorders, e.g., narcolepsy, cataplexy, sleep paralysis, and hypnagogic hallucinations; conditions related to brain injury or neuronal degeneration, e.g., multiple sclerosis, Tourette's syndrome, and impotence; and nicotine dependence and withdrawal. Preferred indications include ADD, ADHD, narcolepsy, and obesity, with ADHD being most preferred.

The methods of treatment include combination therapies which further comprise administering one or more therapeutic agents in addition to administering an amphetamine prodrug. The active ingredients can be formulated into a single dosage form, or they can be formulated together or separately among multiple dosage forms. The active ingredients can be administered simultaneously or sequentially in any order. Exemplary combination therapies include the administration of the drugs listed in Table 1:

TABLE 1

Exemplary drug therapies contemplated for use in combination with an amphetamine prodrug

| Condition | Exemplary drug class | Specific exemplary drugs |
|---|---|---|
| ADHD | Amphetamine | Ritalin ®, Dexedrine ®, Adderall ®, Cylert ®, Clonidine, Guanfacine |
| Alzheimer's disease | | Reminyl ®, Cognex ®, Aricept ®, Exelon ®, Akatinol ®, Neotropin, Eldepryl ®, Estrogen, Clioquinol, Ibuprofen, *Ginko Biloba* |
| Anxiety | Antidepressant (SSRI, benzodiazepine, MAOI), anxiolytic | Elavil, Asendin ®, Wellbutrin ®, Tegretol ®, Anafranil ®, Norpramine ®, Adapin ®, Sinequan ®, Tofranil ®, Epitol ®, Janimire ®, Pamelor ®, Ventyl ®, Aventyl ®, Surmontil ®, Prozac ®, Luvox ®, Serzone ®, Paxil ®, Zoloft ®, Effexor ®, Xanax ®, Librium ®, Klonopin ®, Valium ®, Zetran ®, Valrelease ®, Dalmane ®, Ativan ®, Alzapam ®, Serax ®, Halcion ®, Aurorix ®, Manerix ®, Nardil ®, Parnate ®. |
| Apathy | | Amisulpride, Olanzapine, Visperidone, Quetiapine, Clozapine, Zotepine |
| Cataplexy | | Xyrem ® |
| Dementia | | Thioridazine, Haloperidol, Risperidone, Cognex ®, Aricept ®, Exelon ® |
| Depression | Antidepressant | Fluoxetine (e.g., Prozac ®), Zoloft ®, Paxil ®, Reboxetine, Wellbutrin ®, Olanzapine, Elavil ®, Totranil ®, Pamelor ®, Nardil ®, Parnate ®, Desyrel ®, Effexor ® |
| Fatigue | Benzodiazepine | Anaprox ®, Naprosen, Prozac ®, Zoloft ®, Paxil ®, Effexor ®, Desyrel ® |

TABLE 1-continued

Exemplary drug therapies contemplated for use in combination with an amphetamine prodrug

| Condition | Exemplary drug class | Specific exemplary drugs |
|---|---|---|
| Fibromyalgia | Non-steroidal anti-inflammatory drugs | Dilantin ®, Carbatrol ®, Epitol ®, Tegretol ®, Depacon ®, Depakote ®, Norpramin ®, Aventyl ®, Pamelor ®, Elavil ®, Enovil ®, Adapin ®, Sinequan ®, Zonalon ® |
| Hallucinations | | Clozapine, Risperidone, Zyprexa ®, Seroquel ® |
| Huntington's disorder | | Haloperidol, Clonzepam |
| Narcolepsy | | Modafinil (e.g., Provigil ®), Dexedrine ®, Ritalin ® |
| Mood disorder | | Thorazine ®, Haldol ®, Navane ®, Mellaril ®, Clozaril ®, Risperidone (e.g., Risperdal ®), Olanzapine (e.g., Zyprexa ®), Clozapine |
| Obsessive-compulsive disorder (OCD) | SSRI | Anafranil ®, Prozac ®, Zoloft ®, Paxil ®, Luvox ® |
| Oppositional defiant disorder (ODD) | | Clonidine, Risperidone, Zyprexa ®, Wellbutrin ®, |
| Parkinson's disease | | Levodopa, Parlodel ®, Permax ®, Mirapex ® |
| Schizophrenia | | Clozapine, Zyprexa ®, Seroquel ®, and Risperdal ® |
| Sleep paralysis | | Perocet ®, Vicodin ®, Lorcet ® |

A "composition" refers broadly to any composition containing one or more amphetamine prodrugs. The composition can comprise a dry formulation, an aqueous solution, or a sterile composition. Compositions comprising the compounds described herein may be stored in freeze-dried form and may be associated with a stabilizing agent such as a carbohydrate. In use, the composition may be deployed in an aqueous solution containing salts, e.g., NaCl, detergents such as sodium dodecyl sulfate (SDS), and other components.

In one embodiment, the amphetamine prodrug itself exhibits a sustained release profile. Thus, the invention provides a pharmaceutical composition exhibiting a sustained release profile due to the amphetamine prodrug.

In another embodiment, a sustained release profile is enhanced or achieved by including a hydrophilic polymer in the pharmaceutical composition. Suitable hydrophilic polymers include, but are not limited to, natural or partially or totally synthetic hydrophilic gums such as acacia, gum tragacanth, locust bean gum, guar gum, and karaya gum; cellulose derivatives such as methyl cellulose, hydroxymethyl cellulose, hydroxypropylmethyl cellulose, hydroxypropyl cellulose, hydroxyethyl cellulose, and carboxymethyl cellulose; proteinaceous substances such as agar, pectin, carrageen, and alginates; hydrophilic polymers such as carboxypolymethylene; gelatin; casein; zein; bentonite; magnesium aluminum silicate; polysaccharides; modified starch derivatives; and other hydrophilic polymers known in the art. Preferably, the hydrophilic polymer forms a gel that dissolves slowly in aqueous acidic media thereby allowing the amphetamine prodrug to diffuse from the gel in the stomach. Then when the gel reaches the higher pH medium of the intestines, the hydrophilic polymer dissolves in controlled quantities to allow further sustained release. Preferred hydrophilic polymers are hydroxypropyl methylcelluloses such as Methocel ethers, e.g., Methocel E10M® (Dow Chemical Company, Midland, Mich.). One of ordinary skill in the art would recognize a variety of structures, such as bead constructions and coatings, useful for achieving particular release profiles. See, e.g., U.S. Pat. No. 6,913,768.

In addition to the amphetamine prodrug, the pharmaceutical compositions of the invention further comprise one or more pharmaceutical additives. Pharmaceutical additives include a wide range of materials including, but not limited to diluents and bulking substances, binders and adhesives, lubricants, glidants, plasticizers, disintegrants, carrier solvents, buffers, colorants, flavorings, sweeteners, preservatives and stabilizers, and other pharmaceutical additives known in the art. For example, in a preferred embodiment, the pharmaceutical composition comprises magnesium stearate. In another preferred embodiment, the pharmaceutical composition comprises microcrystalline cellulose (e.g., Avicel® PH-102), croscarmellose sodium, and magnesium stearate. See, e.g., Table 62.

Diluents increase the bulk of a dosage form and may make the dosage form easier to handle. Exemplary diluents include, but are not limited to, lactose, dextrose, saccharose, cellulose, starch, and calcium phosphate for solid dosage forms, e.g., tablets and capsules; olive oil and ethyl oleate for soft capsules; water and vegetable oil for liquid dosage forms, e.g., suspensions and emulsions. Additional suitable diluents include, but are not limited to, sucrose, dextrates, dextrin, maltodextrin, microcrystalline cellulose (e.g., Avicel®), microfine cellulose, powdered cellulose, pregelatinized starch (e.g., Starch 1500®), calcium phosphate dihydrate, soy polysaccharide (e.g., Emcosoy®), gelatin, silicon dioxide, calcium sulfate, calcium carbonate, magnesium carbonate, magnesium oxide, sorbitol, mannitol, kaolin, polymethacrylates (e.g., Eudragit®), potassium chloride, sodium chloride, and talc. A preferred diluent is microcrystalline cellulose (e.g., Avicel® PH-102). Preferred ranges for the amount of diluent by weight percent include about 40% to about 90%, about 50% to about 85%, about 55% to about 80%, about 50% to about 60%, and increments therein.

In embodiments where the pharmaceutical composition is compacted into a solid dosage form, e.g., a tablet, a binder can help the ingredients hold together. Binders include, but are not limited to, sugars such as sucrose, lactose, and glucose; corn syrup; soy polysaccharide, gelatin; povidone (e.g., Kollidon®, Plasdone®); Pullulan; cellulose derivatives such as microcrystalline cellulose, hydroxypropylmethyl cellulose (e.g., Methocel®), hydroxypropyl cellulose (e.g., Klucel®), ethylcellulose, hydroxyethyl cellulose, carboxymethylcellulose sodium, and methylcellulose; acrylic and methacrylic acid co-polymers; carbomer (e.g., Carbopol®); polyvinylpolypyrrolidine, polyethylene glycol (Carbowax®); pharmaceutical glaze; alginates such as alginic acid and sodium alginate; gums such as acacia, guar gum, and arabic gums; tragacanth; dextrin and maltodextrin; milk derivatives such as whey; starches such as pregelatinized starch and starch paste; hydrogenated vegetable oil; and magnesium aluminum silicate.

For tablet dosage forms, the pharmaceutical composition is subjected to pressure from a punch and dye. Among other purposes, a lubricant can help prevent the composition from sticking to the punch and dye surfaces. A lubricant can also be used in the coating of a coated dosage form. Lubricants include, but are not limited to, magnesium stearate, calcium stearate, zinc stearate, powdered stearic acid, glyceryl monostearate, glyceryl palmitostearate, glyceryl behenate, silica, magnesium silicate, colloidal silicon dioxide, titanium dioxide, sodium benzoate, sodium lauryl sulfate, sodium stearyl fumarate, hydrogenated vegetable oil, talc, polyethylene glycol, and mineral oil. A preferred lubricant is magnesium stearate. The amount of lubricant by weight percent is preferably less than about 5%, more preferably 4%, 3%, 2%, 1.5%, 1%, or 0.5%, or increments therein.

Glidants can improve the flowability of non-compacted solid dosage forms and can improve the accuracy of dosing. Glidants include, but are not limited to, colloidal silicon dioxide, fumed silicon dioxide, silica gel, talc, magnesium trisilicate, magnesium or calcium stearate, powdered cellulose, starch, and tribasic calcium phosphate.

Plasticizers include both hydrophobic and hydrophilic plasticizers such as, but not limited to, diethyl phthalate, butyl phthalate, diethyl sebacate, dibutyl sebacate, triethyl citrate, acetyltriethyl citrate, acetyltributyl citrate, cronotic acid, propylene glycol, castor oil, triacetin, polyethylene glycol, propylene glycol, glycerin, and sorbitol. Plasticizers are particularly useful for pharmaceutical compositions containing a polymer and in soft capsules and film-coated tablets. In one embodiment, the plasticizer facilitates the release of the amphetamine prodrug from the dosage form.

Disintegrants can increase the dissolution rate of a pharmaceutical composition. Disintegrants include, but are not limited to, alginates such as alginic acid and sodium alginate, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), polyvinylpolypyrrolidine (Plasone-XL®), guar gum, magnesium aluminum silicate, methyl cellulose, microcrystalline cellulose, polacrilin potassium, powdered cellulose, starch, pregelatinized starch, sodium starch glycolate (e.g., Explotab®, Primogel®). Preferred disintegrants include croscarmellose sodium and microcrystalline cellulose (e.g., Avicel® PH-102). Preferred ranges for the amount of disintegrant by weight percent include about 1% to about 10%, about 1% to about 5%, about 2% to about 3%, and increments therein.

In embodiments where the pharmaceutical composition is formulated for a liquid dosage form, the pharmaceutical composition may include one or more solvents. Suitable solvents include, but are not limited to, water; alcohols such as ethanol and isopropyl alcohol; methylene chloride; vegetable oil; polyethylene glycol; propylene glycol; and glycerin.

The pharmaceutical composition can comprise a buffer. Buffers include, but are not limited to, lactic acid, citric acid, acetic acid, sodium lactate, sodium citrate, and sodium acetate.

Any pharmaceutically acceptable colorant can be used to improve appearance or to help identify the pharmaceutical composition. See 21 C.F.R., Part 74. Exemplary colorants include D&C Red No. 28, D&C Yellow No. 10, FD&C Blue No. 1, FD&C Red No. 40, FD&C Green #3, FD&C Yellow No. 6, and edible inks. Preferred colors for gelatin capsules include white, medium orange, and light blue.

Flavorings improve palatability and may be particularly useful for chewable tablet or liquid dosage forms. Flavorings include, but are not limited to maltol, vanillin, ethyl vanillin, menthol, citric acid, fumaric acid, ethyl maltol, and tartaric acid. Sweeteners include, but are not limited to, sorbitol, saccharin, sodium saccharin, sucrose, aspartame, fructose, mannitol, and invert sugar.

The pharmaceutical compositions of the invention can also include one or more preservatives and/or stabilizers to improve storagability. These include, but are not limited to, alcohol, sodium benzoate, butylated hydroxy toluene, butylated hydroxyanisole, and ethylenediamine tetraacetic acid.

Other pharmaceutical additives include gelling agents such as colloidal clays; thickening agents such as gum tragacanth and sodium alginate; wetting agents such as lecithin, polysorbates, and laurylsulphates; humectants; antioxidants such as vitamin E, caronene, and BHT; adsorbents; effervescing agents; emulsifying agents, viscosity enhancing agents; surface active agents such as sodium lauryl sulfate, dioctyl sodium sulfosuccinate, triethanolamine, polyoxyethylene sorbitan, poloxalkol, and quaternary ammonium salts; and other miscellaneous excipients such as lactose, mannitol, glucose, fructose, xylose, galactose, sucrose, maltose, xylitol, sorbitol, chloride, sulfate and phosphate salts of potassium, sodium, and magnesium.

The pharmaceutical compositions can be manufactured according to any method known to those of skill in the art of pharmaceutical manufacture such as, for example, wet granulation, dry granulation, encapsulation, direct compression, slugging, etc. For instance, a pharmaceutical composition can be prepared by mixing the amphetamine prodrug with one or more pharmaceutical additives with an aliquot of liquid, preferably water, to form a wet granulation. The wet granulation can be dried to obtain granules. The resulting granulation can be milled, screened, and blended with various pharmaceutical additives such as water-insoluble polymers and additional hydrophilic polymers. In one embodiment, an amphetamine prodrug is mixed with a hydrophilic polymer and an aliquot of water, then dried to obtain granules of amphetamine prodrug encapsulated by hydrophilic polymer.

After granulation, the pharmaceutical composition is preferably encapsulated, e.g., in a gelatin capsule. The gelatin capsule can contain, for example, kosher gelatin, titanium dioxide, and optional colorants. Alternatively, the pharmaceutical composition can be tableted, e.g., compressed and optionally coated with a protective coating that dissolves or disperses in gastric juices.

The pharmaceutical compositions of the invention can be administered by a variety of dosage forms. Any biologically-acceptable dosage form known in the art, and combinations thereof, are contemplated. Examples of preferred dosage forms include, without limitation, tablets including chewable tablets, film-coated tablets, quick dissolve tablets, effervescent tablets, multi-layer tablets, and bi-layer tablets; caplets; powders including reconstitutable powders; granules; dispersible granules; particles; microparticles; capsules including soft and hard gelatin capsules; lozenges; chewable lozenges; cachets; beads; liquids; solutions; suspensions; emulsions; elixirs; and syrups.

The pharmaceutical composition is preferably administered orally. Oral administration permits the maximum release of amphetamine, provides sustained release of amphetamine, and maintains abuse resistance. Preferably, the amphetamine prodrug releases the amphetamine over a more extended period of time as compared to administering unbound amphetamine.

Oral dosage forms can be presented as discrete units, such as capsules, caplets, or tablets. In a preferred embodiment, the invention provides a solid oral dosage form comprising an amphetamine prodrug that is smaller in size compared to a solid oral dosage form containing a therapeutically equivalent amount of unbound amphetamine. In one embodiment, the oral dosage form comprises a gelatin capsule of size 2, size 3, or smaller (e.g., size 4). The smaller size of the amphetamine prodrug dosage forms promotes ease of swallowing.

Soft gel or soft gelatin capsules may be prepared, for example, by dispersing the formulation in an appropriate vehicle (e.g., vegetable oil) to form a high viscosity mixture.

This mixture then is encapsulated with a gelatin based film. The industrial units so formed are then dried to a constant weight.

Chewable tablets can be prepared by mixing the amphetamine prodrug with excipients designed to form a relatively soft, flavored tablet dosage form that is intended to be chewed. Conventional tablet machinery and procedures (e.g., direct compression, granulation, and slugging) can be utilized.

Film-coated tablets can be prepared by coating tablets using techniques such as rotating pan coating methods and air suspension methods to deposit a contiguous film layer on a tablet.

Compressed tablets can be prepared by mixing the amphetamine prodrug with excipients that add binding qualities. The mixture can be directly compressed, or it can be granulated and then compressed.

The pharmaceutical compositions of the invention can alternatively be formulated into a liquid dosage form, such as a solution or suspension in an aqueous or non-aqueous liquid. The liquid dosage form can be an emulsion, such as an oil-in-water liquid emulsion or a water-in-oil liquid emulsion. The oils can be administered by adding the purified and sterilized liquids to a prepared enteral formula, which then is placed in the feeding tube of a patient who is unable to swallow.

For oral administration, fine powders or granules containing diluting, dispersing, and/or surface-active agents can be presented in a draught, in water or a syrup, in capsules or sachets in the dry state, in a non-aqueous suspension wherein suspending agents may be included, or in a suspension in water or a syrup. Liquid dispersions for oral administration can be syrups, emulsions, or suspensions. The syrups, emulsions, or suspensions can contain a carrier, for example, a natural gum, agar, sodium alginate, pectin, methylcellulose, carboxymethylcellulose, saccharose, saccharose with glycerol, mannitol, sorbitol, and polyvinyl alcohol.

The dose range of the amphetamine prodrug for humans will depend on a number of factors including the age, weight, and condition of the patient. Tablets and other dosage forms provided in discrete units can contain a daily dose, or an appropriate fraction thereof, of one or more amphetamine prodrugs. The dosage form can contain a dose of about 2.5 mg to about 500 mg, about 10 mg to about 250 mg, about 10 mg to about 100 mg, about 25 mg to about 75 mg, or increments therein of one or more of the amphetamine prodrugs. In a preferred embodiment, the dosage form contains 30 mg, 50 mg, or 70 mg of an amphetamine prodrug.

The dosage form can utilize any one or any combination of known release profiles including, but not limited to immediate release, extended release, pulse release, variable release, controlled release, timed release, sustained release, delayed release, and long acting.

The pharmaceutical compositions of the invention can be administered in a partial, i.e., fractional dose, one or more times during a 24 hour period. Fractional, single, double, or other multiple doses can be taken simultaneously or at different times during a 24 hour period. The doses can be uneven doses with regard to one another or with regard to the individual components at different administration times. Preferably, a single dose is administered once daily. The dose can be administered in a fed or fasted state.

The dosage units of the pharmaceutical composition can be packaged according to market need, for example, as unit doses, rolls, bulk bottles, blister packs, and so forth. The pharmaceutical package, e.g., blister pack, can further include or be accompanied by indicia allowing individuals to identify the identity of the pharmaceutical composition, the prescribed indication (e.g., ADHD), and/or the time periods (e.g., time of day, day of the week, etc.) for administration. The blister pack or other pharmaceutical package can also include a second pharmaceutical product for combination therapy.

It will be appreciated that the pharmacological activity of the compositions of the invention can be demonstrated using standard pharmacological models that are known in the art. Furthermore, it will be appreciated that the inventive compositions can be incorporated or encapsulated in a suitable polymer matrix or membrane for site-specific delivery, or can be functionalized with specific targeting agents capable of effecting site specific delivery. These techniques, as well as other drug delivery techniques, are well known in the art.

Any feature of the above-describe embodiments can be used in combination with any other feature of the above-described embodiments.

In order to facilitate a more complete understanding of the invention, Examples are provided below. However, the scope of the invention is not limited to specific embodiments disclosed in these Examples, which are for purposes of illustration only.

EXAMPLES

The following abbreviations are used in the Examples and throughout the patent:

Lys-Amp=L-lysine-d-amphetamine, Lysine-Amphetamine, K-Amp, K-amphetamine, or 2,6-diaminohexanoic acid-(1-methyl-2-phenylethyl)-amide, or Lisdexamfetamine Phe-Amp=Phenylalanine-Amphetamine, F-Amp, or 2-amino-3-phenylpropanoic acid-(1-methyl-2-phenylethyl)-amide Ser-Amp=Serine-Amphetamine, S-Amp, or 2-amino-3-hydroxylpropanoic acid-(1-methyl-2-phenylethyl)-amide, $Gly_3$-Amp=GGG-Amphetamine, GGG-Amp, or 2-amino-N-({[(1-methyl-2-phenyl-ethylcarbornyl)-methyl]-carbornyl}-methyl)-acetamide BOC=t-butyloxycarbonyl CMC=carboxymethylcellulose DIPEA=di-isopropyl ethyl amine mp=melting point NMR=nuclear magnetic resonance OSu=hydroxysuccinimido ester Throughout the Examples, unless otherwise specified, doses are described as the amount of d-amphetamine base. Exemplary conversions are provided in Table 2.

TABLE 2

Conversion of d-amphetamine doses (mg)

| L-lysine-d-amphetamine dimesylate (29.5% d-amphetamine) | d-amphetamine base | d-amphetamine sulfate (72.8% d-amphetamine) |
|---|---|---|
| 5.08 | 1.5 | 2.06 |
| 10.17 | 3 | 4.12 |
| 20.34 | 6 | 8.24 |
| 40.68 | 12 | 16.48 |
| 101.69 | 30 | 41.21 |
| 203.39 | 60 | 82.42 |
| 25.00 | 7.375 | 10.13 |
| 75.00 | 22.125 | 30.39 |
| 70.00 | 20.65 | 28.37 |
| 50.00 | 14.75 | 20.26 |
| 30.00 | 8.85 | 12.16 |

Example 1

General Synthesis of Peptide Amphetamine Conjugates

Peptide conjugates were synthesized by the general method described in FIG. 1. An iterative approach can be used to identify favorable conjugates by synthesizing and testing single amino acid conjugates, and then extending the peptide one amino acid at a time to yield dipeptide and tripeptide conjugates, etc. The parent single amino acid prodrug candidate may exhibit more or less desirable characteristics than its di- or tripeptide offspring candidates. The iterative approach can quickly suggest whether peptide length influences bioavailability.

General Synthesis of Single Amino Acid Amphetamine Conjugates

To a solution of a protected amino acid succinimidyl ester (2.0 eq) in 1,4-dioxane (30 mL) was added d-amphetamine sulfate (1.0 eq) and NMM (4.0 eq). The resulting mixture was allowed to stir for 20 h at 20° C. Water (10 mL) was added, and the solution was stirred for 10 minutes prior to removing solvents under reduced pressure. The crude product was dissolved in EtOAc (100 mL) and washed with 2% $AcOH_{aq}$ (3×100 mL), saturated $NaHCO_3$ solution (2×50 mL), and brine (1×100 mL). The organic extract was dried over $MgSO_4$, filtered, and evaporated to dryness to afford the protected amino acid amphetamine conjugate. This intermediate was directly deprotected by adding 4 N HCl in 1,4-dioxane (20 mL). The solution was stirred for 20 h at 25° C. The solvent was evaporated, and the product dried in vacuum to afford the corresponding amino acid amphetamine hydrochloride conjugate. The syntheses of exemplary single amino acid conjugates are depicted in FIG. 2-FIG. 6.

General Synthesis of Dipeptide Amphetamine Conjugates

To a solution of a protected dipeptide succinimidyl ester (1.0 eq) in 1,4-dioxane was added amphetamine sulfate (2.0 eq) and NMM (4.0 eq). The resulting mixture was stirred for 20 h at 25° C. Solvents were removed under reduced pressure. Saturated $NaHCO_3$ solution (20 mL) was added, and the suspension was stirred for 30 min. IPAC (100 mL) was added, and the organic layer was washed with 2% $AcOH_{aq}$ (3×100 mL) and brine (2×100 mL). The organic extract was dried over $Na_2SO_4$, and the solvent was evaporated to dryness to yield the protected dipeptide amphetamine conjugate. The protected dipeptide conjugate was directly deprotected by adding 4 N HCl in 1,4-dioxane (20 mL), and the solution stirred for 20 h at 25° C. The solvent was evaporated, and the product was dried in vacuum to afford the corresponding dipeptide amphetamine hydrochloride conjugate.

General Synthesis of Tripeptide Amphetamine Conjugates

An amino acid conjugate was synthesized and deprotected according to the general procedure described above. To a solution of the amino acid amphetamine hydrochloride (1.0 eq) in dioxane (20 mL) was added NMM (5.0 eq) and a protected dipeptide succinate (1.05 eq). The solution was stirred for 20 h at 25° C. The solvent was removed under reduced pressure. Saturated $NaHCO_3$ solution (20 mL) was added, and the suspension was stirred for 30 min. IPAC (100 mL) was added, and the organic layer was washed with 2% $AcOH_{aq}$ (3×100 mL) and brine (2×100 mL). The organic extract was dried over $Na_2SO_4$, and the solvent was evaporated to dryness to yield the protected tripeptide amphetamine. Deprotection was directly carried out by adding 4 N HCl in 1,4-dioxane (20 mL). The mixture was stirred for 20 h at 25° C., the solvent was evaporated, and the product was dried in vacuum to afford the respective tripeptide amphetamine hydrochloride conjugate.

The hydrochloride conjugates required no further purification, but many of the deprotected hydrochloride salts were hygroscopic and required special handling during analysis and subsequent in vivo testing.

Example 2

Synthesis of L-lysine-d-amphetamine

L-lysine-d-amphetamine was synthesized by the following methods.

a. Preparation of HCl salt (see FIG. 3)
  i. Coupling

| Reagents | MW | Weight | mmoles | Molar Equivalents |
|---|---|---|---|---|
| d-amphetamine free base | 135.2 | 4.75 g | 35.13 | 1 |
| Boc-Lys(Boc)-OSu | 443.5 | 15.58 g | 35.13 | 1 |
| Di-iPr-Et-Amine | 129 | 906 mg | 7.03 | 0.2, d = 0.74, 1.22 mL |
| 1,4-Dioxane | — | 100 mL | — | — |

To a solution of Boc-Lys(Boc)-OSu (15.58 g, 35.13 mmol) in dioxane (100 mL) under an inert atmosphere was added d-amphetamine free base (4.75 g, 35.13 mmol) and DIPEA (0.9 g, 1.22 mL, 7.03 mmol). The resulting mixture was allowed to stir at room temperature overnight. Solvent and excess base were then removed using reduced pressure evaporation. The crude product was dissolved in ethyl acetate and loaded on to a flash column (7 cm wide, filled to 24 cm with silica) and eluted with ethyl acetate. The product was isolated, the solvent reduced by rotary evaporation, and the purified protected amide was dried by high-vac to obtain a white solid. $^1$H NMR (DMSO-$d_6$) δ 1.02-1.11 (m, 2H, Lys γ-$CH_2$), δ 1.04 (d, 3H, Amp α-$CH_3$), δ 1.22-1.43 (m, 4H, Lys-β and δ-$CH_2$), δ 1.37 (18H, Boc, 6×$CH_3$), δ 2.60-2.72 (2H, Amp $CH_2$), δ 3.75-3.83, (m, 1H, Lys α-H) δ 3.9-4.1 (m, 1H, Amp α-H), δ 6.54-6.61 (d, 1H, amide NH), δ 6.7-6.77 (m, 1H, amide NH), δ 7.12-7.29 (m, 5H, ArH), δ 7.65-7.71 (m, 1, amide NH); mp=86-88° C.

ii. Deprotection

| Reagents | MW | Weight | mmoles | Molar Equivalents |
|---|---|---|---|---|
| 4M HCl in dioxane | 4 mmol/mL | 50 mL | 200 | 6.25 |
| Boc-Lys(Boc)-Amp | 463.6 | 14.84 g | 32 | 1 |
| 1,4-Dioxane | — | 50 mL | — | — |

The protected amide was dissolved in 50 mL of anhydrous dioxane and stirred while 50 mL (200 mmol) of 4M HCl/dioxane was added and stirred at room temperature overnight. The solvents were then reduced by rotary evaporation to afford a viscous oil. Addition of 100 mL MeOH followed by rotary evaporation resulted in a golden colored solid material that was further dried by storage at room temperature under high vacuum. $^1$H NMR (DMSO-$d_6$) δ 0.86-1.16 (m, 2H, Lys γ-$CH_2$), δ 1.1 (d, 3H, Amp α-$CH_3$), δ 1.40-1.56 (m, 4H, Lys-β and δ-$CH_2$), δ 2.54-2.78 (m, 2H, Amp $CH_2$, 2H, Lys ε-$CH_2$), 3.63-3.74 (m, 1H, Lys α-H), δ 4.00-4.08 (m, 1H, Amp α-H), δ 7.12-7.31 (m, 5H, Amp ArH), δ 8.13-8.33 (d, 3H, Lys amine) δ 8.70-8.78 (d, 1H, amide NH); mp=120-122° C.

b. Preparation of Mesylate Salt (and See FIG. 2)

Similarly, the mesylate salt of the peptide conjugate can be prepared by using methanesulfonic acid in the deprotection step as described in further detail below.

i. Coupling

A 72-L round-bottom reactor was equipped with a mechanical stirrer, digital thermocouple, and addition funnel and purged with nitrogen. The vessel was charged with Boc-Lys(Boc)-OSu (3.8 kg, 8.568 mol, 1.0 eq) and 1,4-dioxane (20.4 L), and the resulting turbid solution was stirred at 20±5° C. for 10 min. To the mixture was added N-methylmorpholine (950 g, 9.39 mol, 1.09 eq) over a period of 1 min, and the mixture was stirred for 10 min. To the slightly turbid reaction mixture was then added a solution of dextro-amphetamine (1.753 kg, 12.96 mol, 1.51 eq) in 1,4-dioxane (2.9 L) over a period of 30 min, while cooling the reactor externally with an ice/water bath. The internal temperature was kept below 25° C. during the addition. At the end of the addition, a thick white precipitate appeared. The addition funnel was rinsed with 1,4-dioxane (2.9 L) into the reactor, and the reaction mixture was stirred at 22±3° C. TLC monitoring 30 min. after completed addition showed no more remaining Boc-Lys(Boc)-Osu, and the reaction was quenched with DI $H_2O$ (10 L). The mixture was stirred for 1 h at ambient temperature and then concentrated under reduced pressure to afford a dense, white solid.

For the extractions, two solutions were prepared: an acetic acid/salt solution: NaCl (15 kg) and glacial acetic acid (2 kg) in DI $H_2O$ (61 L), and a bicarbonate solution: $NaHCO_3$ (1.5 kg) in DI $H_2O$ (30 L).

The solid was re-dissolved in IPAC (38 L) and acetic acid/salt solution (39 kg) and transferred into a 150-L reactor. The layers were mixed for 10 min. and then allowed to separate. The organic layer was drained and washed with another portion (39 kg) of acetic acid/salt solution, followed by a wash with bicarbonate solution (31.5 kg). All phase separations occurred within 5 min. To the organic solution was then added silica-gel (3.8 kg; Silica-gel 60). The resulting slurry was stirred for 45 min. and then filtered through filter paper. The filter-cake was washed with IPAC (5×7.6 L). The filtrate and washes were analyzed by TLC, and it was determined that all contained product. The filtrate and washes were combined and concentrated under reduced pressure to afford the crude product as a white solid.

ii. Deprotection

A 45-L carboy was charged with di-Boc-Lys-Amp (3.63 kg, 7.829 mol) and 1,4-dioxane (30.8 L, 8.5 vol), and the mixture was stirred rapidly under nitrogen for 30 min. The resulting solution was filtered, and the filter-cake was rinsed with 1,4-dioxane (2×1.8 L).

The filtrates were then transferred into a 72-L round-bottom flask, which was equipped with a mechanical stirrer, digital thermocouple, nitrogen inlet and outlet, and 5 L addition funnel. The temperature of the reaction mixture was regulated at 21±3° C. with a water bath. To the clear, slightly yellow solution was added methanesulfonic acid (3.762 kg, 39.15 mol, 5 eq) over a period of 1 h while keeping the internal temperature at 21±3° C. Approximately 1 h after completed addition, a white precipitate started to appear. The mixture was stirred at ambient temperature for 20.5 h, after which HPLC monitoring showed the disappearance of all starting material. The mixture was filtered through filter-paper, and the reaction vessel was rinsed with 1,4-dioxane (3.6 L, 1 vol). The filter-cake was washed with dioxane (3×3.6 L) and dried with a rubber dam for 1 h. The material was then transferred to drying trays and dried in a vacuum oven at 55° C. for ~90 h. This afforded Lys-Amp dimesylate [3.275 kg, 91.8% yield; >99% (AUC)] as a white solid.

Example 3

Synthesis of Ser-Amp

Ser-Amp was synthesized by a similar method (see FIG. 4) except the amino acid starting material was Boc-Ser(O-tBu)-OSu and the deprotection was done using a solution of trifluoroacetic acid instead of HCl.

Example 4

Synthesis of Phe-Amp

Phe-Amp was synthesized by a similar method (see FIG. 5) except the amino acid starting material was Boc-Phe-OSu.

Phe-Amp hydrochloride: hygroscopic; $^1H$ NMR (400 MHz, DMSO-$d_6$): δ 8.82 (d, J=8.0 Hz, 1H), 8.34 (bs, 3H), 7.29-7.11 (m, 10H), 3.99 (m, 2H), 2.99 (dd, J=13.6, 6.2 Hz, 1H), 2.88 (dd, J=13.6, 7.2 Hz, 1H), 2.64 (dd, J=13.2, 7.6 Hz, 1H), 2.53 (m, 1H), 1.07 (d, J=6.4 Hz, 3H); $^{13}C$ NMR (100 MHz, DMSO-$d_6$): δ 167.31, 139.27, 135.49, 130.05, 129.66, 128.78, 128.61, 127.40, 126.60, 53.83, 47.04, 42.15, 37.27, 20.54; HRMS: (ESI) for $C_{18}H_{23}N_2O$ (M+H)$^+$: calcd, 283.1810: found, 283.1806.

Example 5

Synthesis of Gly$_3$-Amp

Gly$_3$-Amp was synthesized by a similar method (see FIG. 6) except the amino acid starting material was Boc-GGG-OSu.

Gly$_3$-Amp hydrochloride: mp 212-214° C.; $^1H$ NMR (400 MHz, DMSO-$d_6$) δ 7.28 (m, 5H), 3.96 (m, 1H), 3.86 (m, 2H), 3.66 (m, 4H), 2.76 (m, 1H), 2.75 (m, 1H), 1.02 (d, J=6.8 Hz, 3H); $^{13}C$ NMR (100 MHz, DMSO-$d_6$) δ 168.91, 168.14, 166.85, 139.45, 129.60, 128.60, 126.48, 46.60, 42.27, 20.30. HRMS: (ESI) for $C_{15}H_{22}N_4O_3Na$ (M+Na)$^+$: calcd, 329.1590: found, 329.1590.

Example 6

Pharmacokinetics of L-lysine-d-amphetamine diHCl Compared to d-amphetamine Sulfate (ELISA Analysis)

Male Sprague-Dawley rats were provided water ad libitum, fasted overnight, and dosed by oral gavage L-lysine-d-amphetamine diHCl or d-amphetamine sulfate. In all studies, doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. L-lysine-d-amphetamine diHCl was also determined to be essentially unreactive in the ELISA (<1%).

Figure 7:
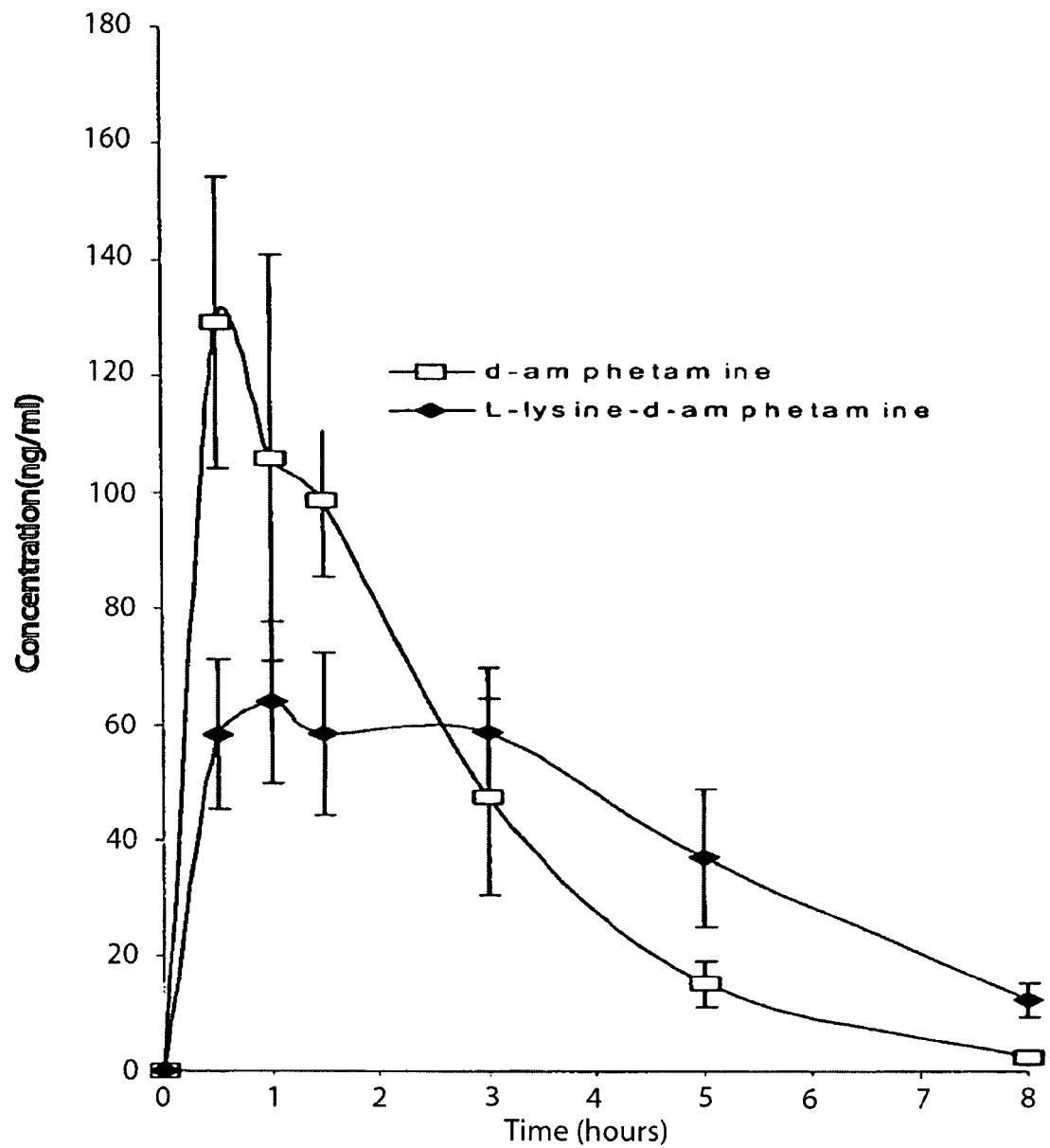
FIG. 7. Plasma concentrations of d-amphetamine from individual rats orally administered d-amphetamine or L-lysine-d-amphetamine hydrochloride.

Mean (n=4) plasma concentration curves of d-amphetamine or L-lysine-d-amphetamine diHCl are shown in FIG. 7. Extended release was observed in all four L-lysine-d-amphetamine diHCl dosed animals, and $C_{max}$ was substantially decreased as compared to animals dosed with d-amphetamine sulfate. Plasma d-amphetamine concentrations of individual animals for d-amphetamine or L-lysine-d-amphetamine diHCl are shown in Table 3. The mean plasma d-amphetamine concentrations are shown in Table 4. The time to peak concentration for L-lysine-d-amphetamine diHCl was similar to that of d-amphetamine. Pharmacokinetic parameters for oral administration of d-amphetamine or L-lysine-d-amphetamine diHCl are summarized in Table 5.

TABLE 3

Plasma concentrations of d-amphetamine from individual animals orally administered d-amphetamine or L-lysine-d-amphetamine diHCl (3 mg/kg d-amphetamine base)

| Time    | d-amphetamine (ng/ml) | | | | L-lysine-d-amphetamine (ng/ml) | | | |
|---------|--------|--------|--------|--------|--------|--------|--------|--------|
| (hours) | Rat #1 | Rat #2 | Rat #3 | Rat #4 | Rat #1 | Rat #2 | Rat #3 | Rat #4 |
| 0.5 | 144 | 157 | 101 | 115 | 52 | 62 | 74 | 44 |
| 1   | 152 | 78  | 115 | 78  | 48 | 72 | 79 | 57 |
| 1.5 | 85  | 97  | 117 | 95  | 42 | 62 | 76 | 53 |
| 3   | 34  | 45  | 72  | 38  | 61 | 60 | 71 | 43 |
| 5   | 20  | 14  | 12  | 15  | 49 | 33 | 44 | 22 |
| 8   | 3   | 3   | 2   | 2   | 15 | 14 | 12 | 8  |

TABLE 4

Mean plasma concentrations of d-amphetamine following oral administration of d-amphetamine or L-lysine-d-amphetamine

| | Plasma d-amphetamine Concentrations (ng/ml) | | | | | |
|---|---|---|---|---|---|---|
| | d-amphetamine | | | L-lysine-d-amphetamine | | |
| Hours | Mean | ±SD | CV | Mean | ±SD | CV |
| 0.5 | 129 | 25 | 20 | 58 | 13 | 22 |
| 1   | 106 | 35 | 33 | 64 | 14 | 22 |
| 1.5 | 99  | 13 | 14 | 58 | 14 | 25 |
| 3   | 47  | 17 | 36 | 59 | 11 | 19 |
| 5   | 15  | 4  | 24 | 37 | 12 | 32 |
| 8   | 2   | 1  | 35 | 12 | 3  | 24 |

TABLE 5

Pharmacokinetic parameters of d-amphetamine following oral administration of d-amphetamine or L-lysine-d-amphetamine

| Drug | AUC (0-8 h) ng·h/mL | Percent Amphetamine | $C_{max}$ (ng/ml) | Percent Amphetamine | Mean Peak (ng/ml) | Percent Amphetamine |
|---|---|---|---|---|---|---|
| Amphetamine | 341 ± 35 | 100 | 111 ± 27 | 100 | 129 | 100 |
| Lys-Amp | 333 ± 66 | 98 | 61 ± 13 | 55 | 64 | 50 |

This example illustrates that when lysine is conjugated to the active agent amphetamine, the peak levels of amphetamine are decreased while bioavailability is maintained approximately equal to amphetamine. The bioavailability of amphetamine released from L-lysine-d-amphetamine is similar to that of amphetamine sulfate at the equivalent dose; thus L-lysine-d-amphetamine maintains its therapeutic value. The gradual release of amphetamine from L-lysine-d-amphetamine and decrease in peak levels reduce the possibility of overdose.

Example 7

Oral Bioavailability of L-lysine-d-amphetamine Dimesylate at Various Doses a. Doses Approximating Therapeutic Human Doses (1.5, 3, and 6 mg/kg)

Mean (n=4) plasma concentration curves of d-amphetamine vs. L-lysine-d-amphetamine are shown for rats orally administered 1.5, 3, and 6 mg/kg in FIG. 8, FIG. 9, and FIG. 10, respectively. Extended release was observed at all three therapeutic doses for L-lysine-d-amphetamine dosed animals. The mean plasma concentrations for 1.5, 3, and 6 mg/kg are shown in Table 6, Table 7, and Table 8, respectively.

Pharmacokinetic parameters for oral administration of d-amphetamine vs. L-lysine-d-amphetamine at the various doses are summarized in Table 9.

TABLE 6

Mean plasma concentrations of d-amphetamine vs. L-lysine-d-amphetamine following oral administration (1.5 mg/kg)

| | Plasma Amphetamine Concentrations (ng/ml) | | | | | |
|---|---|---|---|---|---|---|
| | d-amphetamine | | | L-lysine-d-amphetamine | | |
| Hours | Mean | ±SD | CV | Mean | ±SD | CV |
| 0    | 0   | 0  | 0  | 0  | 0  | 0  |
| 0.25 | 103 | 22 | 21 | 31 | 11 | 37 |
| 0.5  | 126 | 20 | 16 | 51 | 23 | 45 |
| 1    | 101 | 27 | 27 | 68 | 23 | 34 |
| 1.5  | 116 | 28 | 24 | 72 | 10 | 14 |
| 3    | 66  | 13 | 20 | 91 | 5  | 5  |
| 5    | 40  | 7  | 18 | 75 | 16 | 22 |
| 8    | 17  | 2  | 15 | 39 | 13 | 34 |

TABLE 7

Mean plasma concentrations of d-amphetamine vs. L-lysine-d-amphetamine following oral administration (3 mg/kg)

Plasma Amphetamine Concentrations (ng/ml)

| | d-amphetamine | | | L-lysine-d-amphetamine | | |
|---|---|---|---|---|---|---|
| Hours | Mean | ±SD | CV | Mean | ±SD | CV |
| 0 | 0 | | | 0 | | |
| 0.25 | 96 | 41 | 43 | 51 | 49 | 97 |
| 0.5 | 107 | 49 | 46 | 36 | 35 | 96 |
| 1 | 121 | 17 | 14 | 81 | 44 | 54 |
| 1.5 | 120 | 33 | 27 | 97 | 32 | 33 |
| 3 | 91 | 30 | 33 | 88 | 13 | 15 |
| 5 | 62 | 22 | 36 | 91 | 21 | 23 |
| 8 | 19 | 6 | 33 | 46 | 16 | 34 |

TABLE 8

Mean plasma concentrations of d-amphetamine vs. L-lysine-d-amphetamine following oral administration (6 mg/kg)

Plasma Amphetamine Concentrations (ng/ml)

| | d-amphetamine | | | L-lysine-d-amphetamine | | |
|---|---|---|---|---|---|---|
| Hours | Mean | ±SD | CV | Mean | ±SD | CV |
| 0 | 0 | | | 0 | | |
| 0.25 | 204 | 14 | 7 | 74 | 38 | 51 |
| 0.5 | 186 | 9 | 5 | 106 | 39 | 37 |
| 1 | 167 | 12 | 7 | 133 | 33 | 24 |
| 1.5 | 161 | 24 | 15 | 152 | 22 | 15 |
| 3 | 111 | 29 | 26 | 157 | 15 | 10 |
| 5 | 78 | 9 | 11 | 134 | 18 | 13 |
| 8 | 35 | 5 | 15 | 79 | 12 | 15 |

TABLE 9

Pharmacokinetic parameters of d-amphetamine following oral administration of d-amphetamine or L-lysine-d-amphetamine

| | 1.5 mg/kg | | 3 mg/kg | | 6 mg/kg | |
|---|---|---|---|---|---|---|
| Parameter | Amp | K-Amp | Amp | K-Amp | Amp | K-Amp |
| AUC (ng · h/ml) | 481 | 538 | 587 | 614 | 807 | 1005 |
| Percent | 100 | 112 | 100 | 105 | 100 | 125 |
| $C_{max}$ (ng/ml) | 133 | 93 | 141 | 104 | 205 | 162 |
| Percent | 100 | 70 | 100 | 74 | 100 | 79 |
| $T_{max}$ (hours) | 0.938 | 3.5 | 1 | 1.56 | 0.563 | 2.625 |
| Percent | 100 | 373 | 100 | 156 | 100 | 466 | b. Increased doses (12, 30, and 60 mg/kg)

Mean (n=4) plasma concentration curves of d-amphetamine vs. L-lysine-d-amphetamine are shown for rats orally administered 12, 30, and 60 mg/kg. At these higher doses, the bioavailability of L-lysine-d-amphetamine was markedly decreased as compared to d-amphetamine.

TABLE 10

Mean plasma concentrations of d-amphetamine vs. L-lysine-d-amphetamine following oral administration (12 mg/kg)

Plasma Amphetamine Concentrations (ng/ml)

| | d-amphetamine | | | L-lysine-d-amphetamine | | |
|---|---|---|---|---|---|---|
| Hours | Mean | ±SD | CV | Mean | ±SD | CV |
| 0 | NA | NA | NA | NA | NA | NA |
| 0.25 | 530 | 279 | 53 | 53 | 34 | 64 |
| 0.5 | 621 | 76 | 12 | 99 | 32 | 33 |
| 1 | 512 | 91 | 18 | 220 | 77 | 35 |
| 1.5 | 519 | 113 | 22 | 224 | 124 | 55 |
| 3 | 376 | 149 | 40 | 300 | 153 | 51 |
| 5 | 314 | 123 | 39 | 293 | 153 | 52 |
| 8 | 103 | 64 | 63 | 211 | 45 | 22 |

TABLE 11

Mean plasma concentrations of d-amphetamine vs. L-lysine-d-amphetamine following oral administration (30 mg/kg)

Plasma Amphetamine Concentrations (ng/ml)

| | d-amphetamine | | | L-lysine-d-amphetamine | | |
|---|---|---|---|---|---|---|
| Hours | Mean | ±SD | CV | Mean | ±SD | CV |
| 0 | NA | NA | NA | NA | NA | NA |
| 0.25 | 2,036 | 1,262 | 62 | 29 | 16 | 54 |
| 0.5 | 2,583 | 1,465 | 57 | 88 | 29 | 34 |
| 1 | 3,162 | 772 | 24 | 328 | 30 | 9 |
| 1.5 | 3,445 | 191 | 6 | 368 | 99 | 27 |
| 3 | 2,620 | 72 | 3 | 620 | 79 | 13 |
| 5 | 1,535 | 21 | 1 | 730 | 169 | 23 |
| 8 | 164 | 52 | 32 | NA | NA | NA |

TABLE 12

Mean plasma concentrations of d-amphetamine vs. L-lysine-d-amphetamine following oral administration (60 mg/kg)

Plasma Amphetamine Concentrations (ng/ml)

| | d-amphetamine | | | L-lysine-d-amphetamine | | |
|---|---|---|---|---|---|---|
| Hours | Mean | ±SD | CV | Mean | ±SD | CV |
| 0 | NA | NA | NA | NA | NA | NA |
| 0.25 | 3,721 | 286 | 8 | 169 | 93 | 55 |
| 0.5 | 3,566 | 560 | 16 | 259 | 138 | 53 |
| 1 | 3,556 | 442 | 12 | 420 | 173 | 41 |
| 1.5 | 4,142 | 381 | 9 | 506 | 169 | 33 |
| 3 | NA | NA | NA | 686 | 222 | 32 |
| 5 | NA | NA | NA | 612 | 67 | 11 |
| 8 | NA | NA | NA | 870 | NA | NA |

TABLE 13

Pharmacokinetic parameters of d-amphetamine following oral administration of d-amphetamine or L-lysine-d-amphetamine

| Parameter | 12 mg/kg | | 30 mg/kg | | 60 mg/kg | |
|---|---|---|---|---|---|---|
| | Amp | K-Amp | Amp | K-Amp | Amp | K-Amp |
| AUC (ng · h/ml) | 2,738 | 1,958 | 12,623* | 2,387* | 5,081** | 476** |
| Percent | 100 | 72 | 100 | 19 | 100 | 9 |
| $C_{max}$ (ng/ml) | 621 | 352 | 3,726 | 231 | 4,101 | 647 |
| Percent | 100 | 57 | 100 | 6 | 100 | 16 |
| $T_{max}$ (hours) | 0.938 | 3.5 | NA | NA | NA | NA |
| Percent | 100 | 373 | NA | NA | NA | NA |

*0-5 h
**0-1.5 h

Example 8

Oral Bioavailability of L-lysine-d-amphetamine Dimesylate at Various Doses Approximating a Range of Therapeutic Human Doses Compared to a Suprapharmacological Dose Male Sprague-Dawley rats were provided water ad libitum, fasted overnight, and dosed by oral gavage with 1.5, 3, 6, 12, and 60 mg/kg of amphetamine sulfate or L-lysine-d-amphetamine containing the equivalent amounts of d-amphetamine. Concentrations of d-amphetamine were measured by ELISA.

It has been demonstrated that when lysine is conjugated to the active agent d-amphetamine, the levels of d-amphetamine at 30 minutes post-administration are decreased by approximately 50% over a dosage range of 1.5 to 12 mg/kg. However, when a suprapharmacological dose (60 mg/kg) is given, the levels of d-amphetamine from L-lysine-d-amphetamine only reached 8% of those seen for d-amphetamine sulfate (See Table 14, Table 15, and FIG. 15). The substantial decrease in oral bioavailability at a high dose greatly reduces the abuse potential of L-lysine-d-amphetamine.

TABLE 14

Levels of d-amphetamine vs. dosage at 0.5 h post dosing with d-amphetamine sulfate

| | Dose mg/kg | | | | |
|---|---|---|---|---|---|
| | 1.5 | 3 | 6 | 12 | 60 |
| ng/ml 0.5 h | 109 ± 59 | 196 ± 72 | 294 ± 202 | 344 ± 126 | 3239 ± 73 |
| Percent | 100 | 100 | 100 | 100 | 100 |

TABLE 15

Levels of d-amphetamine vs. dosage at 0.5 h post dosing with L-lysine-d-amphetamine

| | Dose mg/kg | | | | |
|---|---|---|---|---|---|
| | 1.5 | 3 | 6 | 12 | 60 |
| ng/ml 0.5 h | 45 ± 10 | 86 ± 26 | 129 ± 46 | 172 ± 113 | 266 ± 18 |
| Percent | 41 | 44 | 44 | 50 | 8 |

Example 9

Decreased Oral Bioavailability of L-lysine-d-amphetamine Dimesylate at a High Dose An additional oral PK study illustrated in FIG. 16 shows the d-amphetamine blood levels of a 60 mg/kg dose over an 8 h time course. In the case of d-amphetamine, blood levels quickly reached a very high level, and 8 of 12 animals either died or were sacrificed due to acute symptoms of toxicity. Blood levels (Table 16 and Table 17) of animals administered L-lysine-d-amphetamine, on the other hand, did not peak until 5 hours and reached only a fraction of the levels of the animals receiving amphetamine. (Note: Valid data past 3 h for d-amphetamine could not be determined due to death and sacrifice of animals).

TABLE 16

Mean plasma concentrations of d-amphetamine vs. L-lysine-d-amphetamine following oral administration of a high dose (60 mg/kg)

| | Plasma Amphetamine Concentrations (ng/ml) | | | | | |
|---|---|---|---|---|---|---|
| | d-amphetamine | | | L-lysine-d-amphetamine | | |
| Hours | Mean | ±SD | CV | Mean | ±SD | CV |
| 0 | NA | NA | NA | NA | NA | NA |
| 0.25 | 2174 | 907 | 42 | 35 | 17 | 48 |
| 0.5 | 2643 | 578 | 22 | 81 | 33 | 41 |
| 1 | 2828 | 1319 | 47 | 212 | 30 | 14 |
| 1.5 | 2973 | 863 | 29 | 200 | 79 | 40 |
| 3 | 2944* | 95 | 3 | 440 | 133 | 30 |
| 5 | 153* | NA | NA | 565 | 100 | 18 |
| 8 | 1309** | NA | NA | 410 | 206 | 50 |

*n = 2
**n = 1

TABLE 17

Pharmacokinetic parameters of d-amphetamine vs. L-lysine-d-amphetamine

| Drug | AUC ng · h/ml | Percent d-Amp | $C_{max}$ (ng/ml) | Percent d-Amp | Mean Peak (ng/ml) | Percent d-Amp |
|---|---|---|---|---|---|---|
| d-amphetamine | 13420 | 100 | 3623 | 100 | 2973 | 100 |
| L-lysine-d-amphetamine | 3,143 | 39 | 582 | 16 | 565 | 19 |

Example 10

Oral Bioavailability of d-amphetamine Following Administration of an Extended Release Formulation (Intact or Crushed) or L-lysine-d-amphetamine Dimesylate Doses of an extended release formulation of d-amphetamine sulfate (Dexedrine Spansule® capsules, GlaxoSmithKline) were orally administered to rats as intact capsules or as crushed capsules and compared to a dose of L-lysine-d-amphetamine containing an equivalent amount of d-amphetamine base (FIG. 20). The crushed capsules showed an increase in $C_{max}$ and $AUC_{inf}$ of 84 and 13 percent, respectively, as compared to intact capsules (Table 18 and Table 19). In contrast, $C_{max}$ and $AUC_{inf}$ of d-amphetamine following administration of L-lysine-d-amphetamine were similar to that of the intact capsule illustrating that extended release is inherent to the compound itself and can not be circumvented by simple manipulation.

TABLE 18

Time-course concentrations of d-amphetamine following oral administration of extended release Dexedrine Spansule ® capsules, crushed extended release Dexedrine Spansule ® capsules, or L-lysine-d-amphetamine (3 mg/kg d-amphetamine base)

| | Plasma Concentration (ng/ml) | | |
|---|---|---|---|
| Hours | Intact Spansule ® Capsule | Crushed Spansule ® Capsule | L-lysine-d-amphetamine |
| 0 | 0 | 0 | 0 |
| 0.25 | 32 | 46 | 3 |
| 0.5 | 33 | 85 | 5 |
| 1 | 80 | 147 | 34 |
| 1.5 | 61 | 101 | 60 |
| 3 | 64 | 66 | 76 |
| 5 | 46 | 39 | 66 |
| 8 | 34 | 12 | 38 |

TABLE 19

Pharmacokinetic parameters of d-amphetamine following oral administration of extended release Dexedrine Spansule ® capsules, crushed extended release Dexedrine Spansule ® capsules, or L-lysine-d-amphetamine (3 mg/kg d-amphetamine base)

| Parameter | Intact Spansule ® Capsule | Crushed Spansule ® Capsule | L-lysine-d-amphetamine |
|---|---|---|---|
| $AUC_{0-8h}$ (ng · h/ml) | 399 | 449 | 434 |
| Percent | 100 | 113 | 109 |
| $C_{max}$ (ng/ml) | 80 | 147 | 76 |
| Percent | 100 | 184 | 95 |
| $T_{max}$ (hours) | 1 | 1 | 3 |
| Percent | 100 | 100 | 300 |

This example illustrates the advantage of the invention over conventional controlled release formulations of d-amphetamine.

Example 11

Decreased Intranasal Bioavailability of L-lysine-d-amphetamine vs. Amphetamine a. Intranasal (IN) Bioavailability of L-lysine-d-amphetamine Hydrochloride Male Sprague-Dawley rats were dosed by intranasal administration with 3 mg/kg of amphetamine sulfate or L-lysine-d-amphetamine hydrochloride containing the equivalent amounts of d-amphetamine. L-lysine-d-amphetamine did not release any significant amount of d-amphetamine into circulation by IN administration. Mean (n=4) plasma amphetamine concentration curves of amphetamine vs. L-lysine-d-amphetamine are shown in FIG. 17. Pharmacokinetic parameters for 1N administration of L-lysine-d-amphetamine are summarized in Table 20.

TABLE 20

Pharmacokinetic parameters of d-amphetamine vs. L-lysine-d-amphetamine hydrochloride by IN administration

| Drug | AUC (0-1.5 h) ng · h/ml | Percent d-amphetamine | $C_{max}$ (ng/ml) | Percent d-amphetamine |
|---|---|---|---|---|
| Amphetamine | 727 | 100 | 1,377 | 100 |
| L-lysine-d-amphetamine | 4 | 0.5 | 7 | 0.5 |

The process of part a was repeated using L-lysine-d-amphetamine mesylate salt:

TABLE 21

Pharmacokinetic parameters of d-amphetamine vs. L-lysine-d-amphetamine mesylate salt by IN administration

| Drug | AUC (0-1.0 h) ng · h/ml | Percent d-amphetamine | $C_{max}$ (ng/ml) | Percent d-amphetamine |
|---|---|---|---|---|
| Amphetamine | 573 | 100 | 1114 | 100 |
| L-lysine-d-amphetamine mesylate salt | 25 | 4 | 26 | 2 |

This example illustrates that when lysine is conjugated to the active agent d-amphetamine, the bioavailability by the intranasal route is substantially decreased, thereby diminishing the ability to abuse the drug by this route.

Example 12

Intravenous Bioavailability of Amphetamine vs. L-lysine-d-amphetamine Dimesylate Male Sprague-Dawley rats were dosed by intravenous tail vein injection with 1.5 mg/kg of d-amphetamine or L-lysine-d-amphetamine containing the equivalent amount of amphetamine. As observed with IN dosing, the conjugate did not release a significant amount of d-amphetamine. Mean (n=4) plasma concentration curves of amphetamine vs. L-lysine-d-amphetamine are shown in FIG. 19. Pharmacokinetic parameters for IV administration of L-lysine-d-amphetamine are summarized in Table 22.

TABLE 22

Pharmacokinetic parameters of d-amphetamine vs. L-lysine-d-amphetamine by IV administration

| Drug | AUC (0-1.5 h) ng · h/ml | Percent Amphetamine | $C_{max}$ (ng/ml) | Percent Amphetamine |
|---|---|---|---|---|
| Amphetamine | 190 | 100 | 169 | 100 |
| K-amphetamine | 6 | 3 | 5 | 3 |

This example illustrates that when lysine is conjugated to the active agent amphetamine, the bioavailability of amphetamine by the intravenous route is substantially decreased, thereby diminishing the ability to abuse the drug by this route.

Example 13

Oral Bioavailability of L-lysine-d-amphetamine Dimesylate Compared to d-amphetamine at Escalating Doses The fraction of intact L-lysine-d-amphetamine absorbed following oral administration in rats increased non-linearly in proportion to escalating doses from 1.5 to 12 mg/kg (FIG. 21-FIG. 25). The fraction absorbed at 1.5 mg/kg was only 2.6 percent whereas it increased to 24.6 percent by 12 mg/kg. The fraction absorbed fell to 9.3 percent at the high dose of 60 mg/kg. $T_{max}$ ranged from 0.25 to 3 hours, and peak concentrations occurred earlier for L-lysine-d-amphetamine than for d-amphetamine. L-lysine-d-amphetamine was cleared more rapidly than d-amphetamine with nearly undetectable concentrations by 8 hours at the lowest dose.

The bioavailability (AUC) of d-amphetamine from each drug administered was approximately equivalent at low doses. $T_{max}$ for d-amphetamine from L-lysine-d-amphetamine ranged from 1.5 to 5 hours as compared to 0.5 to 1.5 following administration of d-amphetamine sulfate. The difference in $T_{max}$ was greater at higher doses. $C_{max}$ of d-amphetamine from L-lysine-d-amphetamine was reduced by approximately half as compared to the $C_{max}$ of d-amphetamine from d-amphetamine sulfate administration at doses of 1.5 to 6 mg/kg, doses approximating therapeutic human equivalent doses (HEDs). Thus, at therapeutic doses, the pharmacokinetics of d-amphetamine from L-lysine-d-amphetamine resembled that of a sustained release formulation.

HEDs are defined as the equivalent dose for a 60 kg person in accordance to the body surface area of the animal model. The adjustment factor for rats is 6.2. The HED for a rat dose of 1.5 mg/kg of d-amphetamine, for example, is equivalent to 1.5/6.2×60=14.52 d-amphetamine base; which is equivalent to 14.52/0.7284=19.9 mg d-amphetamine sulfate, when adjusted for the salt content.

TABLE 23

Human Equivalent Doses (HEDs) of d-amphetamine sulfate

| Rat dose of d-amphetamine (mg/kg) | Human equivalent dose (HED) of d-amphetamine sulfate (mg) |
| --- | --- |
| 1.5 | 19.9 |
| 3 | 39.9 |
| 6 | 79.7 |
| 12 | 159.4 |
| 30 | 399 |
| 60 | 797.2 |

At suprapharmacological doses (12 and 60 mg/kg), $C_{max}$ was reduced by 73 and 84 percent, respectively, as compared to d-amphetamine sulfate. For these high doses, the AUCs for d-amphetamine from L-lysine-d-amphetamine were substantially decreased compared to those of d-amphetamine sulfate, with the $AUC_{inf}$ reduced by 76% at the highest dose (60 mg/kg). At 60 mg/kg, the levels of d-amphetamine from d-amphetamine sulfate spiked rapidly; the experimental time course could not be completed due to extreme hyperactivity necessitating humane euthanasia.

In summary, oral bioavailability of d-amphetamine from L-lysine-d-amphetamine decreased to some degree at higher doses. However, pharmacokinetics with respect to dose were nearly linear for L-lysine-d-amphetamine at doses from 1.5 to 60 mg/kg with the fraction absorbed ranging from 52 to 81 percent (extrapolated from 1.5 mg/kg dose). Pharmacokinetics of d-amphetamine sulfate was also nearly linear at lower doses of 1.5 to 6 mg/kg with the fraction absorbed ranging from 62 to 84 percent. In contrast to L-lysine-d-amphetamine, however, parameters were disproportionately increased at higher doses for d-amphetamine sulfate with the fraction absorbed calculated as 101 and 223 percent (extrapolated from 1.5 mg/kg dose), respectively, for the suprapharmacological doses of 12 and 60 mg/kg.

The results suggest that the capacity for clearance of d-amphetamine when delivered as the sulfate salt becomes saturated at the higher doses whereas the gradual hydrolysis of L-lysine-d-amphetamine precludes saturation of d-amphetamine elimination at higher doses. The difference in proportionality of dose to bioavailability ($C_{max}$ and AUC) for d-amphetamine and L-lysine-d-amphetamine is illustrated in FIG. 26-FIG. 28. The pharmacokinetic properties of L-lysine-d-amphetamine as compared to d-amphetamine at the higher doses decrease the ability to escalate doses. This improves the safety and reduces the abuse liability of L-lysine-d-amphetamine as a method of delivering d-amphetamine for the treatment of ADHD or other indicated conditions.

Example 14

Intranasal Bioavailability of L-lysine-d-amphetamine Dimesylate Compared to d-amphetamine As shown in FIG. 31 and FIG. 32, bioavailability of d-amphetamine following bolus intranasal administration of L-lysine-d-amphetamine was approximately 5 percent of that of the equivalent d-amphetamine sulfate dose with $AUC_{inf}$ values of 56 and 1032, respectively. $C_{max}$ of d-amphetamine following L-lysine-d-amphetamine administration by the intranasal route was also about 5 percent of that of the equivalent amount of d-amphetamine sulfate with values of 78.6 ng/mL and 1962.9 ng/mL, respectively. $T_{max}$ of d-amphetamine concentration was delayed substantially for L-lysine-d-amphetamine (60 minutes) as compared to $T_{max}$ of d-amphetamine sulfate (5 minutes), reflecting the gradual hydrolysis of L-lysine-d-amphetamine. Also, a high concentration of intact L-lysine-d-amphetamine was detected following intranasal administration. These results suggest that intranasal administration of L-lysine-d-amphetamine provides only minimal hydrolysis of L-lysine-d-amphetamine and thus only minimal release of d-amphetamine.

Example 15

Intravenous Bioavailability of L-lysine-d-amphetamine Dimesylate Compared to d-amphetamine As shown in FIG. 33 and FIG. 34, bioavailability of d-amphetamine following bolus intravenous administration of L-lysine-d-amphetamine was approximately one-half that of the equivalent d-amphetamine sulfate dose with $AUC_{inf}$ values of 237.8 and 420.2, respectively. $C_{max}$ of d-amphetamine following L-lysine-d-amphetamine administration was only about one-fourth that of the equivalent amount of d-amphetamine with values of 99.5 and 420.2, respectively. $T_{max}$ of d-amphetamine concentration was delayed substantially for L-lysine-d-amphetamine (30 minutes) as compared to $T_{max}$ of d-amphetamine sulfate (5 minutes), reflecting the gradual hydrolysis of L-lysine-d-amphetamine. In conclusion, the bioavailability of d-amphetamine by the intravenous route is substantially decreased and delayed when given as L-lysine-d-amphetamine. Moreover, bioavailability is less than that obtained by oral administration of the equivalent dose of L-lysine-d-amphetamine.

Summary of LC/MS/MS Bioavailability Data in Rats

The following tables summarize the bioavailability data collected in the experiments discussed in Examples 13-15.

Table 24, Table 25, and Table 26 summarize the pharmacokinetic parameters of d-amphetamine following oral, intranasal, and intravenous administration, respectively, of d-amphetamine or L-lysine-d-amphetamine.

TABLE 24

Pharmacokinetic parameters of d-amphetamine following oral administration of L-lysine-d-amphetamine or d-amphetamine at escalating doses

| Drug | Dose (mg/kg) | $C_{max}$ (ng/mL) | $T_{max}$ (h) | $AUC_{0-8}$ (ng·h/mL) | $AUC_{inf}$ (ng·h/mL) | $AUC_{inf}$ alt. calc.* | F (%) | AUC/Dose (ng·h·kg/mL/mg) | $C_{max}$/Dose (ng·kg/mL/mg) |
|---|---|---|---|---|---|---|---|---|---|
| K-Amp | 1.5 | 59.6 | 3 | 308 | 331 | 376 | 61 | 220.7 | 39.7 |
| Amp | 1.5 | 142.2 | 0.5 | 446 | 461 | 483 | 84 | 307.3 | 94.8 |
| K-Amp | 3 | 126.9 | 1.5 | 721 | 784 | 963 | 72 | 261.3 | 42.3 |
| Amp | 3 | 217.2 | 1.5 | 885 | 921 | 1,059 | 84 | 307.0 | 72.4 |
| K-Amp | 6 | 310.8 | 3 | 1,680 | 1,797 | 2,009 | 82 | 299.5 | 51.8 |
| Amp | 6 | 815.3 | 0.25 | 1,319 | 1,362 | 1429 | 62 | 227.0 | 135.9 |
| K-Amp | 12 | 412.6 | 5 | 2,426 | 2,701 | 2,701 | 62 | 225.1 | 34.4 |
| Amp | 12 | 1,533.1 | 0.25 | 4,252 | 4,428 | 4,636 | 101 | 369.0 | 127.8 |
| K-Amp | 60 | 2,164.3 | 5 | 9995.1 | 11,478 | 11,478 | 52 | 191.3 | 36.1 |
| Amp | 60 | 13,735 | 1 | 14,281** | 48,707 | 48,707 | 223 | 811.8 | 228.9 |

*An alternative calculation of $AUC_{inf}$ can be performed using WinNonlin ® software (Version 4.1, Pharsight, Inc., Mountain View, California).
**AUC (0-1.5)

TABLE 25

Pharmacokinetic parameters of d-amphetamine following bolus intravenous administration of L-lysine-d-amphetamine (1.5 mg/kg)

| Route | Drug | Dose (mg/kg) | $C_{max}$ (ng/mL) | $T_{max}$ (h) | $AUC_{0-24}$ (ng·h/mL) | $AUC_{0-24}$ alt. calc.* | $AUC_{inf}$ (ng·h/mL) | $AUC_{inf}$ alt. calc.* |
|---|---|---|---|---|---|---|---|---|
| IV | K-Amp | 1.5 | 99.5 | 0.5 | 237.8 | 207 | 237.9 | 218 |
| IV | Amp | 1.5 | 420.2 | 0.083 | 546.7 | 511 | 546.9 | 521 |

TABLE 26

Pharmacokinetic parameters of d-amphetamine following intranasal administration of L-lysine-d-amphetamine

| Route | Drug | Dose (mg/kg) | $C_{max}$ (ng/mL) | $T_{max}$ (h) | $AUC_{0-1}$ (ng·h/mL) | $AUC_{inf}$ (ng·h/mL) | $AUC_{inf}$ alt. calc.* |
|---|---|---|---|---|---|---|---|
| IN | K-Amp | 3 | 78.6 | 1 | 56 | 91 | NA |
| IN | Amp | 3 | 1962.9 | 0.083 | 1032 | 7291 | 1,267 |

Table 27, Table 28, and Table 29 summarize the pharmacokinetic parameters of L-lysine-d-amphetamine following oral, intravenous, and intranasal administration of L-lysine-d-amphetamine.

TABLE 27

Pharmacokinetic parameters of L-lysine-d-amphetamine following oral administration of L-lysine-d-amphetamine at escalating doses

| Route | Drug | Dose (mg/kg) | $C_{max}$ (ng/ml) | $T_{max}$ (ng/ml) | $AUC_{0-8}$ (ng·h/mL) | $AUC_{inf}$ (ng·h/mL) | $AUC_{inf}$ alt. calc.* | F (%) |
|---|---|---|---|---|---|---|---|---|
| Oral | K-Amp | 1.5 | 36.5 | 0.25 | 59.4 | 60 | 60 | 2.6 |
| Oral | K-Amp | 3 | 135.4 | 1.5 | 329.7 | 332.1 | 331 | 7.2 |
| Oral | K-Amp | 6 | 676.8 | 0.25 | 1156.8 | 1170.8 | 1,176 | 12.8 |
| Oral | K-Amp | 12 | 855.9 | 1 | 4238.6 | 4510.4 | 5,169 | 24.6 |
| Oral | K-Amp | 60 | 1870.3 | 3 | 8234.3 | 8499.9 | 8,460 | 9.3 |

TABLE 28

Pharmacokinetic parameters of L-lysine-d-amphetamine following bolus intravenous administration of L-lysine-d-amphetamine

| Route | Drug | Dose (mg/kg) | $C_{max}$ (ng/mL) | $T_{max}$ (h) | $AUC_{0-24}$ (ng·h/mL) | $AUC_{inf}$ (ng·h/mL) |
|---|---|---|---|---|---|---|
| IV | K-Amp | 1.5 | 4513.1 | 0.083 | 2,282 | 2,293 |

TABLE 29

Pharmacokinetic parameters of L-lysine-d-amphetamine following intranasal administration of L-lysine-d-amphetamine

| Route | Drug | Dose (mg/kg) | $C_{max}$ (ng/mL) | $T_{max}$ (h) | $AUC_{0-1}$ (ng·h/mL) | $AUC_{inf}$ (ng·h/mL) |
|---|---|---|---|---|---|---|
| IN | K-Amp | 3 | 3345.1 | 0.25 | 2,580 | 9,139 |

Table 30 and Table 31 summarize the percent bioavailability of d-amphetamine following oral, intranasal, and intravenous administration of L-lysine-d-amphetamine as compared to d-amphetamine sulfate.

TABLE 30

Percent bioavailability ($AUC_{inf}$) of d-amphetamine following administration of L-lysine-d-amphetamine by various routes as compared to bioavailability following administration of d-amphetamine sulfate

| | Dose (mg/kg) d-amphetamine base | | | | |
|---|---|---|---|---|---|
| | 1.5 | 3 | 6 | 12 | 60 |
| HED | 19.9 | 39.9 | 79.7 | 159.4 | 797.2 |
| Oral | 72 | 85 | 132 | 61 | 24 |
| IV | 43 | NA | NA | NA | NA |
| IN | NA | 1 | NA | NA | NA |

TABLE 31

Percent bioavailability ($C_{max}$) of d-amphetamine following administration of L-lysine-d-amphetamine by various routes as compared to bioavailability following administration of d-amphetamine sulfate

| | Dose (mg/kg) d-amphetamine base | | | | |
|---|---|---|---|---|---|
| | 1.5 | 3 | 6 | 12 | 60 |
| HED | 19.9 | 39.9 | 79.7 | 159.4 | 797.2 |
| Oral | 42 | 58 | 38 | 27 | 16 |
| IV | 24 | NA | NA | NA | NA |
| IN | NA | 4 | NA | NA | NA |

Table 32-Table 37 summarize the time-course concentrations of d-amphetamine and L-lysine-d-amphetamine following oral, intranasal, and intravenous administration of d-amphetamine or L-lysine-d-amphetamine.

TABLE 32

Time-course concentrations of d-amphetamine following bolus intravenous administration of L-lysine-d-amphetamine or d-amphetamine sulfate (1.5 mg/kg)

| Time (hours) | Concentration (ng/ml) | |
|---|---|---|
| | K-Amp | Amp sulfate |
| 0 | 0 | 0 |
| 0.083 | 52.8 | 420.2 |
| 0.5 | 99.5 | 249.5 |
| 1.5 | 47.1 | 97.9 |
| 3 | 21.0 | 38.3 |
| 5 | 9.0 | 13.2 |
| 8 | 3.7 | 4.3 |
| 24 | 0.1 | 0.2 |

TABLE 33

Time-course concentrations of L-lysine-d-amphetamine following bolus intravenous administration of L-lysine-d-amphetamine (1.5 mg/kg)

| Time (hours) | K-Amp concentration (ng/ml) |
|---|---|
| 0 | 0 |
| 0.083 | 4513.1 |
| 0.5 | 1038.7 |
| 1.5 | 131.4 |
| 3 | 19.3 |
| 5 | 17.9 |
| 8 | 8.7 |
| 24 | 11.5 |

TABLE 34

Time-course concentrations of d-amphetamine following oral administration of L-lysine-d-amphetamine at various doses

| Time (hours) | Concentration (ng/ml) | | | | |
|---|---|---|---|---|---|
| | 1.5 mg/kg | 3 mg/kg | 6 mg/kg | 12 mg/kg | 60 mg/kg |
| 0 | 0 | 0 | 0 | 0 | 0 |
| 0.25 | 20.5 | 25.3 | 96 | 54.3 | 90.9 |
| 0.5 | 34 | 40.9 | 140.2 | 96 | 175.1 |
| 1 | 46.7 | 95.1 | 225.9 | 233.3 | 418.8 |
| 1.5 | 40.7 | 126.9 | 268.4 | 266 | 440.7 |
| 3 | 59.6 | 105 | 310.8 | 356.8 | 1145.5 |
| 5 | 38.6 | 107.6 | 219.5 | 412.6 | 2164.3 |
| 8 | 17.1 | 48 | 86 | 225.1 | 1227.5 |

TABLE 35

Time-course concentrations of d-amphetamine following oral administration of d-amphetamine sulfate at various doses

| Time (hours) | Concentration (ng/ml) | | | | |
|---|---|---|---|---|---|
| | 1.5 mg/kg | 3 mg/kg | 6 mg/kg | 12 mg/kg | 60 mg/kg |
| 0 | 0 | 0 | 0 | 0 | 0 |
| 0.25 | 107.1 | 152.6 | 815.3 | 1533.1 | 6243.6 |
| 0.5 | 142.2 | 198.4 | 462.7 | 1216 | 7931.6 |
| 1 | 105.7 | 191.3 | 301.3 | 828.8 | 13735.2 |
| 1.5 | 129.5 | 217.2 | 314 | 904.8 | 11514.9 |
| 3 | 52.6 | 135.3 | 134.6 | 519.9 | NA |
| 5 | 29.5 | 73.5 | 77.4 | 404.3 | NA |
| 8 | 11.5 | 25.7 | 31.8 | 115.4 | NA |

TABLE 36

Time-course concentrations of d-amphetamine following intranasal administration of L-lysine-d-amphetamine or d-amphetamine sulfate (3 mg/kg)

| Time | Concentration (ng/ml) | |
|---|---|---|
| (hours) | K-Amp | Amp sulfate |
| 0 | 0 | 0 |
| 0.083 | 31.2 | 1962.9 |
| 0.25 | 45.3 | 1497.3 |
| 0.5 | 61.3 | 996.2 |
| 1 | 78.6 | 404.6 |
| AUC | 56 | 1032.3 |

TABLE 37

Time-course concentrations of L-lysine-d-amphetamine following intranasal administration of L-lysine-d-amphetamine (3 mg/kg)

| Time (hours) | Concentration (ng/ml) K-Amp |
|---|---|
| 0 | 0 |
| 0.083 | 3345.1 |
| 0.25 | 3369.7 |
| 0.5 | 2985.8 |
| 1 | 1359.3 |

Example 16

Bioavailability of L-lysine-d-amphetamine Dimesylate or d-amphetamine Sulfate in Dogs (LC/MS/MS Analysis)

Example Experimental Design:

This was a non-randomized, two-treatment crossover study. All animals were maintained on their normal diet and were fasted overnight prior to each dose administration. L-lysine-d-amphetamine dose was based on the body weight measured on the morning of each dosing day. The actual dose delivered was based on syringe weight before and after dosing. Serial blood samples were obtained from each animal by direct venipuncture of a jugular vein using vacutainer tubes containing sodium heparin as the anticoagulant. Derived plasma samples were stored frozen until shipment to Quest Pharmaceutical Services, Inc. (Newark, Del.). Pharmacokinetic analysis of the plasma assay results was conducted by Calvert. Animals were treated as follows:

| Number of Dogs/Sex | Route of Administration | Treatment | Dose Conc. (mg/mL) | Dose Vol. (mL/kg) | Dose Level (mg/kg) |
|---|---|---|---|---|---|
| 3/M | PO | 1 | 0.2 | 10 | 1 |
| 3/M | IV | 2 | 1 | 2 | 1 |

Administration of the Test Article:

Oral: The test article was administered to each animal via a single oral gavage. On Day 1, animals received the oral dose by gavage using an esophageal tube attached to a syringe. Dosing tubes were flushed with approximately 20 mL tap water to ensure the required dosing solution was delivered.

Intravenous: On Day 8, animals received L-lysine-d-amphetamine as a single 30-minute intravenous infusion into a cephalic vein.

Sample Collection:

Dosing Formulations: Post-dosing, remaining dosing formulation was saved and stored frozen.

Blood: Serial blood samples (2 mL) were collected using venipuncture tubes containing sodium heparin. Blood samples were taken at 0, 0.25, 0.5, 1, 2, 4, 8, 12, 24, 48, and 72 hours post-oral dosing. Blood samples were collected at 0, 0.167, 0.33, 0.49 (prior to stop of infusion), 0.583, 0.667, 0.75, 1, 2, 3, 4, 8, 12, and 23 hours post-intravenous infusion start. Collected blood samples were chilled immediately.

Plasma: Plasma samples were obtained by centrifugation of blood samples. Duplicate plasma samples (about 0.2 mL each) were transferred into prelabeled plastic vials and stored frozen at approximately –70° C.

Sample Assay:

Plasma samples were analyzed for L-lysine-d-amphetamine and d-amphetamine using a validated LC-MS/MS method with an LLOQ of 1 ng/mL for both analytes.

Microsoft Excel (Version 6, Microsoft Corp., Redmond, Wash.) was used for calculation of mean plasma concentration and graphing of the plasma concentration-time data. Pharmacokinetic analysis (non-compartmental) was performed using the WinNonlin® software program (Version 4.1, Pharsight, Inc. Mountain View, Calif.). The maximum concentration ($C_{max}$) and the time to $C_{max}(T_{max})$ were observed values. The area under the plasma concentration-time curve (AUC) was determined using linear-log trapezoidal rules. The apparent terminal rate constant ($\lambda z$) was derived using linear least-squares regression with visual inspection of the data to determine the appropriate number of points (minimum of 3 data points) for calculating $\lambda z$. The $AUC_{0-inf}$ was calculated as the sum of $AUC_{0-t}$ and Cpred/$\lambda z$, where Cpred was the predicted concentration at the time of the last quantifiable concentration. The plasma clearance (CL/F) was determined as the ratio of Dose/$AUC_{0-inf}$. The mean residence time (MRT) was calculated as the ratio of $AUMC_{0-inf}/AUC_{0-inf}$ where $AUMC_{0-inf}$ was the area under the first moment curve from the time zero to infinity. The volume of distribution at steady state ($V_{ss}$) was estimated as CL*MRT. Half-life was calculated as ln 2/$\lambda z$. The oral bioavailability (F) was calculated as the ratio of $AUC_{0-inf}$ following oral dosing to $AUC_{0-inf}$ following intravenous dosing. Descriptive statistics (mean and standard deviation) of the pharmacokinetic parameters were calculated using Microsoft Excel.

The objectives of this study were to characterize the pharmacokinetics of L-lysine-d-amphetamine and d-amphetamine following administration of L-lysine-d-amphetamine in male beagle dogs. As shown in FIG. 35, in a cross-over design, L-lysine-d-amphetamine was administered to 3 male beagle dogs orally and intravenously. Blood samples were collected up to 24 and 72 hours after the intravenous and oral doses, respectively.

The mean L-lysine-d-amphetamine and d-amphetamine plasma concentration-time profiles following an intravenous or oral dose of L-lysine-d-amphetamine are presented in FIG. 37 and FIG. 38, respectively. Comparative profiles of L-lysine-d-amphetamine to d-amphetamine following both routes are depicted in FIG. 35 and FIG. 36. Individual plots are depicted in FIG. 39 and FIG. 40. The pharmacokinetic parameters are summarized in Table 38-Table 46.

Following a 30-minute intravenous infusion of L-lysine-d-amphetamine, the plasma concentration reached a peak at the end of the infusion. Post-infusion L-lysine-d-amphetamine concentration declined very rapidly in a biexponential manner, and fell below the quantifiable limit (1 ng/mL) by approximately 8 hours post-dose. Results of non-compartmental pharmacokinetic analysis indicate that L-lysine-d-amphetamine is a high clearance compound with a moderate volume of distribution ($V_{ss}$) approximating total body water (0.7 L/kg). The mean clearance value was 2087 mL/h·kg (34.8 mL/min·kg) and was similar to the hepatic blood flow in the dog (40 mL/min·kg).

L-lysine-d-amphetamine was rapidly absorbed after oral administration with $T_{max}$ at 0.5 hours in all three dogs. Mean absolute oral bioavailability was 33%, which suggests that L-lysine-d-amphetamine is very well absorbed in the dog. The apparent terminal half-life was 0.39 hours, indicating rapid elimination, as observed following intravenous administration.

Plasma concentration-time profiles of d-amphetamine following intravenous or oral administration of L-lysine-d-amphetamine were similar. See Table 39. At a 1 mg/kg oral dose of L-lysine-d-amphetamine, the mean $C_{max}$ of d-amphetamine was 104.3 ng/mL. The half-life of d-amphetamine was 3.1 to 3.5 hours, much longer when compared to L-lysine-d-amphetamine.

In this study, L-lysine-d-amphetamine was infused over a 30 minute time period. Due to rapid clearance of L-lysine-d-amphetamine it is likely that bioavailability of d-amphetamine from L-lysine-d-amphetamine would decrease if a similar dose were given by intravenous bolus injection. Even when given as an infusion the bioavailability of d-amphetamine from L-lysine-d-amphetamine did not exceed that of a similar dose given orally and the time to peak concentration was substantially delayed. This data further supports that L-lysine-d-amphetamine affords a decrease in the abuse liability of d-amphetamine by intravenous injection.

TABLE 38

Pharmacokinetic parameters of L-lysine-d-amphetamine in male beagle dogs following oral or intravenous administration of L-lysine-d-amphetamine (1 mg/kg d-amphetamine base)

| Route | Dose mg/kg | $C_{max}$ ng/mL | $T_{max}^a$ h | $AUC_{inf}$ ng·h/mL | $t_{1/2}$ h | MRT h | CL/F mL/h·kg | $V_{ss}$ mL/kg | F % |
|---|---|---|---|---|---|---|---|---|---|
| IV | 1 (0.00) | 1650 (178) | 0.49 (0.49-0.49) | 964 (97.1) | 0.88 (0.2) | 0.33 (0.03) | 2087 (199) | 689 (105.9) | NA |
| Oral | 1 (0.00) | 328.2 (91.9) | 0.5 (0.5-0.5) | 319 (46.3) | 0.39 (0.1) | 0.81 (0.19) | 6351 (898.3) | NA | 33 (1.9) |

$^a$median (range)
Abbreviations of pharmacokinetic parameters are as follows:
$C_{max}$, maximum observed plasma concentration;
$T_{max}$, time when $C_{max}$ observed;
$AUC_{0-t}$, total area under the plasma concentration versus time curve from 0 to the last data point;
$AUC_{0-inf}$, total area under the plasma concentration versus time curve;
$t_{1/2}$, apparent terminal half-life;
MRT, mean residence time;
CL/F, oral clearance;
$V_{ss}$, volume of distribution at steady state;
F, bioavailability.

TABLE 39

Pharmacokinetic parameters of d-amphetamine in male beagle dogs following oral or intravenous administration of L-lysine-d-amphetamine (1 mg/kg d-amphetamine base)

| Route | Dose (mg/kg) | $C_{max}$ (ng/mL) | $T_{max}^a$ (h) | $AUC_{inf}$ (ng·h/mL) | $t_{1/2}$ (h) |
|---|---|---|---|---|---|
| IV | 1 (0.00) | 113.2 (3.2) | 1.0 (0.67-2.0) | 672.5 (85.7) | 3.14 (0.4) |
| Oral | 1 (0.00) | 104.3 (21.8) | 2.0 (2-2) | 728.0 (204.9) | 3.48 (0.4) |

$^a$median (range)

TABLE 40

Pharmacokinetics of L-lysine-d-amphetamine in male beagle dogs following 30 min intravenous administration of L-lysine-d-amphetamine (1 mg/kg d-amphetamine base)

| Dog ID | $C_{max}$ (ng/mL) | $T_{max}^a$ (h) | $AUC_{0-t}$ (ng·h/mL) | $AUC_{inf}$ (ng·h/mL) | $t_{1/2}$ (h) | CL (mL/h/kg) | $V_{ss}$ (mL/kg) | MRT (h) |
|---|---|---|---|---|---|---|---|---|
| 1 | 1470.3 | 0.49 | 898.2 | 900.2 | 0.72 | 2222 | 807.4 | 0.36 |
| 2 | 1826.4 | 0.49 | 1072.3 | 1076.1 | $ND^b$ | 1859 | 603.4 | 0.32 |

TABLE 40-continued

Pharmacokinetics of L-lysine-d-amphetamine in male beagle dogs following 30 min intravenous administration of L-lysine-d-amphetamine (1 mg/kg d-amphetamine base)

| Dog ID | $C_{max}$ (ng/mL) | $T_{max}^{a}$ (h) | $AUC_{0-t}$ (ng·h/mL) | $AUC_{inf}$ (ng·h/mL) | $t_{1/2}$ (h) | CL (mL/h/kg) | $V_{ss}$ (mL/kg) | MRT (h) |
|---|---|---|---|---|---|---|---|---|
| 3 | 1654.2 | 0.49 | 914.1 | 916.9 | 1.05 | 2181 | 656.0 | 0.30 |
| Mean | 1650 | 0.49 | 961.5 | 964.4 | 0.88 | 2087 | 689.0 | 0.33 |
| SD | 178 | 0.49-0.49 | 96.0 | 97.1 | 0.2 | 199 | 105.9 | 0.03 |

$^{a}$median (range);
$^{b}$not determined
CL, clearance following IV administration

TABLE 41

Pharmacokinetic parameters of L-lysine-d-amphetamine in male beagle dogs following oral administration of L-lysine-d-amphetamine (1 mg/kg d-amphetamine base)

| Dog ID | $C_{max}$ (ng/mL) | $T_{max}^{a}$ (h) | $AUC_{0-t}$ (ng·h/mL) | $AUC_{inf}$ (ng·h/mL) | $t_{1/2}$ (h) | CL/F (mL/h/kg) | MRT (h) | F (%) |
|---|---|---|---|---|---|---|---|---|
| 1 | 350.2 | 0.5 | 275.3 | 277.1 | 0.24 | 7218 | 0.68 | 30.8 |
| 2 | 407.2 | 0.5 | 367.8 | 368.7 | 0.48 | 5424 | 0.74 | 34.3 |
| 3 | 227.4 | 0.5 | 310.8 | 312.0 | 0.45 | 6410 | 1.03 | 34.0 |
| Mean | 328.2 | 0.5 | 318.0 | 319.3 | 0.39 | 6351 | 0.81 | 33.0 |
| SD | 91.9 | 0.0 | 46.7 | 46.3 | 0.1 | 898.3 | 0.19 | 1.9 |

$^{a}$median (range)

TABLE 42

Pharmacokinetics of d-amphetamine in male beagle dogs following 30 min. intravenous administration of L-lysine-d-amphetamine (1 mg/kg d-amphetamine base)

| Dog ID | $C_{max}$ (ng/mL) | $T_{max}^{a}$ (h) | $AUC_{0-t}$ (ng·h/mL) | $AUC_{inf}$ (ng·h/mL) | $t_{1/2}$ (h) |
|---|---|---|---|---|---|
| 1 | 111.2 | 2.0 | 751.9 | 757.6 | 3.35 |
| 2 | 116.8 | 0.67 | 668.5 | 673.7 | 3.43 |
| 3 | 111.4 | 1.0 | 557.8 | 586.1 | 2.65 |
| Mean | 113.2 | 1.00 | 659.4 | 672.5 | 3.14 |
| SD | 3.2 | 0.67-2.0 | 97 | 85.7 | 0.4 |

$^{a}$median (range)

TABLE 43

Pharmacokinetics of d-amphetamine in male beagle dogs following oral administration of L-lysine-d-amphetamine (1 mg/kg d-amphetamine base)

| Dog ID | $C_{max}$ (ng/mL) | $T_{max}^{a}$ (h) | $AUC_{0-t}$ (ng·h/mL) | $AUC_{inf}$ (ng·h/mL) | $t_{1/2}$ (h) |
|---|---|---|---|---|---|
| 1 | 102.1 | 2.0 | 686.34 | 696.89 | 3.93 |
| 2 | 127.2 | 2.0 | 937.57 | 946.62 | 3.44 |
| 3 | 83.7 | 2.0 | 494.61 | 540.38 | 3.06 |
| Mean | 104.3 | 2.0 | 706.2 | 728.0 | 3.48 |
| SD | 21.8 | 2.0-2.0 | 222.1 | 204.9 | 0.4 |

$^{a}$median (range)

TABLE 44

Pharmacokinetics of d-amphetamine in male beagle dogs following oral administration of L-lysine-d-amphetamine or d-amphetamine sulfate (1.8 mg/kg d-amphetamine base)

| Time (hours) | Mean Plasma Concentration | | Standard Deviation (SD) | | Coefficient of Variation (CV) | |
|---|---|---|---|---|---|---|
| | Amp | K-Amp | Amp | K-Amp | Amp | K-Amp |
| 0 | 0 | 0 | 0 | 0 | 0 | 0 |
| 1 | 431.4 | 223.7 | 140.7 | 95.9 | 32.6 | 42.9 |
| 2 | 360 | 291.8 | 87.6 | 93.6 | 24.3 | 32.1 |
| 4 | 277.7 | 247.5 | 68.1 | 66 | 24.5 | 26.7 |
| 6 | 224.1 | 214.7 | 59.3 | 62.1 | 26.5 | 28.9 |
| 8 | 175.4 | 150 | 66.7 | 40.1 | 38.0 | 26.7 |
| 12 | 81.4 | 47.6 | 58.7 | 19 | 72.1 | 39.9 |
| 16 | 33 | 19.6 | 28.1 | 9 | 85.2 | 45.9 |
| 24 | 7.2 | 4.5 | 4.5 | 1.7 | 62.5 | 37.8 |

TABLE 45

Pharmacokinetics of d-amphetamine in female beagle dogs following oral administration of L-lysine-d-amphetamine or d-amphetamine sulfate (1.8 mg/kg d-amphetamine base)

| Time (hours) | Mean Plasma Concentration | | Standard Deviation (SD) | | Coefficient of Variation (CV) | |
|---|---|---|---|---|---|---|
| | Amp | K-Amp | Amp | K-Amp | Amp | K-Amp |
| 0 | 0 | 0 | 0 | 0 | 0 | 0 |
| 1 | 217.8 | 308.8 | 141.7 | 40.7 | 65.1 | 13.2 |
| 2 | 273.5 | 308 | 113.7 | 29.6 | 41.6 | 9.6 |
| 4 | 266 | 260.9 | 132.7 | 37.3 | 49.9 | 14.3 |
| 6 | 204.7 | 212.1 | 84.5 | 38.7 | 41.3 | 18.2 |
| 8 | 160.1 | 164.3 | 72.7 | 43.5 | 45.4 | 26.5 |
| 12 | 79.4 | 68.7 | 41.3 | 31 | 52.0 | 45.1 |

TABLE 45-continued

Pharmacokinetics of d-amphetamine in female beagle dogs following oral administration of L-lysine-d-amphetamine or d-amphetamine sulfate (1.8 mg/kg d-amphetamine base)

| Time | Mean Plasma Concentration | | Standard Deviation (SD) | | Coefficient of Variation (CV) | |
|---|---|---|---|---|---|---|
| (hours) | Amp | K-Amp | Amp | K-Amp | Amp | K-Amp |
| 16 | 25.5 | 22.3 | 13.4 | 4.7 | 52.5 | 21.1 |
| 24 | 5.6 | 5.4 | 4.1 | 1.9 | 73.2 | 35.2 |

TABLE 46

Pharmacokinetic parameters of d-amphetamine in male and female beagle dogs following oral administration of L-lysine-d-amphetamine or d-amphetamine sulfate (1.8 mg/kg d-amphetamine base)

| Parameter | Males Compound | | Females Compound | |
|---|---|---|---|---|
| | Amp | K-Amp | Amp | K-Amp |
| AUC$_{inf}$ | 3088.9 | 2382.2 | 2664.5 | 2569.9 |
| Percent | 100 | 77 | 100 | 96 |
| C$_{max}$ | 431.4 | 291.8 | 308.8 | 273.5 |
| Percent | 100 | 67 | 100 | 89 |
| T$_{max}$ (hours) | 1 | 2 | 1 | 2 |
| Percent | 100 | 200 | 100 | 200 |

Example 17

Delayed Cardiovascular Effects of L-lysine-d-amphetamine Dimesylate as Compared to d-amphetamine Following Intravenous Infusion Systolic and diastolic blood pressure (BP) are increased by d-amphetamine even at therapeutic doses. Since L-lysine-d-amphetamine is expected to release d-amphetamine (albeit slowly) as a result of systemic metabolism, a preliminary study was done using equimolar doses of d-amphetamine or L-lysine-d-amphetamine to 4 dogs (2 male and 2 female). The results suggest that the amide prodrug is inactive and that slow release of some d-amphetamine, occurs beginning 20 minutes after the first dose. Relative to d-amphetamine, however, the effects are less robust. For example, the mean blood pressure is graphed in FIG. 43. Consistent with previously published data (Kohli and Goldberg, 1982), small doses of d-amphetamine were observed to have rapid effects on blood pressure. The lowest dose (0.202 mg/kg, equimolar to 0.5 mg/kg of L-lysine-d-amphetamine) produced an acute doubling of the mean BP followed by a slow recovery over 30 minutes.

By contrast, L-lysine-d-amphetamine produced very little change in mean BP until approximately 30 minutes after injection. At that time, pressure increased by about 20-50%. Continuous release of d-amphetamine is probably responsible for the slow and steady increase in blood pressure over the remaining course of the experiment. Upon subsequent injections, d-amphetamine is seen to repeat its effect in a non-dose dependent fashion. That is, increasing dose 10-fold from the first injection produced a rise to the same maximum pressure. This may reflect the state of catecholamine levels in nerve terminals upon successive stimulation of d-amphetamine bolus injections. Note that the rise in mean blood pressure seen after successive doses of L-lysine-d-amphetamine (FIG. 43) produces a more gradual and less intense effect. Similar results were observed for left ventricular pressure (FIG. 44). These results further substantiate the significant decrease in d-amphetamine bioavailability by the intravenous route when given as L-lysine-d-amphetamine. As a result the rapid onset of the pharmacological effect of d-amphetamine that is sought by persons injecting the drug is eliminated.

TABLE 47

Effects of L-lysine-d-amphetamine on cardiovascular parameters in the anesthetized dog (mean values, n = 2)

| Treatment | Time | SAP | % Change | DAP | % Change | MAP | % Change | LVP | % Change |
|---|---|---|---|---|---|---|---|---|---|
| 0.9% Saline | 0 | 81 | 0 | 48 | 0 | 61 | 0 | 87 | 0 |
| 1 ml/kg | 30 | 87 | 7 | 54 | 11 | 67 | 10 | 87 | 0 |
| K-Amp | 0 | 84 | 0 | 51 | 0 | 64 | 0 | 86 | 0 |
| 0.5 mg/kg | 5 | 87 | 4 | 52 | 3 | 66 | 3 | 87 | 2 |
| | 15 | 93 | 11 | 51 | 1 | 67 | 5 | 95 | 11 |
| | 25 | 104 | 25 | 55 | 8 | 73 | 15 | 105 | 22 |
| | 30 | 107 | 28 | 58 | 14 | 77 | 21 | 108 | 26 |
| K-Amp | 0 | 105 | 0 | 55 | 0 | 74 | 0 | 108 | 0 |
| 1.0 mg/kg | 5 | 121 | 15 | 63 | 15 | 85 | 15 | 120 | 11 |
| | 15 | 142 | 35 | 73 | 33 | 100 | 35 | 140 | 29 |
| | 25 | 163 | 55 | 97 | 75 | 124 | 68 | 162 | 50 |
| | 30 | 134 | 28 | 73 | 32 | 98 | 32 | 144 | 33 |
| K-Amp | 0 | 132 | 0 | 71 | 0 | 95 | 0 | 144 | 0 |
| 5.0 mg/kg | 5 | 142 | 7 | 71 | 0 | 99 | 4 | 151 | 5 |
| | 15 | 176 | 33 | 98 | 39 | 130 | 37 | 184 | 28 |
| | 25 | 126 | −5 | 69 | −3 | 96 | 1 | 160 | 11 |
| | 30 | 132 | 0 | 70 | −1 | 99 | 4 | 163 | 13 |

SAP: systolic arterial pressure (mmHg);
MAP: mean arterial pressure (mmHg);
DAP: diastolic arterial pressure (mmHg);
LVP: left ventricular pressure (mmHg);
% Change: percent change from respective Time 0.

TABLE 48

Effects of d-amphetamine on cardiovascular parameters in the anesthetized dog (mean values, n = 2)

| Treatment | Time | SAP | % Change | DAP | % Change | MAP | % Change | LVP | % Change |
|---|---|---|---|---|---|---|---|---|---|
| 0.9% Saline | 0 | 110 | 0 | 67 | 0 | 84 | 0 | 105 | 0 |
| 1 ml/kg | 30 | 108 | −2 | 65 | −3 | 82 | −2 | 101 | −3 |
| d-amphetamine | 0 | 111 | 0 | 67 | 0 | 84 | 0 | 104 | 0 |
| 0.202 mg/kg | 5 | 218 | 97 | 145 | 117 | 176 | 109 | 214 | 107 |
|  | 15 | 168 | 52 | 97 | 45 | 125 | 49 | 157 | 52 |
|  | 25 | 148 | 34 | 87 | 30 | 110 | 31 | 142 | 37 |
|  | 30 | 140 | 26 | 80 | 20 | 103 | 23 | 135 | 30 |
| d-amphetamine | 0 | 139 | 0 | 78 | 0 | 101 | 0 | 133 | 0 |
| 0.404 mg/kg | 5 | 240 | 73 | 147 | 88 | 187 | 85 | 238 | 79 |
|  | 15 | 193 | 39 | 112 | 44 | 145 | 43 | 191 | 43 |
|  | 25 | 166 | 19 | 92 | 17 | 122 | 20 | 168 | 26 |
|  | 30 | 160 | 16 | 87 | 11 | 117 | 16 | 163 | 22 |
| d-amphetamine | 0 | 158 | 0 | 87 | 0 | 115 | 0 | 162 | 0 |
| 2.02 mg/kg | 5 | 228 | 44 | 128 | 48 | 169 | 47 | 227 | 40 |
|  | 15 | 196 | 24 | 107 | 23 | 142 | 23 | 200 | 24 |
|  | 25 | 189 | 20 | 102 | 17 | 135 | 17 | 192 | 19 |
|  | 30 | 183 | 16 | 98 | 13 | 129 | 12 | 187 | 16 |

Example 18

Pharmacodynamic (Locomotor) Response to Amphetamine vs. L-lysine-d-amphetamine diHCl by Oral Administration Male Sprague-Dawley rats were provided water ad libitum, fasted overnight, and dosed by oral gavage with 6 mg/kg of amphetamine or L-lysine-d-amphetamine containing the equivalent amount of d-amphetamine. Horizontal locomotor activity (HLA) was recorded during the light cycle using photocell activity chambers (San Diego Instruments). Total counts were recorded every 12 minutes for the duration of the test. Rats were monitored in three separate experiments for 5, 8, and 12 hours, respectively. Time vs. HLA counts for d-amphetamine vs. L-lysine-d-amphetamine is shown in FIG. 45 and FIG. 46. In each experiment the time until peak activity was delayed, and the pharmacodynamic effect was evident for an extended period of time for L-lysine-d-amphetamine as compared to d-amphetamine. The total activity counts for HLA of Lys-Amp dosed rats were increased (11-41%) over those induced by d-amphetamine in all three experiments.

TABLE 49

Locomotor activity of rats orally administered d-amphetamine vs. L-lysine-d-amphetamine (5 h)

| Test Material | Total Activity Counts | Total Activity Counts Above Baseline | Peak of activity (Counts per 0.2 h) | Time of Peak (Counts per 0.2 h) | Time of Last Count Above 200 per 0.2 h |
|---|---|---|---|---|---|
| Vehicle | 4689 | 4174 | 80 | 1.4 | — |
| K-Amp | 6417 | 5902 | 318 | 1.8 | 5 h |
| Amp | 515 | 0 | 291 | 0.6 | 2.6 h |

TABLE 50

Locomotor activity of rats orally administered d-amphetamine vs. L-lysine-d-amphetamine (12 h)

| Test Material | Total Activity Counts | Total Activity Counts Above Baseline | Peak of activity (Counts per 0.2 h) | Time of Peak (Counts per 0.2 h) | Time of Last Count Above 200 per 0.2 h |
|---|---|---|---|---|---|
| Vehicle | 936 | 0 | 81 | 7.2 | — |
| K-Amp | 8423 | 7487 | 256 | 1.8 | 8.6 h |
| Amp | 6622 | 5686 | 223 | 0.6 | 6.4 h |

Example 19

Pharmacodynamic Response to d-amphetamine vs. L-lysine-d-amphetamine diHCl by Intranasal Administration Male Sprague-Dawley rats were dosed by intranasal administration with d-amphetamine or L-lysine-d-amphetamine (1.0 mg/kg). In a second set of similarly dosed animals, carboxymethyl cellulose (CMC) was added to the drug solutions at a concentration of 62.6 mg/ml (approximately 2-fold higher than the concentration of L-lysine-d-amphetamine and 5-fold higher than the d-amphetamine content). The CMC drug mixtures were suspended thoroughly before each dose was delivered. Locomotor activity was monitored using the procedure described in Example 18. As shown in FIG. 47 and FIG. 48, the activity vs. time (1 hour or 2 hours) is shown for amphetamine/CMC vs. L-lysine-d-amphetamine and compared to that of amphetamine vs. L-lysine-d-amphetamine CMC. As seen in FIG. 47, addition of CMC to L-lysine-d-amphetamine decreased the activity response of IN dosed rats to levels similar to the water/CMC control, whereas no effect was seen on amphetamine activity by the addition of CMC. The increase in activity over baseline of L-lysine-d-amphetamine with CMC was only 9% compared to 34% for L-lysine-d-amphetamine without CMC when compared to activity observed for d-amphetamine dosed animals (Table 51). CMC had no observable effect on d-amphetamine activity induced by IN administration.

TABLE 51

Locomotor activity of intranasal d-amphetamine vs.
L-lysine-d-amphetamine with and without CMC

| Drug | n | Total Activity Counts (1 h) | Total Activity Counts Above Baseline | Percent Amp |
|---|---|---|---|---|
| Amp | 3 | 858 | 686 | 100 |
| Amp CMC | 3 | 829 | 657 | 100 |
| K-Amp | 4 | 408 | 237 | 35 |
| K-Amp CMC | 4 | 232 | 60 | 9 |
| Water | 1 | 172 | 0 | 0 |
| Water CMC | 1 | 172 | 0 | 0 |

Example 20

Pharmacodynamic Response to d-amphetamine vs. L-lysine-d-amphetamine diHCl by Intravenous Administration Male Sprague-Dawley rats were dosed by intravenous administration with d-amphetamine or L-lysine-d-amphetamine (1.0 mg/kg). The activity expressed as total activity counts over a three hour period of time is shown in FIG. 49. The activity induced by L-lysine-d-amphetamine was substantially decreased, and time to peak activity was delayed. The increase in activity over baseline of L-lysine-d-amphetamine was 34% for L-lysine-d-amphetamine when compared to activity observed for d-amphetamine dosed animals (Table 52).

TABLE 52

Total activity counts after intravenous administration of
d-amphetamine vs. L-lysine-d-amphetamine

| Drug | n | Total Activity Counts (3 h) | Above Baseline | Percent Amp |
|---|---|---|---|---|
| Amp | 3 | 1659 | 1355 | 100 |
| K-Amp | 4 | 767 | 463 | 34 |
| Water | 1 | 304 | 0 | 0 |

Example 21

Decrease in Toxicity of Orally Administered L-lysine-d-amphetamine diHCl

Three male and three female Sprague Dawley rats per group were given a single oral administration of L-lysine-d-amphetamine at 0.1, 1.0, 10, 60, 100, or 1000 mg/kg (Table 53). Each animal was observed for signs of toxicity and death on Days 1-7 (with Day 1 being the day of the dose), and one rat/sex/group was necropsied upon death (scheduled or unscheduled).

TABLE 53

Dosing chart for oral administration of L-lysine-d-amphetamine
toxicity testing

| Groups | No. of Animals M | No. of Animals F | Test Article | Dose (mg/kg) | Concentration (mg/mL) |
|---|---|---|---|---|---|
| 1 | 3 | 3 | L-lysine-d-amphetamine | 0.1 | 0.01 |
| 2 | 3 | 3 | L-lysine-d-amphetamine | 1.0 | 0.1 |
| 3 | 3 | 3 | L-lysine-d-amphetamine | 10 | 1.0 |

TABLE 53-continued

Dosing chart for oral administration of L-lysine-d-amphetamine
toxicity testing

| Groups | No. of Animals M | No. of Animals F | Test Article | Dose (mg/kg) | Concentration (mg/mL) |
|---|---|---|---|---|---|
| 4 | 3 | 3 | L-lysine-d-amphetamine | 60 | 6.0 |
| 5 | 3 | 3 | L-lysine-d-amphetamine | 100 | 10 |
| 6 | 3 | 3 | L-lysine-d-amphetamine | 1000 | 100 |

Key observations of this study include:

All animals in Groups 1-3 showed no observable signs throughout the conduct of the study.

All animals in Groups 4-6 exhibited increased motor activity within two hours post-dose and which lasted into Day 2.

One female rat dosed at 1000 mg/kg was found dead on Day 2. Necropsy revealed chromodacryorrhea, chromorhinorrhea, distended stomach (gas), enlarged adrenal glands, and edematous and distended intestines.

A total of 4 rats had skin lesions of varying degrees of severity on Day 3.

One male rat dosed at 1000 mg/kg was euthanatized on Day 3 due to open skin lesions on the ventral neck.

All remaining animals appeared normal from Day 4 through Day 7.

Animals were observed for signs of toxicity at 1, 2, and 4 h post-dose, and once daily for 7 days after dosing and cage-side observations were recorded. Animals found dead, or sacrificed moribund were necropsied and discarded.

Cage-side observations and gross necropsy findings are summarized above. The oral LD50 of d-amphetamine sulfate is 96.8 mg/kg. For L-lysine-d-amphetamine dimesylate, although the data are not sufficient to establish a lethal dose, the study indicates that the lethal oral dose of L-lysine-d-amphetamine is above 1000 mg/kg because only one death occurred out of a group of six animals. Although a second animal in this dose group was euthanatized on Day 3, it was done for humane reasons and it was felt that this animal would have fully recovered. Observations suggested drug-induced stress in Groups 4-6 that is characteristic of amphetamine toxicity (NTP, 1990; NIOSH REGISTRY NUMBER: SI1750000; Goodman et. al., 1985). All animals showed no abnormal signs on Days 4-7 suggesting full recovery at each treatment level.

The lack of data to support an established lethal dose is believed to be due to a putative protective effect of conjugating amphetamine with lysine. Intact L-lysine-d-amphetamine has been shown to be inactive, but becomes active upon metabolism into the unconjugated form (d-amphetamine). Thus, at high doses, saturation of metabolism of L-lysine-d-amphetamine into the unconjugated form may explain the lack of observed toxicity, which was expected at doses greater than 100 mg/kg, which is consistent with d-amphetamine sulfate (NTP, 1990). The formation rate of d-amphetamine and the extent of the formation of amphetamine may both attribute to the reduced toxicity. Alternatively, oral absorption of L-lysine-d-amphetamine may also be saturated at such high concentrations, which may suggest low toxicity due to limited bioavailability of L-lysine-d-amphetamine.

Example 22

In vitro Assessment of L-lysine-d-amphetamine diHCl Pharmacodynamic Activity

It was anticipated that the acylation of amphetamine, as in the amino acid conjugates discussed here, would significantly reduce the stimulant activity of the parent drug. For example, Marvola (1976) showed that N-acetylation of amphetamine completely abolished the locomotor activity increasing effects in mice. To confirm that the conjugate was not directly acting as a stimulant, we tested (NovaScreen, Hanover, Md.) the specific binding of Lys-Amp ($10^{-9}$ to $10^{-5}$ M) to human recombinant dopamine and norepinephrine transport binding sites using standard radioligand binding assays. The results (Table 54) indicate that the Lys-Amp did not bind to these sites. It seems unlikely that the conjugate retains stimulant activity in light of these results. (Marvola M. (1976) "Effect of acetylated derivatives of some sympathomimetic amines on the acute toxicity, locomotor activity and barbiturate anesthesia time in mice." Acta Pharmacol Toxicol (Copenh) 38(5): 474-89).

TABLE 54

Results from radioligand binding experiments with L-lysine-d-amphetamine

| Assay | Radioligand | Reference Compound | Ki (M) for Ref. Cpd. | Activity* |
|---|---|---|---|---|
| NE Transporter | [3H]-Nisoxetine | Desipramine | $4.1 \times 10^{-9}$ | No |
| DA Transporter | [3H]-WIN35428 | GBR-12909 | $7.7 \times 10^{-9}$ | No |

*No activity is defined as producing between −20% and 20% inhibition of radioligand binding (Novascreen).

TABLE 55

Percent inhibition of DAT and NET with L-lysine-d-amphetamine

| L-lysine-d-amphetamine (mol/L) | % inhibition DAT | % inhibition NET |
|---|---|---|
| $10^{-9}$ | −10.46 | 8.15 |
| $10^{-7}$ | 11.52 | −11.75 |
| $10^{-5}$ | −0.71 | 13.89 |

Example 23

In vitro Assessment to Release Amphetamine from L-lysine-d-amphetamine Dimesylate "Kitchen tests" were performed in anticipation of attempts by illicit chemists to release free amphetamine from the amphetamine conjugate. Preferred amphetamine conjugates are resistant to such attempts. Initial kitchen tests assessed the amphetamine conjugates' resistance to water, acid (vinegar), and base (baking powder and baking soda) where in each case, the sample was heated to boiling for 20-60 minutes. L-lysine-d-amphetamine and GGG-Amp released no detectable free amphetamine.

TABLE 56

In vitro assessment

| | Vinegar | Tap Water | Baking Powder | Baking Soda |
|---|---|---|---|---|
| L-lysine-d-amphetamine | 0% | 0% | 0% | 0% |
| Gly$_3$-Amp | 0% | 0% | 0% | 0% |

Amphetamine conjugate stability was assessed under concentrated conditions, including concentrated HCl and in 10 N NaOH solution at elevated temperatures. Lys-Amp stock solutions were prepared in H$_2$O and diluted 10-fold with concentrated HCl to a final concentration of 0.4 mg/mL and a final volume of 1.5 mL. Samples were heated in a water bath to about 90° C. for 1 hour, cooled to 20° C., neutralized, and analyzed by HPLC for free d-amphetamine. The results suggest that only a minimal amount of d-amphetamine is released under these concentrated conditions.

TABLE 57

Stability under concentrated conditions

| | % AUC | |
|---|---|---|
| solution | Lys-Amp | d-amphetamine |
| 10 N NaOH | 99 | <1 |
| conc. HCl | 96 | 4 |

Amphetamine conjugate stability was assessed under acidic conditions.

TABLE 58

Acids used for stability study

| Acid | Concentrations |
|---|---|
| Hydrochloric acid | 10%, 25%, 50%, 75%, and concentrated |
| Acetic acid | 10%, 25%, 50%, 75%, and concentrated |
| Sulfuric acid | 10%, 25%, 50%, 75%, and concentrated |
| Phosphoric acid | 10%, 25%, 50%, 75%, and concentrated |
| Nitric acid | 10%, 25%, 50%, 75%, and concentrated |
| Citric acid | 10%, 25%, 50%, 75%, and saturated |

At ambient temperature, only a limited amount of d-amphetamine was released. At 90° C., only a limited amount of d-amphetamine was released, but the decomposition of L-lysine-d-amphetamine was more pronounced. This suggested that the amide bond is stable, and that the conjugate usually degrades before an appreciable amount is hydrolyzed. At reflux conditions, concentrated hydrochloric acid and 50% sulfuric acid released 85% and 59%, respectively, of the d-amphetamine content, but rendered the drug in undesirable acidic solution. The process for recovering d-amphetamine from the acidic solution further reduces the yield.

In a similar test, reflux in concentrated HCl resulted in some hydrolysis after 5 hours (28%) with further hydrolysis occurring after 22 hours (76%). Reflux in concentrated H$_2$SO$_4$ for 2 hours resulted in complete decomposition of Lys-Amp and potentially released d-amphetamine. As described above, recovery of d-amphetamine from the acidic solution would further reduce the yield.

Amphetamine conjugate stability was also assessed under basic conditions, including variable concentrations of sodium hydroxide, potassium hydroxide, sodium carbonate, ammonium hydroxide, diethyl amine, and triethyl amine. The maximum d-amphetamine release was 25.4% obtained by 3M sodium hydroxide; all other basic conditions resulted in a release of less than 3%.

Example 24

Stability of L-lysine-d-amphetamine Dimesylate Under Treatment with Commercially Available Products The stability of L-lysine-d-amphetamine dimesylate was assessed under treatment commercially available acids, bases, and enzyme cocktails. For acids and bases (Table 59), 10 mg of Lys-Amp was mixed with 2 mL of each stock solution, and the solution was shaken at 20° C. For enzyme treatment (Table 60), 10 mg Lys-Amp was mixed with 5 mL of each enzyme cocktail, and the solution was shaken at 37° C. Each aliquot (0, 1, and 24 h) was neutralized and filtered prior to analysis by HPLC. Many of the commercially available reagents also contained various solvents and/or surfactants.

Unless otherwise indicated, solutions were used directly from the container and were combined with neat Lys-Amp solid. Lewis Red Devil® Lye, Enforcer Drain Care® Septic Treatment, and Rid-X® Septic Treatment were prepared as saturated solutions in $H_2O$. Enzymes used were purchased from Sigma and directly dissolved in water (3 mg/mL pepsin, 10 mg/mL pancreatin, 3 mg/mL pronase, 3 mg/mL esterase), while enzyme-containing nutraceuticals such as Omnigest® and VitälZym® were first either crushed or opened (1 tablet or capsule per 5 mL of $H_2O$).

The commercial acids and bases were ineffective in hydrolyzing Lys-Amp. Only treatment with Miracle-Gro® (7% release) and Olympic® Deck Cleaner (4% release) showed any release, but even after 24 hours, the amount of d-amphetamine was negligible. Among the enzyme products, only pure esterase (19% release) or pronase (24% release) mixtures successfully cleaved lysine (after 24 hours).

TABLE 59

Stability of L-lysine-d-amphetamine dimesylate under treatment with commercially available acids and bases

| Solution (active ingredients) | d-amphetamine (1) (w.t. % d-amphetamine) | |
|---|---|---|
| | 1 h | 24 h |
| Lysol ® Toilet (HCl) | 0 | 0 |
| Crete-nu (75% $H_3PO_4$) | 0 | 0 |
| CLR ® (sulfamic acid, hydroxyacetic acid) | 0 | 0 |
| Roebic ® Drain Flow (90% $H_2SO_4$) | 0 | 0 |
| Crown ® Muriatic Acid (31.45% HCl) | 0 | 0 |
| Liquid-Plumr ® (NaOH, NaClO, $H_2O_2$) | 0 | 0 |
| Brasso ® ($NH_4OH$) | 0 | 0 |
| Johnson ® Wax Degreaser ($K_2CO_3$) | 0 | 0 |
| Miracle-Gro ® (Urea, $K_3PO_4$) | 0 | 7 |
| Lewis Red Devil ® Lye (NaOH) | 0 | 0 |
| Drain Power (NaOH, NaClO) | 0 | 0 |
| Savogran TSP ($Na_3PO_4$) | 0 | 0 |
| Johnson ® Wax Stripper (NaOH) | 0 | 0 |
| Olympic ® Deck Cleaner (NaOH, NaClO) | 0 | 4 |
| Windex ® ($NH_4OH$) | 0 | 0 |
| Greased Lightning ® (basic components) | 0 | 0 |

TABLE 60

Stability of L-lysine-d-amphetamine dimesylate under treatment with commercially available enzyme cocktails

| Solution | d-amphetamine (1) (w.t. % d-amphetamine) | |
|---|---|---|
| | 1 h | 24 h |
| Cellfood ® | 0 | 0 |
| Drano ® Max with Bacteria | 0 | 0 |
| VitälZym ® | 0 | 0 |
| Omnigest ® | 0 | 0 |
| Enforcer ® Septic | 0 | 0 |
| Rid-X ® Septic | 0 | 0 |
| Esterase | 0 | 19 |
| Pancreatin | 0 | 0 |
| Pepsin | 0 | 0 |
| Pronase | 0 | 24 |

Example 25

Bioavailability of Various Peptide Amphetamine Conjugates (HCl Salts) Administered by Oral, Intranasal, and Intravenous Routes Oral administration: Male Sprague-Dawley rats were provided water ad libitum, fasted overnight, and dosed by oral gavage with amphetamine or amino acid-amphetamine conjugates containing the equivalent amount of amphetamine.

Intranasal administration: Male Sprague-Dawley rats were dosed by intranasal administration with amphetamine or lysine-amphetamine (1.8 mg/kg).

The relative in vivo performance of various amino acid-amphetamine compounds is shown in FIG. 50-FIG. 58 and summarized in Table 61. Intranasal bioavailability of amphetamine from Ser-Amp was decreased to some degree relative to free amphetamine. However, this compound was not bioequivalent with amphetamine by the oral route of administration. Phenylalanine was bioequivalent with amphetamine by the oral route of administration, however, little or no decrease in bioavailability by parenteral routes of administration was observed. $Gly_3$-Amp had nearly equal bioavailability (90%) by the oral route accompanied by a decrease in $C_{max}$ (74%). Additionally, $Gly_3$-Amp showed a decrease in bioavailability relative to amphetamine by intranasal and intravenous routes.

TABLE 61

Percent bioavailability of amino acid amphetamine compounds administered by oral, intranasal, or intravenous routes

| Drug | Oral | | Intranasal | | Intravenous | |
|---|---|---|---|---|---|---|
| | Percent AUC | Percent $C_{max}$ | Percent AUC | Percent $C_{max}$ | Percent AUC | Percent $C_{max}$ |
| Amphetamine | 100 | 100 | 100 | 100 | 100 | 100 |
| E-Amp | 73 | 95 | NA | NA | NA | NA |
| EE-Amp | 26 | 74 | NA | NA | NA | NA |
| EEE-Amp | 69 | 53 | 10 | 10 | NA | NA |
| L-Amp | 65 | 81 | NA | NA | NA | NA |
| S-Amp | 79/55 | 62/75 | 76 | 65 | NA | NA |
| G-Amp | 81 | 78 | 65 | 53 | NA | NA |
| GG-Amp | 79 | 88 | 88 | 85 | NA | NA |
| GGG-Amp | 111/68 | 74/73 | 32 | 38 | 45 | 46 |
| F-Amp | 95 | 91 | 97 | 95 | 87 | 89 |
| EEF-Amp | 42 | 73 | 39 | 29 | NA | NA |
| FF-Amp | 27 | 64 | NA | NA | NA | NA |

TABLE 61-continued

Percent bioavailability of amino acid amphetamine compounds administered by oral, intranasal, or intravenous routes

| Drug | Oral | | Intranasal | | Intravenous | |
|---|---|---|---|---|---|---|
| | Percent AUC | Percent $C_{max}$ | Percent AUC | Percent $C_{max}$ | Percent AUC | Percent $C_{max}$ |
| Gulonate-Amp | 1 | 1 | 0.4 | 0.5 | 3 | 5 |
| K-Amp | 98 | 55 | 0.5 | 0.5 | 3 | 3 |
| KG-Amp | 69 | 71 | 13 | 12 | NA | NA |
| dKlK-Amp | 16 | 7 | 2 | 2 | NA | NA |
| LE-Amp | 40 | 28 | 6 | 6 | NA | NA |
| H-Amp | 16 | 21 | 22 | 42 | NA | NA |
| P-Amp | 6 | 3 | 2 | 2 | NA | NA |
| PP-Amp | 61 | 80 | 47 | 43 | NA | NA |
| Y-Amp | 25 | 20 | 21 | 20 | NA | NA |
| I-Amp | 71 | 52 | 73 | 97 | NA | NA |

Several single amino acid amphetamine conjugates had comparable oral bioavailability (80-100%) to d-amphetamine. Lys, Gly, and Phe conjugates, for example, all demonstrated similar oral bioavailability to the parent drug. Dipeptide prodrugs generally showed lower bioavailability than the respective amino acid analogs, and tripeptide compounds displayed no discernable trend. Several amino acid amphetamine conjugates had decreased parenteral bioavailability. Preferred conjugates, such as Lys-Amp, exhibit both oral bioavailability comparable to d-amphetamine and decreased parenteral bioavailability compared to d-amphetamine.

Example 26

Decreased Oral $C_{max}$ of d-amphetamine Conjugates

Male Sprague-Dawley rats were provided water ad libitum, fasted overnight, and dosed by oral gavage with amphetamine conjugate or d-amphetamine sulfate. All doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. Plasma d-amphetanine and L-lysine-d-amphetamine concentrations were measured by LC/MS/MS where indicated in examples.

Example 27

Decreased Intranasal Bioavailability (AUC and $C_{max}$) of d-amphetamine Conjugates Male Sprague-Dawley rats were provided water ad libitum and doses were administered by placing 0.02 ml of water containing amphetamine conjugate or d-amphetamine sulfate into the nasal flares. All doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. Plasma d-amphetamine and L-lysine-d-amphetamine concentrations were measured by LC/MS/MS where indicated in examples.

Example 28

Decreased Intravenous Bioavailability (AUC and $C_{max}$) of d-amphetamine Conjugates Male Sprague-Dawley rats were provided water ad libitum, and doses were administered by intravenous tail vein injection of 0.1 ml of water containing amphetamine conjugate or d-amphetamine sulfate. All doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. Plasma d-amphetamine and L-lysine-d-amphetamine concentrations were measured by LC/MS/MS where indicated in examples.

Example 29

Attachment of Amphetamine to Variety of Chemical Moieties

The above examples demonstrate the use of an amphetamine conjugated to a chemical moiety, such as an amino acid, which is useful in reducing the potential for overdose while maintaining its therapeutic value. The effectiveness of binding amphetamine to a chemical moiety was demonstrated through the attachment of amphetamine to lysine (K), however, the above examples are meant to be illustrative only. The attachment of amphetamine to any variety of chemical moieties (i.e., peptides, glycopeptides, carbohydrates, nucleosides, or vitamins) as described below through similar procedures using the following exemplary starting materials.

Amphetamine Synthetic Examples:

Synthesis of $Gly_2$-Amp $Gly_2$-Amp was synthesized by a similar method except the amino acid starting material was Boc-Gly-Gly-OSu.

Synthesis of $Glu_2$-Phe-Amp

Glu2-Phe-Amp was synthesized by a similar method except the amino acid starting material was Boc-Glu(OtBu)-Glu(OtBu)-OSu and the starting drug conjugate was Phe-Amp (see Phe-Amp synthesis).

Synthesis of His-Amp

His-Amp was synthesized by a similar method except the amino acid starting material was Boc-His(Trt)-OSu.

Synthesis of Lys-Gly-Amp

Lys-Gly-Amp was synthesized by a similar method except the amino acid starting material was Boc-Lys(Boc)-OSu and the starting drug conjugate was Gly-Amp (see Gly-Amp synthesis).

Synthesis of Lys-Glu-Amp

Lys-Glu-Amp was synthesized by a similar method except the amino acid starting material was Boc-Lys(Boc)-OSu and the starting drug conjugate was Glu-Amp.

Synthesis of Glu-Amp

Glu-Amp was synthesized by a similar method except the amino acid starting material was Boc-Glu(OtBu)-OSu.

Synthesis of (d)-Lys-(l)-Lys-Amp (d)-Lys-(l)-Lys-Amp was synthesized by a similar method except the amino acid starting material was Boc-(d)-Lys(Boc)-(l)-Lys(Boc)-OSu.

Synthesis of Gulonic Acid-Amp

Gul-Amp was synthesized by a similar method except the carbohydrate starting material was gulonic acid-OSu.

Example 30

Lack of Detection of L-lysine-d-amphetamine diHCl in Brain Tissue Following Oral Administration Male Sprague-Dawley rats were provided water ad libitum, fasted overnight, and dosed by oral gavage with L-lysine-d-amphetamine or d-amphetamine sulfate. All doses contained equivalent amounts of d-amphetamine base. As shown in FIG. 59, similar levels of d-amphetamine were detected in serum as well as in brain tissue following administration of d-amphetamine sulfate or L-lysine-d-amphetamine. The d-amphetamine from L-lysine-d-amphetamine showed a sustained presence in the brain as compared to levels of d-amphetamine from d-amphetamine sulfate. The conjugate L-lysine-d-amphetamine was present in appreciable amounts in serum but was not detected in brain tissue indicating that the conjugate does not cross the blood brain barrier to access the central nervous system site of action.

Example 31

Pharmaceutical Composition of L-lysine-d-amphetamine Dimesylate

A gelatin capsule dosage form was prepared in three dosage strengths. The hard gelatin capsules were printed with NRP104 and the dosage strength. The capsule fill contains a white to off-white finely divided powder uniform in appearance.

Example 32

Clinical Pharmacokinetic Evaluation and Oral Bioavailability of L-lysine-d-amphetamine Dimesylate 70 mg Capsules Administered to Healthy Adults Under Fasting Conditions for 7 Days In this open-label, single-arm study, healthy adults between the ages of 18 to 55 years were administered 70 mg of L-lysine-d-amphetamine dimesylate with 8 ounces of water once daily (7 am) for 7 consecutive days. Patients fasted for at least 10 hours before and 4 hours after final dosing. Venous blood samples (7 mL) were drawn into EDTA vacutainers both before medication dosing on days 0, 1, 6, and 7 (in the morning) and at 16 time points (hours 0.5, 1, 1.5, 2, 3, 4, 5, 6, 7, 8, 10, 12, 16, 24, 48, and 72) after final dosing on day 7. Immediately after sample collection, vacutainer tubes were centrifuged at 3000 rpm at 4° C. for 10 minutes; within 1 hour of collection, they were stored at −20° C. Plasma samples were analyzed for L-lysine-d-amphetamine and d-amphetamine using a validated LC/MS/MS method.

By dose 5, d-amphetamine reached steady state. After dose 7, mean $AUC_{0-24}$ was 1113 ng·h/mL, mean $AUC_{0-\infty}$ was 1453 ng·h/mL, mean $C_{max}$ was 90.1 ng·h/mL, and mean $T_{max}$ was 3.68 hours. See Table 63 and FIG. 60. In comparison, extended-release amphetamine salts exhibit a $T_{max}$ of 5.8 hours and $AUC_{0-\infty}$ 853 ng·h/mL after an overnight fast. J. F. Auiler et al., "Effect of food on early drug exposure from extended-release stimulants: results from the Concerta, Adderall XR Food Evaluation (CAFE) study," *Curr Med Res Opin* 18: 311-316 at 313 (2002).

Intact L-lysine-d-amphetamine was rapidly converted to d-amphetamine. After dose 7, mean $AUC_{0-24}$ was 60.66 ng·h/

TABLE 62

Composition of L-lysine-d-amphetamine dimesylate capsules

| Ingredient | Quantity (mg) 30 | 50 | 70 | Placebo | Function | Grade |
|---|---|---|---|---|---|---|
| L-lysine-d-amphetamine dimesylate | 30.0 | 50.0 | 70.0 | 0.0 | Active | |
| Microcrystalline Cellulose | 151 | 70.0 | 98.0 | 144.0 | Filler/diluent, disintegrant | NF (Avicel ® PH-102) |
| Croscarmellose Sodium | 4.69 | 3.12 | 4.37 | 3.75 | Disintegrant | NF |
| Magnesium Stearate | 1.88 | 1.88 | 2.63 | 2.25 | Lubricant | NF (5712) |
| Gelatin Capsule Size 3 | White/Med. Orange | White/Lt. Blue | Med. Orange/Lt. Blue | White/White | Carrier | NF |
| Total | 187.5 | 125 | 175 | 150 | | |

Other diluents, disintegrants, lubricants, and colorants, etc. may be used. Also, a particular ingredient can be used to serve a different function than those listed above.

The pharmaceutical composition was prepared by milling de-lumped L-lysine-d-amphetamine dimesylate (size 20 mesh) with microcrystalline cellulose. The mixture was sieved through a 30 mesh screen and then mixed with croscarmellose sodium. Pre-screened magnesium stearate (size 30 mesh) was added, and the composition was mixed until uniform to form the capsule fill.

mL, and mean $AUC_{0-\infty}$ was 61.06 ng·h/mL. See Table 63 and FIG. 60. In addition, mean $C_{max}$ was 47.9 ng·h/mL, and mean $T_{max}$ was 1.14 hours for intact L-lysine-d-amphetamine. L-lysine-d-amphetamine was completely eliminated within approximately 6 hours.

There were no gender differences in systemic exposure to d-amphetamine, though $C_{max}$ was 12% higher in men after normalization by body weight.

The multidose pharmacokinetic profile of d-amphetamine released from the prodrug L-lysine-d-amphetamine is consistent with extended-release properties. The adverse events that occurred in this setting are consistent with other stimulants and suggest that suggest that L-lysine-d-amphetamine 70 mg is well tolerated.

TABLE 63

Steady-state pharmacokinetics parameters (n = 11)

| Parameter | Mean | SD | CV % |
|---|---|---|---|
| d-amphetamine | | | |
| $C_{max}$ (ng/mL) | 90.1 | 29.6 | 32.84 |
| $C_{min}$ (ng/mL) | 18.2 | 14.2 | 78.12 |
| $T_{max}$ (h) | 3.68 | 1.42 | 38.54 |
| $t_{1/2}$ (h) | 10.08 | 2.76 | 27.37 |
| $AUC_{0-24}$ (ng · h/mL) | 1113 | 396.8 | 35.65 |
| $AUC_{0-\infty}$ (ng · h/mL) | 1453 | 645.7 | 44.45 |
| $AUC_{0-t}$ (ng · h/mL) | 1371 | 633.5 | 46.19 |
| FI (%) | 163.55 | 37.20 | 22.74 |
| Intact L-lysine-d-amphetamine | | | |
| $C_{max}$ (ng/mL) | 47.9 | 18.6 | 38.81 |
| $C_{min}$ (ng/mL) | 0.0 | 0.0 | — |
| $T_{max}$ (h) | 1.14 | 0.32 | 28.45 |
| $t_{1/2}$ (h) | 0.43 | 0.09 | 21.90 |
| $AUC_{0-24}$ (ng · h/mL) | 60.66 | 21.00 | 34.61 |
| $AUC_{0-\infty}$ (ng · h/mL) | 61.06 | 20.63 | 33.79 |
| $AUC_{0-t}$ (ng · h/mL) | 59.44 | 21.47 | 36.12 |
| FI (%) | 1896.06 | 340.24 | 17.94 |

Example 33

Clinical Pharmacokinetic Evaluation and Oral Bioavailability of L-lysine-d-amphetamine Dimesylate Compared to Amphetamine Extended Release Products Adderall XR® and Dexedrine Spansule® Used in the Treatment of ADHD

TABLE 64

Treatment groups and dosage for clinical pharmacokinetic evaluation of L-lysine-d-amphetamine compared to Adderall XR ® or Dexedrine Spansule ®

| Drug | Treatment Group | No. of Subjects | Dose | Dose (mg) | Dose (amphetamine base) |
|---|---|---|---|---|---|
| L-lysine-d-amphetamine | A | 10 | 1 × 25 mg capsule | 25 | 7.37 |
| L-lysine-d-amphetamine | B | 10 | 3 × 25 mg capsules | 75 | 22.1 |
| Dexedrine Spansule ® | C | 10 | 3 × 10 mg capsules | 30 | 22.1 |
| Adderall XR ® | D | 10 | 1 × 30 mg capsules plus 1 × 5 mg capsule | 35 | 21.9 |

A clinical evaluation of the pharmacokinetics and oral bioavailability of L-lysine-d-amphetamine in humans was conducted. L-lysine-d-amphetamine was orally administered at doses approximating the lower (25 mg) and higher (75 mg) end of the therapeutic range based on d-amphetamine base content of the doses. Additionally, the higher dose was compared to doses of Adderall XR® (Shire) or Dexedrine Spansule® (GlaxoSmithKline) containing equivalent amphetamine base to that of the higher L-lysine-d-amphetamine dose. Treatment groups and doses are summarized in Table 64. All levels below limit quantifiable (blq<0.5 ng/mL) were treated as zero for purposes of pharmacokinetic analysis.

The concentrations of d-amphetamine and L-lysine-d-amphetamine intact conjugate following administration of L-lysine-d-amphetamine at the low and high dose for each individual subject as well as pharmacokinetic parameters are presented in Table 65-Table 70. The concentrations of d-amphetamine following administration of Adderall XR® or Dexedrine Spansule® for each individual subject as well as pharmacokinetic parameters are presented in Table 69 and Table 70, respectively. Concentration-time curves showing L-lysine-d-amphetamine intact conjugate and d-amphetamine are presented in FIG. 61 and FIG. 62. Extended release of d-amphetamine from L-lysine-d-amphetamine was observed for both doses and pharmacokinetic parameters ($C_{max}$ and AUC) were proportional to doses when the lower and higher dose results were compared (FIG. 61 and FIG. 62). Significant levels of d-amphetamine were not observed until one-hour post administration. Only small amounts (1.6 and 2.0 percent of total drug absorption, respectively for 25 and 75 mg doses; $AUC_{inf}$-molar basis) of L-lysine-d-amphetamine intact conjugate were detected with levels peaking at about one hour (Table 66 and Table 68). The small amount of intact conjugate absorbed was rapidly and completely eliminated, with no detectable concentrations present by five hours, even at the highest dose.

In a cross-over design (identical subjects received Adderall XR® doses following a 7-day washout period), the higher L-lysine-d-amphetamine dose was compared to an equivalent dose of Adderall XR®. Adderall XR® is a once-daily extended release treatment for ADHD that contains a mixture of d-amphetamine and l-amphetamine salts (equal amounts of d-amphetamine sulfate, d-/l-amphetamine sulfate, d-amphetamine saccharate, and d-/l-amphetamine aspartate). An equivalent dose of extended release Dexedrine Spansule® (contains extended release formulation of d-amphetamine sulfate) was also included in the study. As observed in pharmacokinetic studies in rats, oral administration of L-lysine-d-amphetamine resulted in d-amphetamine concentration-time curves similar to those of Adderall XR® and Dexedrine Spansule® (FIG. 63 and FIG. 64). The bioavailability ($AUC_{inf}$) of d-amphetamine following administration of L-lysine-d-amphetamine was approximately equivalent to both extended release amphetamine products (Table 71). Over the course of twelve hours, typically the time needed for effective once-daily treatment of ADHD, the bioavailability for L-lysine-d-amphetamine was approximately equivalent to that of Adderall XR® (d-amphetamine plus l-amphetamine levels) and over twenty percent higher than that of Dexedrine Spansule®. Based on the results of this clinical study, L-lysine-d-amphetamine would be an effective once-daily treatment for ADHD. Moreover, L-lysine-d-amphetamine afforded similar pharmacokinetics in humans and animal models, namely, delayed release of d-amphetamine resulting in extended release kinetics. Based on these observations L-lysine-d-amphetamine should also have abuse-resistant properties in humans.

TABLE 65

Individual subject d-amphetamine concentrations and pharmacokinetic parameters following oral administration of a 25 mg dose of L-lysine-d-amphetamine to humans

| | Subject 102 | Subject 103 | Subject 105 | Subject 107 | Subject 110 | Subject 112 | Subject 113 | Subject 116 | Subject 117 | Subject 120 | Mean | SD | CV % |
|---|---|---|---|---|---|---|---|---|---|---|---|---|---|
| Time Hours | | | | | | | | | | | | | |
| 0 | 0 | 0 | 0 | 0 | 0 | 0 | 0 | 0 | 0 | 0 | 0 | 0 | 0 |
| 0.5 | 0 | 0 | 0.625 | 0 | 0 | 0 | 0 | 0.78 | 0.769 | 0 | 0.2 | 0.4 | 162.1 |
| 1 | 4.29 | 2.95 | 8.67 | 3.36 | 8.33 | 1.1 | 10 | 10.5 | 14 | 3.15 | 6.6 | 4.2 | 63.6 |
| 1.5 | 10 | 12.7 | 16 | 13.8 | 21.4 | 3.94 | 24.7 | 19.5 | 24 | 15.1 | 16.1 | 6.5 | 40.3 |
| 2 | 16.3 | 18.4 | 17 | 21 | 25.9 | 9.29 | 30.9 | 23.6 | 30 | 21.7 | 21.4 | 6.6 | 30.8 |
| 3 | 16.5 | 19.6 | 16.7 | 26.1 | 27 | 17.7 | 30.2 | 23.5 | 27.6 | 28.9 | 23.4 | 5.3 | 22.7 |
| 4 | 23.9 | 18.8 | 14.1 | 24.5 | 30.1 | 17.9 | 33.2 | 21.2 | 24.7 | 25.3 | 23.4 | 5.7 | 24.3 |
| 5 | 21.2 | 18.9 | 14.6 | 21.6 | 22.6 | 17.2 | 27 | 20 | 20.2 | 24.2 | 20.8 | 3.5 | 16.9 |
| 6 | 21.8 | 18 | 12.5 | 21.6 | 23.7 | 15.7 | 25.8 | 18.2 | 20.3 | 20.5 | 19.8 | 3.9 | 19.6 |
| 7 | 18.9 | 15.8 | 12.1 | 17.8 | 20.6 | 14.5 | 26.6 | 21 | 18.3 | 21.8 | 18.7 | 4.1 | 21.9 |
| 8 | 19.3 | 16.6 | 10.4 | 17.9 | 20 | 14.2 | 25.7 | 13.6 | 18.8 | 20.1 | 17.7 | 4.2 | 24.1 |
| 10 | 18.8 | 13.6 | 9.8 | 15.3 | 19.3 | 13.7 | 22.4 | 15.1 | 15.3 | 15.9 | 15.9 | 3.5 | 22.1 |
| 12 | 15.8 | 12.6 | 6.92 | 11.5 | 15.8 | 11.2 | 17.9 | 12 | 13.7 | 15.2 | 13.3 | 3.1 | 23.6 |
| 16 | 13.4 | 10.5 | 6.56 | 9.53 | 14.3 | 10.7 | 12.5 | 10.3 | 10 | 13 | 11.1 | 2.3 | 20.5 |
| 24 | 8.03 | 5.81 | 2.65 | 4.9 | 5.8 | 5.9 | 6.57 | 6.13 | 4.52 | 5.45 | 5.6 | 1.4 | 25.1 |
| 48 | 1.57 | 1.36 | 0 | 1.26 | 0.795 | 1.44 | 1.24 | 1.23 | 0.864 | 0.586 | 1.0 | 0.5 | 46.1 |
| 72 | 0 | 0 | 0 | 0 | 0 | 0 | 0 | 0 | 0 | 0 | 0 | 0 | 0 |
| Parameter | | | | | | | | | | | | | |
| $AUC_{0-12\,h}$ (ng·h/mL) | 204.0 | 177.4 | 140.4 | 204.9 | 242.7 | 152.4 | 284.6 | 199.2 | 225.5 | 223.3 | 205.4 | 42.5 | 20.7 |
| $AUC_{last}$ (ng·h/mL) | 463.3 | 375.1 | 201.4 | 378.5 | 462.7 | 350.7 | 515.2 | 397.9 | 395.7 | 426.1 | 396.7 | 84.8 | 21.4 |
| $AUC_{inf}$ (ng·h/mL) | 486.7 | 397.1 | 233.5 | 398.8 | 472 | 374 | 532.5 | 416.4 | 407 | 432.2 | 415.0 | 80.1 | 19.3 |
| $C_{max}$ (ng/mL) | 23.9 | 19.6 | 17 | 26.1 | 30.1 | 17.9 | 33.2 | 23.6 | 30 | 28.9 | 25.0 | 5.6 | 22.3 |
| $T_{max}$ (hours) | 4 | 3 | 2 | 3 | 4 | 4 | 4 | 2 | 2 | 3 | 3.1 | 0.876 | 28.2 |
| $T_{1/2}$ (hours) | 10.32 | 11.18 | 8.36 | 11.18 | 8.16 | 11.22 | 9.68 | 10.43 | 9.06 | 7.22 | 9.68 | 1.43 | 14.7 |

TABLE 66

Individual subject L-lysine-d-amphetamine intact conjugate concentrations and pharmacokinetic parameters following oral administration of a 25 mg dose of L-lysine-d-amphetamine to humans

| | Subject 102 | Subject 103 | Subject 105 | Subject 107 | Subject 110 | Subject 112 | Subject 113 | Subject 116 | Subject 117 | Subject 120 | Mean | SD | CV % |
|---|---|---|---|---|---|---|---|---|---|---|---|---|---|
| Time Hours | | | | | | | | | | | | | |
| 0 | 0 | 0 | 0 | 0 | 0 | 0 | 0 | 0 | 0 | 0 | 0 | 0 | 0 |
| 0.5 | 4.1 | 5.5 | 10.0 | 0.0 | 3.6 | 0.0 | 9.2 | 9.6 | 8.9 | 0.0 | 5.1 | 4.2 | 82.0 |
| 1 | 9.2 | 11.2 | 15.2 | 12.5 | 9.1 | 2.7 | 20.1 | 10.5 | 10.8 | 10.9 | 11.2 | 4.5 | 39.7 |
| 1.5 | 4.0 | 4.4 | 6.1 | 7.5 | 3.6 | 6.2 | 6.6 | 2.8 | 4.2 | 8.4 | 5.4 | 1.8 | 34.1 |
| 2 | 2.1 | 1.4 | 2.5 | 2.9 | 1.9 | 4.0 | 2.3 | 0 | 1.7 | 3.1 | 2.2 | 1.1 | 48.8 |
| 3 | 0 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | 0 | 0 |
| 48 | 0 | 0 | 0 | 0 | 0 | 0 | 0 | 0 | 0 | 0 | 0 | 0 | 0 |
| 72 | 0 | 0 | 0 | 0 | 0 | 0 | 0 | 0 | 0 | 0 | 0 | 0 | 0 |
| Parameter | | | | | | | | | | | | | |
| $AUC_{last}$ (ng·h/mL) | 9.18 | 10.95 | 16.31 | 10.68 | 8.583 | 5.439 | 18.51 | 10.77 | 12.35 | 10.41 | 11.32 | 3.74 | 33.1 |
| $AUC_{inf}$ (ng·h/mL) | 10.62 | 11.64 | 17.66 | 12.65 | 9.759 | — | 19.56 | — | 13.3 | 12.83 | 13.50 | 3.40 | 25.2 |
| $C_{max}$ (ng/mL) | 9.18 | 11.2 | 15.2 | 12.5 | 9.05 | 6.18 | 20.1 | 10.5 | 10.8 | 10.9 | 11.56 | 3.80 | 32.9 |
| $T_{max}$ (hours) | 1 | 1 | 1 | 1 | 1 | 1.5 | 1 | 1 | 1 | 1 | 1.05 | 0.16 | 15.1 |
| $T_{1/2}$ (hours) | 0.47 | 0.34 | 0.38 | 0.47 | 0.44 | — | 0.32 | — | 0.38 | 0.55 | 0.419 | 0.077 | 18.5 |

TABLE 67

Individual subject d-amphetamine concentrations and pharmacokinetic parameters following oral administration of a 75 mg dose of L-lysine-d-amphetamine to humans

| Time Hours | Subject 101 | Subject 104 | Subject 106 | Subject 108 | Subject 109 | Subject 111 | Subject 114 | Subject 115 | Subject 118 | Subject 119 | Mean | SD | CV % |
|---|---|---|---|---|---|---|---|---|---|---|---|---|---|
| 0 | 0 | 0 | 0 | 0 | 0 | 0 | 0 | 0 | 0 | 0 | 0 | 0 | 0 |
| 0.5 | 0 | 0.748 | 0.506 | 0 | 0 | 0.779 | 0.525 | 0 | 3 | 1.85 | 0.7 | 1.0 | 132.2 |
| 1 | 11.9 | 14.4 | 12.6 | 7.26 | 5.9 | 10.3 | 7.2 | 23.1 | 23 | 27.9 | 14.4 | 7.7 | 53.6 |
| 1.5 | 40.3 | 34.6 | 30.4 | 22.8 | 19.3 | 38.4 | 19 | 52.8 | 51.5 | 55.8 | 36.5 | 13.8 | 37.8 |
| 2 | 84.6 | 48.9 | 68.2 | 34.8 | 32.7 | 57.2 | 33.1 | 91.3 | 61.7 | 70.4 | 58.3 | 21.0 | 36.0 |
| 3 | 72.9 | 64.3 | 55.7 | 60.3 | 62.3 | 61.1 | 44.8 | 95.8 | 62.1 | 83.6 | 66.3 | 14.5 | 21.9 |
| 4 | 84.6 | 65.3 | 58.8 | 51.1 | 77.9 | 63.3 | 47.6 | 89.2 | 54.2 | 86 | 67.8 | 15.5 | 22.8 |
| 5 | 65 | 55.6 | 60.2 | 74 | 83.9 | 59.1 | 56.9 | 77.7 | 54.9 | 82.8 | 67.0 | 11.5 | 17.2 |
| 6 | 71 | 53.5 | 49.4 | 51.5 | 78.3 | 50.8 | 55.1 | 68.8 | 52.9 | 64 | 59.5 | 10.2 | 17.1 |
| 7 | 53.8 | 55.7 | 52.9 | 69.5 | 73.1 | 52.9 | 55.9 | 71.2 | 45.1 | 74.6 | 60.5 | 10.5 | 17.4 |
| 8 | 63.7 | 40.3 | 47.3 | 45.7 | 72.2 | 46.5 | 54.2 | 61.1 | 44.3 | 66.2 | 54.2 | 10.9 | 20.2 |
| 10 | 43.7 | 41.7 | 37 | 58.4 | 67 | 44.3 | 48.4 | 68 | 34.1 | 55.9 | 49.9 | 11.9 | 24.0 |
| 12 | 46.4 | 26.1 | 36.7 | 37.4 | 49.9 | 32.4 | 37.1 | 54.1 | 34.5 | 45.1 | 40.0 | 8.6 | 21.6 |
| 16 | 35.4 | 22.2 | 25.7 | 48 | 44.9 | 24.3 | 28.9 | 44.7 | 31.7 | 34.5 | 34.0 | 9.2 | 27.1 |
| 24 | 16.4 | 11.4 | 14.9 | 13.2 | 18.4 | 16.8 | 20.5 | 21.7 | 15.7 | 18.1 | 16.7 | 3.1 | 18.8 |
| 48 | 2.74 | 2.14 | | 4.17 | 2.73 | 3.75 | 4.81 | 2.81 | 4.26 | 3.36 | 3.4 | 0.9 | 25.9 |
| 72 | 0 | 0 | 0 | 1.07 | 0.661 | 0.687 | 1.49 | 0 | 0 | 0.553 | 0.4 | 0.5 | 120.2 |
| Parameter | | | | | | | | | | | | | |
| $AUC_{0-12\,h}$ (ng·h/mL) | 666.2 | 525.9 | 531.6 | 570.3 | 704.8 | 545.6 | 513.7 | 790.9 | 523.4 | 742.8 | 611.5 | 104.5 | 17.1 |
| $AUC_{last}$ (ng·h/mL) | 1266 | 918.7 | 1031 | 1257 | 1442 | 1123 | 1223 | 1549 | 1143 | 1417 | 1237.0 | 194.0 | 15.7 |
| $AUC_{inf}$ (ng·h/mL) | 1301 | 948.3 | 1072 | 1278 | 1451 | 1133 | 1251 | 1582 | 1154 | 1425 | 1259.5 | 191.3 | 15.2 |
| $C_{max}$ (ng/mL) | 84.6 | 65.3 | 68.2 | 74 | 83.9 | 63.3 | 56.9 | 95.8 | 62.1 | 86 | 74.0 | 12.9 | 17.4 |
| $T_{max}$ (hours) | 4 | 4 | 2 | 5 | 5 | 4 | 5 | 3 | 3 | 4 | 3.9 | 1.0 | 25.5 |
| $T_{1/2}$ (hours) | 8.78 | 9.59 | 10.02 | 13.26 | 9.24 | 10.41 | 12.8 | 8.05 | 10.92 | 9.47 | 10.3 | 1.7 | 16.3 |

TABLE 68

Individual subject L-lysine-d-amphetamine intact conjugate concentrations and pharmacokinetic parameters following oral administration of a 75 mg dose of L-lysine-d-amphetamine to humans

| Time Hours | Subject 101 | Subject 104 | Subject 106 | Subject 108 | Subject 109 | Subject 111 | Subject 114 | Subject 115 | Subject 118 | Subject 119 | Mean | SD | CV % |
|---|---|---|---|---|---|---|---|---|---|---|---|---|---|
| 0 | 0 | 0 | 0 | 0 | 0 | 0 | 0 | 0 | 0 | 0 | 0 | 0 | 0 |
| 0.5 | 10.4 | 22.6 | 6.92 | 10.3 | 0 | 9.21 | 7.88 | 14.5 | 87.8 | 35.5 | 20.5 | 25.6 | 124.7 |
| 1 | 48 | 40.5 | 29 | 41.5 | 21.2 | 30.8 | 23.4 | 127 | 88.9 | 80.1 | 53.0 | 34.6 | 65.2 |
| 1.5 | 28.4 | 15.7 | 16.1 | 20.3 | 26.5 | 19 | 12.7 | 38.7 | 28.6 | 38 | 24.4 | 9.2 | 37.5 |
| 2 | 8.87 | 5.53 | 4.91 | 9 | 18.1 | 5.62 | 6.29 | 12.1 | 9.75 | 11.3 | 9.1 | 4.0 | 44.0 |
| 3 | 2.15 | 1.29 | 1.76 | 1.82 | 10.6 | 0 | 2.31 | 2.57 | 1.73 | 1.73 | 2.6 | 2.9 | 111.6 |
| 4 | 0 | 0 | 1.09 | 0 | 4.65 | 0 | 1.53 | 1.01 | 0 | 0 | 0.8 | 1.5 | 176.9 |
| 5 | 0 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | 0 | 0 |
| 48 | 0 | 0 | 0 | 0 | 0 | 0 | 0 | 0 | 0 | 0 | 0 | 0 | 0 |
| 72 | 0 | 0 | 0 | 0 | 0 | 0 | 0 | 0 | 0 | 0 | 0 | 0 | 0 |
| Parameter | | | | | | | | | | | | | |
| $AUC_{last}$ (ng·h/mL) | 51.2 | 44.2 | 32.0 | 43.7 | 50.4 | 30.9 | 29.8 | 102.1 | 110.8 | 86.1 | 58.1 | 30.2 | 52.0 |
| $AUC_{inf}$ (ng·h/mL) | 52.5 | 45.0 | 33.0 | 44.9 | 52.3 | 34.2 | 31.4 | 102.9 | 111.7 | 87.0 | 59.5 | 29.9 | 50.2 |
| $C_{max}$ (ng/mL) | 48.0 | 40.5 | 29.0 | 41.5 | 26.5 | 30.8 | 23.4 | 127.0 | 88.9 | 80.1 | 53.6 | 34.1 | 63.6 |
| $T_{max}$ (hours) | 1 | 1 | 1 | 1 | 1.5 | 1 | 1 | 1 | 1 | 1 | 1.05 | 0.16 | 15.1 |
| $T_{1/2}$ (hours) | 0.43 | 0.4 | 0.61 | 0.43 | 1.02 | 0.41 | 0.75 | 0.56 | 0.38 | 0.35 | 0.534 | 0.211 | 39.6 |

TABLE 69

Individual subject d-amphetamine concentrations and pharmacokinetic parameters following oral administration of a 35 mg dose of Adderall XR ® (equivalent to 75 mg dose of L-lysine-d-amphetamine based on amphetamine base content) to humans

| | Subject 101 | Subject 104 | Subject 106 | Subject 108 | Subject 109 | Subject 111 | Subject 114 | Subject 115 | Subject 118 | Subject 119 | Mean | SD | CV % |
|---|---|---|---|---|---|---|---|---|---|---|---|---|---|
| Time Hours | | | | | | | | | | | | | |
| 0 | 0 | 0 | 0 | 0 | 0 | 0 | 0 | 0 | 0 | 0 | 0 | 0 | 0 |
| 0.5 | 7.9 | 2.3 | 2.8 | 0.6 | 2.2 | 5.7 | 0 | 16 | 2.3 | 5.3 | 4.5 | 4.7 | 104.3 |
| 1 | 37.6 | 28.9 | 23.3 | 13.7 | 29.8 | 38.2 | 17.9 | 46.2 | 28.8 | 48.8 | 31.3 | 11.5 | 36.6 |
| 1.5 | 49.9 | 42.3 | 31.1 | 23.7 | 39.1 | 34.4 | 30.8 | 65.4 | 34.1 | 53 | 40.4 | 12.5 | 31.0 |
| 2 | 65.9 | 45.8 | 29.2 | 37.4 | 46.2 | 65.4 | 40 | 64.4 | 37 | 67.8 | 49.9 | 14.6 | 29.2 |
| 3 | 95.3 | 51.7 | 36.7 | 23.6 | 64.7 | 62.9 | 44.7 | 56.5 | 31.1 | 64.8 | 53.2 | 20.7 | 38.9 |
| 4 | 83.7 | 73.3 | 56.7 | 40 | 67 | 76.6 | 56.3 | 53.1 | 33.5 | 73.3 | 61.4 | 16.3 | 26.6 |
| 5 | 77.4 | 75.2 | 71.6 | 62.1 | 75.9 | 76.4 | 51.5 | 61.4 | 56.8 | 82.4 | 69.1 | 10.3 | 14.9 |
| 6 | 71.5 | 72.1 | 64 | 59.8 | 66.9 | 63.5 | 56.8 | 59.8 | 58.7 | 85.7 | 65.9 | 8.7 | 13.2 |
| 7 | 72.3 | 63.6 | 71 | 57.9 | 70.6 | 69.7 | 51.9 | 48.1 | 53.7 | 79.7 | 63.9 | 10.5 | 16.4 |
| 8 | 60.4 | 57.1 | 53.8 | 53 | 72 | 66.9 | 56.2 | 56.4 | 51.7 | 66.7 | 59.4 | 6.9 | 11.6 |
| 10 | 50.4 | 45.5 | 53 | 50.7 | 67.6 | 57.4 | 49.1 | 66.6 | 48 | 71.3 | 56.0 | 9.3 | 16.6 |
| 12 | 42.5 | 41.3 | 45.4 | 32.9 | 53.1 | 46 | 37.3 | 74.7 | 42.2 | 60.2 | 47.6 | 12.2 | 25.7 |
| 16 | 31.1 | 29.6 | 35.7 | 39 | 45.2 | 33.9 | 34.3 | 64.9 | 29 | 40.5 | 38.3 | 10.6 | 27.7 |
| 24 | 14.9 | 15.1 | 22.1 | 19.5 | 21.7 | 21.2 | 20.7 | 35.7 | 17.9 | 20.5 | 20.9 | 5.8 | 27.7 |
| 48 | 2.5 | 4.2 | 3.8 | 5.9 | 5.4 | 3.8 | 7.3 | 5.1 | 3.9 | 3 | 4.5 | 1.4 | 32.1 |
| 72 | 0 | 0.3 | 1 | 1 | 0.3 | 1.1 | 2.7 | 0.3 | 0 | 0 | 0.7 | 0.8 | 124.7 |
| Parameter | | | | | | | | | | | | | |
| $AUC_{0-12h}$ (ng·h/mL) | 731.2 | 625.0 | 582.6 | 504.3 | 711.6 | 698.5 | 535.4 | 683.5 | 509.8 | 793.2 | 637.5 | 101.1 | 15.9 |
| $AUC_{last}$ (ng·h/mL) | 1270 | 1230 | 1343 | 1269 | 1568 | 1436 | 1354 | 1920 | 1101 | 1520 | 1401.1 | 229.0 | 16.3 |
| $AUC_{inf}$ (ng·h/mL) | 1301 | 1234 | 1358 | 1286 | 1571 | 1454 | 1418 | 1923 | 1164 | 1557 | 1426.6 | 218.9 | 15.3 |
| $C_{max}$ (ng/mL) | 95.3 | 75.2 | 71.5 | 62 | 75.9 | 76.5 | 56.8 | 74.7 | 58.8 | 85.8 | 73.3 | 11.9 | 16.3 |
| $T_{max}$ (hours) | 3 | 5 | 5 | 5 | 5 | 4 | 6 | 12 | 6 | 6 | 5.70 | 2.41 | 42.2 |
| $T_{1/2}$ (hours) | 8.65 | 9.01 | 10.57 | 11.58 | 8.37 | 10.78 | 16.4 | 7.25 | 11.05 | 8.54 | 10.22 | 2.59 | 25.3 |

TABLE 70

Individual subject d-amphetamine concentrations and pharmacokinetic parameters following oral administration of a 30 mg dose of Dexedrine Spansule ® (equivalent to 75 mg dose of L-lysine-d-amphetamine based on amphetamine base content) to humans

| | Subject 102 | Subject 103 | Subject 105 | Subject 107 | Subject 110 | Subject 112 | Subject 113 | Subject 116 | Subject 117 | Subject 120 | Mean | SD | CV % |
|---|---|---|---|---|---|---|---|---|---|---|---|---|---|
| Time Hours | | | | | | | | | | | | | |
| 0 | 0 | 0 | 0 | 0 | 0 | 0 | 0 | 0 | 0 | 0 | 0 | 0 | 0 |
| 0.5 | 1.2 | 2.68 | 1.37 | 1.4 | 1.16 | 2.36 | 6.75 | 2.63 | 4.95 | 3.43 | 2.8 | 1.8 | 65.5 |
| 1 | 14.8 | 26.5 | 16.7 | 21.4 | 25.2 | 12.7 | 33.1 | 22.3 | 26 | 21.5 | 22.0 | 6.1 | 27.8 |
| 1.5 | 24.2 | 36.9 | 23.2 | 28.5 | 37.2 | 21.3 | 42.4 | 29.2 | 33.7 | 39.2 | 31.6 | 7.3 | 23.2 |
| 2 | 28.6 | 43.4 | 27.3 | 34.6 | 38.5 | 27.6 | 46.2 | 31.3 | 38.5 | 42 | 35.8 | 6.9 | 19.4 |
| 3 | 27.4 | 37.3 | 30.6 | 40.1 | 41.7 | 30.9 | 52 | 36.5 | 42.9 | 60.1 | 40.0 | 10.0 | 25.2 |
| 4 | 27.1 | 44.1 | 33.5 | 48.7 | 45.2 | 34.7 | 49.1 | 40.7 | 42.4 | 53.2 | 41.9 | 8.1 | 19.2 |
| 5 | 35.1 | 53 | 40.2 | 43.4 | 46.5 | 42.4 | 58.1 | 47 | 52.1 | 68.7 | 48.7 | 9.7 | 20.0 |
| 6 | 33.8 | 58.5 | 40.2 | 46.5 | 43.5 | 37.5 | 56.2 | 40 | 51 | 63 | 47.0 | 9.8 | 20.8 |
| 7 | 37.2 | 50.7 | 31.2 | 41.4 | 44.9 | 42 | 57.8 | 43.6 | 51.6 | 65.7 | 46.6 | 10.1 | 21.7 |
| 8 | 35.9 | 54.3 | 34.9 | 45 | 45 | 36 | 58.7 | 41.8 | 53.9 | 59.2 | 46.5 | 9.5 | 20.4 |
| 10 | 33.1 | 49.1 | 34.3 | 35.5 | 45 | 37 | 51.4 | 38.9 | 46.3 | 60.1 | 43.1 | 8.8 | 20.4 |
| 12 | 34 | 51 | 28.6 | 34.1 | 40.8 | 32.6 | 51.6 | 37.7 | 38.1 | 50.9 | 39.9 | 8.4 | 21.1 |
| 16 | 30.2 | 40.8 | 25.2 | 28 | 33 | 25.8 | 41 | 26.8 | 29.6 | 44.9 | 32.5 | 7.1 | 22.0 |
| 24 | 20.5 | 27.8 | 18.2 | 19.5 | 17.1 | 17.8 | 22.5 | 19.1 | 15.5 | 27.3 | 20.5 | 4.2 | 20.3 |
| 48 | 3.83 | 6.89 | 3.7 | 5.11 | 2.56 | 4.31 | 6.51 | 4.43 | 2.77 | 5.47 | 4.6 | 1.4 | 31.8 |
| 72 | 0.715 | 1.63 | 1 | 1.7 | 0 | 0.622 | 1.29 | 1.22 | 0 | 1.31 | 0.9 | 0.6 | 64.0 |
| Parameter | | | | | | | | | | | | | |
| $AUC_{0-12h}$ (ng·h/mL) | 356.2 | 539.8 | 366.4 | 444.3 | 480.8 | 387.0 | 591.4 | 436.5 | 512.8 | 634.2 | 474.9 | 94.7 | 19.9 |
| $AUC_{last}$ (ng·h/mL) | 1033 | 1517 | 966 | 1135 | 1065 | 1003 | 1473 | 1100 | 1048 | 1589 | 1193 | 236 | 19.8 |
| $AUC_{inf}$ (ng·h/mL) | 1043 | 1544 | 983.5 | 1168 | 1097 | 1013 | 1495 | 1121 | 1085 | 1610 | 1216 | 238 | 19.5 |
| $C_{max}$ (ng/mL) | 37.2 | 58.5 | 40.2 | 48.7 | 46.5 | 42.4 | 58.7 | 47 | 53.9 | 68.7 | 50.18 | 9.74 | 19.4 |
| $T_{max}$ (hours) | 7 | 6 | 5 | 4 | 5 | 5 | 8 | 5 | 8 | 5 | 5.80 | 1.40 | 24.1 |
| $T_{1/2}$ (hours) | 9.92 | 11.74 | 12.07 | 13.8 | 8.7 | 10.76 | 11.47 | 12.23 | 9.36 | 10.92 | 11.10 | 1.50 | 13.6 |

TABLE 71

Pharmacokinetic parameters of amphetamine following oral administration of L-lysine-d-amphetamine, Adderall XR ® or Dexedrine Spansule ®.

| | Drug | | | | | | |
|---|---|---|---|---|---|---|---|
| Parameter | L-lysine-d-amphetamine 25 mg | Percent[1] | L-lysine-d-amphetamine 75 mg | Percent[1] | Adderall XR ® | Percent[1] | Dexedrine Spansule ® | Percent[1] |
| $AUC_{0-12\,h}$ (ng · h/mL) | 205.4 | 33.6 | 611.5 | 100 | 637.5 | 104 | 474.9 | 78 |
| $AUC_{last}$ (ng · h/mL) | 396.7 | 31.5 | 1237 | 100 | 1401.1 | 113 | 1193 | 96 |
| $AUC_{inf}$ (ng · h/mL) | 415 ± 80.3 | 32.9 | 1260 ± 192 | 100 | 1429 ± 223 | 113 | 1217 ± 237 | 97 |
| $C_{max}$ (ng/mL) | 25.0 ± 5.57 | 33.8 | 74.0 ± 12.9 | 100 | 73.3 ± 11.9 | 99 | 50.2 ± 9.74 | 68 |
| $T_{max}$ (hours) | 3.10 ± 0.88 | 79.5 | 3.90 ± 0.99 | 100 | 5.70 ± 2.41 | 146 | 5.8 ± 1.40 | 149 |
| $T_{1/2}$ (hours) | 9.66 ± 1.45 | 94 | 10.3 ± 1.66 | 100 | 10.2 ± 2.62 | 99 | 11.1 ± 1.48 | 108 |

[1] Percent relative to L-lysine-d-amphetamine 75 mg dose

Example 34

Clinical Pharmacokinetic Evaluation and Oral Bioavailability of L-lysine-d-amphetamine Dimesylate In pediatric patients (6-12 yrs) with ADHD, the $T_{max}$ of d-amphetamine was approximately 3.5 hours following single-dose oral administration of L-lysine-d-amphetamine dimesylate either 30 mg, 50 mg, or 70 mg after a 8-hour overnight fast. See FIG. 65. The $T_{max}$ of L-lysine-d-amphetamine dimesylate was approximately 1 hour. Linear pharmacokinetics of d-amphetamine after single-dose oral administration of L-lysine-d-amphetamine dimesylate was established over the dose range of 30 mg to 70 mg in children.

TABLE 72

Pharmacokinetic parameters of d-amphetamine and L-lysine-d-amphetamine dimesylate

| Dose | $C_{max}$ (ng/mL) | $T_{max}$ (h) | AUC (ng · h/mL) | $t_{1/2}$ (h) |
|---|---|---|---|---|
| | d-amphetamine | | | |
| 30 mg | 53.2 ± 9.62 | 3.41 ± 1.09 | 845 ± 117 | 8.90 ± 1.33 |
| 50 mg | 93.3 ± 18.2 | 3.58 ± 1.18 | 1510 ± 242 | 8.61 ± 1.04 |
| 70 mg | 134 ± 26.1 | 3.46 ± 1.34 | 2157 ± 383 | 8.64 ± 1.32 |
| | Intact L-lysine-d-amphetamine dimesylate | | | |
| 30 mg | 21.9 | 0.97 | 27.9 | |
| 50 mg | 46.0 | 0.98 | 57.9 | |
| 70 mg | 89.5 | 1.07 | 108.9 | |

There is no unexpected accumulation of d-amphetamine at steady state in children with ADHD and no accumulation of L-lysine-d-amphetamine dimesylate after once-daily dosing for 7 consecutive days.

Food does not affect the extent of absorption of d-amphetamine in healthy adults after single-dose oral administration of 70 mg of L-lysine-d-amphetamine dimesylate capsules but delays $T_{max}$ by approximately 1 hour (from 3.78 hrs at fasted state to 4.72 hrs after a high fat meal). After an 8-hour fast, the extent of absorption of d-amphetamine following oral administration of L-lysine-d-amphetamine dimesylate in solution and as intact capsules was equivalent.

There were no apparent differences between males and females in exposure as measured by dose-normalized $C_{max}$ and AUC although the range of values in children was higher than that in adults. This is a consequence of the significant correlation between dose-normalized $C_{max}$ and AUC and body weight and thus the differences are due to the higher doses in mg/kg administered to children. There were no apparent differences in $t_{1/2}$ between male and female subjects nor were there any apparent relationships between $t_{1/2}$ and either age or body weight.

Exemplary results of clinical pharmacokinetic evaluation are presented in FIG. 66 (AUC), FIG. 67 ($C_{max}$), and FIG. 68 ($T_{max}$).

Example 35

Efficacy of L-lysine-d-amphetamine Dimesylate in Pediatric Clinical Trials

The efficacy of L-lysine-d-amphetamine dimesylate was established in a double-blind, randomized, placebo-controlled, parallel-group study conducted in children aged 6-12 (N=290) who met DSM-IV criteria for ADHD (either the combined type or the hyperactive-impulsive type). Patients were randomized to fixed dose treatment groups receiving final doses of 30, 50, or 70 mg of L-lysine-d-amphetamine dimesylate or placebo once daily in the morning for four weeks. For patients randomized to 50 and 70 mg L-lysine-d-amphetamine dimesylate, dosage was increased by forced titration. Significant improvements in the signs and symptoms of ADHD, as rated by investigators (ADHD Rating Scale; ADHD-RS) and parents (Connor's Parent Rating Scale; CPRS), were demonstrated for all L-lysine-d-amphetamine dimesylate doses compared to placebo, for all four weeks, including the first week of treatment, when all L-lysine-d-amphetamine dimesylate patients were receiving a dose of 30 mg/day. Additional dose-responsive improvement was demonstrated in the 50 and 70 mg groups, respectively. L-lysine-d-amphetamine dimesylate-treated patients showed significant improvements, as measured by CPRS scores, in the morning (~10 am), afternoon (~2 pm), and evening (~6 pm) compared with placebo-treated patients, demonstrating effectiveness throughout the day. The results of the primary efficacy analysis, ADHD-RS total score change from baseline to endpoint for the ITT population, are shown in FIG. 69.

Efficacy was also measured by the SKAMP score. A total of 52 children ages 6 to 12 who met DSM-IV criteria for ADHD (either the combined type or the hyperactive-impulsive type) were enrolled in a double-blind, randomized, placebo-controlled crossover study. Patients were randomized to receive fixed and optimal doses of L-lysine-d-amphetamine (30, 50, 70 mg), Adderall XR® (10, 20, or 30 mg), or placebo once daily in the morning for 1 week each treatment. The primary efficacy endpoint in this study was SKAMP-Deportment score (Swanson, Kotkin, Agler, M. Flynn and Pelham rating scale). Both L-lysine-d-amphetamine and Adderall XR® were highly effective compared to placebo. The significant effects of L-lysine-d-amphetamine occurred within 2 hours post morning dose and continued throughout the last assessment time point, 12 hours post morning dose, compared to placebo, yielding a 12-hour duration of action. See FIG. 70.

Example 36

Abuse Liability of Intravenous L-lysine-d-amphetamine

L-lysine-d-amphetamine 50 mg, d-amphetamine 20 mg, and placebo were given intravenously over 2 minutes at 48 hour intervals to 9 stimulant abusers in a double blind crossover design to assess abuse liability. Drugs were given according to 3×3 balanced latin squares. Each dosing day, vital sign measures and subjective and behavioral effects were assessed with questionnaires before dosing and at 0.5, 1, 1.5, 2, 3, 4, 5, 6, 9, 12, 16 and 24 hours after dosing. At these times and at 5 minutes, a blood sample (5 ml) was taken for d-amphetamine levels.

For d-amphetamine, mean peak plasma level of 77.7 ng/ml of d-amphetamine occurred at 5 minutes and then rapidly subsided. Administration of d-amphetamine produced expected d-amphetamine-like effects with mean peak responses at 15 minutes. The mean maximum response to d-amphetamine on the primary variable of Subject Liking VAS was significantly greater than placebo (p=0.01).

For L-lysine-d-amphetamine, mean peak plasma level of 33.8 ng/ml of d-amphetamine occurred at 3 hours and remained at this level through the 4 hour observation. L-lysine-d-amphetamine produced d-amphetamine-like subjective, behavioral, and vital sign effects with mean peak responses at 1 to 3 hours. For the primary variable of Subject Liking VAS, the response was not greater than placebo (p=0.29). Changes in blood pressure following L-lysine-d-amphetamine were significant.

At the end of the study, subjects were asked which treatment they would take again. Six subjects chose d-amphetamine 20 mg, two subjects chose none of the treatments, and one subject chose L-lysine-d-amphetamine 50 mg. In summary, L-lysine-d-amphetamine 50 mg did not produce euphoria or amphetamine-like subjective effects although there were late occurring blood pressure increases. The findings suggest that L-lysine-d-amphetamine itself is inactive. After 1 to 2 hours, L-lysine-d-amphetamine is converted to d-amphetamine. Taken intravenously, L-lysine-d-amphetamine has significantly less abuse potential than immediate release d-amphetamine containing an equal amount of d-amphetamine base.

Example 37

Preliminary Estimates of Decreased Abuse Liability with L-lysine-d-amphetamine vs. d-amphetamine in Healthy Adults with a History of Stimulant Abuse This randomized, single-center, single-blind, dose-escalation study used pharmacokinetic parameters to obtain preliminary estimates of abuse liability for L-lysine-d-amphetamine (30-150 mg) vs. d-amphetamine sulfate (40 mg) and placebo in healthy adults meeting DSM-IV criteria for stimulant abuse. Subjects were divided into 3 cohorts of 4 patients each; all received single doses of L-lysine-d-amphetamine at a minimum interval of 48 hours, with d-amphetamine sulfate (40 mg) and placebo randomly dispersed. Cohort 1 was administered L-lysine-d-amphetamine doses of 30, 50, 70, 100 mg; cohort 2 received 50, 70, 100, 130 mg doses; and cohort 3 received 70, 100, 130, and 150 mg doses.

$AUC_{last}$ d-amphetamine over the first 4 hours was substantially lower with 100 mg L-lysine-d-amphetamine (165.3-213.1 ng/mL) vs. 40 mg d-amphetamine (245.5-316.8 ng/mL). $C_{max}$ and $AUC_{last}$ increased with dose for 30-130 mg L-lysine-d-amphetamine, attenuating between the 130 mg and 150 mg dose. $T_{max}$ ranged from 3.78-4.25 h with L-lysine-d-amphetamine vs. d-amphetamine sulfate (1.88-2.74 h). The half-life of L-lysine-d-amphetamine (range, 0.44-0.76 h) indicated rapid clearance. Adverse reactions were mild in severity with no significant changes in vital signs or ECG parameters. L-lysine-d-amphetamine had a slower release of d-amphetamine compared with d-amphetamine sulfate. At doses as high as 150 mg, there appears to be an attenuation of the maximum concentration, suggesting higher doses of L-lysine-d-amphetamine will not lead to further increases in $C_{max}$ and $AUC_{last}$. These results suggest a drug profile consistent with reduced abuse liability.

It will be understood that the specific embodiments of the invention shown and described herein are exemplary only. Numerous variations, changes, substitutions and equivalents will occur to those skilled in the art without departing from the spirit and scope of the invention. In particular, the terms used in this application should be read broadly in light of similar terms used in the related applications. Accordingly, it is intended that all subject matter described herein and shown in the accompanying drawings be regarded as illustrative only and not in a limiting sense and that the scope of the invention be solely determined by the appended claims.

The invention claimed is:

1. A pharmaceutical composition comprising (a) L-lysine-d-amphetamine or a pharmaceutically acceptable salt thereof and (b) a pharmaceutically acceptable additive.

2. A pharmaceutical composition as defined in claim 1, wherein said pharmaceutical composition is suitable for oral dosing.

3. A pharmaceutical composition as defined in claim 2, comprising from 2.5 mg to 500 mg of L-lysine-d-amphetamine or a pharmaceutically acceptable salt thereof.

4. A pharmaceutical composition as defined in claim 3, comprising from 10 mg to 250 mg of L-lysine-d-amphetamine or a pharmaceutically acceptable salt thereof.

5. A pharmaceutical composition as defined in claim 4, comprising from 25 mg to 75 mg of L-lysine-d-amphetamine or a pharmaceutically acceptable salt thereof.

6. A pharmaceutical composition as defined in claim 5, comprising 30 mg of L-lysine-d-amphetamine or a pharmaceutically acceptable salt thereof.

7. A pharmaceutical composition as defined in claim 5, comprising 50 mg of L-lysine-d-amphetamine or a pharmaceutically acceptable salt thereof.

8. A pharmaceutical composition as defined in claim 5, comprising 70 mg of L-lysine-d-amphetamine or a pharmaceutically acceptable salt thereof.

9. A pharmaceutical composition as defined in claim 2, comprising a salt of L-lysine-d-amphetamine.

10. A pharmaceutical composition as defined in claim 9, wherein said salt is a mesylate salt.

11. A pharmaceutical composition as defined in claim 10, wherein said salt is a dimesylate salt.

12. A pharmaceutical composition comprising L-lysine-d-amphetamine dimesylate and a pharmaceutically acceptable additive, wherein said pharmaceutical composition has a water content of about 1% to about 10% by Karl Fischer analysis.

13. A pharmaceutical composition as defined in claim 12, wherein said pharmaceutical composition has a water content of about 1% to about 8% by Karl Fischer analysis.

14. A pharmaceutical composition as defined in claim 13, wherein said water content is about 2% to about 7% by Karl Fischer analysis.

* * * * *